(12) United States Patent
Tajima et al.

(10) Patent No.: US 6,506,757 B1
(45) Date of Patent: Jan. 14, 2003

(54) CARBOXYLIC ACID DERIVATIVES AND DRUGS CONTAINING THE SAME AS THE ACTIVE INGREDIENT

(75) Inventors: Hisao Tajima, Osaka (JP); Yoshisuke Nakayama, Osaka (JP); Daikichi Fukushima, Osaka (JP)

(73) Assignee: ONO Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/623,913

(22) PCT Filed: Mar. 9, 1999

(86) PCT No.: PCT/JP99/01134

§ 371 (c)(1),
(2), (4) Date: Sep. 11, 2000

(87) PCT Pub. No.: WO99/46232

PCT Pub. Date: Sep. 16, 1999

(30) Foreign Application Priority Data

Mar. 10, 1998 (JP) ............................................. 10-058444
Mar. 31, 1998 (JP) ........................................... 10-087560

(51) Int. Cl.$^7$ ................... C07D 213/30; C07D 263/32; C07D 277/24; A61K 31/42; A61K 31/215

(52) U.S. Cl. .................. 514/254.02; 514/340; 514/361; 514/365; 514/374; 544/369; 546/271.4; 548/127; 548/204; 548/236

(58) Field of Search ................................. 548/204, 236, 548/127; 546/271.4; 544/369; 514/365, 374, 361, 254.02, 340

(56) References Cited

U.S. PATENT DOCUMENTS 5,262,540 A  11/1993  Meanwell .................... 514/374

FOREIGN PATENT DOCUMENTS

| EP | 0 402 246 | 12/1990 | ........ C07D/277/30 |
| EP | 0 930 299 | 7/1999 | ........ C07D/213/30 |

OTHER PUBLICATIONS

Fayer et al., PubMed Abstract, J. Clin. Pharmacol., 41(3):305–16, Mar. 2001.*

* cited by examiner

*Primary Examiner*—Deepak R. Rao
(74) *Attorney, Agent, or Firm*—Sughrue Mion, PLLC

(57) ABSTRACT

A peroxisome proliferator activated receptor regulator containing a carboxylic acid derivative of formula (I)

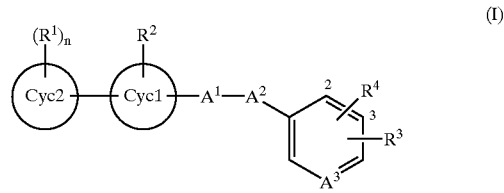

(wherein all symbols are as defined in the specification), a non-toxic acid thereof or a hydrate thereof as active ingredient. Because of having an effect of regulating PPAR, a compound of formula (I) is useful as a hypoglycemic agent, a hypolipidemic agent, a preventive and/or a remedy for diseases associating metabolic disorders (diabetes, obesity, syndrome X, hypercholesterolemia, hyperlipoproteinemia, etc.), hyperlipemia, atherosclerosis, hypertension, circulatory diseases, overeating, coronary heart diseases, etc., an HDL cholesterol-elevating agent, an LDL cholesterol and/or VLDL cholesterol-lowering agent and a drug for relief from risk factors of diseases or syndrome X.

10 Claims, No Drawings

CARBOXYLIC ACID DERIVATIVES AND DRUGS CONTAINING THE SAME AS THE ACTIVE INGREDIENT

This application is a 371 of PCT/JP99/01134 filed Mar. 9, 1999.

TECHNICAL FIELD

The present invention relates to a carboxylic acid derivative and a peroxisome proliferator activated receptor regulator containing carboxylic acid derivative as active ingredient.

More particularly, the present invention relates to a peroxisome proliferator activated regulator containing a compound of formula (I)

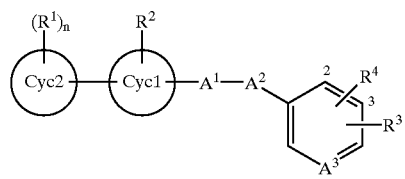

(wherein all symbols are as hereinafter described), a non-toxic salt thereof and a hydrate thereof as active ingredient, a novel carboxylic acid derivative of formula (I), a non-toxic salt thereof, a hydrate thereof and a process for the preparation thereof.

BACKGROUND

Recently in the study of transcription factors concerned with genes expression in adipocytes differentiation, peroxisome proliferator activated receptor (abbreviated as PPAR hereinafter) has been focused. cDNAs of PPAR were cloned from various kinds of animals, and plural isoform genes were found, particularly in mammals three types of isoforms (α, δ, γ) are known (see J. Steroid Biochem. Molec. Biol., 51, 157 (1994); Gene Expression,. 4, 281 (1995); Biochem Biophys. Res. Commun., 224, 431 (1996); Mol. Endocrinology., 6, 1634 (1992)). PPAR γ isoform is predominantly expressed in adipose tissues, immune cells, adrenal gland, spleen, small intestine. PPAR α isoform is mainly expressed in adipose tissue, liver, retina, and δ isoform shows the expression with no tissue specificity, which is widely expressed (see Endocrinology., 137, 354 (1996)).

On the other hand, the following thiazolidine derivatives are known as agents for the treatment of non-insulin dependent diabetes mellitus (NIDDM) and are hypoglycemic agents which are used for the improvement of hyperglycemia in the patients suffering from diabetes. They are also effective for the improvement of hyperinsulinemia, glucose tolerance and decrease of serum lipid and therefore they are thought to be considerably hopeful as agents for the treatment of insulin resistance.

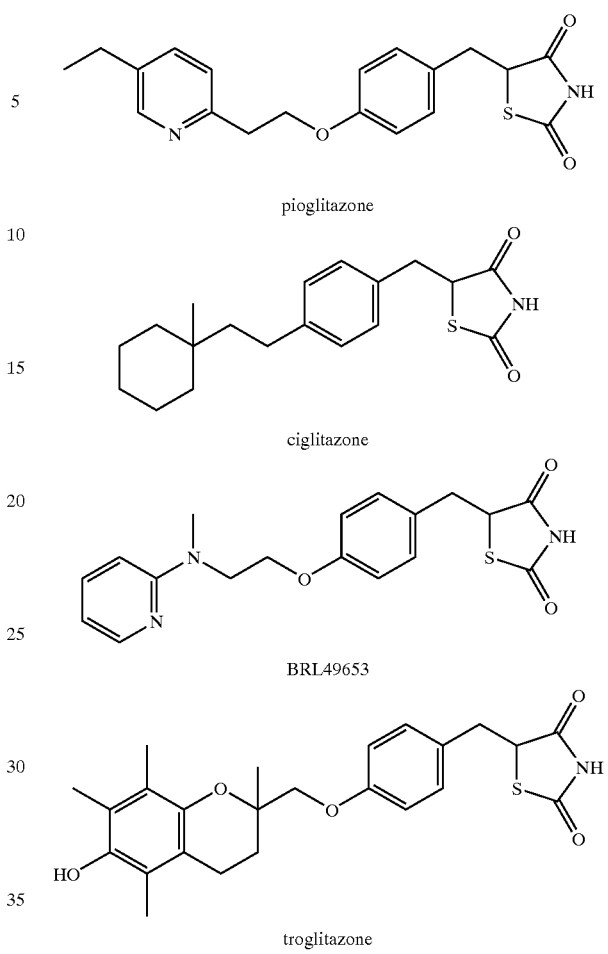

One of the target proteins in the cells of these thiazolidine derivatives is exactly PPAR γ and it is resolved that they enhance the transcription activity of PPAR γ (see Endocrinology., 137, 4189 (1996); Cell., 83, 803 (1995); Cell., 83, 813 (1995); J. Biol. Chem., 270, 12953 (1995)). Therefore, a PPAR activator (agonist) which enhances its transcription activity is thought to be hopeful as a hypoglycemic agent and/or a hypolipidemic agent. Furthermore, since a PPAR γ agonist is known to promote the expression of PPAR γ protein itself (Genes & Development., 10, 974 (1996)), an agent which increases the expression of PPAR γ protein itself as well as PPAR γ activating agent is also clinically useful.

Among all of nuclear receptors, PPAR γ is related to adipocytes differentiation (see J. Biol. Chem., 272, 5637 (1997) and Cell., 83, 803 (1995)). It is known that thiazolidine derivatives which activate this receptor promote adipocytes differentiation. Recently it was reported that thiazolidine derivatives increase fat mass and cause man to gain weight and to become obese (see Lancet., 349, 952 (1997)). Therefore, it is also thought that antagonists which inhibit PPAR γ activity and agents that decrease the expression of PPAR γ protein itself are also clinically applicable. On the other hand, a compound that phosphorylates PPAR γ protein and decreases its activity is reported (Science., 274, 2100 (1996)). This implies that an agent which does not bind on PPAR γ protein as a ligand, but inhibits its activity is also clinically applicable.

From these, PPAR γ activators (agonists) and PPAR γ regulators for its expression that can increase the expression of the protein itself are expected to be useful as hypoglycemic agents, hypolipidemic agents, preventives and/or remedies for diseases associated with metabolic disorders (diabetes, obesity, syndrome X, hypercholesterolemia, hyperlipoproteinemia, etc.), hyperlipidemia, atherosclerosis, hypertension, circulatory diseases, overeating, etc.

On the other hand, antagonists that inhibit the transcription activity of PPAR γ or PPAR γ regulators that inhibit the expression of the protein itself are expected to be useful as hypoglycemic agents, preventives and/or remedies for diseases associated with metabolic disorders (diabetes, obesity, syndrome X, etc.), hyperlipidemia, atherosclerosis, hypertension, overeating, etc.

The following fibrate compound (e.g. chlofibrate) is known as a hypolipidemic agent.

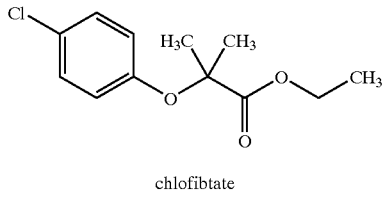

chlofibtate

It is also resolved that one of the target proteins in the cells of fibrate compounds is PPAR α (See Nature., 347, 645 (1990); J. Steroid Biochem. Molec. Biol., 51, 157 (1994); Biochemistry., 32, 5598 (1993)). From these facts, PPAR α regulators, which can be activated by fibrate compounds are thought to have a hypolipidemic effect, and so they are expected to be useful as preventives and/or remedies for hyperlipidemia etc.

Besides, it was recently reported that biological activation of PPAR α linked anti-obese effect in the specification of WO 9736579. It was reported that the elevation of high density lipoprotein (HDL) cholesterol and the reduction of low density lipoprotein (LDL) cholesterol, very low density lipoprotein (VLDL) cholesterol and triglyceride were induced by PPAR α activation (J. Lipid Res., 39, 17 (1998)). It was also reported that improvement of fatty acid composition in the blood, hypertension and insulin resistance by the treatment of bezafibrate (one of fibtrate compounds) (Diabetes., 46, 348 (1997)). Therefore, agonists that activate PPAR α and PPAR α regulators that promote expression of PPAR α protein itself are useful as hypolipidemic agents and remedies for hyperlipidemia , and are expected to have HDL cholesterol-elevating effect, LDL cholesterol and/or VLDL cholesterol-lowering effect, inhibition on the progress of atherosclerosis and anti-obese effect. Therefore, they are thought to be hopeful agents for the treatment and/or prevention of diabetes as hypoglycemic agents, for the improvement of hypertension, for the relief from risk factor of syndrome X and for the prevention of occurrence of coronary heart diseases.

On the other hand, few reports are found on ligands that activate PPAR δ significantly or on biological activities associated with PPAR δ.

PPAR δ is sometimes called PPAR β, or it is also called NUC1 in human. So far it was shown that in the specification of WO 9601430 hNUC1B (PPAR subtype whose structure is different from that of human NUC1 in one amino acid) inhibited the transcription activities of human PPAR α and thyroid hormone receptor. Recently in the specification of WO 9728149, it was reported that compounds bound to PPAR δ protein with high affinity activated PPAR δ significantly (i.e. agonists) and they had HDL (high density lipoprotein) cholesterol-elevating activity. Therefore, agonists :that activate PPAR δ are expected to have HDL cholesterol-elevating effect, and so they are expected to be useful for the inhibition on the progress of atherosclerosis and its treatment, as hypolipidemic agents and/or hypoglycemic agents, for the treatment of hyperlipidemia, as hypoglycemic agents, for the treatment of diabetes, for the relief from risk factor of syndrome X, and for the prevention of occurrence of coronary heart diseases.

The following PPAR regulators have been reported.
(1) For example, in the specification of WO 9728115, it is described that a compound of formula (A)

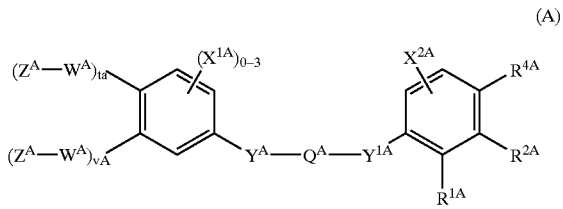

(A)

(wherein $R^{1A}$ is selected from hydrogen, C3~10 cycloalkyl, etc., $R^{2A}$ is selected from hydrogen, C5~10 aryl, C5~10 heteroaryl, etc., $R^{4A}$ is selected from $R^{2A}$ etc., ($Z^A$—$W^A$—) is $Z^A$—$CR^{6A}R^{7A}$ or $Z^A$—$CR^{6A}R^{7A}$—$R^{8A}$—, etc., $R^{8A}$ is selected from $CR^{6A}R^{7A}$, O, $S(O)_{pA}$, etc., $R^{6A}$ and $R^{7A}$ are each independently, selected from hydrogen, C1~6 alkyl, etc., $X^{1A}$ and $X^{2A}$ are each independently, hydrogen, C1~15 alkyl, halogen, etc., $Y^A$ is selected from $S(O)_{pA}$, —O—, etc., $Y^{1A}$ is selected from O, C, etc., $Z^A$ is selected from $CO_2R^{3A}$ etc., tA and vA are each independently 0 or 1, tA+vA is 1, $Q^A$ is saturated or unsaturated 2~4 straight-chained hydrocarbon, pA is 0~2, $R^{3A}$ is hydroxy, C1~15 alkoxy, etc.) or a pharmaceutically acceptable salt thereof is a PPAR δ modulator (necessary part is extracted in the explanation of the group). In the specifications of WO 9727857 and WO 9728137, it is described that analogous compounds therewith are also PPAR δ modulators.

(2) In the specification of WO 9731907, it is described that a compound of formula (B)

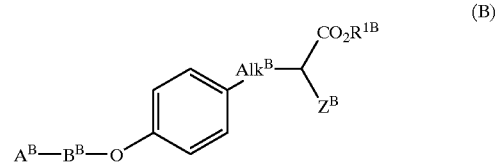

(B)

(wherein $A^B$ is phenyl, said phenyl may be substituted by one or more of halogen, C1~6 alkyl, C1~3 alkoxy, C1~3 fluoroalkoxy, nitrile or —$NR^{7B}R^{8B}$ ($R^{7B}$ and $R^{8B}$ are each independently hydrogen or C1~3 alkyl);

$B^B$ is 5 or 6-membered hetero ring—C1~6 alkylene-, said hetero ring may be substituted by C1~3 alkyl;

$Alk^B$ is C1~3 alkylene;

$R^{1B}$ is hydrogen or C1~3 alkyl;

$Z^B$ is selected from —(C1~3 alkylene)phenyl or —$NR^{3B}R^{4B}$) or a pharmaceutically acceptable salt thereof has PPAR γ agonist activity (necessary part is extracted in the explanation of the group).

(3) In the specification of JP Kokai Hei 9-323982, it is described that a propionic acid derivative of formula (C)

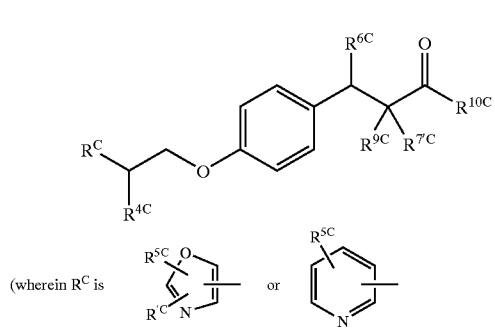

(wherein R$^C$ is (wherein R$^{1C}$ is an optionally substituted aromatic hydrocarbon, an optionally substituted cyclic aliphatic hydrocarbon, an optionally substituted hetero ring or an optionally substituted fused hetero ring and R$^{5C}$ is lower alkyl), R$^{4C}$ is hydrogen or lower alkyl, R$^{6C}$ is hydrogen or taken together with R$^{9C}$ to form a double bond, R$^{7C}$ is hydrogen, hydroxy, carboxy, acyl, optionally substituted alkoxycarbonyl, optionally substituted lower alkyl, optionally substituted carbamoyl, optionally substituted aryloxycarbonyl, optionally substituted aralkyloxycarbonyl or a group represented by formula —Y$^C$—R$^C$ (wherein Y$^C$ is —NH— or oxygen, R$^{8C}$ is optionally substituted acyl, optionally substituted alkoxycarbonyl, aryloxycarbonyl or aralkyloxycarbonyl), R$^{9C}$ is hydrogen, optionally substituted lower alkyl or optionally substituted lower alkoxycarbonyl, R$^{10C}$ is hydroxy, optionally substituted amino, optionally substituted lower alkoxy, optionally substituted lower alkyl, optionally substituted aryloxy or optionally substituted aralkyloxy) or a pharmaceutical composition containing a pharmaceutically acceptable salt thereof has hypoglycemic effect and hypolipidemic effect. In the specifications of JP Kokai Hei 8-325264, JP Kokai Hei 8-325250, WO 9638415 and WO 9800137, it is described that analogous compounds therewith have hypoglycemic effect and hypolipidemic effect.

(4) In the specification of JP Kokai Hei 8-104688, it is described that a compound of formula (D)

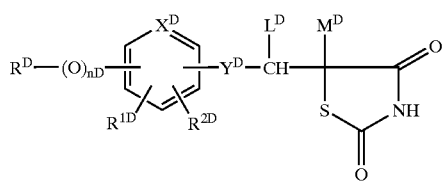

(wherein R$^D$ is an optionally substituted hydrocarbon residue or a hetero ring which may be bound through carbon chain(s), n$^D$ is 0 or 1, X$^D$ is CH or N, Y$^D$ is a bivalent hydrocarbon residue. R$^{1D}$ and R$^{2D}$ are the same or different to represent hydrogen, halogen, optionally substituted hydroxyl or an optionally substituted hydrocarbon residue, and either of R$^{1D}$ or R$^{2D}$ may be taken attached to a part of Y$^D$ to form a ring) or a salt thereof has hypoglycemic effect and hypolipidemic effect. In the specification of JP Kokai Sho 61-85372, it is described that analogous compounds therewith also have hypoglycemic effect and hypolipidemic effect.

(5) In the specification of JP Kokai Hei 1-143856, it is described that a compound of formula (E)

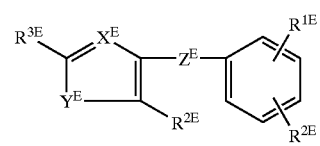

(wherein X$^E$ is —CR$^{4E}$═ or —N═, Y$^E$ is —CR$^{4E}$═N—, —N═CR$^{4E}$—, —CR$^{4E}$═CR$^{4E}$—, —O—, —S— or —NR$^{4E}$—, Z$^E$ is —(CH$_2$)$_{nE}$O—, —(CH$_2$)$_{nE}$S—, etc., R$^{1E}$ is —(CHR$^{7E}$)$_{nE}$COOR$^{6E}$ etc., nE is each independently 0~5, R$^{2E}$ is each hydrogen, lower alkyl, lower alkoxy, trifluoromethyl, nitro, cyano or halogen, etc., R$^{3E}$ is

W$^E$ is a bond or —O—, —S— or —NR$^{4E}$—, mE is 1~15, R$^{4E}$ is each independently hydrogen or lower alkyl, R$^{7E}$ is hydrogen or methyl) or a pharmaceutically acceptable salt thereof has an inhibitory activity against lipoxygenase and a competitive activity against leucotriene.

(6) In the specification of JP Kohyo Hei 8-504194, it is described that a compound of formula (F)

$$X^F—Y^F—Z^F—\text{"Aryl}^F\text{"}—A^F—B^F \quad (F)$$

(wherein "Aryl F" is a monocyclic 6-membered hetero ring system containing 0, 1, 2, 3 or 4 of N atom and having no substituents or substituted by R$^{5F}$;

X$^F$ is a mono- or multi-cyclic aromatic or non-aromatic 4~10 membered ring system etc. containing 0, 1, 2, 3 or 4 of hetero atom selected from N, O and S and having no substituents or substituted by R$^{1F}$, R$^{2F}$, R$^{3F}$ or R$^{4F}$, R$^{1F}$, R$^{2F}$, R$^{3F}$ and R$^{4F}$ are independently selected from a group of hydrogen, C1~10 alkyl, C3~8 cycloalkyl, aryl C0~8 alkyl, amino C0~8 alkyl, C1~6 alkylamino C0~8 alkyl, C1~6 dialkylamino C0~8 alkyl, C1~4 alkoxy C0~6 alkyl, etc.;

Y$^F$ is C0~8 alkyl, C0~8 alkyl-O-C0~8 alkyl, C0~8 alkyl-SO$_{nF}$—C0~8 alkyl, etc., wherein nF is an integer of 0~2, Z$^F$ and A$^F$ are independently selected from (CH$_2$)$_{mF}$, (CH$_2$)$_{mF}$O(CH$_2$)$_{nF}$, (CH$_2$)$_{mF}$SO$_2$(CH$_2$)$_{nF}$, (CH$_2$)$_{mF}$S (CH$_2$)$_{nF}$, (CH$_2$)$_{mF}$SO(CH$_2$)$_{nF}$, etc., wherein mF and nF are integers independently selected from 0~6, with the proviso that when A$^F$ is (CH$_2$)$_{mF}$, "Aryl F" which is attached to Z$^F$ and A$^F$ must contain at least 1 hetero atom;

R$^{5F}$ is hydrogen, C1~6 alkyl, C0~6 alkyloxy C0~6 alkyl, or halogen, etc., B$^F$ is

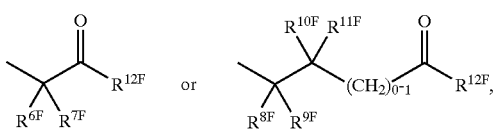 or wherein
$R^{6F}$, $R^{7F}$, $R^{8F}$, $R^{9F}$, $R^{10F}$ and $R^{11F}$ are independently selected from hydrogen, C1~8 alkyl, etc.,
$R^{12F}$ is selected from hydroxy, C1~8 alkyloxy, etc.) and a pharmaceutically acceptable salt have fibrinogen receptor antagonist activity (necessary part is extracted in the explanation of the group).

DISCLOSURE OF THE INVENTION

As a result of energetic investigations in order to find compounds which possess PPAR regulating activity, the present inventors have found that the purpose is accomplished by the compound of formula (I).

Part of the compounds of formula (I) is known by the said specifications of JP Kokai Hei 1-143856 and JP Kohyo Hei 8-504194. The effects of these compounds, that is to say, lipoxygenase inhibitory activity, leucotriene competitive activity and fibrinogen receptor antagonist activity are also known, but PPAR regulating effect of these compounds is not easily expected from these facts.

The other part of the compounds of formula (I) is novel which has never been known so far.

The present invention relates to
1) a peroxisome proliferator activated receptor regulator containing a carboxylic acid derivative of formula (I)

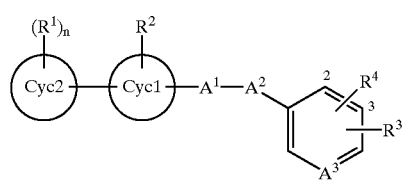 (I)

(wherein
$A^1$ is C1~4 alkylene or C2~4 alkenylene,
$A^2$ is —O— or —S—,
$A^3$ is CH or N,
n is 1~5,
$R^1$ is
  (i) hydrogen,
  (ii) C1~8 alkyl,
  (iii) halogen,
  (iv) C1~4 alkoxy,
  (v) nitro,
  (vi) trihalomethyl,
  (vii) trihalomethoxy,
  (viii) trihalomethylthio,
  (ix) cyano,
  (x) C1~4 alkylthio,
  (xi) NR$^5$R$^6$ (wherein R$^5$ and R$^6$ are each independently, hydrogen or C1~4 alkyl),
  (xii) carbocyclic ring or
  (xiii) hetero ring,
$R^2$ is
  (i) hydrogen,
  (ii) C1~4 alkyl,
  (iii) halogen or
  (iv) trihalomethyl,
$Cyc^1$ is

 (i)

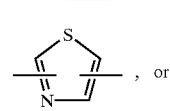 , or (ii)

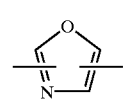 (iii)

$Cyc^2$ is
  (i) carbocyclic ring or
  (ii) hetero ring,
$R^3$ is
  (i) hydrogen,
  (ii) C1~8 alkyl,
  (iii) halogen,
  (iv) C1~4 alkoxy,
  (v) nitro,
  (vi) trihalomethyl,
  (vii) trihalomethoxy,
  (viii) trihalomethylthio,
  (ix) cyano or
  (x) C1~4 alkylthio,
$R^4$ is

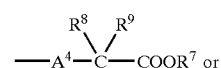 (i)

(ii) 2,4-thiazolidindion-5-yl,
$A^4$ is
  (i) bond,
  (ii) C1~4 alkylene,
  (iii) —C1~4 alkylene-O— or
  (iv) —C1~4 alkylene-S—,
$R^7$, $R^8$ and $R^9$ are each independently hydrogen or C1~4 alkyl, with the proviso that
  (1) $R^4$ is attached to 2- or 3-position and
  (2) when $R^4$ is attached to 3-position, $A^4$ is bond or methylene, $A^3$ is CH and $Cyc^1$ is benzene, then $A^1$ is methylene, ethylene or vinylene.), its non-toxic salt or hydrate thereof as active ingredient,
2) a carboxylic acid derivative of formula (I)

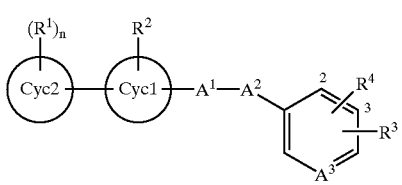 (I)

(wherein
$A^1$ is C1~4 alkylene or C2~4 alkenylene,
$A^2$ is —O— or —S—,
$A^3$ is CH or N, n is 1~5, $R^1$ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano,
(x) C1~4 alkylthio,
(xi) $NR^5R^6$ (wherein $R^5$ and $R^6$ are each independently hydrogen or C1~4 alkyl),
(xii) carbocyclic ring or
(xiii) hetero ring, $R^2$ is
(i) hydrogen,
(ii) C1~4 alkyl,
(iii) halogen or
(iv) trihalomethyl, $Cyc^1$ is

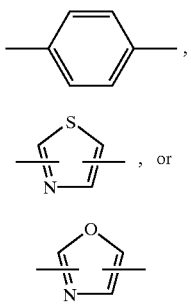

$Cyc^2$ is
(i) a carbocyclic ring or
(ii) a hetero ring, $R^3$ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano or
(x) C1~4 alkylthio, $R^4$ is

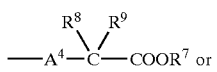

(ii) 2,4-thiazolidindion-5-yl, $A^4$ is
(i) bond,
(ii) C1~4 alkylene,
(iii) —C1~4 alkylene-O— or
(iv) —C1~4 alkylene-S—, $R^7$, $R^8$ and $R^9$ are each independently hydrogen or C1~4 alkyl, with the proviso that (1) $R^4$ is attached to 2- or 3-position and
(2) when $R^4$ is attached to 3-position, $A^4$ is a bond or methylene, $A^3$ is CH and $Cyc^1$ is benzene, $A^1$ is methylene, ethylnene or vinylene.), a non-toxic acid thereof or a hydrate thereof and 3) a method for the preparation of a compound of formula (I).

DETAILED EXPLANATION OF THE INVENTION

Unless otherwise specified, all isomers are included in the present invention. For example, alkyl, alkenyl, alkynyl, alkoxy, alkylthio, alkylene, alkenylene and alkynylene include straight-chain and branched-chain ones. Moreover, the isomers in the structure of double bond, ring, fused ring (E, Z, cis, trans), the isomers generated by the presence of asymmetric carbon atom(s) etc. (R, S isomers, α, β isomers, enantiomers, diastereomers) optically active isomers having optical rotation (D, L, d, l isomers), isomers separated by chromatography (more polar or less polar isomers), equilibrium compounds, compounds of arbitrary ratio of these compounds.

In the present invention, C1~4 alkyl is methyl, ethyl, propyl, butyl and isomers thereof.

C1~8 alkyl is methyl, ethyl, propyl, butyl, pentyl, hexyl, heptyl, octyl and isomers thereof.

C1~4 alkoxy is methoxy, ethoxy, propoxy, butoxy and isomers thereof.

C1~4 alkylthio is methylthio, ethylthio, propylthio, butylthio and isomers thereof.

C1~4 alkylene is methylene, ethylene, trimethylene, tetramethylene and isomers thereof.

C2~4 alkenylene is ethenylene, propenylene, butenylene and isomers thereof.

Halogen is iodine, bromine, fluorine and chlorine.

Trihalomethyl is methyl group which is tri-substituted by iodine, bromine, fluorine or chlorine.

Trihalomethoxy is methoxy group which is tri-substituted by iodine, bromine, fluorine or chlorine.

Trihalomethylthio is methylthio group which is tri-substituted by iodine, bromine, fluorine or chlorine.

Carbocyclic ring represents C3~15 mono-, bi-, or tri-cyclic carbon ring and bridged carbocyclic ring. C3~15 mono-, bi-, or tri-cyclic carbon ring and bridged carbocyclic ring contains, for example, cyclopropane, cyclobutane, cyclopentane, cyclohexane, cycloheptane, cyclooctane, cyclononane, cyclodecane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydronaphthalene, indane (dihydroindene), perhydroindene, dihydronaphthalene, tetrahydronaphthalene, perhydronaphthalene, perhydroazulene, perhydrofluorene, perhydrophenanthrene, perhydroanthracene, perhydroacenaphthylene, perhydrophenylene, bicyclopentane, bicyclohexane, bicycloheptane ([2.2.1]bicycloheptane), bicyclooctane, bicyclononane, bicyclodecane, adamantane, etc.

Hetero ring includes a 4~18 membered mono-, di- or tri-cyclic hetero aryl, or partially or completely saturated one containing 1~4 of nitrogen, 1~2 of oxygen and/or 1 of sulfur.

Said 4~18 membered mono-, di- or tri-cyclic hetero aryl containing 1~4 of nitrogen, 1~2 of oxygen and/or 1 of sulfur includes pyrrole, imidazole, triazole, tetrazole, pyrazole, pyridine, pyrazine, pyrimidine, pyridazine, azepine, diazepine, furan, pyran, oxepin, oxazepin, thiophene, thiain (thiopyran), thiepin, oxazole, isoxazole, thiazole, isothiazole, oxadiazole, oxazine, ozadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, carbazole, acridine, etc.

Said 4~18 membered mono-, di- or tri-cyclic hetero aryl or partially or completely saturated one containing 1~4 of nitrogen, 1~2 of oxygen and/or 1 of sulfur includes pyrroline, pyrrolidine, imidazoline, imidazolidine, triazoline, triazolidine, tetrazoline, tetrazolidine, dihydropyridine, dihydropyrazine, dihydropyrimidine, dihydropyridazine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydroxazole, tetrahydroxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzothiadiazepine, benzazepine, benzodiazepine, indoloxazepine, indolotetrahydroxazepine, indoloxadiazepine, indolotetrahydroxadiazepine, indolothiazepine, indolotetrahydrothiazepine, indolothiadiazepine, indolotetrahydrothiadiazepine, indolazepine, indolotetrahydroazepine, indolodiazepine, indolotetrahydrodiazepine, benzofurazane, benzothiadiazole, benzotriazole, camphor, imidazothiazole, dihydrocarbazole, tetrahydrocarbazole, perhydrocarbazole, dihydroacridine, tetrahydroacridine, perhydroacridine, 1,3-dioxaindane, 1,4-dioxaindane ring, etc.

In the formula (I), $R^2$ is preferably C1~4 alkyl, more preferably methyl and ethyl.

In the formula (I), $Cyc^1$ is preferably,

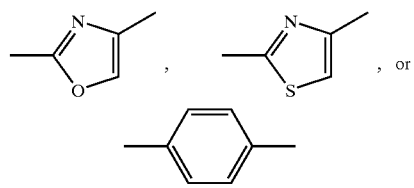

(wherein the bond in the right hand is attached to $A^1$), more preferably

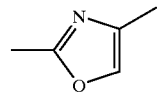

(wherein the bond in the right hand is attached to $A^1$.).

In the formula (I), $A^1$ is preferably C1~4 alkylene, more preferably C1~2 alkylene (—$CH_2$—, —$(CH_2)_2$—).

In the formula (I), $A^2$ is preferably —O—.

In the formula (I), $A^3$ is preferably CH.

In the formula (I), $R^4$ is preferably attached to 3-position.

In the formula (I), $R^4$ is preferably

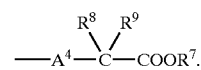

In the formula (I), $A^4$ is preferably a bond, —C1~4 alkylene-O— or —C1~4 alkylene-S—, more preferably a bond or —$CH_2$—S—. In the formula (I), $R^8$ and $R^9$ are preferably hydrogen or methyl, more preferably hydrogen.

In the formula (I), $R^1$ is preferably hydrogen, C1~8alkyl, halogen, trihalomethoxy or trihalomethylthio, more preferably hydrogen, halogen or trihalomethoxy.

In the formula (I), a carbocyclic ring represented by $Cyc^2$ is, preferably C3~10 mono- or bi-cyclic carbon ring, more preferably cyclopropane, cyclobutane, cyclopentane, cyclohexane, cycloheptane, cyclooctane, cyclononane, cyclodecane or benzene, particularly preferably, cyclopropane, cyclopentane, cyclohexane or benzene.

In the formula (I), a hetero ring represented by $Cyc^2$ is preferably 3~10 membered mono- or bi-cyclic hetero aryl containing 1~2 of nitrogen, 1~2 of oxygen and/or 1 of sulfur or partly or totally saturated one, more preferably furan, thiophene, pyridine, quinoline, thiadiazole (1,2,3-thiadiazole), piperazine or dioxaindane (1,3-dioxaindane), particularly preferably dioxaindane (1,3-dioxaindane).

In the formula (I), a carbocyclic ring represented by $R^1$ is preferably C3~10 mono- or bi-cyclic carbon ring, more preferably cyclopropane, cyclobutane, cyclopentane, cyclohexane, cycloheptane, cyclooctane, cyclononane, cyclodecane or benzene, particularly preferably cyclopropane, cyclopentane, cyclohexane or benzene.

In the formula (I), a hetero ring represented by $R^1$ is preferably a 5~10 membered mono- or bi-cyclic hetero aryl or partially or completely saturated one containing 1~2 of nitrogen, 1~2 of oxygen and/or 1 of sulfur, more preferably furan, thiophene, pyridine, thiadiazole (1,2,3-thiazole), piperazine or dioxaindane (1,3-dioxaindane), particularly preferably thiadiazole (1,2,3-thiadiazole).

In the present invention, PPAR regulator includes all the regulators of PPAR α, γ, δ, α+γ, α+δ, γ+δ and α+γ+δ. Preferable regulatory fashion is, PPAR α regulator, PPAR δ regulator, PPAR α+γ regulator, PPAR α+δ regulator, more preferably PPAR α+γ regulator or PPAR δ regulator.

PPAR regulator also includes PPAR agonist and PPAR antagonist, preferably PPAR agonist, more preferably PPAR α agonist, PPAR δ agonist, PPAR α+γ agonist or PPAR α+γ agonist or PPAR α+δ agonist, particularly preferably PPAR α+γ agonist or PPAR δ agonist.

Among the..compounds of formula (I), preferable ones are, a compound of formula (I-a)

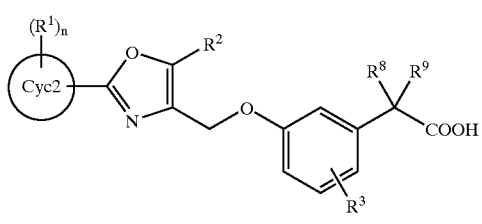
(I-a)

(wherein all symbols are as hereinbefore described), a compound of formula (I-b)

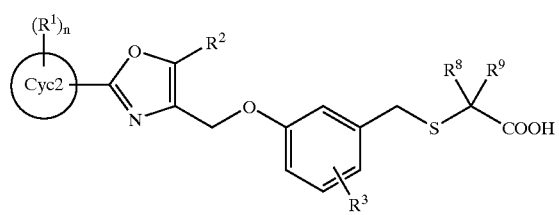
(I-b)

(wherein all symbols are as hereinbefore described), a compound of formula (I-c)

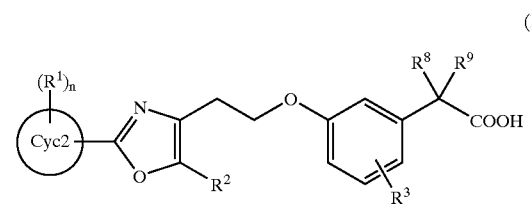
(I-c)

(wherein all symbols are as hereinbefore described), a compound of formula (I-d)

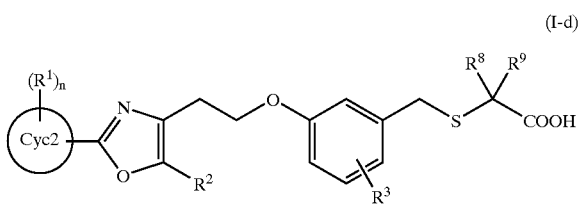
(I-d)

(wherein all symbols are as hereinbefore described), a compound of formula (I-e)

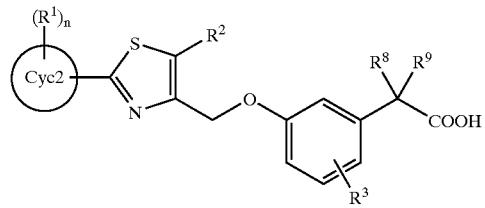
(I-e)

(wherein all symbols are as hereinbefore described), a compound of formula (I-f)

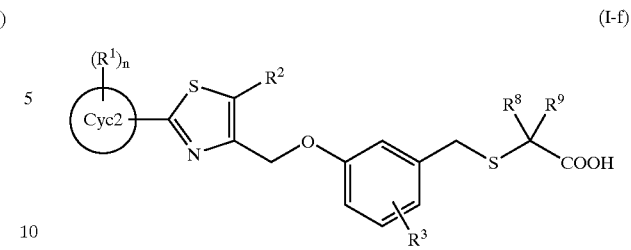
(I-f)

(wherein all symbols are as hereinbefore described), a compound of formula (I-g)

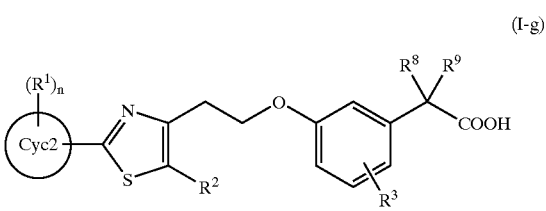
(I-g)

(wherein all symbols are as hereinbefore described), a compound of formula (I-h)

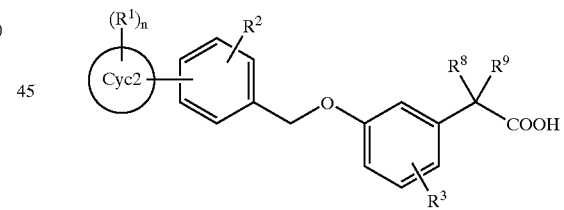
(I-h)

(wherein all symbols are as hereinbefore described), a compound of formula (I-j)

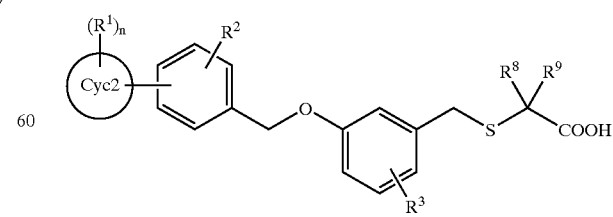
(I-j)

(wherein all symbols are as hereinbefore described), a compound of formula (I-k)

(I-k)

(wherein all symbols are as hereinbefore described), a compound of formula (I-l)

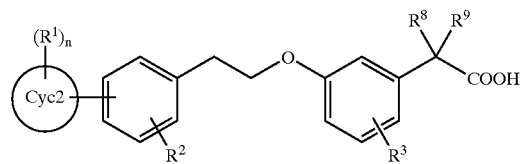

(I-l)

(wherein all symbols are as hereinbefore described), a compound of formula (I-m)

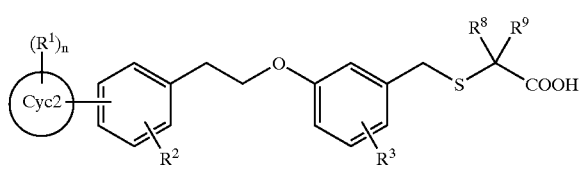

(I-m)

a non-toxic salt thereof and a hydrate thereof.

Concrete compounds include the ones described in the following tables 1–20, non-toxic salts thereof and hydrates thereof.

In the following tables, Me represents methyl, Et represents ethyl, t-Bu represents t-butyl and the other symbols are as hereinbefore described.

TABLE 1

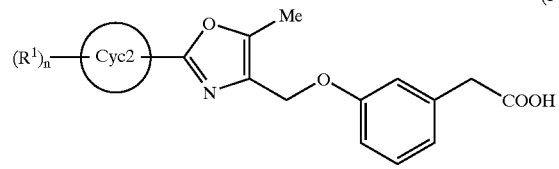
(I-a-1)

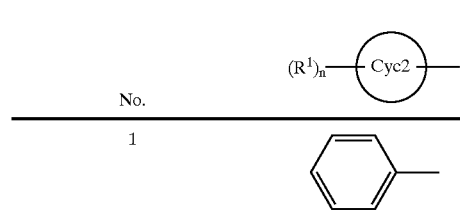

| No. | (R¹)ₙ—Cyc2— |
|---|---|
| 1 | 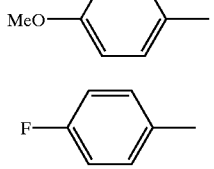 |
| 2 | Me— phenyl |
| 3 | t-Bu— phenyl |
| 4 | MeO— phenyl |
| 5 | F— phenyl |

TABLE 1-continued

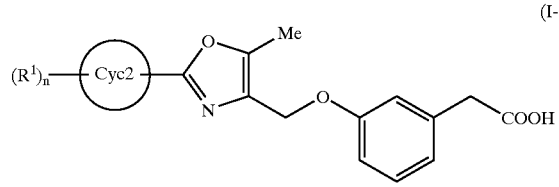
(I-a-1)

| No. | (R¹)ₙ—Cyc2— |
|---|---|
| 6 | 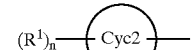 Cl— |
| 7 | 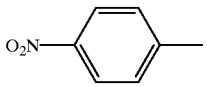 O₂N— |
| 8 | 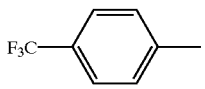 F₃C— |
| 9 | 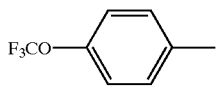 F₃CO— |
| 10 | 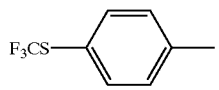 F₃CS— |
| 11 | 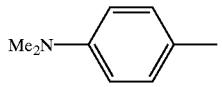 Me₂N— |
| 12 | 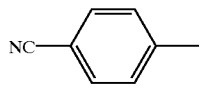 NC— |
| 13 | 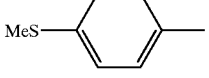 MeS— |
| 14 | 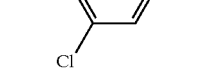 Me—, Cl— |
| 15 | 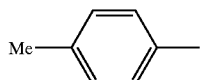 Me—, O₂N— |
| 16 | 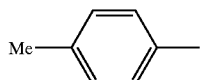 MeO—, MeO— |

TABLE 1-continued
(I-a-1)
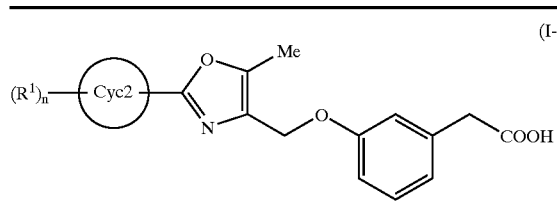
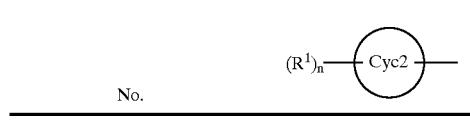
| No. | |
|---|---|
| 17 | 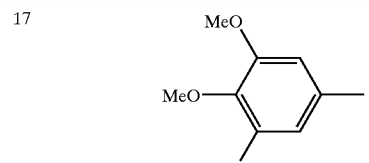 |
| 18 | 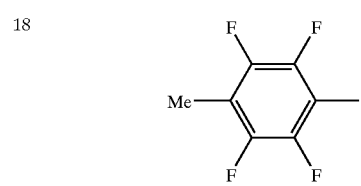 |
| 19 |  |
| 20 |  |
| 21 |  |
| 22 | 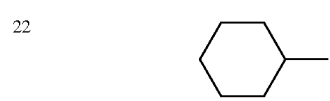 |
| 23 |  |
| 24 | 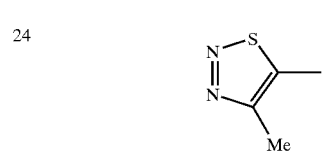 |
| 25 |  |
| 26 | 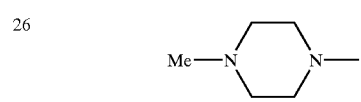 |
| 27 | 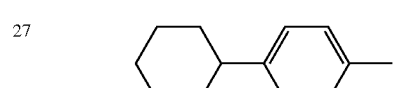 |
TABLE 1-continued
(I-a-1)
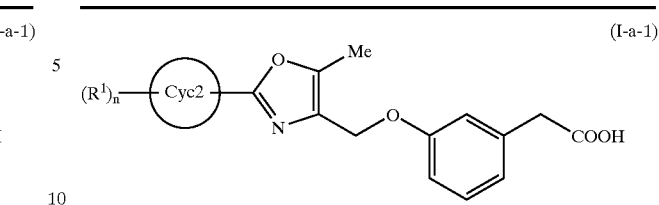
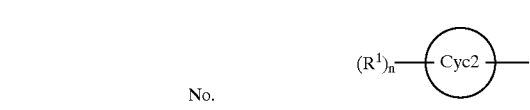
| No. | |
|---|---|
| 28 | 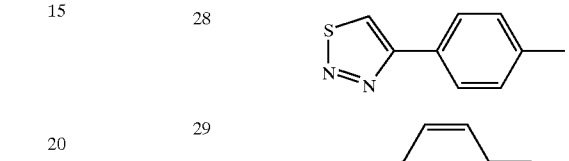 |
| 29 | 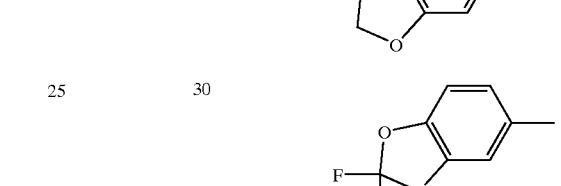 |
| 30 | 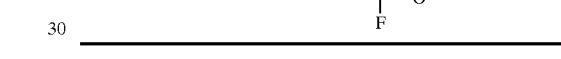 |
TABLE 2
(I-a-2)
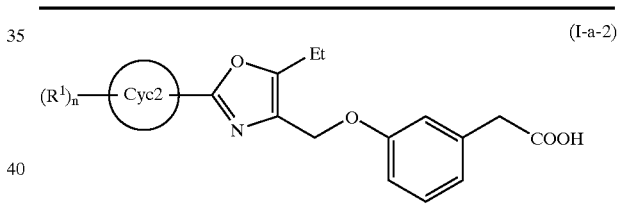
| No. | |
|---|---|
| 1 |  |
| 2 | 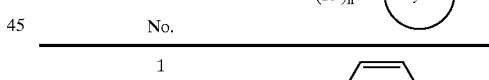 |
| 3 |  |
| 4 |  |
| 5 |  |

TABLE 2-continued (I-a-2)

[Structure: (R¹)ₙ-Cyc2-oxazole(Et)-CH₂-O-phenyl-CH₂COOH]

(R¹)ₙ—Cyc2—

| No. | (R¹)ₙ—Cyc2— |
|---|---|
| 6 | 4-Cl-C₆H₄— |
| 7 | 4-O₂N-C₆H₄— |
| 8 | 4-F₃C-C₆H₄— |
| 9 | 4-F₃CO-C₆H₄— |
| 10 | 4-F₃CS-C₆H₄— |
| 11 | 4-Me₂N-C₆H₄— |
| 12 | 4-NC-C₆H₄— |
| 13 | 4-MeS-C₆H₄— |
| 14 | 4-Me-3-Cl-C₆H₃— |
| 15 | 4-Me-3-O₂N-C₆H₃— |
| 16 | 3,4-(MeO)₂-C₆H₃— |
| 17 | 3,4,5-(MeO)₃-C₆H₂— |
| 18 | 2,3,5,6-tetrafluoro-4-Me-C₆— |
| 19 | cyclopropyl |
| 20 | cyclopentyl |
| 21 | 2-thienyl |
| 22 | cyclohexyl |
| 23 | 2-furyl |
| 24 | 4-methyl-1,2,3-thiadiazol-5-yl |
| 25 | 4-pyridyl |
| 26 | 4-methylpiperazin-1-yl (Me-N-piperazine) |
| 27 | 4-cyclohexylphenyl |

TABLE 2-continued
(I-a-2)
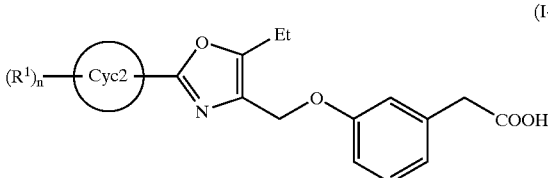
| No. | (R¹)ₙ—Cyc2— |
|---|---|
| 28 | 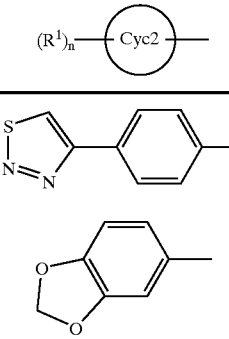 |
| 29 | 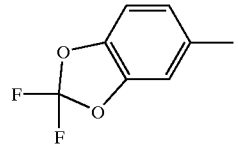 |
| 30 | 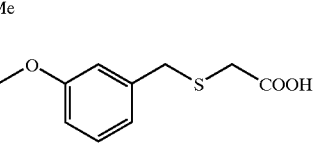 |
TABLE 3
(I-b-1)
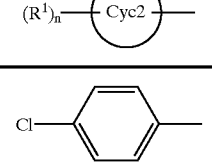
| No. | (R¹)ₙ—Cyc2— |
|---|---|
| 1 | 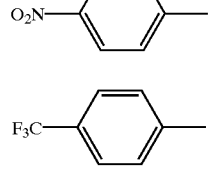 |
| 2 | 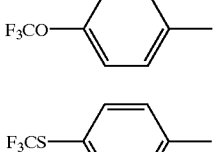 |
| 3 | 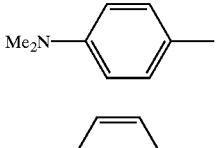 |
| 4 | 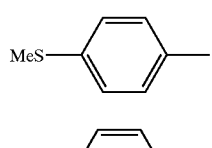 |
| 5 | 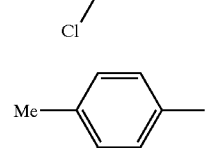 |
TABLE 3-continued
(I-b-1)
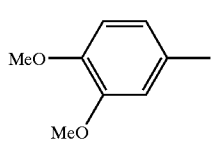
| No. | (R¹)ₙ—Cyc2— |
|---|---|
| 6 |  |
| 7 | 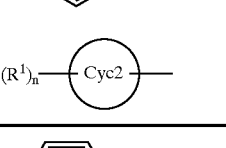 |
| 8 | 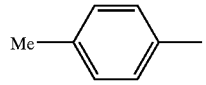 |
| 9 | 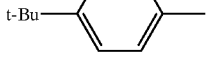 |
| 10 | 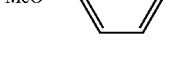 |
| 11 | 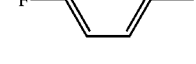 |
| 12 | NC—⟨phenyl⟩— |
| 13 | MeS—⟨phenyl⟩— |
| 14 | Me,Cl-substituted phenyl |
| 15 | Me,O₂N-substituted phenyl |
| 16 | MeO,MeO-substituted phenyl |

TABLE 3-continued (I-b-1)

[Structure: (R¹)ₙ–Cyc2–oxazole(5-Me)–CH₂O–phenyl–CH₂–S–CH₂COOH]

(R¹)ₙ–Cyc2–

| No. | Cyc2 group |
|-----|-----|
| 17 | 3,4,5-trimethoxyphenyl (MeO, MeO, MeO) |
| 18 | tetrafluoro-methylphenyl (Me, F, F, F, F) |
| 19 | cyclopropyl |
| 20 | cyclopentyl |
| 21 | 2-thienyl |
| 22 | cyclohexyl |
| 23 | 2-furyl |
| 24 | 4,5-dimethyl-1,2,3-thiadiazolyl (Me, Me) |
| 25 | 4-pyridyl |
| 26 | 4-methylpiperazin-1-yl (Me–N, N–) |
| 27 | 4-cyclohexylphenyl |
| 28 | 4-(1,2,3-thiadiazol-4-yl)phenyl |
| 29 | benzo[1,3]dioxol-5-yl (methylenedioxyphenyl) |
| 30 | 2,2-difluorobenzo[1,3]dioxol-5-yl |

TABLE 4

(I-b-2)

[Structure: (R¹)ₙ–Cyc2–oxazole(5-Et)–CH₂O–phenyl–CH₂–S–CH₂COOH]

(R¹)ₙ–Cyc2–

| No. | Cyc2 group |
|-----|-----|
| 1 | phenyl |
| 2 | 4-methylphenyl (Me) |
| 3 | 4-tert-butylphenyl (t-Bu) |
| 4 | 4-methoxyphenyl (MeO) |
| 5 | 4-fluorophenyl (F) |

TABLE 4-continued
(I-b-2)
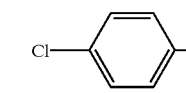
| No. | (R¹)ₙ—Cyc2— |
|---|---|
| 6 | 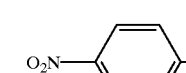 |
| 7 | 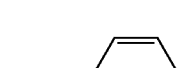 |
| 8 | 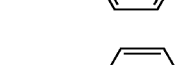 |
| 9 | 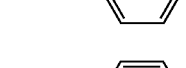 |
| 10 | 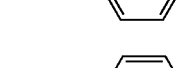 |
| 11 | 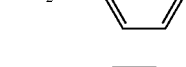 |
| 12 | 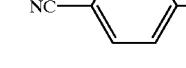 |
| 13 | 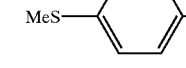 |
| 14 | 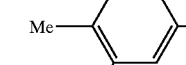 |
| 15 | 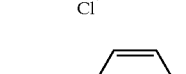 |
| 16 | MeO—⟨benzene⟩—, MeO |
| 17 | MeO, MeO, MeO-trisubstituted benzene |
| 18 | F,F,F,F-tetrafluoro-Me benzene |
| 19 | cyclopropyl |
| 20 | cyclopentyl |
| 21 | 2-thienyl |
| 22 | cyclohexyl |
| 23 | 2-furyl |
| 24 | 4,5-dimethyl-thiadiazolyl |
| 25 | 4-pyridyl |
| 26 | 4-methylpiperazin-1-yl (Me-N\_/N—) |
| 27 | 4-cyclohexylphenyl |

TABLE 4-continued (I-b-2)

$(R^1)_n$—Cyc2—[oxazole with Et]—CH₂—O—[phenyl]—CH₂—S—CH₂COOH

| No. | (R¹)ₙ—Cyc2— |
|---|---|
| 28 | 4-(1,2,3-thiadiazol-4-yl)phenyl |
| 29 | 5-(benzo[1,3]dioxol)yl |
| 30 | 2,2-difluoro-benzo[1,3]dioxol-5-yl |

TABLE 5

(I-c-1)

$(R^1)_n$—Cyc2—[oxazole with Me]—CH₂CH₂—O—[phenyl]—CH₂COOH

| No. | (R¹)ₙ—Cyc2— |
|---|---|
| 1 | phenyl |
| 2 | 4-Me-phenyl |
| 3 | 4-t-Bu-phenyl |
| 4 | 4-MeO-phenyl |
| 5 | 4-F-phenyl |

TABLE 5-continued (I-c-1)

$(R^1)_n$—Cyc2—[oxazole with Me]—CH₂CH₂—O—[phenyl]—CH₂COOH

| No. | (R¹)ₙ—Cyc2— |
|---|---|
| 6 | 4-Cl-phenyl |
| 7 | 4-O₂N-phenyl |
| 8 | 4-F₃C-phenyl |
| 9 | 4-F₃CO-phenyl |
| 10 | 4-F₃CS-phenyl |
| 11 | 4-Me₂N-phenyl |
| 12 | 4-NC-phenyl |
| 13 | 4-MeS-phenyl |
| 14 | 4-Me, 3-Cl-phenyl |
| 15 | 4-Me, 2-O₂N-phenyl |
| 16 | 3,4-(MeO)₂-phenyl |

TABLE 5-continued (I-c-1)

(R¹)ₙ-Cyc2- [oxazole with 5-Me, linked via CH₂CH₂O to 3-(carboxymethyl)phenyl] -COOH (R¹)ₙ-Cyc2-

| No. | Cyc2 structure |
|---|---|
| 17 | 3,4,5-trimethoxyphenyl |
| 18 | 3-methyl-2,4,5,6-tetrafluorophenyl |
| 19 | cyclopropyl |
| 20 | cyclopentyl |
| 21 | 2-thienyl |
| 22 | cyclohexyl |
| 23 | 2-furyl |
| 24 | 5-methyl-1,2,3-thiadiazol-4-yl (4-Me) |
| 25 | 4-pyridyl |
| 26 | 4-methylpiperazin-1-yl (Me-N, N-Me) |
| 27 | 4-cyclohexylphenyl |
| 28 | 4-(4-methylphenyl)-1,2,3-thiadiazol-... |
| 29 | 6-methyl-1,3-benzodioxol-5-yl |
| 30 | 2,2-difluoro-6-methyl-1,3-benzodioxol-5-yl |

TABLE 6

(I-c-2)

(R¹)ₙ-Cyc2- [oxazole with 5-Et, linked via CH₂CH₂O to 3-(carboxymethyl)phenyl] -COOH (R¹)ₙ-Cyc2-

| No. | Cyc2 structure |
|---|---|
| 1 | phenyl |
| 2 | 4-methylphenyl |
| 3 | 4-t-butylphenyl |
| 4 | 4-methoxyphenyl |
| 5 | 4-fluorophenyl |
| 6 | 4-chlorophenyl |

TABLE 6-continued
(I-c-2)
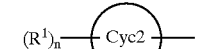
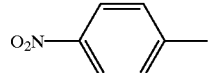
| No. | (R¹)ₙ—Cyc2— |
|---|---|
| 7 | 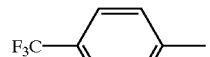 |
| 8 | 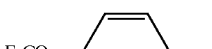 |
| 9 | 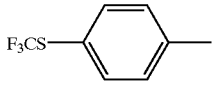 |
| 10 | 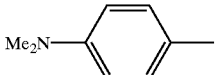 |
| 11 | 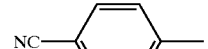 |
| 12 | 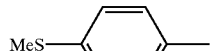 |
| 13 | 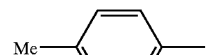 |
| 14 | 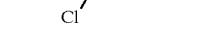 |
| 15 | 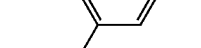 |
| 16 | 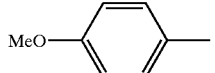 |
| 17 | 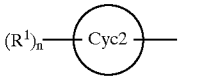 |
| 18 | 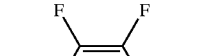 |
| 19 | 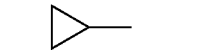 |
| 20 | 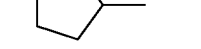 |
| 21 | 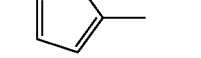 |
| 22 | 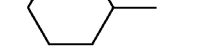 |
| 23 | 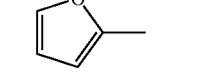 |
| 24 | 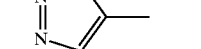 |
| 25 | 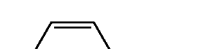 |
| 26 | 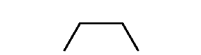 |
| 27 | 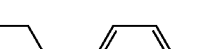 |
| 28 | 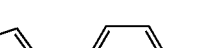 |
| 29 | 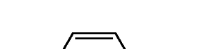 |

TABLE 6-continued
(I-c-2)
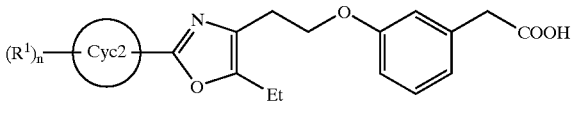
| No. | (R¹)ₙ—Cyc2— |
|-----|-------------|
| 30  | 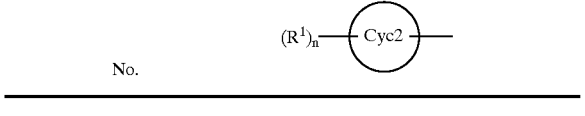 |
TABLE 7
(I-d-1)
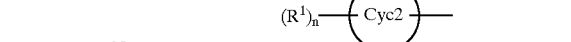
| No. | (R¹)ₙ—Cyc2— |
|-----|-------------|
| 1 | 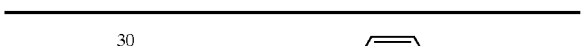 |
| 2 | Me—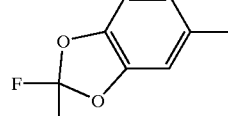 |
| 3 | t-Bu—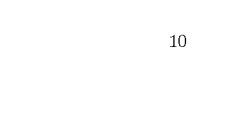 |
| 4 | MeO—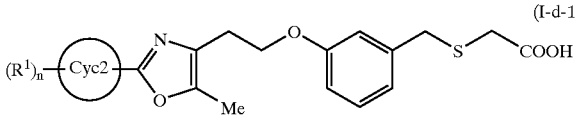 |
| 5 | F—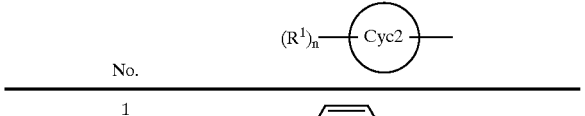 |
| 6 | Cl—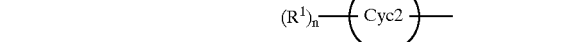 |
| 7 | O₂N—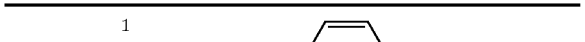 |
| 8 | F₃C—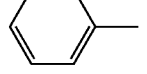 |
TABLE 7-continued
(I-d-1)
| No. | (R¹)ₙ—Cyc2— |
|-----|-------------|
| 9 | F₃CO—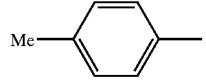 |
| 10 | F₃CS— |
| 11 | Me₂N—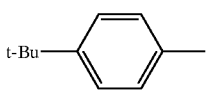 |
| 12 | NC— |
| 13 | MeS—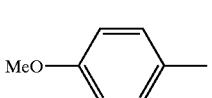 |
| 14 |  |
| 15 | 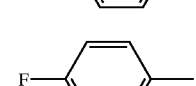 |
| 16 |  |
| 17 | 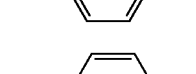 |
| 18 |  |
| 19 | 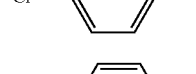 |

TABLE 7-continued (I-d-1)

Structure: (R¹)ₙ-Cyc2-[oxazole with Me]-CH₂CH₂-O-[phenyl]-CH₂-S-CH₂-COOH

| No. | (R¹)ₙ—Cyc2— |
|---|---|
| 20 | cyclopentyl |
| 21 | 2-thienyl |
| 22 | cyclohexyl |
| 23 | 2-furyl |
| 24 | 4-methyl-1,2,3-thiadiazol-5-yl |
| 25 | 4-pyridyl |
| 26 | 4-methylpiperazin-1-yl (Me—N-piperazine-N—Me) |
| 27 | 4-cyclohexylphenyl |
| 28 | 4-(1,2,3-thiadiazol-4-yl)phenyl |
| 29 | 6-methyl-1,3-benzodioxol-5-yl |
| 30 | 2,2-difluoro-1,3-benzodioxol-5-yl |

TABLE 8

(I-d-2)

Structure: (R¹)ₙ-Cyc2-[oxazole with Et]-CH₂CH₂-O-[phenyl]-CH₂-S-CH₂-COOH

| No. | (R¹)ₙ—Cyc2— |
|---|---|
| 1 | phenyl |
| 2 | 4-Me-phenyl |
| 3 | 4-t-Bu-phenyl |
| 4 | 4-MeO-phenyl |
| 5 | 4-F-phenyl |
| 6 | 4-Cl-phenyl |
| 7 | 4-O₂N-phenyl |
| 8 | 4-F₃C-phenyl |
| 9 | 4-F₃CO-phenyl |
| 10 | 4-F₃CS-phenyl |
| 11 | 4-Me₂N-phenyl |
| 12 | 4-NC-phenyl |
| 13 | 4-MeS-phenyl |

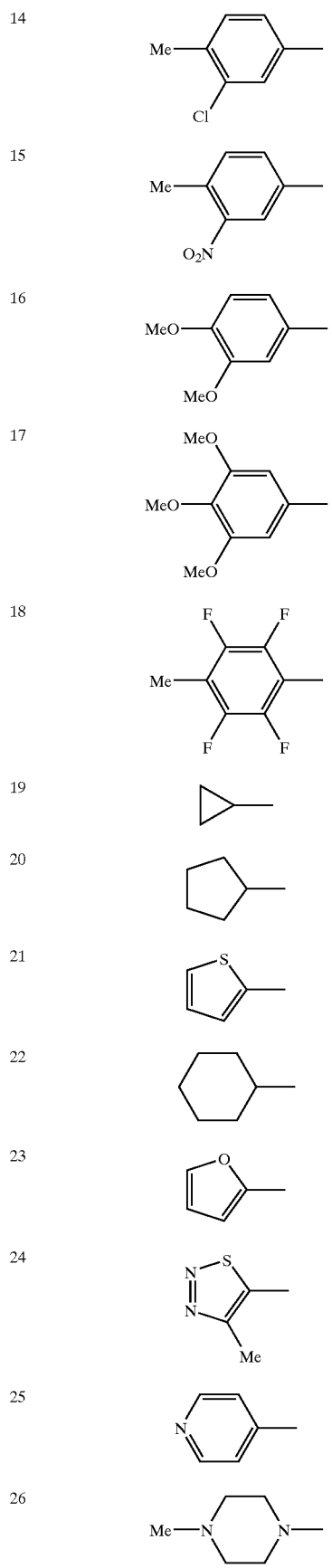
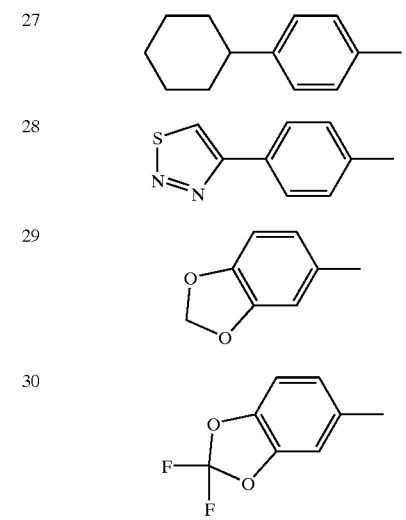
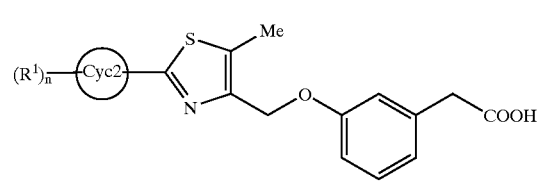
TABLE 9
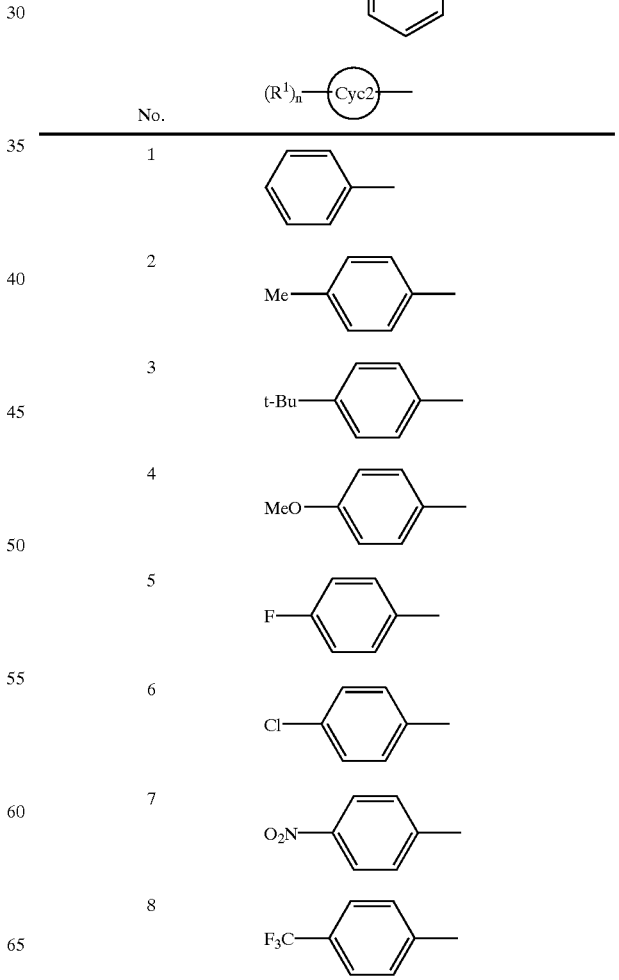

TABLE 9-continued (I-e-1)

Structure: (R¹)ₙ–Cyc2–[thiazole with Me]–CH₂O–[phenyl]–CH₂COOH

| No. | (R¹)ₙ–Cyc2– |
|---|---|
| 9 | F₃CO–C₆H₄– |
| 10 | F₃CS–C₆H₄– |
| 11 | Me₂N–C₆H₄– |
| 12 | NC–C₆H₄– |
| 13 | MeS–C₆H₄– |
| 14 | 4-Me-3-Cl-C₆H₃– |
| 15 | 4-Me-3-NO₂-C₆H₃– |
| 16 | 3,4-(MeO)₂-C₆H₃– |
| 17 | 3,4,5-(MeO)₃-C₆H₂– |
| 18 | 4-Me-2,3,5,6-tetrafluoro-C₆– |
| 19 | cyclopropyl |
| 20 | cyclopentyl |
| 21 | 2-thienyl |
| 22 | cyclohexyl |
| 23 | 2-furyl |
| 24 | 4-Me-1,2,3-thiadiazol-5-yl |
| 25 | 4-pyridyl |
| 26 | 4-Me-piperazin-1-yl (N-Me) |
| 27 | 4-cyclohexylphenyl |
| 28 | 4-(1,2,3-thiadiazol-4-yl)phenyl |
| 29 | benzo[1,3]dioxol-5-yl |

TABLE 9-continued (I-e-1)

[Structure: (R¹)ₙ-Cyc2-thiazole(5-Me)-CH₂-O-phenyl-CH₂-COOH]

| No. | (R¹)ₙ—Cyc2— |
|---|---|
| 30 | 5-methyl-2,2-difluoro-benzo[1,3]dioxole |

TABLE 10

(I-e-2)

[Structure: (R¹)ₙ-Cyc2-thiazole(5-Et)-CH₂-O-phenyl-CH₂-COOH]

| No. | (R¹)ₙ—Cyc2— |
|---|---|
| 1 | phenyl |
| 2 | 4-Me-phenyl |
| 3 | 4-t-Bu-phenyl |
| 4 | 4-MeO-phenyl |
| 5 | 4-F-phenyl |
| 6 | 4-Cl-phenyl |
| 7 | 4-O₂N-phenyl |

TABLE 10-continued (I-e-2)

| No. | (R¹)ₙ—Cyc2— |
|---|---|
| 8 | 4-F₃C-phenyl |
| 9 | 4-F₃CO-phenyl |
| 10 | 4-F₃CS-phenyl |
| 11 | 4-Me₂N-phenyl |
| 12 | 4-NC-phenyl |
| 13 | 4-MeS-phenyl |
| 14 | 4-Me-3-Cl-phenyl |
| 15 | 4-Me-3-O₂N-phenyl |
| 16 | 3,4-diMeO-phenyl |
| 17 | 3,4,5-triMeO-phenyl |

TABLE 10-continued
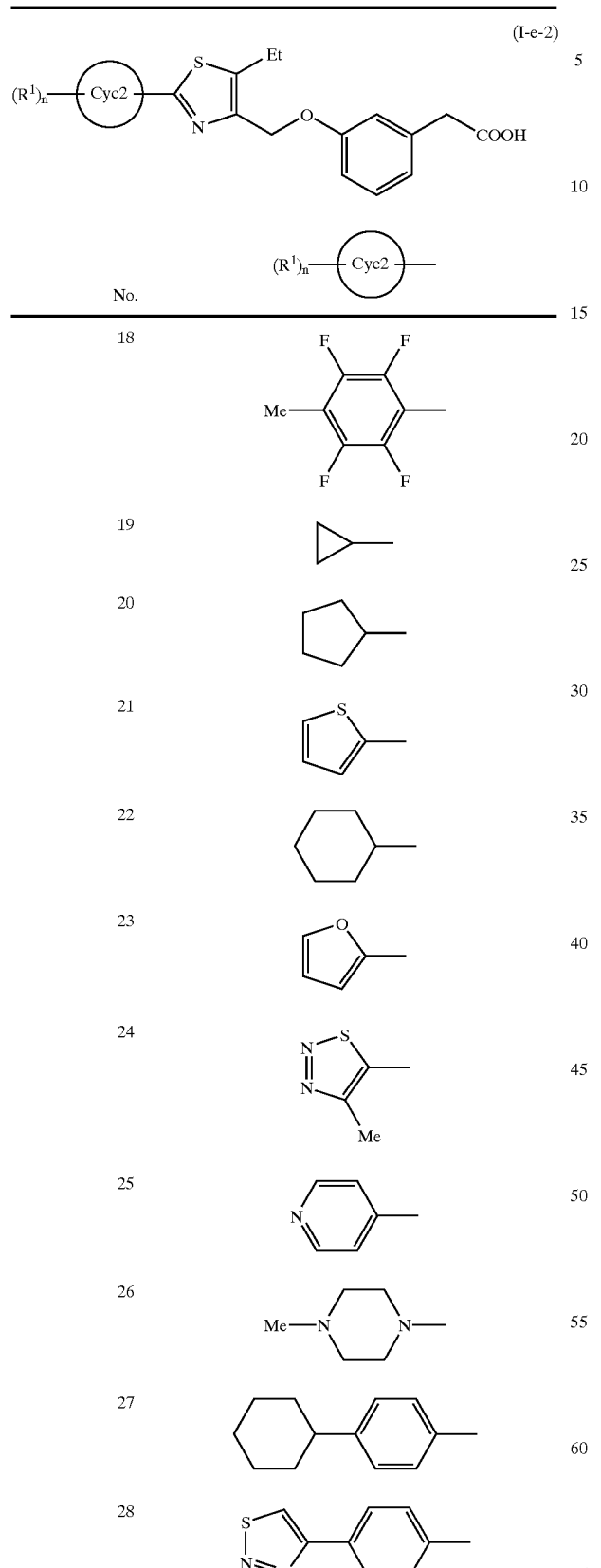
TABLE 10-continued
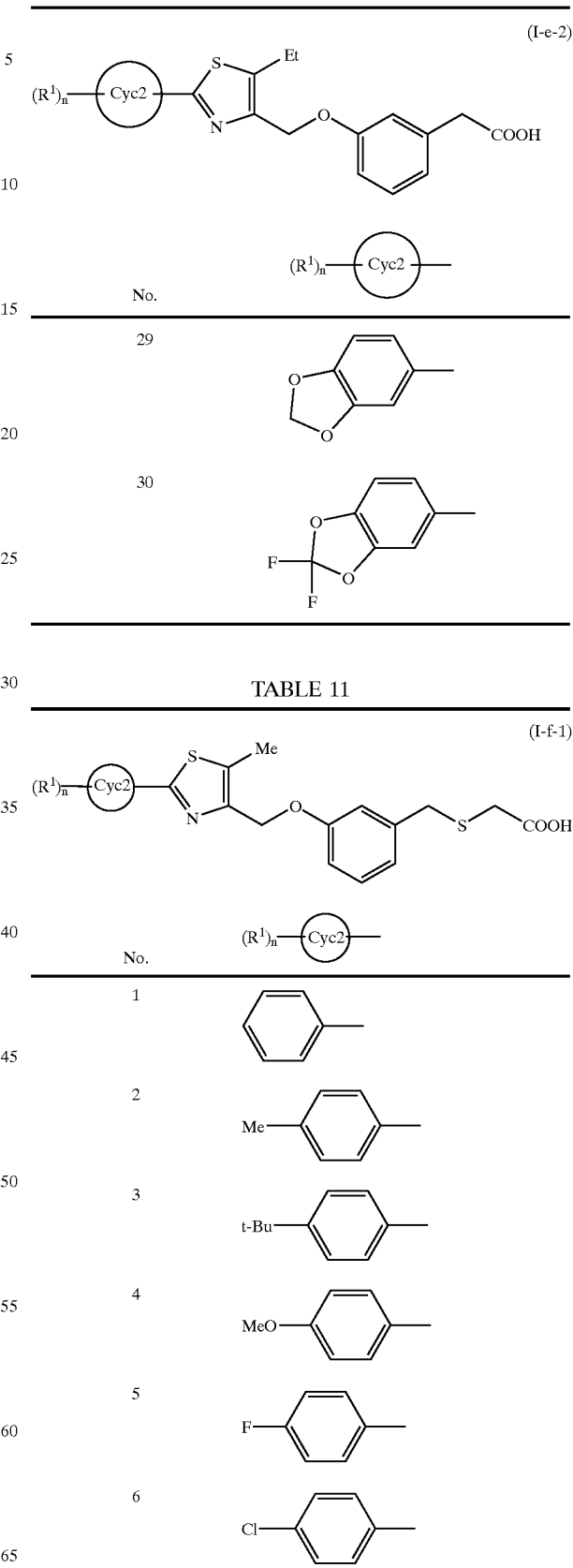

TABLE 11-continued (I-f-1)

[Structure: (R¹)ₙ-Cyc2-thiazole(5-Me)-CH₂-O-phenyl-CH₂-S-CH₂-COOH]

| No. | (R¹)ₙ—Cyc2— |
|---|---|
| 7 | 4-O₂N-C₆H₄— |
| 8 | 4-F₃C-C₆H₄— |
| 9 | 4-F₃CO-C₆H₄— |
| 10 | 4-F₃CS-C₆H₄— |
| 11 | 4-Me₂N-C₆H₄— |
| 12 | 4-NC-C₆H₄— |
| 13 | 4-MeS-C₆H₄— |
| 14 | 4-Me-3-Cl-C₆H₃— |
| 15 | 4-Me-3-O₂N-C₆H₃— |
| 16 | 3,4-(MeO)₂-C₆H₃— |
| 17 | 3,4,5-(MeO)₃-C₆H₂— |
| 18 | 2,3,5,6-tetrafluoro-4-Me-C₆— (Me, F, F, F, F ring) |
| 19 | cyclopropyl— |
| 20 | cyclopentyl— |
| 21 | 2-thienyl— |
| 22 | cyclohexyl— |
| 23 | 2-furyl— |
| 24 | 4-Me-1,2,3-thiadiazol-5-yl— |
| 25 | 4-pyridyl— |
| 26 | 4-Me-piperazin-1-yl— |
| 27 | 4-cyclohexyl-C₆H₄— |
| 28 | 4-(1,2,3-thiadiazol-4-yl)-C₆H₄— |

TABLE 11-continued (I-f-1)

Structure: (R¹)ₙ-Cyc2-[thiazole with Me]-CH₂-O-[phenyl]-CH₂-S-CH₂-COOH

| No. | (R¹)ₙ-Cyc2- |
|-----|-------------|
| 29  | methylenedioxyphenyl (benzo[1,3]dioxole) |
| 30  | difluoromethylenedioxyphenyl (2,2-difluorobenzo[1,3]dioxole) |

TABLE 13

(I-g-1)

Structure: (R¹)ₙ-Cyc2-[thiazole with Me]-CH₂CH₂-O-[phenyl]-CH₂-COOH

| No. | (R¹)ₙ-Cyc2- |
|-----|-------------|
| 1   | phenyl |
| 2   | 4-Me-phenyl |
| 3   | 4-t-Bu-phenyl |
| 4   | 4-MeO-phenyl |
| 5   | 4-F-phenyl |
| 6   | 4-Cl-phenyl |
| 7   | 4-O₂N-phenyl |

TABLE 13-continued (I-g-1)

| No. | (R¹)ₙ-Cyc2- |
|-----|-------------|
| 8   | 4-F₃C-phenyl |
| 9   | 4-F₃CO-phenyl |
| 10  | 4-F₃CS-phenyl |
| 11  | 4-Me₂N-phenyl |
| 12  | 4-NC-phenyl |
| 13  | 4-MeS-phenyl |
| 14  | 4-Me, 3-Cl-phenyl |
| 15  | 4-Me, 3-O₂N-phenyl |
| 16  | 3,4-diMeO-phenyl |
| 17  | 3,4,5-triMeO-phenyl |

TABLE 13-continued (I-g-1)

Structure: (R¹)ₙ-Cyc2-[thiazole with Me]-CH₂CH₂-O-[phenyl]-CH₂COOH

| No. | (R¹)ₙ-Cyc2- |
|---|---|
| 18 | 2,3,5,6-tetrafluoro-4-methylphenyl (Me and 4 F substituents) |
| 19 | cyclopropyl |
| 20 | cyclopentyl |
| 21 | 2-thienyl |
| 22 | cyclohexyl |
| 23 | 2-furyl |
| 24 | 4,5-dimethyl-1,2,3-thiadiazol-yl |
| 25 | 4-pyridyl |
| 26 | 4-methylpiperazin-1-yl (Me-N-piperazine-N-) |
| 27 | 4-cyclohexylphenyl |
| 28 | 4-(1,2,3-thiadiazol-4-yl)phenyl |
| 29 | 1,3-benzodioxol-5-yl |

TABLE 13-continued (I-g-1)

| No. | (R¹)ₙ-Cyc2- |
|---|---|
| 30 | 2,2-difluoro-1,3-benzodioxol-5-yl (with Me) |

TABLE 14

(I-g-2)

Structure: (R¹)ₙ-Cyc2-[thiazole with Et]-CH₂CH₂-O-[phenyl]-CH₂COOH

| No. | (R¹)ₙ-Cyc2- |
|---|---|
| 1 | phenyl |
| 2 | 4-methylphenyl (Me) |
| 3 | 4-tert-butylphenyl (t-Bu) |
| 4 | 4-methoxyphenyl (MeO) |
| 5 | 4-fluorophenyl (F) |
| 6 | 4-chlorophenyl (Cl) |
| 7 | 4-nitrophenyl (O₂N) |
| 8 | 4-trifluoromethylphenyl (F₃C) |
| 9 | 4-trifluoromethoxyphenyl (F₃CO) |

TABLE 14-continued
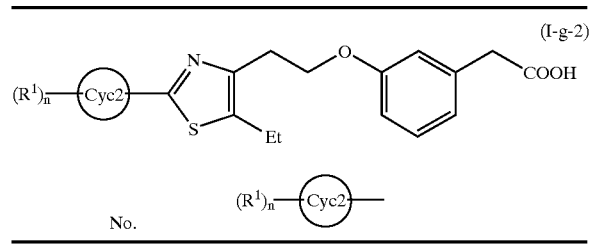
(I-g-2)
| No. | (R¹)ₙ—Cyc2— |
|---|---|
| 10 | F₃CS—C₆H₄— |
| 11 | Me₂N—C₆H₄— |
| 12 | NC—C₆H₄— |
| 13 | MeS—C₆H₄— |
| 14 | 4-Me, 3-Cl—C₆H₃— |
| 15 | 4-Me, 3-NO₂—C₆H₃— |
| 16 | 3,4-(MeO)₂—C₆H₃— |
| 17 | 3,4,5-(MeO)₃—C₆H₂— |
| 18 | Me-C₆F₄— |
| 19 | cyclopropyl— |
| 20 | cyclopentyl— |
TABLE 14-continued
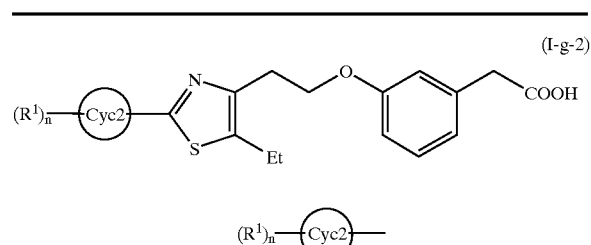
(I-g-2)
| No. | (R¹)ₙ—Cyc2— |
|---|---|
| 21 | 2-thienyl— |
| 22 | cyclohexyl— |
| 23 | 2-furyl— |
| 24 | 4-Me-1,2,3-thiadiazol-5-yl— |
| 25 | 4-pyridyl— |
| 26 | 4-Me-piperazin-1-yl— (N-methylpiperazinyl-phenyl) |
| 27 | 4-cyclohexyl-C₆H₄— |
| 28 | 4-(1,2,3-thiadiazol-4-yl)-C₆H₄— |
| 29 | benzo[1,3]dioxol-5-yl— |
| 30 | 2,2-difluoro-benzo[1,3]dioxol-5-yl— |

TABLE 15

![Structure I-h-1: (R¹)ₙ-Cyc2-thiazole(5-Me)-CH₂CH₂-O-phenyl-CH₂-S-CH₂-COOH]

(I-h-1)

(R¹)ₙ—Cyc2—

| No. | (R¹)ₙ—Cyc2— |
|---|---|
| 1 | phenyl |
| 2 | 4-Me-phenyl |
| 3 | 4-t-Bu-phenyl |
| 4 | 4-MeO-phenyl |
| 5 | 4-F-phenyl |
| 6 | 4-Cl-phenyl |
| 7 | 4-O₂N-phenyl |
| 8 | 4-F₃C-phenyl |
| 9 | 4-F₃CO-phenyl |
| 10 | 4-F₃CS-phenyl |
| 11 | 4-Me₂N-phenyl |
| 12 | 4-NC-phenyl |
| 13 | 4-MeS-phenyl |
| 14 | 2-Cl-4-Me-phenyl (Me, Cl substituents) |
| 15 | 2-NO₂-4-Me-phenyl (Me, O₂N substituents) |
| 16 | 3,4-(MeO)₂-phenyl |
| 17 | 3,4,5-(MeO)₃-phenyl |
| 18 | 2,3,5,6-tetrafluoro-4-Me-phenyl |
| 19 | cyclopropyl |
| 20 | cyclopentyl |
| 21 | 2-thienyl |
| 22 | cyclohexyl |
| 23 | 2-furyl |

TABLE 15-continued
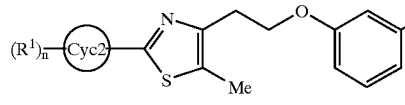
(I-h-1)
| No. | (R¹)ₙ—Cyc2— |
|---|---|
| 24 | 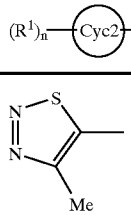 |
| 25 | 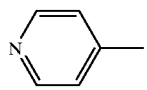 |
| 26 | 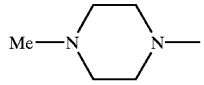 |
| 27 | 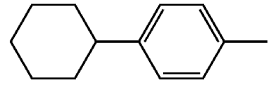 |
| 28 | 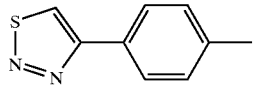 |
| 29 | 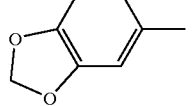 |
| 30 | 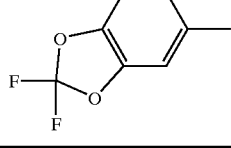 |
TABLE 16
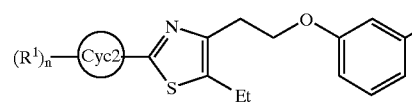
(I-h-2)
| No. | (R¹)ₙ—Cyc2— |
|---|---|
| 1 | 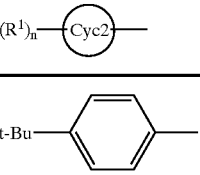 |
| 2 | 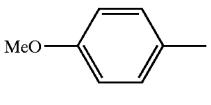 |
| 3 | 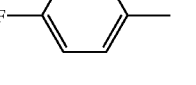 |
| 4 | 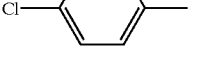 |
| 5 | 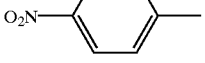 |
| 6 | 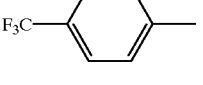 |
| 7 | 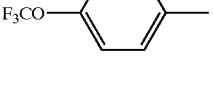 |
| 8 | 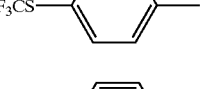 |
| 9 | 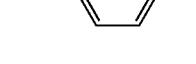 |
| 10 | 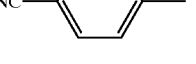 |
| 11 | 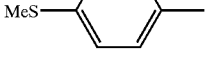 |
| 12 | 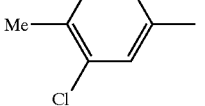 |
| 13 | 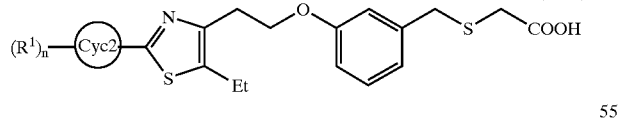 |
| 14 | 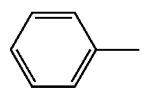 |

TABLE 16-continued (I-h-2)

(R¹)ₙ—Cyc2—[thiazole-Et]—CH₂CH₂—O—[phenyl]—CH₂—S—CH₂COOH

| No. | (R¹)ₙ—Cyc2— |
|---|---|
| 15 | 4-Me, 2-NO₂, Me-phenyl |
| 16 | 3,4-(MeO)₂-phenyl |
| 17 | 3,4,5-(MeO)₃-phenyl |
| 18 | 2,3,5,6-tetrafluoro-4-Me-phenyl |
| 19 | cyclopropyl |
| 20 | cyclopentyl |
| 21 | 2-thienyl |
| 22 | cyclohexyl |
| 23 | 2-furyl |
| 24 | 4-Me-1,2,3-thiadiazol-5-yl |
| 25 | 4-pyridyl |
| 26 | 4-Me-piperazin-1-yl (N-Me) |
| 27 | 4-cyclohexylphenyl |
| 28 | 4-(1,2,3-thiadiazol-4-yl)phenyl |
| 29 | benzo[1,3]dioxol-5-yl (methylenedioxyphenyl) |
| 30 | 2,2-difluoro-benzo[1,3]dioxol-5-yl |

TABLE 17

(I-j-1)

(R¹)ₙ—Cyc2—[phenyl]—CH₂—O—[phenyl]—CH₂COOH

| No. | (R¹)ₙ—Cyc2— |
|---|---|
| 1 | phenyl |
| 2 | 4-Me-phenyl |
| 3 | 4-t-Bu-phenyl |

TABLE 17-continued
(I-j-1)
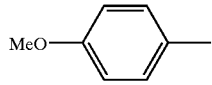
| No. | (R¹)ₙ—Cyc2— |
|---|---|
| 4 | MeO—C₆H₄— |
| 5 | F—C₆H₄— |
| 6 | Cl—C₆H₄— |
| 7 | O₂N—C₆H₄— |
| 8 | F₃C—C₆H₄— |
| 9 | F₃CO—C₆H₄— |
| 10 | F₃CS—C₆H₄— |
| 11 | Me₂N—C₆H₄— |
| 12 | NC—C₆H₄— |
| 13 | MeS—C₆H₄— |
| 14 | Me, Cl-disubstituted phenyl |
| 15 | Me, O₂N-disubstituted phenyl |
| 16 | (MeO)₂-disubstituted phenyl |
| 17 | (MeO)₃-trisubstituted phenyl |
| 18 | Me, F₄-pentasubstituted phenyl |
| 19 | cyclopropyl |
| 20 | cyclopentyl |
| 21 | 2-thienyl |
| 22 | cyclohexyl |
| 23 | 2-furyl |
| 24 | 4,5-dimethyl-1,2,3-thiadiazolyl |

TABLE 17-continued
(I-j-1)
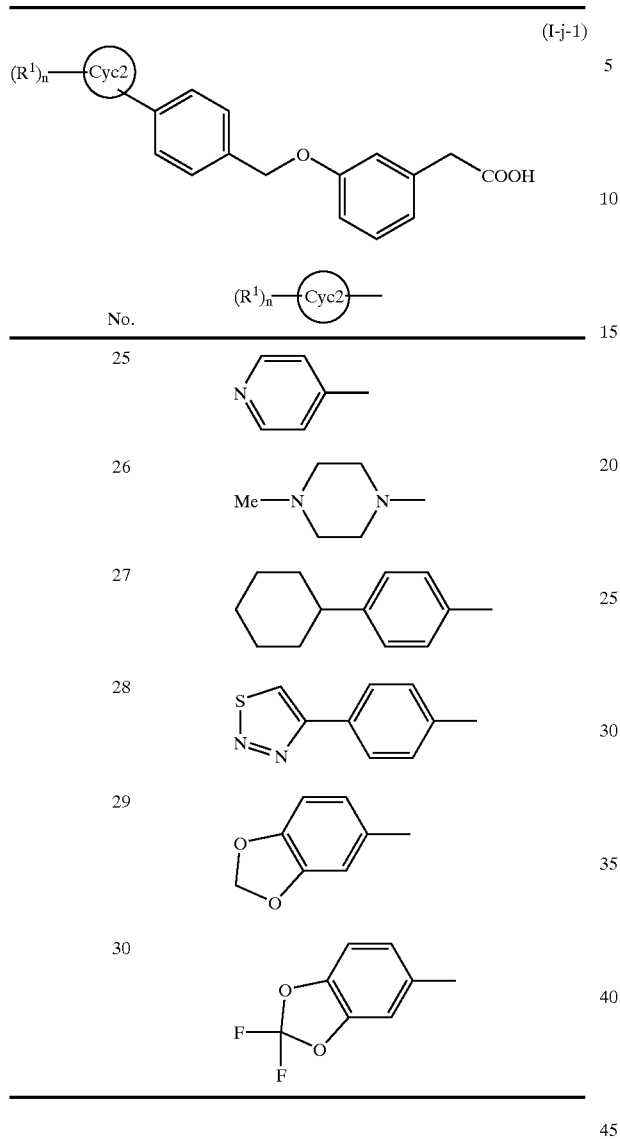
TABLE 18
(I-k-1)
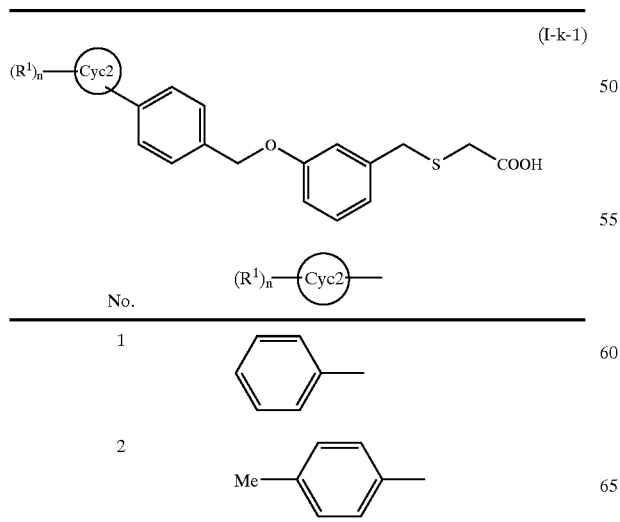
TABLE 18-continued
(I-k-1)
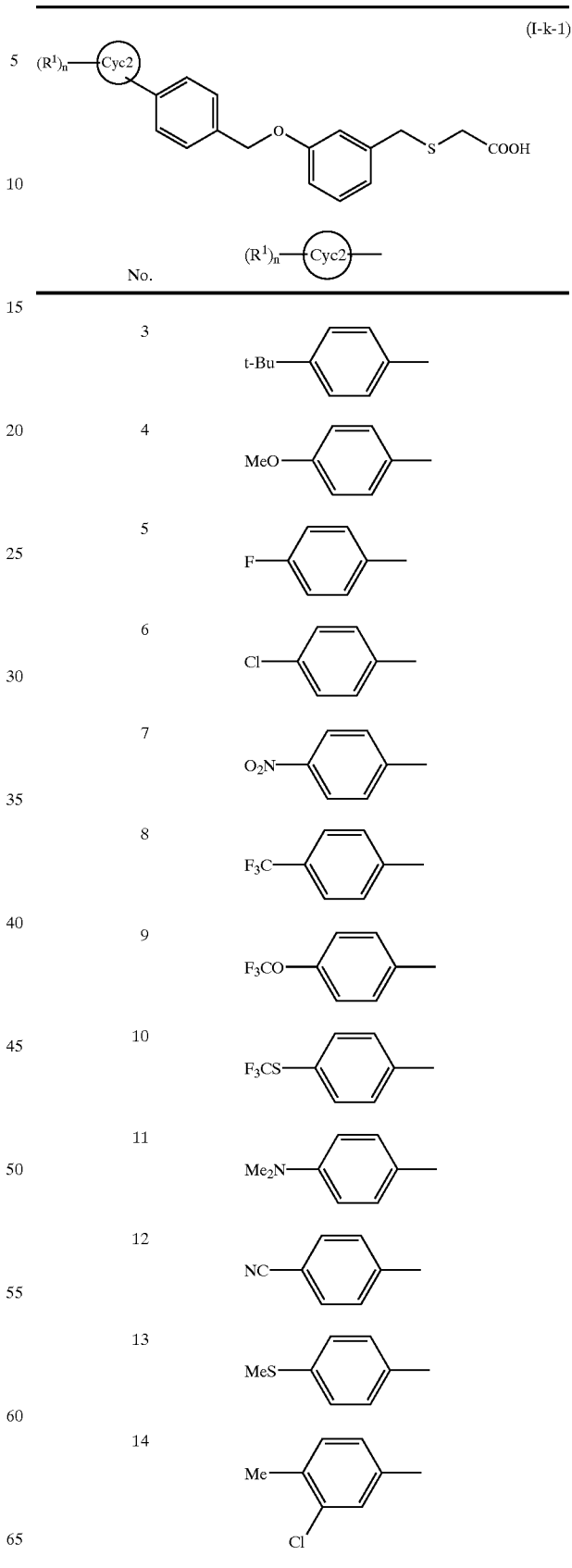

TABLE 18-continued
(I-k-1)
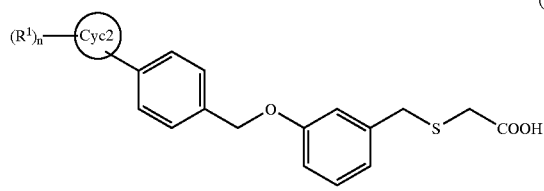
| No. | (R¹)ₙ—Cyc2— |
|---|---|
| 15 | 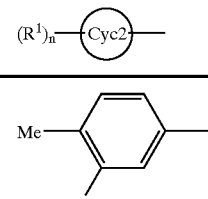 |
| 16 | 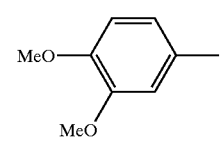 |
| 17 | 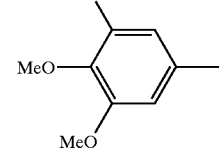 |
| 18 | 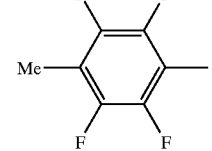 |
| 19 |  |
| 20 | 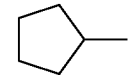 |
| 21 | 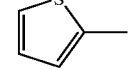 |
| 22 |  |
| 23 | 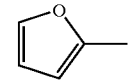 |
| 24 | 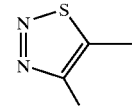 |
| 25 | 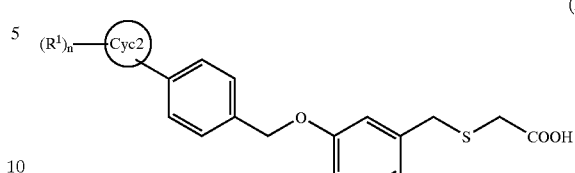 |
| 26 | 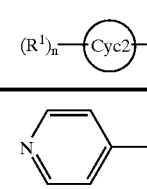 |
| 27 | 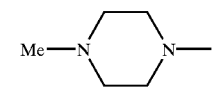 |
| 28 | 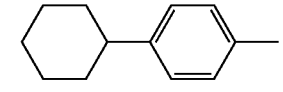 |
| 29 | 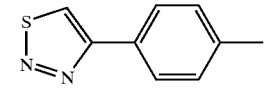 |
| 30 | 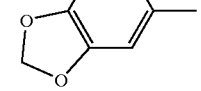 |
TABLE 19
(I-l-1)
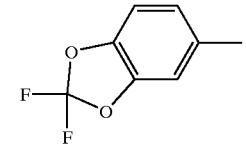
| No. | (R¹)ₙ—Cyc2— |
|---|---|
| 1 |  |
| 2 | 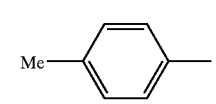 |

TABLE 19-continued
(I-l-1)
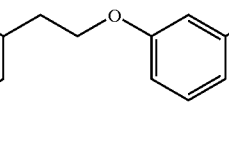
| No. | (R¹)ₙ—Cyc2— |
|---|---|
| 3 | 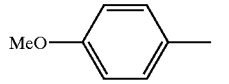 |
| 4 | 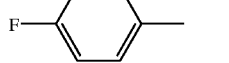 |
| 5 | 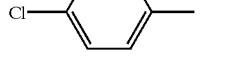 |
| 6 | 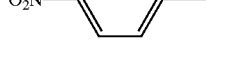 |
| 7 | 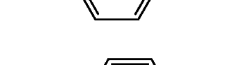 |
| 8 | 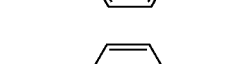 |
| 9 | 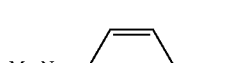 |
| 10 |  |
| 11 |  |
| 12 |  |
| 13 |  |
| 14 |  |
TABLE 19-continued
(I-l-1)
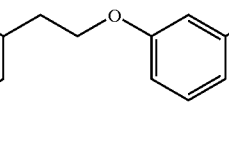
| No. | (R¹)ₙ—Cyc2— |
|---|---|
| 15 | 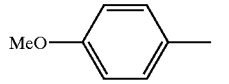 |
| 16 | 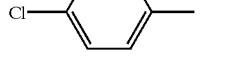 |
| 17 | 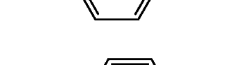 |
| 18 | 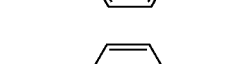 |
| 19 | 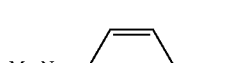 |
| 20 |  |
| 21 |  |
| 22 |  |
| 23 |  |
| 24 |  |

TABLE 19-continued
(I-l-1)
| No. | (R¹)ₙ—Cyc2— |
|---|---|
| 25 | 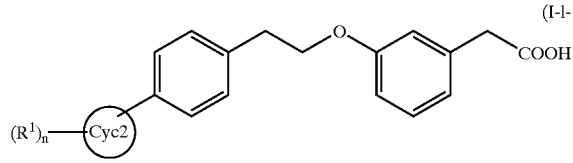 |
| 26 | 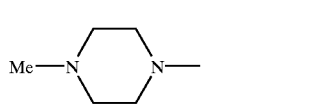 |
| 27 | 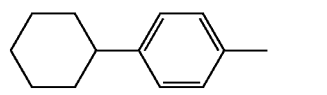 |
| 28 | 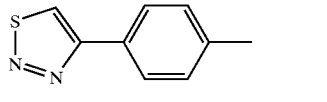 |
| 29 | 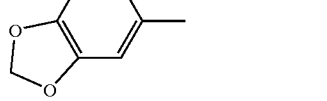 |
| 30 | 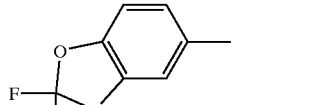 |
TABLE 20
(I-m-1)
| No. | (R¹)ₙ—Cyc2— |
|---|---|
| 1 | 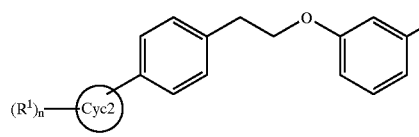 |
| 2 | 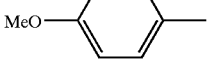 |
| 3 | 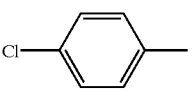 |
TABLE 20-continued
(I-m-1)
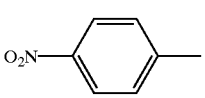
| No. | (R¹)ₙ—Cyc2— |
|---|---|
| 4 | 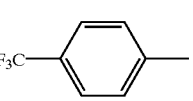 |
| 5 | 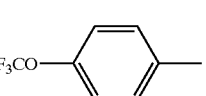 |
| 6 | 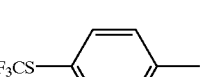 |
| 7 | 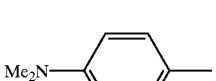 |
| 8 | 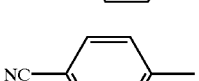 |
| 9 | 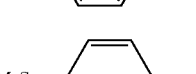 |
| 10 | 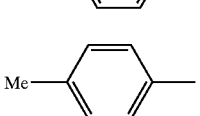 |
| 11 | 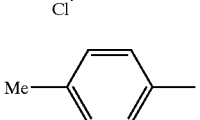 |
| 12 | 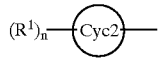 |
| 13 | 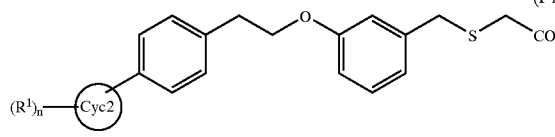 |
| 14 | 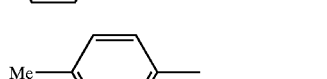 |
| 15 | 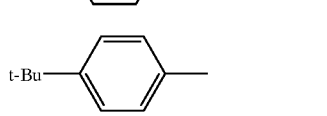 |

TABLE 20-continued (I-m-1)

| No. | (R¹)ₙ—Cyc2— |
|---|---|
| 16 | MeO-phenyl-, with MeO substituent |
| 17 | MeO-, MeO-, MeO-phenyl- (trimethoxyphenyl) |
| 18 | Me-, F, F, F, F-phenyl- |
| 19 | cyclopropyl- |
| 20 | cyclopentyl- |
| 21 | thienyl (2-)- |
| 22 | cyclohexyl- |
| 23 | furyl (2-)- |
| 24 | 4-methyl-thiadiazolyl- |
| 25 | pyridin-4-yl- |
| 26 | Me—N(piperazinyl)N— |
| 27 | cyclohexyl-phenyl- |
| 28 | thiadiazolyl-phenyl- |
| 29 | benzo[1,3]dioxol-yl- |
| 30 | 2,2-difluoro-benzo[1,3]dioxol-yl- |

Processes for the Preparation of the Compound of the Present Invention (1) Among the compounds of the present invention of formula (I), the compounds wherein $R^4$ is $$—A^4—\underset{R^9}{\overset{R^8}{C}}—COOR^{7'}$$

i.e. the compounds of formula (I-1)

(I-1)

(wherein $R^{1-1}$ and $COOR^{7-1}$ are the same meanings as $R^1$ and $COOR^7$ respectively, with the proviso that amino group represented by $R^{1-1}$ is protected if necessary, COOH group represented by $COOR^{7-1}$ is protected if necessary.

Protective groups for amino include, for example, benzyloxycarbonyl, t-butoxycarbonyl, trifluoroacetyl, etc., protective groups for COOH include, for example, methyl, ethyl, t-butyl, benzyl, etc. The other symbols are as hereinbefore described) may be prepared by subjecting to a reaction a compound of formula (II)

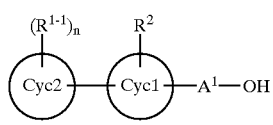
(II)

(wherein all symbols are as hereinbefore described) and a compound of formula (III)

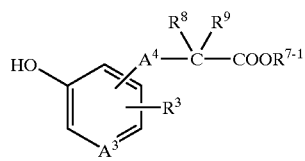
(III)

(wherein all symbols are as hereinbefore described) or subjecting to a reaction a compound of formula (IV)

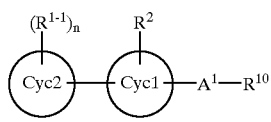
(IV)

(wherein $R^{10}$ is halogen or methanesulfonyloxy and the other symbols are as hereinbefore described) and a compound of formula (V)

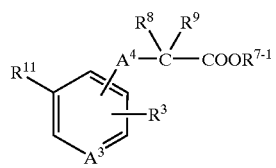
(V)

(wherein $R^{11}$ is hydroxy or mercapto and the other symbols are as hereinbefore described).

The reaction of a compound of formula (II) and a compound of formula (III) is known, for example, it is carried out in an organic solvent (dichloromethane, ether, tetrahydrofuran, acetonitrile, benzene, toluene, etc.) in the presence of azo compound (azodicarboxylic acid diethyl, azodicarboxylic acid diisopropyl, 1,1'-(azodicarbonyl)dipiperidine, 1,1'-azobis(N,N-dimethylformamide), etc.) and phosphine compound (triphenylphosphine, tributylphosphine, trimethylphosphine, etc.) at a temperature of from 0° C. to 60° C. for 3~20 hours.

The reaction of a compound of formula (IV) and a compound of formula (V) is known, for example, it is carried out in an inert organic solvent (tetrahydrofuran (THF), diethyl ether, dichloromethane, chloroform, carbon tetrachloride, pentane, hexane, benzene, toluene, dimethylformamide (DMF), dimethylsulfoxide (DMSO), hexamethylphosphoramide (HMPA), etc.) in the presence of base (sodium hydride, potassium carbonate, triethylamine, pyridine, cesium carbonate, etc.), optionally using an additive (sodium iodide, potassium iodide, etc.) at a temperature of from 0° C. to 80° C.

(2) Among the compounds of formula (I), the compounds wherein $R^4$ is 2,4-thiazolidindion-5-yl, i.e. the compounds of formula (I-2)

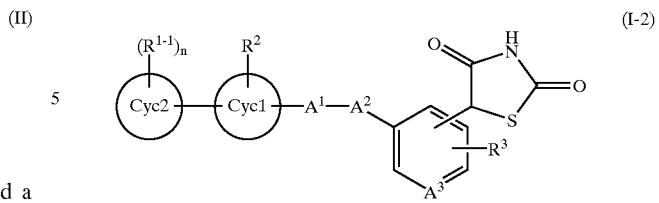
(I-2)

(wherein all symbols are as hereinbefore described) may be prepared by subjecting to a reaction a compound of formula (VI)

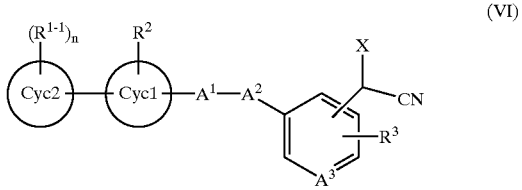
(VI)

(wherein X is halogen and the other symbols are as hereinbefore described) and thiourea.

The above reaction is known, for example, it is carried out in an organic solvent (methanol, ethanol, propanol, etc.) subjecting to a reaction a compound of formula (VI) and thiourea at a temperature of from 0° C. to refluxing temperature for 3~20 hours, followed by addition of acid (concentrated sulfuric acid etc.) and then subjecting to a reaction at a temperature of 0° C. to refluxing temperature for another 3~20 hours.

(3) Among the compounds of formula (I), the compounds wherein at least one of $R^1$ and $COOR^7$ is COOH or amino, i.e. the compounds of formula (I-3)

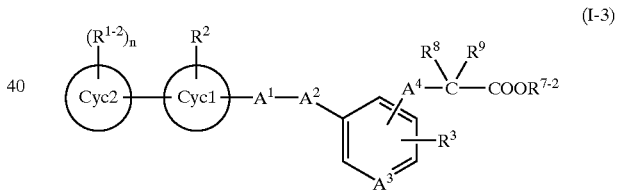
(I-3)

(wherein $R^{1-2}$ and $COOR^{7-2}$ are the same meanings as $R^1$ and $COOR^7$, with the proviso that at least one of $R^{1-2}$ and $COOR^{7-2}$ is amino or COOH and the other symbols are as hereinbefore described) may be prepared by subjecting a compound of formula (I-1) to alkali hydrolysis, deprotection reaction under acidic conditions or deprotection reaction by hydration.

Deprotection reaction by alkali hydrolysis is known, for example, it is carried out in an organic solvent (methanol, ethanol, tetrahydrofuran, dioxane, etc.) using hydroxide of alkali metal (sodium hydroxide, potassium hydroxide, lithium hydroxide, etc.), hydroxide of alkaline earth metal (barium hydroxide, calcium hydroxide, etc.) or carbonate (sodium carbonate, potassium carbonate, etc.) or an aqueous solution thereof or a mixture thereof at a temperature of from 0° C. to 40° C.

Deprotection reaction under acidic conditions is known, for example, it is carried out in an organic solvent (dichloromethane, chloroform, dioxane, ethyl acetate, anisole, etc.), in organic acid (acetic acid, trifluoroacetic acid, methanesulfonic acid, trimethylsilyl iodide etc.) or inorganic acid (hydrochloric acid, sulfuric acid, etc.) or a mixture thereof (hydrobromic acid-acetic acid etc.) at a temperature of from 0° C. to 100° C.

Deprotection reaction by hydration is known, for example, it is carried out in an inert solvent [ether (e.g. tetrahydrofuran, dioxane, dimethoxyethane, diethyl ether, etc.), alcohol (e.g. methanol, ethanol, etc.), benzene (e.g. benzene, toluene, etc.), ketone (e.g. acetone, methylethylketone, etc.), nitrile (e.g. acetonitrile etc.), amide (e.g. dimethylformamide etc.), water, ethyl acetate, acetic acid or a mixture of two or more thereof], in the presence of hydrating catalyst (e.g. palladium-carbon, palladium black, palladium, palladium hydroxide, platinum hydroxide, platinum dioxide, nickel, Raney-nickel, ruthenium chloride, etc.) in the presence or absence of inorganic acid (e.g. hydrochloric acid, sulfuric acid, hypochlorous acid, boronic acid, tetrafluoroboronic acid, etc.) or organic acid (e.g. acetic acid, p-toluenesulfonic acid, oxalic acid, trifluoroacetic acid, formic acid etc.), under normal atmosphere or suppressed atmosphere of hydrogen or in the presence of ammonium formate, at a temperature of from 0° C. to 200° C. In use of acid, its salt may be used.

(4) Among the compounds of formula (I), the compounds wherein $R^4$ is 2,4-thiazolidinedion-5-yl and at least one of $R^1$ is amino, i.e. the compounds of formula (I-4)

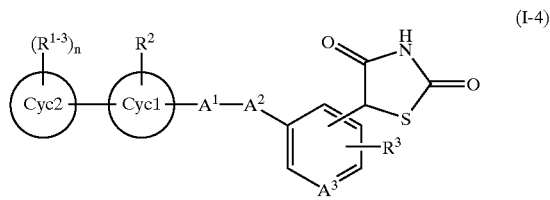

(I-4)

(wherein $R^{1-3}$ is the same meaning as $R^1$, with the proviso that at least one of $R^{1-3}$ is amino, and the other symbols are the same meaning as hereinbefore described) may be prepared by subjecting the said compound of formula (I-2) to deprotection reaction under acidic conditions or deprotection reaction by hydration.

Deprotection reaction under acidic conditions or deprotection reaction by hydration is carried out by the same procedure as hereinbefore described.

In the present invention deprotection reaction means a comprehensive deprotection reaction easily understood by those skilled in the art, for example, alkali hydrolysis, deprotection reaction under acidic condition, deprotection reaction by hydration. The desired compounds of the present invention can be easily prepared by these reactions.

As should be easily understood by those skilled in the art, methyl, ethyl, t-butyl and benzyl are included in the protective groups for carboxyl, but other groups that can be easily and selectively eliminated may also be used instead. For example, the groups described in T. W. Greene, Protective Groups in Organic Synthesis, Wiley, N.Y., 1991 may be used.

Benzyloxycarbonyl, t-butoxycarbonyl and trifluoroacetyl are included in the protective groups for amino, but other groups that can be easily and selectively eliminated may also be used instead. For example, the groups described in T. W. Greene, Protective Groups in Organic Synthesis, Wiley, N.Y., 1991 may be used.

The compounds of formula (II), (III), (IV), (V) and (VI) are known per se or may be easily prepared by known methods.

For example, among the compounds of formula (II), 2-(5-methyl-2-phenyloxazol-4-yl)ethanol can be prepared by the method described in J. Med. Chem., 41, 5037–5054 (1998).

For example, the compounds of formula (IV), (V) and (VI) may be prepared by the method described in the following reaction schemes.

The symbols in the reaction schemes represent the followings and the other symbols are as hereinbefore described.

$R^{11-1}$: protected hydroxy or mercapto;

$A^{4-1}$: a bond or C1~4 alkylene;

$A^{4-2}$: —C1~4 alkylene-O— or —C1~4 alkylene-S—;

TMSCN: trimethylsilylcyanide;

$Ph_3P$: triphenylphosphine;

ADDP: 1,1'-(azodicarbonyl)dipiperidine.

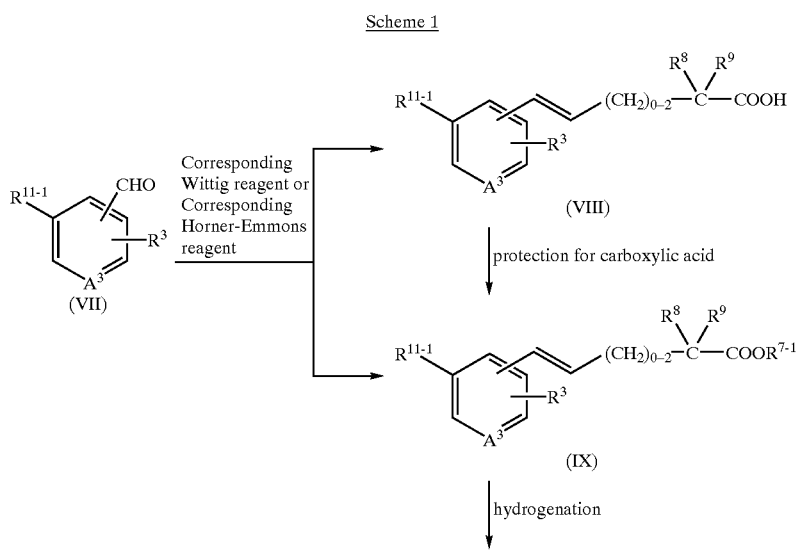

-continued
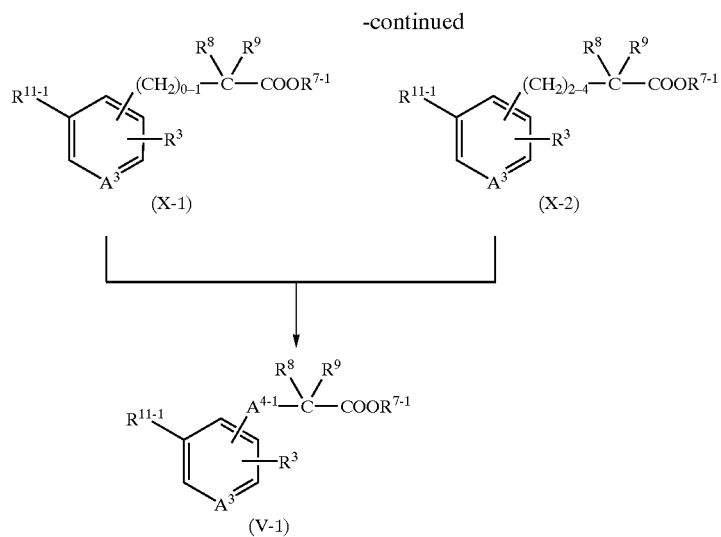
Scheme 2
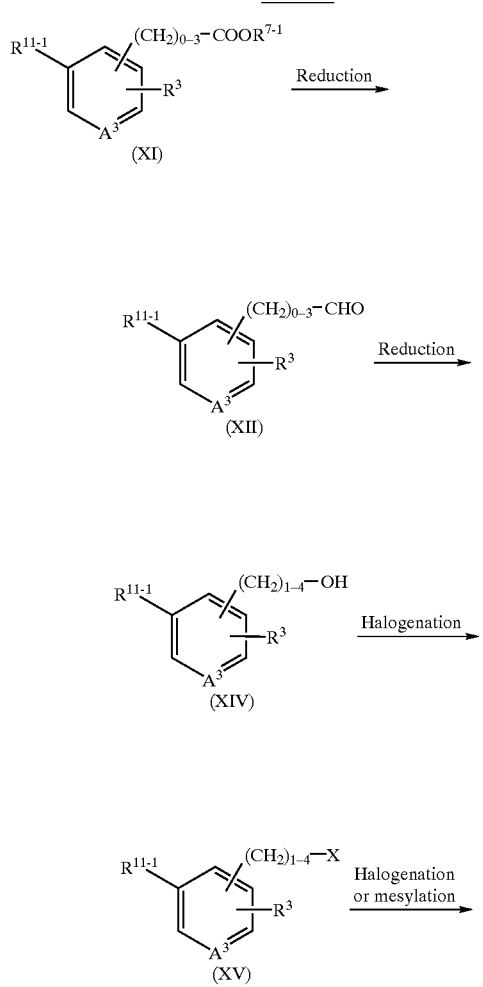
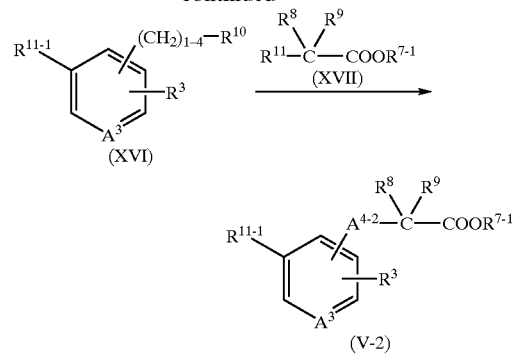
Scheme 3
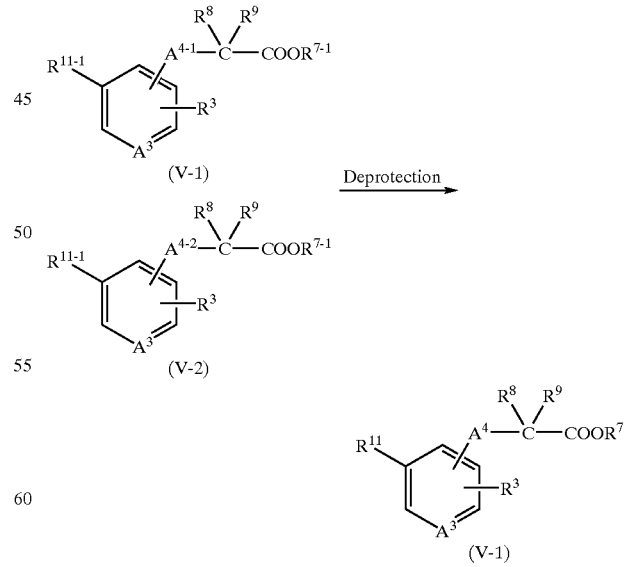

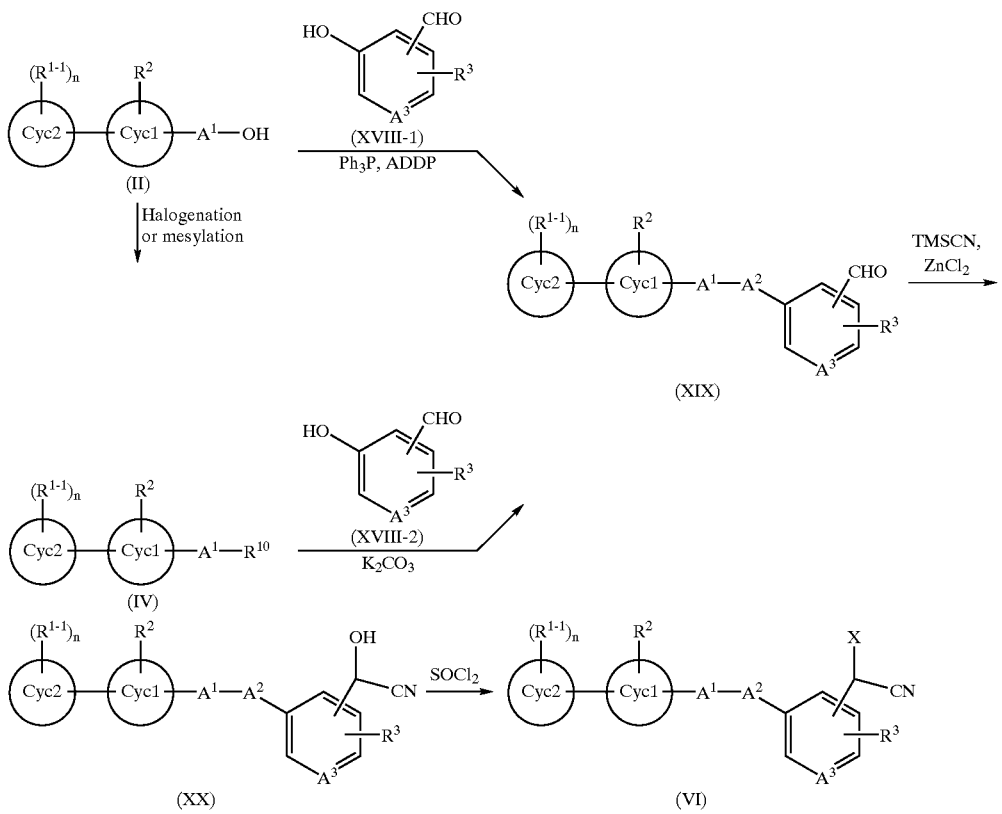

Scheme 4

The starting materials in the reaction schemes are known per se or may be prepared by known methods.

The reactions of the reaction schemes may be carried out by known methods.

The other starting materials and reagents in the present invention are known per se or may be prepared by known methods.

In each reaction described in the present specification, reaction products may be purified by conventional techniques. For example, purification may be carried out by distillation at atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

The compounds described in the present specification may be converted to corresponding salts by known methods. Non-toxic and water-soluble salts are preferable. Suitable salts include a salt of alkali metal (potassium, sodium, etc.), a salt of alkali earth metal (calcium, magnesium, etc.), an ammonium salt, a pharmaceutically acceptable salt of organic amine (tetramethylammonium, triethylamine, methylamine, dimethylamine, cyclopentylamine, benzylamine, phenethylamine, piperidine, monoethanolamine, diethanolamine, tris(hydroxymethyl) aminomethane, lysine, arginine, N-methyl-D-glucamine, etc.)

The compounds of formula (I) may be converted to corresponding acid addition salts by known methods. Non-toxic and water-soluble acid addition salts are preferable. Suitable acid addition salts include salts of inorganic acid (e.g. salts of hydrochloric acid, hydrobromic acid, sulfuric acid, phosphoric acid, nitric acid) and salts of organic acid (e.g. salts of acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid,, toluenesulfonic acid, isethionic acid, glucuronic acid and gluconic acid), etc.

The compounds of the present invention described in the present specification or salts thereof may be converted to hydrates by a known method.

PHARMACOLOGICAL ACTIVITY

It was confirmed that a compound of the present invention of formula (I) has PPAR regulating activities by the following experiments.

Measurement of PPAR α, PPAR γ and PPAR δ Agonist Activities

1) Preparation of Materials Using Human PPAR α, γ or δ in Luciferase Assay

The whole operation was based on basic gene engineering techniques, and in the operation conventional methods in yeast One-hybrid or Two-hybrid system were used.

As a luciferase gene expression vector under the control of thymidine kinase (TK) promotor, luciferase structural gene was excised from PicaGene Basic Vector 2 (A Brand Name, Toyo Ink Inc., catalogue No. 309-04821), to prepare luciferase gene expression vector pTK-Luc. under the control of TK promotor (−105/+51) as a minimum essential promotor activity from pTKβ having TK promotor (Chrontech Inc., catalogue No.6179-9). In the upper stream of TK promotor, four times repeated UAS sequence was inserted, which is the response element of Ga14 protein, a basic transcription factor in yeast, to construct 4×UAS-TK-Luc. as reporter gene. The following is the enhancer sequence used (Sequence No. 1).
Sequence No. 1: Enhancer sequence repeating Ga14 response element four-times tandemly
5'-T(CGACGGAGTACTGTCCTCCG)×4 AGCT-3'

A vector was prepared as described hereafter which expresses chimeric receptor protein wherein in carboxyl terminus of yeast Ga14 protein DNA binding domain was fused to ligand binding domain of human PPAR α, γ or δ. That is to say, PicaGene Basic Vector 2 (a Brand Name; Toyo Ink Inc., catalogue No. 309-04821) was used as a basic expression vector, the structural gene was exchanged for that of chimeric receptor protein, while promotor and enhancer domains were kept as they were.

DNA encoding a fused protein composed of Ga14 DNA binding domain, amino acids 1–147 linked to the ligand binding domain of human PPAR α, γ or δ in frame was inserted to the downstream of promotor/enhancer in PicaGene Basic Vector 2 (a Brand Name). Here the DNA was aligned as follows; in the amino terminus of human PPAR α, γ or δ ligand binding domain, nuclear translocation signal originated from SV-40 T-antigen, Ala Pro Lys Lys Lys Arg Lys Val Gly (sequence No. 2) was added to make fusion protein localizing intranuclearly. On the other hand, in the carboxy terminus of them, influenza hemagglutinin epitope, Tyr Pro Tyr Asp Val Pro Asp Tyr Ala (sequence No. 3) and stop codon for translation was added in this order, to detect an expressed fused protein tagged epitope sequence.

The portion of structural gene used as ligand binding domain of human PPAR α, γ or δ is as follows: human PPAR α ligand binding domain: $Ser^{167}$-$Tyr^{468}$ human PPAR γ ligand binding domain: $Ser^{176}$-$Tyr^{478}$ human PPAR δ ligand binding domain: $Ser^{139}$-$Tyr^{441}$ in comparison with human PPAR γ 1 and human PPAR γ 2, $Ser^{204}$-$Tyr^{506}$ in human γ 2 is corresponding and identical to $Ser^{176}$-$Tyr^{478}$ in human PPAR γ 1), according to the comparison of human PPAR structures described in the literatures by R. Mukherjee et al. (See J. Steroid Biochem. Molec. Biol., 51, 157 (1994)), M. E. Green et al., (See Gene Expression., 4, 281 (1995)), A. Elbrecht et al. (See Biochem Biophys. Res. Commun., 224, 431 (1996)) or A. Schmidt et al. (See Mol. Endocrinology., 6, 1634 (1992)). In order to measure basal level of transcription, an expression vector containing DNA binding domain of Gal4 protein lacking in PPAR ligand binding domain, which is exclusively encoding the amino acids of No. 1~No. 147 in Gal4 protein was also prepared.

2) Luciferase Assay Using Human PPAR α, γ or δ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 μg/ml of streptomycin sulfate were used to culture CV-1 cells under the atmosphere of 5% carbon dioxide gas at 37° C.

$2 \times 10^6$ cells were seeded in a 10 cm dish, and once washed with the medium without serum, followed by addition of the medium (10 ml) thereto. Reporter gene (10 μg), Gal4-PPAR expression vector (0.5 μg) and 50 μl of LipofectAMINE (a Brand Name, GIBRO BRL Inc., catalogue No. 18324-012) were well mixed and added to the culture to introduce these DNAs into the cells. They were cultured at 37° C. for 5–6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin, and they were again seeded in 96-well plates in a density of 8000 cells/100 μl of DMEM-10% dialyzed serum/well. Several hours after the cultivation, cells were attached to the plastic ware, then 100 μl of DMEM-10% dialyzed serum containing the compounds of the present invention, whose concentration is twice as high as the final concentration of them. The culture was settled at 37° C. for 42 hours and the cells were dissolved, to measure luciferase activity according to manufacturer's instruction.

As to PPAR α agonist activity, the relative activity of the compounds of the present invention (0.3 μM) was shown in table 21, under the condition that luciferase activity was defined as 1.0 when a positive control compound carbaprostacyclin made a final concentration of 10 μM, which apparently activated PPAR α (See Eur. J. Biochem., 233, 242 (1996); Genes & Development., 10, 974 (1996)).

As to PPAR γ agonist activity, the relative activity of the compounds of the present invention (1.0 μM) was shown in table 22, under the condition that luciferase activity was defined as 1.0 when a positive control compound troglitazone made a final concentration of 10 μM, which significantly activated PPAR γ (See Cell., 83, 863 (1995); Endocrinology., 137, 4189 (1996) and J. Med. Chem., 39, 665 (1996)) and has already launched.

As to PPAR δ agonist activity, the relative activity of the compounds of the present invention was shown in table 23, under the condition that luciferase activity was defined as 1.0 when solvent containing no compound was added.

Furthermore, the reproducibility was very good in each point examined in triplicate. And dose dependent activation of PPARs thereof was also confirmed.

TABLE 21

PPAR α agonist activity

| Compound No. | Relative Activity |
| --- | --- |
| Example 2 | 2.1 |
| Example 2 (5) | 0.8 |
| Example 2 (11) | 3.2 |
| Example 2 (12) | 1.7 |

TABLE 22

PPAR γ agonist activity

| Compound No. | Relative Activity |
| --- | --- |
| Example 2 (12) | 1.4 |

TABLE 23

PPAR δ agonist activity

| | Concentration (μM) | | |
| --- | --- | --- | --- |
| Compound No. | 0 | 1.0 | 10.0 |
| Example 2 (22) | 1.0 | 9.3 | 66.7 |
| Example 2 (93) | 1.0 | 36.1 | 54.7 |
| Example 6 | 1.0 | 11.0 | 61.6 |

Hypoglycemic and Hypolipidemic Effects in KKAy Mice

Male, 7-weeks old KKAy/Ta mice weighed from 35 to 40 g (seven mice per group) were pre-breaded for approximately one week and acclimatized for three days on milled diet. On the first day of the experiment (Day 0), mice were divided into some groups by weight, plasma glucose and triglyceride (TG) levels to minimize the differences among groups. From the next day for two days they were given compounds by food mixture containing 0.03% (w/w) of the compound of the present invention or by milled diet only. At 13:00 of the third day, blood samples were collected and glucose and TG were measured. These results are shown in table 24. Additionally, there was no significant difference in the food intake between control group (milled diet only) and compounds-treated group (milled diet containing 0.03% compounds).

TABLE 24

| Compound No. | glycemic value (mg/dl) 3 days | TG value (mg/dl) 3 days |
|---|---|---|
| control | 495 ± 35 | 558 ± 107 |
| food containing compound of Example 2 (12) 38.9 mg/kg/day (converted) | 214 ± 19* | 221 ± 66* |

*p < 0.01 v.s. control (seven mice per group)

Hypocholesterolemic and Hypolipidemic Effects in Normal Rats

Male, six-weeks old SD rats (seven rats per group) were left to take milled diet and water ad libitum and were acclimatized for 1 week.

At 9:00 on the first day of the experiment (Day 0) blood sampling was done from tail vein. The rats were divided into some groups by body weight, trigiyceride(TG), non-esterified fatty acid (NEFA), total cholesterol (TC) values to minimize differences of the parameters among the groups. At 17:00 of the day the compound of the present invention suspended in 0.5%,aqueous solution of carboxymethylcellulose (CMC) was orally administered at a dose of 10 mg/kg, and thereafter, with hypercholesterolemic food (5.5% peanut oil, 1.5% cholesterol and 0.5% cholic acid were mixed with milled CRF-1 diet, Charles River Inc.) was given to the rats.

At 9:00 of the next day, blood sampling was done from tail vein. The lipid values in blood (TG, NEFA and TC values) were measured. The results are shown in table 25.

There was no significant difference of the food intake between the control group (provided only 0.5% CMC) and the group treated with the compounds of the present invention.

TABLE 25

| Compound No. | TC value (mg/dl) | TG value (mg/dl) | NEFA value (µEq/l) |
|---|---|---|---|
| control | 188 ± 5 | 147 ± 9 | 489 ± 66 |
| Example 2 (12) | 70 ± 5** | 100 ± 14* | 178 ± 14** |

*p < 0.05 vs control (seven rats per group)
**p < 0.01 vs control (seven rats per group)

The hypoglycemic or hypolipidemic effects observed in KKAy mice imply the possibility of preventives and/or remedies for diabetes and hyperlipidemia, etc. Cholesterol-lowering and free fatty acid-lowering effects observed in high cholesterol diet-fed rats imply that the compounds of the present invention are useful as preventives and/or remedies of atherosclerosis etc.

INDUSTRIAL APPLICABILITY

[Effect]

The compounds of formula (I), non-toxic salts thereof and hydrates thereof have PPAR regulating effect, and therefore are expected to be applied as hypoglycemic agents, hypolipidemic agents, preventives and/or remedies for diseases associated with metabolic disorders (diabetes, obesity, syndrome X, hypercholesterolemia, hyperlipoproteinemia, etc.), hyperlipidemia, atherosclerosis, hypertension, circulatory diseases, overeating, coronary heart diseases, etc., HDL cholesterol-elevating agents, LDL cholesterol and/or VLDL cholesterol-lowering agents and agents for relieving risk factors of diabetes or syndrome X.

The compounds of formula (I), non-toxic salts thereof and hydrates thereof have particularly PPAR α agonist and/or PPAR γ agonist effect, and therefore are thought to be useful as hypoglycemic agents, hypolipidemic agents, preventives and/or remedies for diseases associated with metabolic disorders (diabetes, obesity, syndrome X, hypercholesterolemia, hyperlipoproteinemia, etc.), hyperlipidemia, atherosclerosis, hypertension, circulatory diseases, overeating, etc. coronary heart diseases, etc. Since they are expected to have HDL cholesterol-elevating effect, LDL cholesterol and/or VLDL cholesterol-lowering effect, inhibition of progress of atherosclerosis and its treatment, and inhibitory effect against obesity, they are also expected to be useful for the treatment and/or prevention of diabetes as hypoglycemic agents, for the amelioration of hypertension, for the relief from risk factors of syndrome X, and as preventives against occurrence of coronary heart diseases.

Since the compounds of formula (I), non-toxic salts thereof and hydrates thereof also have PPAR δ agonist activity, they are expected to have HDL cholesterol-elevating effect, and therefore, they are expected to be useful as agents for the inhibition of progress of atherosclerosis and its treatment, hypolipidemic agents and/or hypoglycemic agents. Furthermore, they are also expected to be useful for the treatment of hyperglycemia, as hypoglycemic agents, for the treatment of diabetes, for the relief from risk factors of syndrome X, and as preventives against occurrence of coronary heart diseases.

[Toxicity]

The toxicity of the compounds of the present invention are very low and the compounds are safe enough for pharmaceutical use.

[Application to Pharmaceuticals]

For the purpose above described, the compounds of the present invention of formula (I), non-toxic salts, acid addition salts or hydrates thereof may normally be administered usually systemically or topically, orally or parenterally.

The doses to be administered are determined depending upon, for example, age, body weight, symptom, the desired therapeutic effect, the route of administration, and the duration of the treatment. In the human adult, the doses per person are generally in the range of from 1 mg to 1000 mg, by oral administration, up to several times per day, and in the range of from 0.1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules, etc. Capsules include hard capsules and soft capsules.

In these solid forms, one or more of the active compound(s) may be admixed with excipients (e.g. lactose, mannitol, glucose, microcrystalline cellulose, starch), binders (e.g. hydroxypropyl cellulose, polyvinylpyrrolidone or magnesium metasilicate aluminate), disintegrants (e.g. cellulose calcium glycolate), lubricants (e.g. magnesium stearate), stabilizing agents, and adjuvants to assist dissolution (e.g. glutamic acid, aspartic acid) and prepared according to methods well known to those skilled in the art. The solid forms may, if desired, be coated with coating agents (e.g. sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable aqueous solutions, suspensions and emulsions, syrups and elixirs, etc. In such forms, one or more of the active compound(s) may be dissolved, suspended or emulsified into diluent(s) commonly used in the art (e.g. purified water, ethanol or a mixture thereof). Besides such liquid forms may also comprise wetting agents, suspending agents, emulsifying agents, sweetening agents, flavoring agents, aroma, preservative or buffering agent, etc.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, physiological salt solution, vegetable oil, propylene glycol, polyethylene glycol, alcohol, e.g. ethanol, or a mixture thereof.

Injections may comprise some additives, such as stabilizing agents, solution adjuvants (e.g. glutamic acid, aspartic acid or POLYSORBATE80 (registered trademark)), suspending agents, emulsifying agents, soothing agent, buffering agents, preservatives. They may be sterilized at the final step, or may be prepared and compensated according to sterile methods. They may also be manufactured in the form of sterile solid forms, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se. Sprays may comprise additional substances other than diluents, such as stabilizing agents (e.g. sodium sulfate), isotonic buffers (e.g. sodium chloride, sodium citrate or citric acid). For preparation of such sprays, for example, the method described in the U.S. Pat. No. 2,868,691 or 3,095,355 may be used.

BEST MODE FOR CARRYING OUT THE INVENTION

The following Reference Examples and Examples illustrate the present invention, but do not limit the present invention.

The solvents in the parentheses show the developing or eluting solvents and the ratios of the solvents used are by volume in chromatographic separations and TLC.

Solvents in the parentheses of NMR show the solvents used for measurement.

REFERENCE EXAMPLE 1

3-methoxymethoxybenzaldehyde

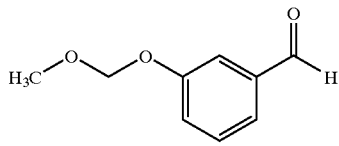

A solution of 3-hydroxybenzaldehyde (20 g), chloromethylmethyl ether (25 ml) and diisopropylethylamine (114 ml) intetrahydrofuran (300 ml) was stirred at room temperature overnight. To the reaction mixture was added ice water and was extracted with ethyl acetate. The extract was washed with a saturated aqueous solution of sodium bicarbonate, water and a saturated aqueous solution of sodium chloride, successively, dried over anhydrous magnesium sulfate and concentrated. The residue was purified by column chromatography on silica gel (hexane:ethyl acetate=25:1) to give the title compound (23 g) having the following physical data.

TLC: Rf 0.65 (hexane:ethyl acetate=3:1);

NMR (CDCl$_3$): δ9.98 (s, 1H), 7.42–7.56 (m, 3H), 7.30 (m, 1H), 5.24 (s, 2H), 3.50 (s, 3H).

REFERENCE EXAMPLE 2

3-methoxymethoxybenzylalcohol

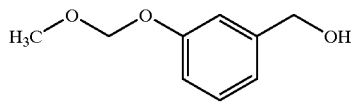

To a suspension of lithium aluminum hydride (690 mg) in tetrahydrofuran (60 ml), was added a solution of the compound prepared in Reference Example 1 (3.0 g) in tetrahydrofuran (40 ml) and the reaction mixture was stirred at room temperature for 30 minutes. To the reaction mixture were added a saturated aqueous solution of sodium sulfate and magnesium sulfate and the mixture was filtered through Celite. The filtrate was concentrated. The residue was purified by column chromatography on silica gel (hexane:ethyl acetate=3:1) to give the title compound (2.5 g) having the following physical data.

TLC: Rf 0.39 (hexane:ethyl acetate=3:1);

NMR (CDCl$_3$): δ7.25 (t, J=7.5 Hz, 1H), 7.10–6.95 (m, 3H), 5.20 (s, 2H), 4.70 (d, J=6 Hz, 2H), 3.50 (s, 3H), 1.75 (t, J=6 Hz, 1H).

REFERENCE EXAMPLE 3

3-methoxymethoxybenzyl bromide

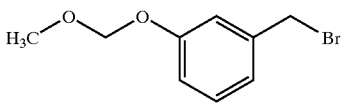

To a solution of the compound prepared in Reference Example 2 (2.48 g) and triphenylphosphine (4.64 g) in dichloromethane (150 ml), carbon tetrabromide (7.34 g) was added and the mixture was stirred at room temperature for 30 minutes. To the reaction mixture was added a saturated aqueous solution of sodium bicarbonate and was extracted with dichloromethane. The extract was washed with a saturated aqueous solution of sodium chloride, dried over anhydrous magnesium sulfate and concentrated. The residue was purified by column chromatography on silica gel (hexane:ethyl acetate=5:1) to give the tittle compound (4.41 g) having the following physical data.

TLC: Rf 0.71 (hexane:ethyl acetate=2:1);

NMR (CDCl₃): δ7.25 (t, J=7.5 Hz, 1H), 7.10–6.95 (m, 3H), 5.20 (s, 2H), 4.45 (s, 2H), 3.50 (s, 3H).

REFERENCE EXAMPLE 4

2-(3-methoxymethoxyphenylmethylthio)acetic acid.methyl ester

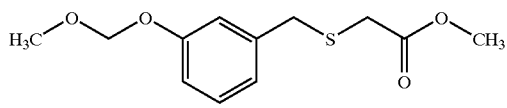

A suspension of the compound prepared in Reference Example 3 (4.41 g), methyl thioglycolate (1.5 ml), potassium carbonate (2.45 g) and potassium iodide (250 mg) in acetonitrile (50 ml) was refluxed for 3 hours. The reaction mixture was filtered. The filtrate was concentrated. The residue was purified by column chromatography on silica gel (hexane:ethyl acetate=5:1) to give the title compound (2.81 g) having the following physical data.

TLC: Rf 0.57 (hexane:ethyl acetate=2:1);

NMR (CDCl₃): δ7.25 (t, J=7.5 Hz, 1H), 7.05–6.90 (m, 3H), 5.20 (s, 2H), 3.80 (s, 2H), 3.75 (s, 3H), 3.50 (s, 3H), 3.10 (s, 2H).

REFERENCE EXAMPLE 5

2-(3-hydroxyphenylmethylthio)acetic acid methyl ester

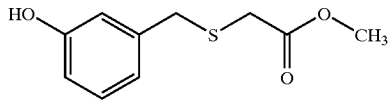

To a solution of the compound prepared in Reference Example 4 (2.81 g) in methanol (20 ml), was added 4N solution of hydrogen chloride in dioxane (11 ml) and the mixture was stirred at room temperature for 30 minutes. The reaction mixture was concentrated. The residue was purified by column chromatography on silica gel (hexane:ethyl acetate=5:1) to give the title compound (2.16 g )having the following physical data.

TLC: Rf 0.45 (hexane:ethyl acetate=2:1);

NMR (CDCl₃): δ7.20 (t, J=7.5 Hz, 1H), 6.90 (d, J=7.5 Hz, 1H), 6.85 (d, J=2 Hz, 1H), 6.75 (dd, J=7.5, 2 Hz, 1H), 5.05 (s, 1H), 3.80 (s, 2H), 3.75 (s, 3H), 3.10 (s, 2H).

EXAMPLE 1

2-(3-(4-(4-methylphenyl)thiazol-2-ylmethoxy) phenylmethylthio)acetic acid.methyl ester

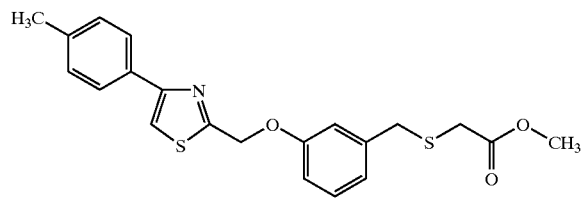

The compound prepared in Reference Example 5 (0.30 g) was dissolved in dichloromethane (10 ml) and thereto were added 2-hydroxymethyl-4-(4-methylphenyl)thiazole (0.34 g) and triphenylphosphine (0.44 g) and the mixture was stirred at room temperature for 5 minutes. To the reaction mixture was added 1,1'-azodicarbonyldipiperidine (0.56 g) and the mixture was stirred at room temperature overnight. To the reaction mixture was added diethyl ether and the mixture was filtered. The filtrate was washed with a saturated aqueous solution of sodium bicarbonate, water and a saturated aqueous solution of sodium chloride, successively, dried over anhydrous magnesium sulfate and concentrated. The residue was purified by column chromatography on silica gel (hexane:ethyl acetate=10:1) to give the compound of the present invention (0.51 g) having the following physical data.

TLC: Rf 0.56 (hexane:ethyl acetate=3:1);

NMR (CDCl₃): δ7.79 (d, J=8.2 Hz, 2H), 7.44 (s, 1H), 7.22–7.30 (m, 3H), 6.91–7.05 (m, 3H), 5.42 (s, 2H), 3.81 (s, 2H), 3.72 (s, 3H), 3.08 (s, 2H), 2.39 (s, 3H).

EXAMPLE 1(1)~EXAMPLE 1(137)

The following. compounds were obtained by the same procedure as shown in Example 1, using the compound prepared in Reference Example 5 or corresponding derivatives, and 2-hydroxymethyl-4-(4-methylphenyl) thiazole or corresponding derivatives.

EXAMPLE 1(1)

6-(3-(4-(4-methylphenyl)thiazol-2-ylmethoxy) phenyl)hexanoic acid.methyl ester

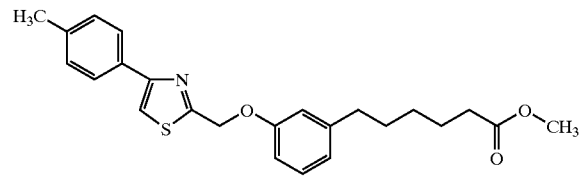

TLC: Rf 0.75 (hexane ethyl acetate=2:1);

NMR (CDCl₃): δ7.48–7.66 (2H, m), 7.43 (1H, s), 7.28–7.10 (3H, m), 6.88–6.72 (3H, m), 5.41 (2H, s), 3.66 (3H, s), 2.59 (2H, t, J=8.0 Hz), 2.39 (3H, s), 2.30 (2H, t, J=7.5 Hz), 1.74–1.46 (4H, m), 1.45–1.16 (2H, m).

EXAMPLE 1(2)

5-(3-(biphenyl-4-ylmethoxy)phenyl)pentanoic acid.methyl ester

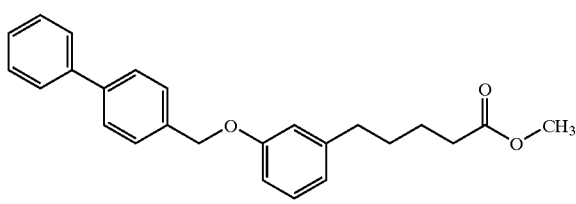

TLC: Rf 0.57 (hexane:ethyl acetate=4:1);

NMR (CDCl$_3$): δ7.30–7.62 (m, 9H), 7.20 (m, 1H), 6.77–6.83 (m, 3H), 5.08 (s, 2H), 3.64 (s, 3H), 2.60 (t, J=6.8 Hz, 2H), 2.32 (t, J=6.8 Hz, 2H), 1.59–1.66 (m, 4H).

EXAMPLE 1(3)

4-(3-(biphenyl-4-ylmethoxy)phenyl)butanoic acid.methyl ester

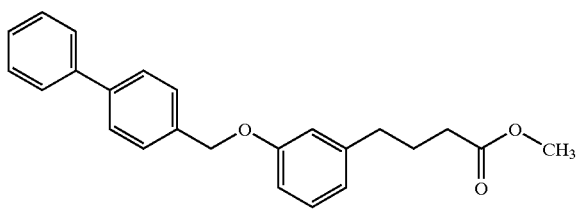

TLC: Rf 0.65 (hexane:ethyl acetate=3:1);

NMR (CDCl$_3$): δ7.57–7.64 (m, 4H), 7.31–7.53 (m, 5H), 7.22 (m, 1H), 6.78–6.87 (m, 3H), 5.09 (s, 2H), 3.66 (s, 3H), 2.64 (t, J=7.5 Hz, 2H), 2.33 (t, J=7.5 Hz, 2H), 1.96 (tt, J=7.5, 7.5 Hz, 2H).

EXAMPLE 1(4)

4-(3-(4-(4-methylphenyl)thiazol-2-ylmethoxy)phenyl)butanoic acid.methyl ester

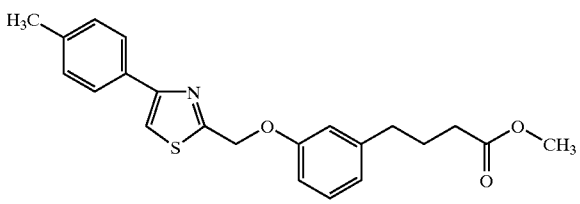

TLC: Rf 0.59 (hexane:ethyl acetate 3:1);

NMR (CDCl$_3$): δ7.79 (d, J=8.0 Hz, 2H), 7.44 (s, 1H), 7.18–7.26 (m, 3H), 6.81–6.87 (m, 3H), 5.41 (s, 2H), 3.66 (s, 3H), 2.64 (t, J=7.5 Hz, 2H), 2.39 (s, 3H), 2.33 (t, J=7.5 Hz, 2H), 1.95 (tt, J=7.5, 7.5 Hz, 2H).

EXAMPLE 1(5)

4-(3-(2-(5-methyl-2-phenyloxazol-4-yl)ethoxy)phenyl)butanoic acid.methyl ester

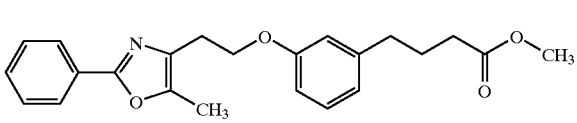

TLC: Rf 0.39 (hexane:ethyl acetate 3:1);

NMR (CDCl$_3$): δ7.98 (m, 2H), 7.38–7.46 (m, 3H), 7.17 (m, 1H), 6.72–6.77 (m, 3H), 4.23 (t, J=7.0 Hz, 2H), 3.66 (s, 3H), 2.98 (t, J=7.0 Hz, 2H), 2.60 (t, J=7.5 Hz, 2H), 2.38 (s, 3H), 2.32 (t, J=7.5 Hz, 2H), 1.93 (tt, J=7.5, 7.5 Hz, 2H).

EXAMPLE 1(6)

6-(3-(2-(5-methyl-2-phenyloxazol-4-yl)ethoxy)phenyl)hexanoic acid.methyl ester

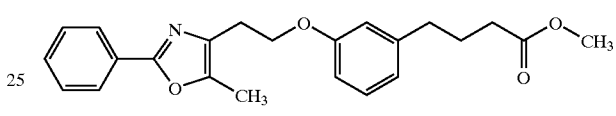

TLC: Rf 0.51 (hexane:ethyl acetate=3:1);

NMR (CDCl$_3$): δ8.04–7.92 (2H, m), 7.50–7.36 (3H, m), 7.16 (1H, t, J=8.0 Hz), 6.80–6.60 (3H, m), 4.23 (2H, t, J=7.0 Hz), 3.65 (3H, s), 2.98 (2H, t, J=7.0 Hz), 2.56 (2H, t, J=7.5 Hz), 2.38 (3H, s), 2.29 (2H, t, J=7.0 Hz), 1.75–1.52 (4H, m), 1.44–1.26 (2H, m).

EXAMPLE 1(7)

5-(3-(2-(5-methyl-2-phenyloxazol-4-yl)ethoxy)phenyl)pentanoic acid.methyl ester

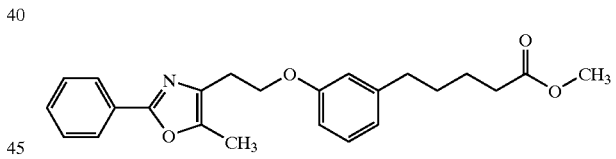

TLC: Rf 0.28 (hexane:ethyl acetate=5:1);

NMR (CDCl$_3$): δ8.03–7.94 (2H, m), 7.49–7.36 (3H, m), 7.23–7.12 (1H, m), 6.78–6.68 (3H, m), 4.23 (2H, t, J=7.0 Hz), 3.65 (3H, s), 2.98 (2H, t, J=7.0 Hz), 2.64–2.52 (2H, m), 2.38 (3H, s), 2.38–2.26 (2H, m), 1.75–1.58 (4H, m).

EXAMPLE 1(8)

2-(3-(3-(biphenyl-4-ylmethoxy)phenyl)propylthio)acetic acid.methyl ester

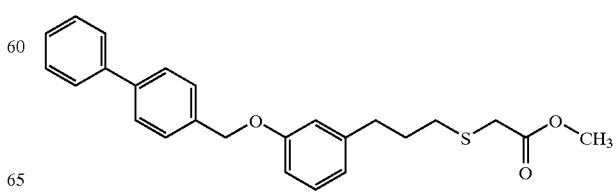

TLC: Rf 0.73 (hexane ethyl acetate=2 1);

NMR (CDCl$_3$): δ7.57–7.64 (m, 4H), 7.31–7.53 (m, 5H), 7.22 (dd, J=9.0, 7.6 Hz, 1H), 6.79–6.86 (m, 3H), 5.10 (s, 2H), 3.72 (s, 3H), 3.23 (s, 2H), 2.71 (t, J=7.4 Hz, 2H), 2.65 (t, J=7.4 Hz, 2H), 1.93 (tt, J=7.4, 7.4 Hz, 2H).

EXAMPLE 1(9)

2-(3-(3-(4-(4-methylphenyl)thiazol-2-ylmethoxy)phenyl)propylthio)acetic acid.methyl ester

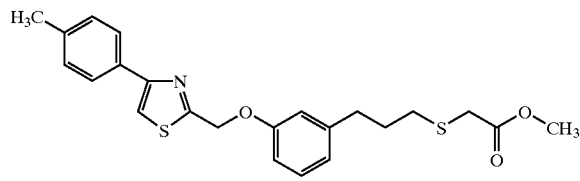

TLC: Rf 0.68 (hexane:ethyl acetate=2 1);

NMR (CDCl$_3$): δ7.79 (d, J=8.0 Hz, 2H), 7.44 (s, 1H), 7.18–7.26 (m, 3H), 6.82–6.88 (m, 3H), 5.41 (s, 2H), 3.72 (s, 3H), 3.22 (s, 2H), 2.71 (t, J=7.5 Hz, 2H), 2.64 (t, J=7.5 Hz, 2H), 2.39 (s, 3H), 1.92 (tt, J=7.5, 7.5 Hz, 2H).

EXAMPLE 1(10)

6-(2-(2-(5-methyl-2-phenyloxazol-4-yl)ethoxy)phenyl)hexanoic acid.methyl ester

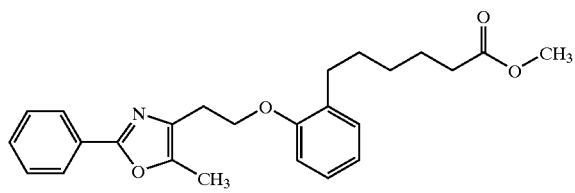

TLC: Rf 0.51 (hexane:ethyl acetate 5:1);

NMR (CDCl$_3$): δ7.95–8.00 (m, 2H), 7.40–7.45 (m, 3H), 7.02–7.17 (m, 2H), 6.81–6.89 (m, 2H), 4.25 (t, J=6.4 Hz, 2H), 3.65 (s, 3H), 2.99 (t, J=6.4 Hz, 2H), 2.56 (t, J=7.8 Hz, 2H), 2.38 (s, 3H), 2.26 (t, J=7.8 Hz, 2H), 1.46–1.76 .(m, 4H), 1.22–1.45 (m, 2H).

EXAMPLE 1(11)

2-(3-(biphenyl-4-ylmethoxy)phenylmethylthio)acetic acid.methyl ester

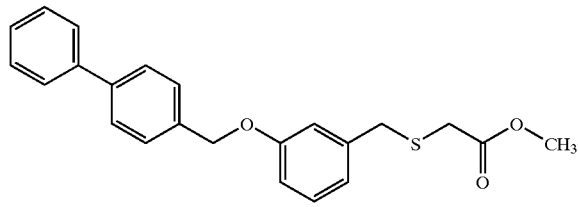

TLC: Rf 0.56 (hexane ethyl acetate=3:1);

NMR (CDCl$_3$): δ7.57–7.63 (m, 4H), 7.34–7.52 (m, 5H), 7.24 (dd, J=8.1, 7.7 Hz, 1H), 6.87–7.00 (m, 3H), 5.10 (s, 2H), 3.80 (s, 2H), 3.71 (s, 3H), 3.07 (s, 2H).

EXAMPLE 1(12)

2-(3-(2-(5-methyl-2-phenyloxazol-4-yl)ethoxy)phenylmethylthio)acetic acid.methyl ester

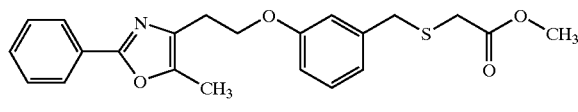

TLC: Rf 0.36 (hexane ethyl acetate=3:1);

NMR (CDCl$_3$): δ7.95–8.00 (m, 2H), 7.37–7.44 (m, 3H), 7.20 (dd, J=8.0, 8.0 Hz, 1H), 6.87–6.90 (m, 2H), 6.80 (dd, J=8.0, 2.5 Hz, 1H), 4.24 (t, J=6.7 Hz, 2H), 3.77 (s, 2H), 3.70 (s, 3H), 3.07 (s, 2H), 2.98 (t, J=6.7 Hz, 2H), 2.37 (s, 3H).

EXAMPLE 1(13)

5-(2-(2-(5-methyl-2-phenyloxazol-4-yl)ethoxy)phenyl)pentanoic acid.methyl ester

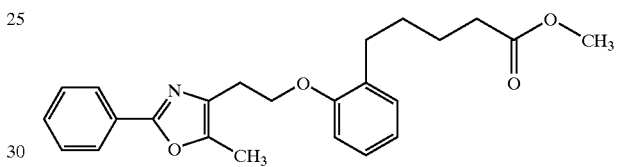

TLC: Rf 0.59 (hexane:ethyl acetate 2:1);

NMR (CDCl$_3$): δ8.05–7.95 (m, 2H), 7.45–7.35 (m, 3H), 7.20–7.05 (m, 2H), 6.90–6.80 (m, 2H);, 4.25 (t, J=6.5 Hz, 2H), 3.65 (s, 3H), 3.00 (t, J=6.5 Hz, 2H), 2.60 (t, J=7 Hz, 2H), 2.40 (s, 3H), 2.25 (t, J=7 Hz, 2H), 1.80–1.45 (m, 4H).

EXAMPLE 1(14)

6-(2-(4-(4-methylphenyl)thiazol-2-ylmethoxy)phenyl)hexanoic acid.methyl ester

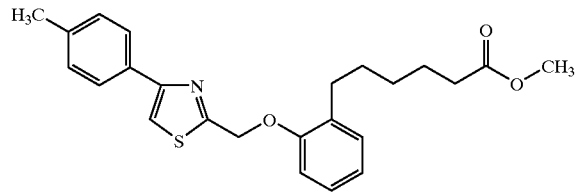

TLC: Rf 0.55 (hexane:ethyl acetate=5:1);

NMR (CDCl$_3$): δ7.79 (d, J=8.0 Hz, 2H), 7.44 (s, 1H), 7.24 (d, J=8.0 Hz, 2H), 7.15–7.22 (m, 2H), 6.91–6.98 (m, 2H), 5.42 (s, 2H), 3.65 (s, 3H), 2.73 (t, J=7.6 Hz, 2H), 2.39 (s, 3H), 2.32 (t, J=7.4 Hz, 2H), 1.61–1.77 (m, 4H), 1.38–1.50 (m, 2H).

EXAMPLE 1(15)

2-(3-(3-(2-(5-methyl-2-phenyloxazol-4-yl)ethoxy)phenyl)propylthio)acetic acid.methyl ester

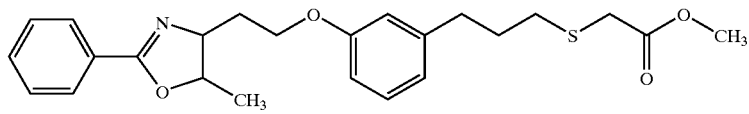

TLC: Rf 0.29 (hexane:ethyl acetate 4:1);
NMR (CDCl₃): δ7.95–8.00 (m, 2H), 7.40–7.46 (m, 3H), 7.17 (dd, J=8.1, 8.1 Hz, 1H), 6.72–6.77 (m, 3H), 4.23 (t, J=6.8 Hz, 2H), 3.71 (s, 3H), 3.22 (s, 2H), 2.98 (t, J=6.8 Hz, 2H), 2.67 (t, J=6.8 Hz, 2H), 2.63 (t, J=6.8 Hz, 2H), 2.38 (s, 3H), 1.90 (tt, J=6.8, 6.8 Hz, 2H).

EXAMPLE 1(16)

2-(3-(2-(biphenyl-4-yl)ethoxy)phenylmethylthio) acetic acid.methyl ester

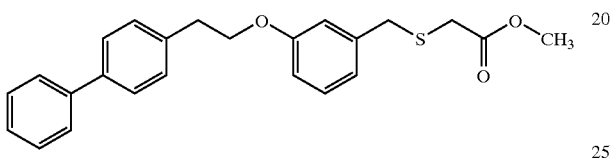

TLC: Rf 0.48 (hexane ethyl acetate=3:1);
NMR (CDCl₃): δ7.53–7.61 (in, 4H), 7.30–7.47 (m, 5H), 7.22 (dd, J=8.2, 8.2 Hz, 1H), 6.78–6.92 (m, 3H), 4.21 (t, J=7.0 Hz, 2H), 3.79 (s, 2H), 3.71 (s, 3H), 3.14 (t, J=7.0 Hz, 2H), 3.09 (s, 2H).

EXAMPLE 1(17)

2-(4-chloro-3-(2-(5-methyl-2-phenyloxazol-4-yl)ethoxy)phenylmethylthio)acetic acid.methyl ester

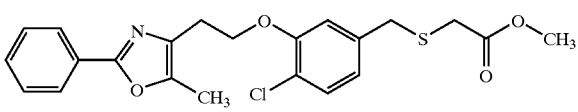

TLC: Rf 0.41 (hexane:ethyl acetate=2:1);
NMR (CDCl₃): δ8.00 (m, 2H), 7.50–7.35 (m. 3H), 7.27 (d, J=8.0 Hz, 1H), 6.94 (d, J=2.0 Hz, 1H), 6.83 (dd, J=8.0, 2.0 Hz, 1H), 4.30 (t, J=6.5 Hz, 2H), 3.75 (s, 2H), 3.71 (s, 3H), 3.05 (s, 2H), 3.05 (t, J=6.5 Hz, 2H), 2.42 (s, 3H).

EXAMPLE 1(8)

2-(4-chloro-3-(4-(4-methylphenyl)thiazol-2-ylmethoxy)phenylmethylthio)acetic acid.methyl ester

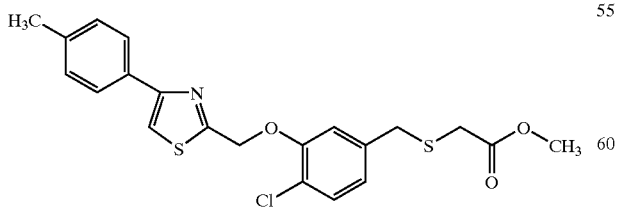

TLC: Rf 0.61 (hexane:ethyl acetate=2:1);
NMR (CDCl₃): δ7.78 (d, J=8.0 Hz, 2H), 7.45 (s. 1H), 7.34 (d, J=8.0 Hz, 1H), 7.23 (d, J=8.0 Hz, 2H), 7.11 (d, J=2.0 Hz, 1H), 6.93 (dd, J=8.0, 2.0 Hz, 1H), 5.49 (s, 2H), 3.77 (s, 2H), 3.69 (s, 3H), 3.01 (s, 2H), 2.38 (s, 3H).

EXAMPLE 1(19)

2-(3-(biphenyl-4-ylmethoxy)-4-chlorophenylmethylthio)acetic acid.methyl ester

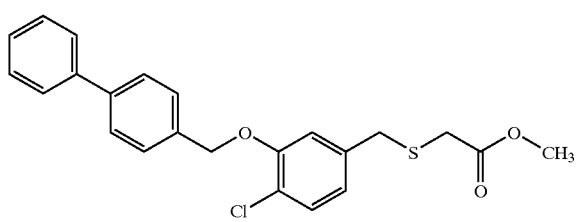

TLC: Rf 0.62 (hexane:ethyl acetate=2:1);
NMR (CDCl₃): δ7.70–7.35 (m, 5H), 7.58 (d, J=8.0 Hz, 2H), 7.43 (d, J=8.0 Hz, 2H), 7.33 (d, J=8.0 Hz, 1H), 7.03 (d, J=2.0 Hz, 1H), 6.88 (dd, J=8.0, 2.0 Hz, 1H), 5.22 (s, 2H), 3.77 (s, 2H), 3.70 (s, 3H), 3.00 (s, 2H).

EXAMPLE 1(20)

2-(3-((2E)-3-(biphenyl-4-yl)propenyloxy)phenylmethylthio)acetic acid.methyl ester

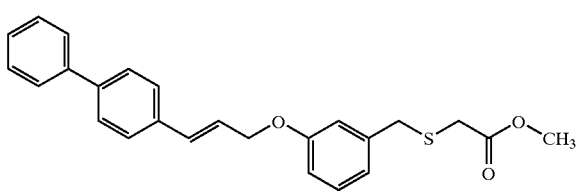

TLC: Rf 0.63 (hexane:ethyl acetate 3:1);
NMR (CDCl₃): δ7.53–7.63 (m, 4H), 7.15–7.50 (m, 6H), 6.74–6.93 (m, 4H), 6.45 (dt, J=16.2, 5.7 Hz, 1H), 4.73 (dd, J=5.7, 1.4 Hz, 2H), 3.81 (s, 2H), 3.72 (s, 3H), 3.09 (s, 2H).

EXAMPLE 1(21)

2-(3-(3-(biphenyl-4-yl)propoxy)phenylmethylthio) acetic acid.methyl ester

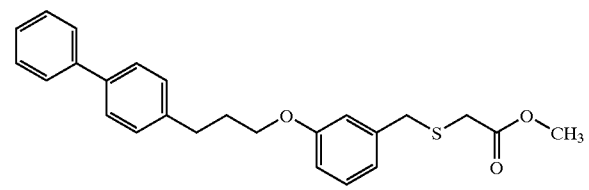

TLC: Rf 0.66 (hexane:ethyl acetate=4:1);
NMR (CDCl₃): δ7.19–7.61 (m, 10H), 6.79–6.92 (m, 3H), 4.00 (t, J=6.2 Hz, 2H), 3.80 (s, 2H), 3.72 (s, 3H), 3.10 (s, 2H), 2.86 (t, J=7.7 Hz, 2H), 2.14 (m, 2H).

EXAMPLE 1(22)

2-(3-(2-(5-methyl-L2-phenyloxazol-4-yl)ethoxy)phenyl)acetic acid.methyl ester

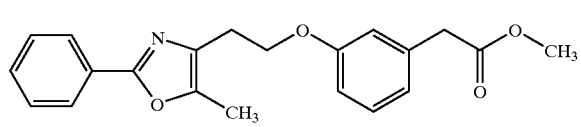

TLC: Rf 0.50 (hexane:ethyl acetate=2:1);

NMR (CDCl$_3$): δ8.00–7.95 (m, 2H), 7.50–7.35 (m, 3H), 7.20 (m, 1H), 6.90–6.75 (m, 3H), 4.25 (t, J=7 Hz, 2H), 3.70 (s, 3H), 3.60 (s, 2H), 3.00 (t, J=7 Hz, 2H), 2.40 (3H, s).

EXAMPLE 1(23)

2-(3-(biphenyl-4-ylmethoxy)pyridin-5-ylmethylthio)acetic acid.methyl ester

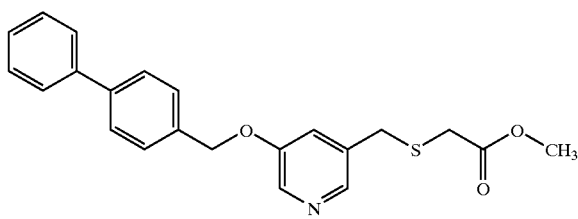

TLC: Rf 0.22 (ethyl acetate:hexane=1:2);

NMR (CDCl$_3$): δ8.32 (d, J=3.0 Hz, 1H), 8.18 (d, J=2.0 Hz, 1H), 7.70–7.30 (m, 10H), 5.16 (s, 2H), 3.81 (s, 2H), 3.72 (s, 3H), 3.06 (s, 2H).

EXAMPLE 1(24)

2-(3-(4'-propylbiphenyl-4-ylmethoxy)phenylmethylthio)acetic acid.methyl ester

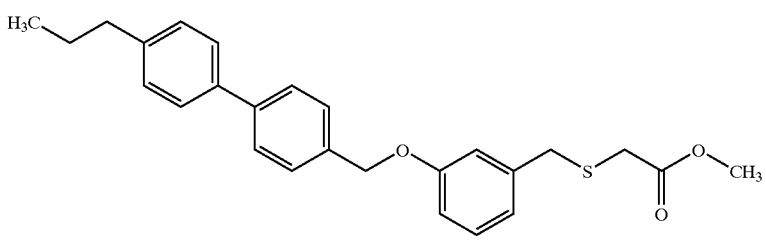

TLC: Rf 0.65 (hexane:ethyl acetate=3:1);

NMR (CDCl$_3$): δ7.60 (d, J=8.4 Hz, 2H), 7.51 (d, J=8.2 Hz, 2H), 7.49 (d, J=8.4 Hz, 2H), 7.25 (d, J=8.2 Hz, 2H), 7.24 (dd, J=7.7, 7.7 Hz, 1H), 6.87–7.0.0 (m, 3H), 5.10 (s, 2H), 3.81 (s, 2H), 3.72 (s, 3H), 3.08 (s, 2H), 2.63 (t, J=7.4 Hz, 2H), 1.68 (tq, J=7.4, 7.4 Hz, 2H), 0.98 (t, J=7.4 Hz, 3H).

EXAMPLE 1(25)

2-(3-(4-(pyridin-4-yl)phenylmethoxy)phenylmethylthio)acetic acid.methyl ester

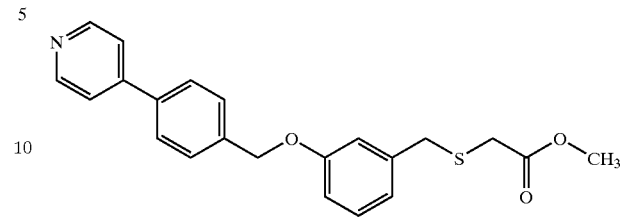

TLC: Rf 0.50 (ethyl acetate);

NMR (CDCl$_3$): δ8.67 (d, J=4.5 Hz, 1H), 8.66 (d, J=4.5 Hz, 1H), 7.67 (d, J=8.6 Hz, 2H), 7.50–7.58 (m, 4H), 7.26 (dd, J=8.0, 8.0 Hz, 1H), 6.80–7.01 (m, 3H), 5.13 (s, 2H), 3.81 (s, 2H), 3.72 (s, 3H), 3.09 (s, 2H).

EXAMPLE 1(26)

2-(3-(4-(pyridin-3-yl)phenylmethoxy)phenylmethylthio)acetic acid.methyl ester

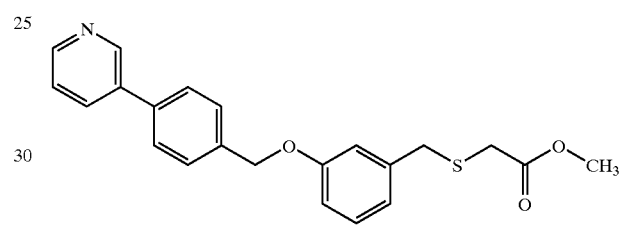

TLC: Rf 0.77 (hexane:ethyl acetate=1:9);

NMR (CDCl$_3$): δ8.86 (d, J=2.4 Hz, 1H), 8.60 (dd, J=5.0, 1.6 Hz, 1H), 7.89 (ddd, J=8.0, 2.4, 1.6 Hz, 1H), 7.62 (d, J=8.2 Hz, 2H), 7.55 (d, J=8.2 Hz, 2H), 7.38 (dd, J=8.0, 5.0 Hz, 1H), 7.26 (dd, J=8.0, 8.0 Hz, 1H)., 6.87–7.01 (m, 3H), 5.13 (s, 2H), 3.81 (s, 2H), 3.72 (s, 3H), 3.09 (s, 2H).

EXAMPLE 1(27)

2-(3-(4-(1,3-dioxaindan-5-yl)phenylmethoxy)phenylmethylthio)acetic acid.methyl ester

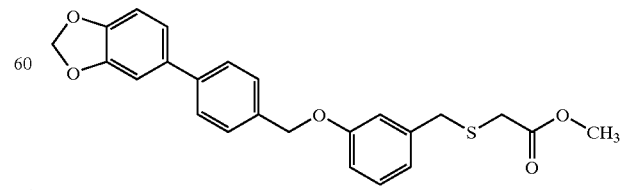

TLC: Rf 0.48 (hexane:ethyl acetate=3:1);

NMR (CDCl₃): δ7.54 (d, J=8.4 Hz, 2H), 7.47 (d, J=8.4 Hz, 2H), 7.25 (dd, J=7.9, 7.9 Hz, 1H), 6.86–7.08 (m, 6H), 6.00 (s, 2H), 5.09 (s, 2H), 3.81 (s, 2H), 3.72 (s, 3H), 3.08 (s, 2H).

EXAMPLE 1(28)

2-(3-(4-(pyridin-2-yl)phenylmethoxy)phenylmethylthio)acetic acid.methyl ester

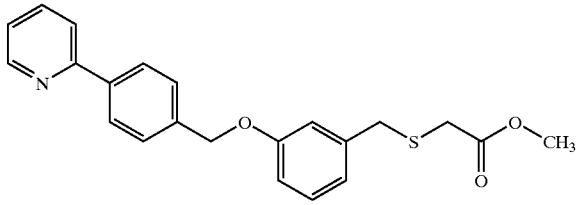

TLC: Rf 0.47 (hexane:ethyl acetate=2:1);

NMR (CDCl₃): δ8.70 (d, J=4. 6 Hz, 1H), 8. 01 (d, J=8.6 Hz, 2H), 7.74–7.77 (m, 3H), 7.54 (d, J=8.6 Hz, 2H), 7.24 (m, 1H), 6.75–7.00 (m, 3H), 5.13 (s, 2H), 3.80 (s, 2H), 3.72 (s, 3H), 3.08 (s, 2H).

EXAMPLE 1(29)

2-(5-(biphenyl-4-ylmethoxy)-2-nitrophenylmethylthio)acetic acid.methyl ester

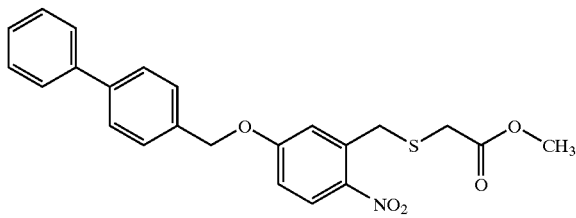

TLC: Rf 0.38 (hexane:ethyl acetate=4:1);

NMR (CDCl₃): δ8.14 (d, J=9.0 Hz, 1H), 7.57–7.65 (m, 4H), 7.45–7.52 (m, 3H), 7.36–7.45 (m, 2H), 7.08 (d, J=2.8 Hz, 1H), 6.97 (dd, J=9.0, 2.8 Hz, 1H), 5.22 (s, 2H), 4.22 (s, 2H), 3.71 (s, 3H), 3.07 (s, 2H).

EXAMPLE 1(30)

2-(3-(biphenyl-4-ylmethoxy)-4-nitro phenylmethylthio)acetic acid.methyl ester

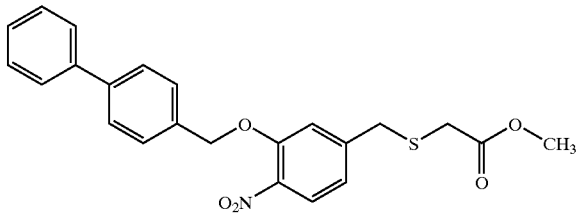

TLC: Rf 0.34 (hexane:ethyl acetate=4:1);

NMR (CDCl₃): δ7.85 (d, J=5.5 Hz, 1H), 7.53–7.63 (m, 6H), 7.42–7.48 (m, 2H), 7.33–7.38 (m, 1H), 7.20 (d, J=1.0 Hz, 1H), 7.01 (dd, J=5.5, 1.0 Hz, 1H), 5.31 (s, 2H), 3.83 (s, 2H), 3.71 (s, 3H), 3.00 (s, 2H).

EXAMPLE 1(31)

2-(3-(4-(1,3-dioxaindan-4-yl)phenylethoxy)phenylmethylthio)acetic acid.methyl ester

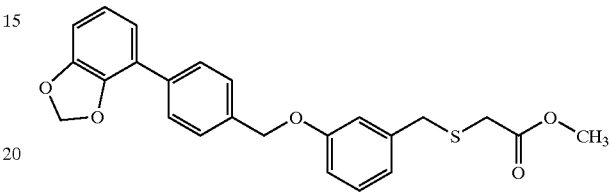

TLC: Rf 0.52 (hexane:ethyl acetate=3:1);

NMR (CDCl₃): δ7.74 (d, J=8.4 Hz, 2H), 7.50 (d, J=8.4 Hz, 2H), 7.24 (dd, J=7.8, 7.8 Hz, 1H), 6.80–7.09 (m, 6H), 6.02 (s, 2H), 5.11 (s, 2H), 3.80 (s, 2H), 3.71 (s, 3H), 3.08 (s, 2H).

EXAMPLE 1(32)

2-(3-(2-phenylthiazol-4-ylmethoxy)phenylmethylthio)acetic acid.methyl ester

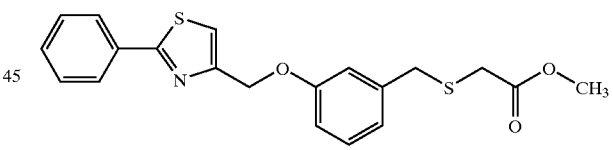

TLC: Rf 0.38 (hexane:ethyl acetate=4:1);

NMR (CDCl₃): δ7.92–7.99 (m, 2H), 7.43–7.48 (m, 3H), 7.32 (t, J=1.0 Hz, 1H), 7.26 (dd J=7.9, 7.9 Hz, 1H), 6.90–7.04 (m, 3H), 5.27 (d, J=1.0 Hz, 2H), 3.81 (s, 2H), 3.72 (s, 3H), 3.09 (s, 2H).

EXAMPLE 1(33)

2-(3-(2-(5-methyl-2-(4-methyl phenyl)oxazol-4-yl)ethoxy)phenylmethylthio)acetic acid.methyl ester

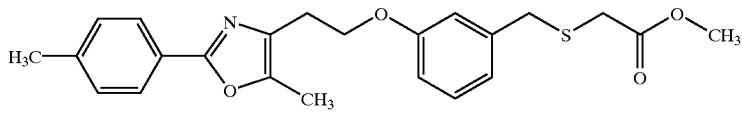

TLC: Rf 0.81 (hexane:ethyl acetate=1:1);

NMR (CDCl$_3$): δ7.86 (d, J=8.2 Hz, 2H), 7.25–7.16 (m, 3H), 6.90–6.76 (m, 3H), 4.24 (t, J=6.7 Hz, 2H), 3.78 (s, 2H), 3.71 (s, 3H), 3.08 (s, 2H), 2.97 (t, J=6.7 Hz, 2H), 2.39 (s, 3H), 2.37 (s, 3H).

EXAMPLE 1(34)

2-(3-(2-(2-phenylthiazol-4-yl)ethoxy)phenylmethylthio)acetic acid.methyl ester

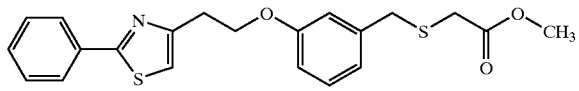

TLC: Rf 0.39 (hexane:ethyl acetate=4:1);

NMR (CDCl$_3$): δ7.92–7.96 (m, 2H), 7.41–7.46 (m, 3H), 7.23 (dd, J=8.4, 8.4 Hz, 1H), 7.07 (s, 1H), 6.81–6.93 (m, 3H), 4.37 (t, J=6.6 Hz, 2H), 3.79 (s, 2H), 3.71 (s, 3H), 3.31 (t, J=6.6 Hz, 2H), 3.09 (s, 2H).

EXAMPLE 1(35)

2-(3-(2-(5-methyl-2-(4-trifluoromethylphenyl)oxazol-4-yl)ethoxy)phenylmethylthio)acetic acid.methyl ester

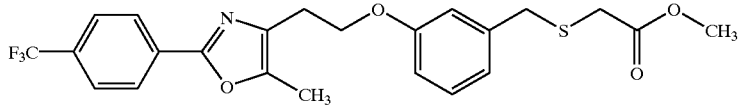

TLC: Rf 0.22 (hexane:ethyl acetate=2:1);

NMR (CDCl$_3$): δ8.09 (d, J=7.6 Hz, 2H), 7.69 (d, J=7.6 Hz, 2H), 7.19 (m, 1H), 6.89 (m, 2H), 6.8 (d, J=7.2 Hz, 1H), 4.25 (t, J=6.5 Hz, 2H), 3.78 (s, 2H), 3.72 (s, 3H), 3.09 (s, 2H), 2.99 (t, J=6.5 Hz, 2H), 2.41 (s, 3H).

EXAMPLE 1(36)

2-(3-(2-(2-phenyloxazol-4-yl)ethoxy)phenylmethylthio)acetic acid.methyl ester

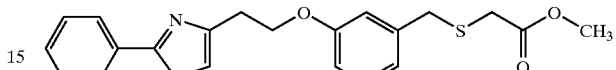

TLC: Rf 0.40 (hexane:ethyl acetate=3:1);

NMR (CDCl$_3$): δ8.00–8.05 (m, 2H), 7.58 (s, 1H), 7.41–7.46 (m, 3H), 7.23 (dd, J=8.0, 8.0 Hz, 1H), 6.81–6.93 (m, 3H), 4.29 (t, J=6.5 Hz, 2H), 3.79 (s, 2H), 3.72 (s, 3H), 3.09 (t, J=6.5 Hz, 2H), 3.09 (s, 2H).

EXAMPLE 1(37)

2-(3-(2-(5-methyl-2-(4-fluorophenyl)oxazol-4-yl)ethoxy)phenylmethylthio)acetic acid.methyl ester

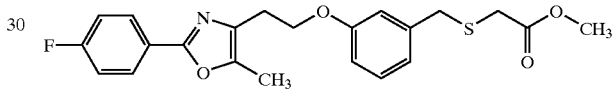

TLC: Rf 0.62 (hexane:ethyl acetate=1:1);

NMR (CDCl$_3$): δ7.96 (m, 2H), 7.06–7.24 (m, 3H), 6.91–6.74 (m, 3H), 4.23 (t, J=6.6 Hz, 2H), 3.77 (s, 2H), 3.71 (s, 3H), 3.08 (s, 2H), 2.97 (t, J=6.6 Hz, 2H), 2.38 (s, 3H).

EXAMPLE 1(38)

2-(3-(2-(5-methyl-2-(1,3-dioxaindan-5-yl)oxazol-4-yl)ethoxy)phenylmethylthio)acetic acid.methyl ester

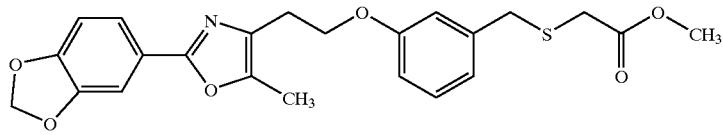

TLC: Rf 0.84 (hexane:ethyl acetate=1:1);

NMR (CDCl₃): δ7.52 (dd, J=8.0, 1.4 Hz, 1H), 7.43 (d, J=1.4 Hz, 1H), 7.19 (d, J=8.0 Hz, 1H), 6.91–6.77 (m, 4H), 6.01 (s, 2H), 4.23 (t, J=6.7 Hz, 2H), 3.78 (s, 2H), 3.71 (s, 3H), 3.08 (s, 2H), 2.95 (t, J=6.7 Hz, 2H), 2.35 (s, 3H).

EXAMPLE 1(39)

5-(3-(3-(5-methyl-2-phenyloxazol-4-yl)propoxy)phenyl)pentanoic acid.methyl ester

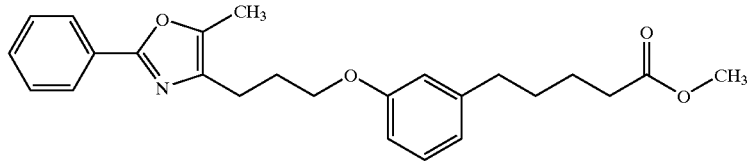

TLC: Rf 0.64 (hexane:ethyl acetate=2:1);

NMR (CDCl₃): δ8.00–7.95 (m, 2H), 7.50–7.35 (m, 3H), 7.20 (dd, J=8, 7.5 Hz, 1H), 6.80–6.70 (m, 3H), 4.00 (t, J=6 Hz, 2H), 3.65 (s, 3H), 2.70 (t, J=6 Hz, 2H), 2.60 (m, 2H), 2.35 (m, 2H), 23.30 (s, 3H), 2.15 (m, 2H), 1.70–1.50 (s, 4H).

EXAMPLE 1(40)

2-(3-(2-(5-methyl-2-(4-chlorophenyl)oxazol-4-yl)ethoxy)phenylmethylthio)acetic acid.methyl ester

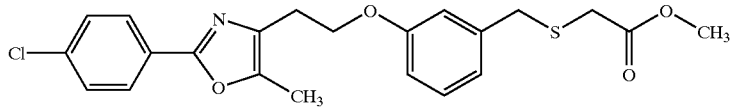

TLC: Rf 0.83 (hexane:ethyl acetate=2:1);

NMR (CDCl₃): δ7.93 (d, J=8.8 Hz, 2H), 7.38 (d, J=8.8 Hz, 2H), 7.27 (t, J=7.9 Hz, 1H), 7.06 (m, 1H), 6.92 (d, J=8.0 Hz, 1H), 6.82 (d, J=8.0 Hz, 1H), 4.27 (t, J=7.8 Hz, 2H), 3.88 (s, 2H), 3.70 (s, 3H), 3.15 (s, 2H), 2.97 (t, J=7.8 Hz, 2H), 2.39 (s, 3H).

EXAMPLE 1(41)

2-(3-(5-methyl-2-phenyloxazol-4-ylmethoxy)phenylmethylthio)acetic acid.methyl ester

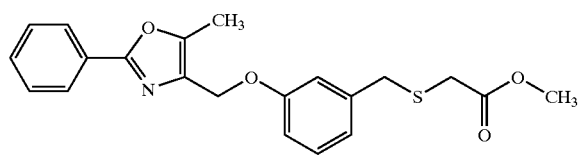

TLC: Rf 0.56 (hexane:ethyl acetate=2:1);

NMR (CDCl₃): δ8.05–8.00 (m, 2H), 7.50–7.40 (m, 3H), 7.25 (dd, J=8, 8 Hz, 1H), 7.05–6.90 (m, 3H), 5.00 (s, 2H), 3.80 (s, 2H), 3.75 (s, 3H), 3.10 (s, 2H), 2.50 (s, 3H).

EXAMPLE 1(42)

2-(3-(3-(5-methyl-2-phenyloxazol-4-yl)propoxy)phenylmethylthio)acetic acid.methyl ester TLC: Rf 0.53 (hexane:ethyl acetate=2:1);

NMR (CDCl₃): δ8.00–7.95 (m, 2H), 7.50–7.40 (m, 3H), 7.25 (dd, J=7.5, 7.5 Hz, 1H), 6.95–6.75 (m, 3H), 4.00 (t, J=6 Hz, 2H), 3.80 (s, 2H), 3.75 (s, 3H), 3.10 (s, 2H), 2.70 (t, J=7 Hz, 2H), 2.30 (s, 3H), 2.15 (m, 2H).

EXAMPLE 1(43)

2-(3-(2-(5-methyl-2-phenyloxazol-4-yl)ethoxy)phenyl)-2-methylpropanoic acid.methyl ester

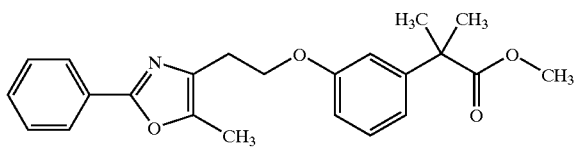

TLC: Rf 0.48 (hexane:ethyl acetate=3:1);

NMR (CDCl$_3$): δ7.97–8.02 (m, 2H), 7.41–7.46 (m, 3H), 7.22 (dd, J=8.0, 8.0 Hz, 1H), 6.76–6.81 (m, 3H), 4.25 (t, J=6.5 Hz, 2H), 3.64 (s, 3H), 2.99 (t, J=6.5 Hz, 2H), 2.38 (s, 3H), 1.55 (S, 6H).

EXAMPLE 1(44)

2-(3-(2-(5-methyl-2-(2-methylphenyl)oxazol-4-yl)ethoxy)phenylmethylthio)acetic acid.methyl ester

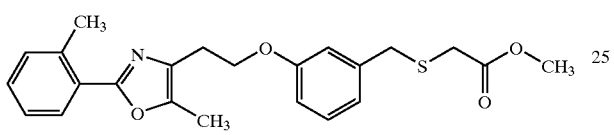

TLC: Rf 0.70 (hexane:ethyl acetate=2:1);

NMR (CDCl$_3$): δ7.91 (m, 1H), 7.25–7.15 (m, 4H), 6.90–6.77 (m, 3H), 4.25 (t, J=6.7 Hz, 2H), 3.77 (s, 2H), 3.68 (s, 3H), 3.06 (s, 2H), 2.98 (t, J=6.7 Hz, 2H), 2.65 (s, 3H), 2.36 (s, 3H).

EXAMPLE 1(45)

2-(3-(2-(5-methyl-2-(3-methylphenyl)oxazol-4-yl)ethoxy)phenylmethylthio)acetic acid.methyl ester

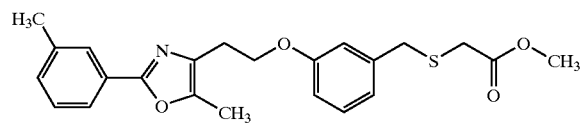

TLC: Rf 0.64 (hexane:ethyl acetate=2:1);

NMR (CDCl$_3$): δ7.81 (s, 1H), 7.76 (d, J=8.0 Hz, 1H), 7.32–7.14 (m, 3H), 6.89–6.76 (m, 3H), 4.23 (t, J=6.6 Hz, 2H), 3.75 (s, 2H), 3.67 (s, 3H), 3.06 (s, 2H), 2.96 (t, J=6.6 Hz, 2H), 2.37 (s, 3H), 2.35 (s, 3H).

EXAMPLE 1(46)

2-(3-(2-(5-methyl-2-(4-methoxyphenyl)oxazol-4-yl)ethoxy)phenylmethylthio)acetic acid.methyl ester

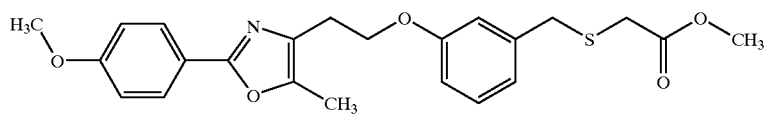

TLC: Rf 0.43 (hexane:ethyl acetate=3:1);

NMR (CDCl$_3$): δ7.92 (d, J=9.0 Hz, 2H), 7.21 (dd, J=8.1, 8.1 Hz, 1H), 6.94 (d, J=9.0 Hz, 2H), 6.88–6.98 (m, 2H), 6.81 (m, 1H), 4.24 (t, J=6.7 Hz, 2H), 3.85 (s, 3H), 3.78 (s, 2H), 3.71 (s, 3H), 3.08 (s, 2H), 2.97 (t, J=6.7 Hz, 2H), 2.36 (s, 3H).

EXAMPLE 1(47)

2-(3-(2-(5-methyl-2-(4-nitrophenyl)oxazol-4-yl)ethoxy)phenylmethylthio)acetic acid.methyl ester

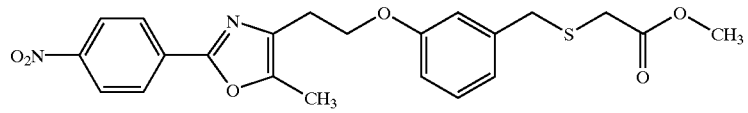

TLC: Rf 0.32 (hexane:ethyl acetate=3:1);

NMR (CDCl$_3$): δ8.30 (d, J=9.0 Hz, 2H), 8.14 (d, J=9.0 Hz, 2H), 7.22 (dd, J=8.0, 8.0 Hz, 1H), 6.77–6.91 (m, 3H), 4.26 (t, J=6.5 Hz, 2H), 3.78 (s, 2H), 3.72 (s, 3H), 3.09 (s, 2H), 3.00 (t, J=6.5 Hz, 2H), 2.43 (s, 3H).

EXAMPLE 1(48)

2-(3-(2-(5-methyl-2-phenyloxazol-4-yl)ethoxy)-5-chlorophenylmethylthio)acetic acid.methyl ester

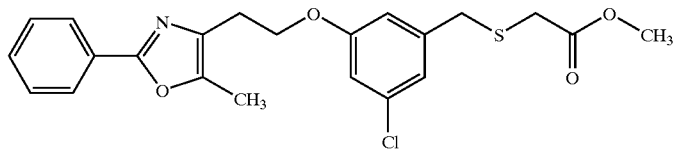

TLC: Rf 0.45 (hexane:ethyl acetate=3:1);

NMR (CDCl₃): δ7.96–8.00 (m, 2H), 7.40–7.46 (m, 3H), 6.91 (m, 1H), 6.77–6.81 (m, 2H), 4.23 (t, J=6.6 Hz, 2H), 3.73 (s, 2H), 3.72 (s, 3H), 3.08 (s, 2H), 2.97 (t, J=6.6 Hz, 2H), 2.38 (s, 3H).

EXAMPLE 1(49)

2-(3-(2-(5-methyl-2-phenyloxazol-4-yl)ethoxy)-2-methylphenylmethylthio)acetic acid.methyl ester

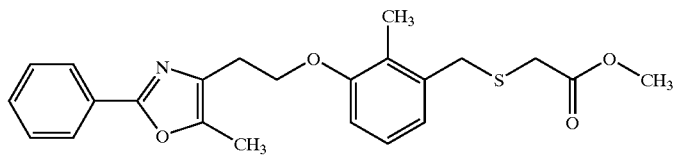

TLC: Rf 0.48 (hexane:ethyl acetate=5 1);

NMR (CDCl₃): δ8.00–7.95 (m, 2H), 7.46–7.39 (m, 3H), 7.07 (t, J=7.9 Hz, 1H), 6.85–6.77 (m, 2H), 4.24 (t, J=6.5 Hz, 2H), 3.83 (s, 2H), 3.73 (s, 3H), 3.11 (s, 2H), 3.00 (t, J=6.5 Hz, 2H), 2.38 (s, 3H), 2.21 (s, 3H).

EXAMPLE 1(50)

2-(1-(3-(2-(5-methyl-2-phenyloxazol-4-yl)ethoxy)phenyl)ethylthio)acetic acid.methyl ester

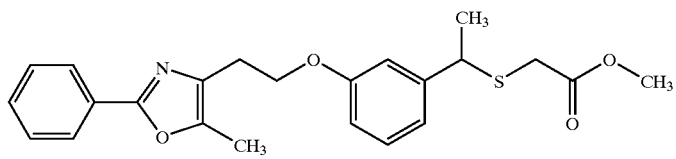

TLC: Rf 0.68 (hexane:ethyl acetate=4:1);

NMR (CDCl₃): δ8.00–7.95 (m, 2H), 7.46–7.39 (m, 3H), 7.21 (t, J=8.2 Hz, 1H), 6.94–6.89 (m, 2H), 6.82–6.76 (m, 1H), 4.25 (t, J=6.7 Hz, 2H), 4.10 (q, J=7.2 Hz, 1H), 3.67 (s, 3H), 3.02 (s, 2H), 2.98 (t, J=6.7 Hz, 2H), 2.39 (s, 3H), 1.55 (d, J=7.2 Hz, 3H).

EXAMPLE 1(51)

2-(3-(2-(5-methyl-2-phenyloxazol-4-yl)-1-methylethoxy)phenylmethylthio)acetic acid.methyl ester

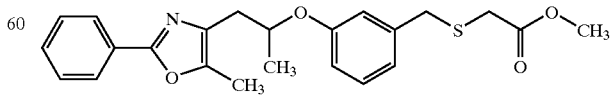

TLC: Rf 0.72 (hexane:ethyl acetate=2:1).

EXAMPLE 1(52)

2-(3-(2-(5-trifluoromethyl-2-phenyloxazol-4-yl)ethoxy)phenylmethylthio)acetic acid.methyl ester

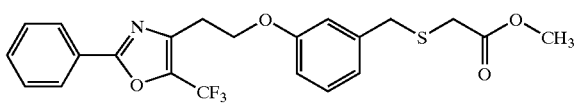

TLC: Rf 0.37 (hexane:ethyl acetate=4:1);

NMR (CDCl$_3$): δ8.10–8.00 (m., 2H), 7.55–7.41 (m., 3H), 7.21 (dd, J=8.0, 8.0 Hz, 1H), 6.94–6.75 (m, 3H), 4.31 (t, J=6.5 Hz, 2H), 3.77 (s, 2H), 3.71 (s, .3H), 3.25–3.14 (m, 2H), 3.08 (s, 2H).

EXAMPLE 1(53)

2-(3-(2-(5-methyl-2-phenyloxazol-4-yl)propoxy)phenylmethylthio)acetic acid.methyl ester

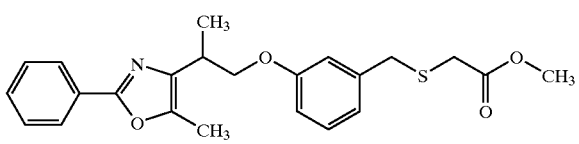

TLC: Rf 0.54:(hexane:ethyl acetate=3:1);

NMR (CDCl$_3$): δ8.00–7.94 (m, 2H), 7.44–7.37 (m, 3H), 7.29 (t, J=8.2 Hz, 1H), 6.89–6.86 (m, 2H), 6.79 (dd, J=8.4, 2.0 Hz, 1H), 4.17–4.03 (m, 2H), 3.77 (s, 2H), 3.71 (s, 3H), 3.26–3.15 (m, 1H), 3.08 (s, 2H), 2.37 (s, 3H), 1.41 (d, J=6.8 Hz, 3H).

EXAMPLE 1(54)

2-(3-(2-(5-methyl-2-phenyloxazol-4-yl)ethoxy)phenylmethylthio)propanoic acid.ethyl ester

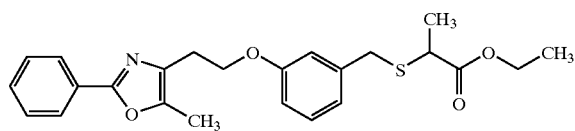

TLC: Rf 0.75 (hexane:ethyl acetate=7:1);

NMR (CDCl$_3$): δ8.00–7.94 (m, 2H), 7.46–7.38 (m, 3H), 7.20 (t, J=8.2 Hz, 1H), 6.90 (m, 2H), 6.82–6.75 (m, 1H), 4.24 (t, J=6.8 Hz, 2H), 4.17 (q, J=7.2 Hz, 2H), 3.82 (d, J=13.4 Hz, 1H), 3.74 (d, J=13.4 Hz, 1H), 3.28 (q, J=7.0 Hz, 1H), 2.98 (t, J=6.8 Hz, 2H), 2.38 (s, 3H), 1.38 (d, J=7.0 Hz, 3H), 1.28 (t, J=7.2 Hz, 3H).

EXAMPLE 1(55)

2-(3-(2-(5-methyl-2-(4-ethylphenyl)oxazol-4-yl)ethoxy)phenylmethylthio)acetic acid.methyl ester

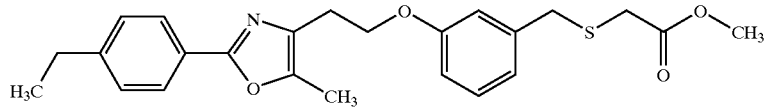

TLC: Rf 0.57 (ethyl acetate:hexane=1:2);

NMR (CDCl$_3$): δ7.88 (d, J=8.0 Hz, 2H), 7.25 (d, J=8.0 Hz, 2H), 7.21 (dd, J=8.0, 8.0 Hz, 1H), 6.95–6.75 (m, 3H), 4.24 (t, J=6.5 Hz, 2H), 3.78 (s, 2H), 3.71 (s, 3H), 3.08 (s, 2H), 2.97 (t, J=6.5 Hz, 2H), 2.68 (q, J=7.5 Hz, 2H), 2.37 (s, 3H), 1.25 (t, J=7.5 Hz, 3H).

EXAMPLE 1(56)

2-(3-(2-(5-methyl-2-(2,2-difluoro-1,3-dioxaindan-5-yl)oxazol-4-yl)ethoxy)phenylmethylthio)acetic acid.methyl ester

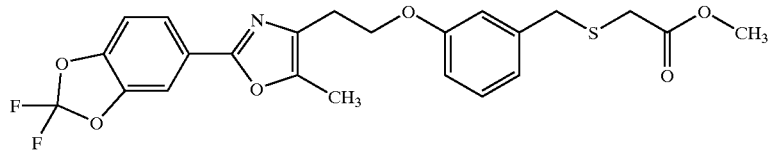

TLC: Rf 0.59 (ethyl acetate:hexane=1:2);

NMR (CDCl$_3$): δ7.75 (dd, J=8.0, 1.0 Hz, 1H), 7.69 (d, J=1.0 Hz, 1H), 7.21 (dd, J=8.0, 8.0 Hz, 1H), 7.10 (d, J=8.0 Hz, 1H), 6.89 (d, J=8.0 Hz, 1H), 6.88 (s, 1H), 6.80 (d, J=8.0 Hz, 1H), 4.23 (t, J=6.5 Hz, 2H), 3.78 (s, 2H), 3.71 (s, 3H), 3.09 (s, 2H), 2.96 (t, J=6.5 Hz, 2H), 2.38 (s, 3H).

EXAMPLE 1(57)

2-(3-(2-(5-methyl-2-(4-propylphenyl)oxazol-4-yl)ethoxy)phenylmethylthio)acetic acid.methyl ester

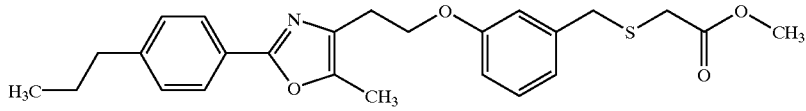

TLC: Rf 0.63 (ethyl acetate:hexane=1:2);

NMR (CDCl$_3$): δ7.88 (d, J=8.5 Hz, 2H), 7.23 (d, J=8.5 Hz, 2H), 7.21 (dd, J=8.0, 8.0 Hz, 1H), 6.95–6.75 (m, 3H), 4.24 (t, J=7.0 Hz, 2H), 3.78 (s, 2H), 3.71 (s, 3H), 3.08 (s, 2H), 2.97 (t, J=7.0 Hz, 2H), 2.62 (t, J=7.5 Hz, 2H), 2.37 (s, 3H), 1.65 (m, 2H), 0.94 (t, J=7.5 Hz, 3H).

EXAMPLE 1(58)

2-(3-(2-(5-methyl-2-(4-isopropylphenyl)oxazol-4-yl)ethoxy)phenylmethylthio)acetic acid.methyl ester

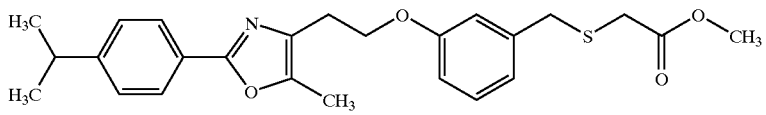

TLC: Rf 0.60 (ethyl acetate:hexane=1:2);

NMR (CDCl$_3$): δ7.89 (d, J=8.5 Hz, 2H), 7.28 (d, J=8.5 Hz, 2H), 7.21 (dd, J=8.0, 8.0 Hz, 1H), 6.95–6.75 (m, 3H), 4.24 (t, J=6.5 Hz, 2H), 3.78 (s, 2H), 3.71 (s, 3H), 3.08 (s, 2H), 2.97 (t, J=6.5 Hz, 2H), 2.94 (m, 1H), 2.37 (s, 3H), 1.26 (d, J=7.0 Hz, 6H).

EXAMPLE 1(59)

2-(3-(2-(5-methyl-2-phenylthiazol-4-yl)ethoxy)phenylmethylthio)acetic acid.methyl ester

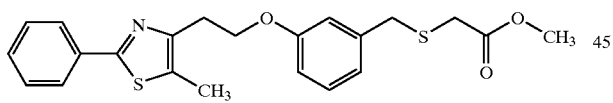

TLC: Rf 0.54 (hexane:ethyl acetate=3:1);

NMR (CDCl$_3$): δ7.89–7.83 (m, 2H), 7.45–7.36 (m, 3H), 7.21 (t, J=8.0 Hz, 1H), 6.91–6.77 (m, 3H), 4.33 (t, J=6.8 Hz, 2H), 3.78 (s, 2H), 3.71 (s, 3H), 3.19 (t, J=6.8 Hz, 2H), 3.08 (s, 2H), 2.47 (s, 3H).

EXAMPLE 1(60)

2-(3(2-(5-methyl-2-(4-butylphenyl)oxazol-4-yl)ethoxy)phenylmethylthio)acetic acid.methyl ester

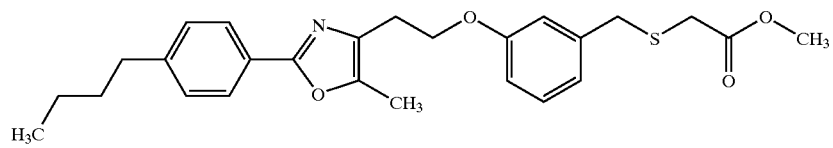

TLC: Rf 0.59 (hexane:ethyl acetate=2:1);

NMR (CDCl$_3$): δ7.90 (d, J=7 Hz, 2H), 7.25–7.15 (m, 3H), 6.90–6.75 (m, 3H), 4.25 (t, J=6.5 Hz, 2H), 3.75 (s, 2H), 3.70 (s, 3H), 3.10 (s, 2H), 3.00 (t, J=6.5 Hz, 2H), 2.65 (t, J=7.5 Hz, 2H), 2.40 (s, 3H), 1.60 (m, 2H), 1.35 (m, 2H), 0.95 (t, J=7 Hz, 3H).

EXAMPLE 1(61)

2-(3-(2-(5-ethyl-2-phenyloxazol-4-yl)ethoxy)phenylmethylthio)acetic acid.methyl ester

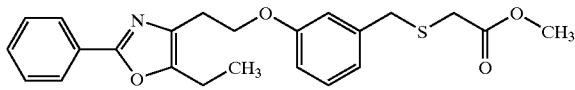

TLC: Rf 0.27 (hexane:ethyl acetate=3:1);

NMR (CDCl$_3$): δ7.96–8.01 (m, 2H), 7.40–7.48 (m, 3H), 7.21 (dd, J=8.0, 8.0 Hz, 1H), 6.87–6.90 (m, 2H), 6.79 (m, 1H), 4.24 (t, J=6.6 Hz, 2H), 3.78 (s, 2H), 3.71 (s, 3H), 3.08 (s, 2H), 2.99 (t, J=6.6 Hz, 2H), 2.75 (q, J=7.6 Hz, 2H), 1.31 (t, J=7.6 Hz, 3H).

EXAMPLE 1(62)

2-(3-(2-(5-methyl-2-(2,3,5,6-tetrafluoro-4-methylphenyl)oxazol-4-yl)ethoxy)phenylmethylthio)acetic acid.methyl ester

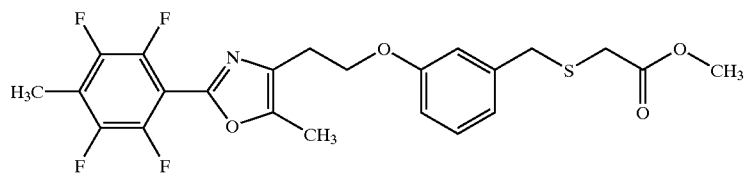

TLC: Rf 0.45 (hexane:ethyl acetate=4:1);

NMR (CDCl$_3$): δ7.21 (dd, J=8.0, 8.0 Hz, 1H), 6.94–6.75 (m, 3H), 4.25 (t, J=6.4 Hz, 2H), 3.78 (s, 2H), 3.72 (s, 3H), 3.09 (s, 2H), 3.03 (t, J=6.4 Hz, 2H), 2.42 (s, 3H), 2.36–2.30 (m, 3H).

EXAMPLE 1(63)

2-(3-(2-(5-methyl-2-(4-pentylphenyl)oxazol-4-yl)ethoxy)phenylmethylthio)acetic acid.methyl ester

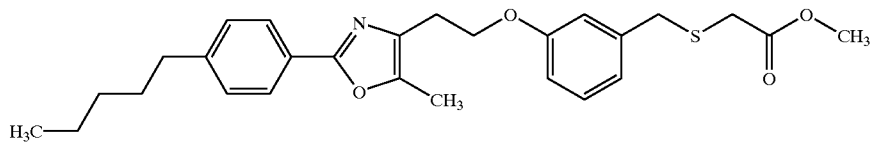

TLC: Rf 0.66 (hexane:ethyl acetate=2:1);

NMR (CDCl$_3$): δ7.90 (d, J=8 Hz, 2H), 7.25–7.20 (m, 3H), 6.95–6.75 (m, 3H), 4.25 (t, J=6.5 Hz, 2H), 3.80 (s, 2H), 3.70 (s, 3H), 3.10 (s, 2H), 3.00 (t, J=6.5 Hz, 2H), 2.65 (t, J=7.5 Hz, 2H), 2.40 (s, 3H), 1.60 (m, 2H), 1.40–1.25 (m, 4H), 0.90 (t, J=6.5 Hz, 3H).

EXAMPLE 1(64)

2-(3-(2-(5-methyl-2-(3-chloro-4-methylphenyl)oxazol-4-yl)ethoxy)phenylmethylthio)acetic acid.methyl ester

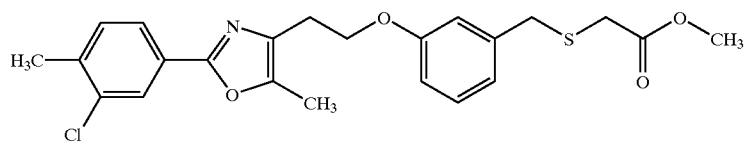

TLC: Rf 0.47 (hexane:ethyl acetate=3:1);

NMR (CDCl$_3$): δ7.96 (d, J=1.8 Hz, 1H), 7.75 (dd, J=7.8, 1.8 Hz, 1H), 7.28 (d, J=7.8 Hz, 1H), 7.21 (dd, J=8.0, 8.0 Hz, 1H), 6.88–6.91 (m, 2H), 6.79 (m, 1H), 4.24 (t, J=6.6 Hz, 2H), 3.78 (s, 2H), 3.72 (s, 3H), 3.08 (s, 2H), 2.97 (t, J=6.6 Hz, 2H), 2.41 (s, 3H), 2.38 (s, 3H).

EXAMPLE 1(65)

2-(3-(2-(5-methyl-2-cyclohexyloxazol-4-yl)ethoxy)
phenylmethylthio)acetic acid.methyl ester

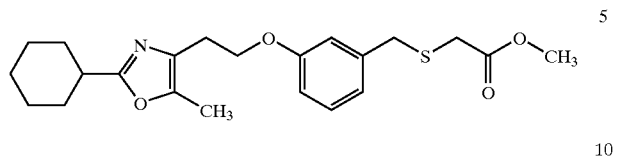

TLC: Rf 0.65 (hexane:ethyl acetate=2:1);
NMR (CDCl$_3$): δ7.20 (m, 1H), 6.95–6.70 (m, 3H), 4.15 (t, J=7.5 Hz, 2H), 3.80 (s, 2H), 3.75 (s, 3H), 3.15 (s, 2H), 2.90 (t, J=7.5 Hz, 2H), 2.70 (m, 1H), 2.25 (s, 3H), 2.10–1.20 (m, 10H).

EXAMPLE 1(66)

2-(3-(2-(5-methyl-2-(4-(2-methylpropyl)phenyl)
oxazol-4-yl)ethoxy)phenylmethylthio)acetic
acid.methyl ester

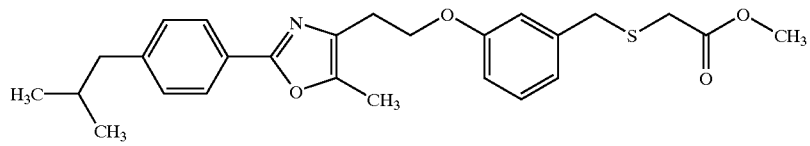

TLC: Rf 0.58 (hexane:ethyl acetate=2:1);
NMR (CDCl$_3$): δ7.90 (d, J=8 Hz, 2H), 7.25–7.20 (m, 3H), 6.90–6.75 (m, 3H), 4.25 (t, J=7 Hz, 2H), 3.80 (s, 2H), 3.70 (s, 3H), 3.10 (s, 2H), 2.95 (t, J=7 Hz, 2H), 2.50 (d, J=8 Hz, 2H), 2.40 (s, 3H), 1.90 (m, 1H), 0.90 (d, J.=7 Hz, 6H).

EXAMPLE 1(67)

2-(3-(2-(5-methyl-2-(4-t-butylphenyl)oxazol-4-yl)
ethoxy)phenylmethylthio)acetic acid.methyl ester

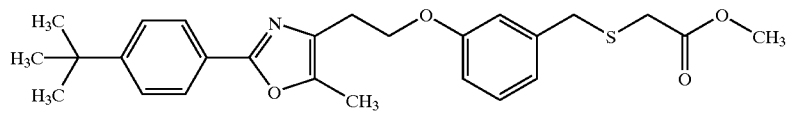

TLC: Rf 0.50 (hexane:ethyl acetate=2:1);

NMR (CDCl$_3$): δ7.90 (d, J=8 Hz, 2H), 7.45 (d, J=8 Hz, 2H), 7.20 (dd, J=8, 8 Hz, 1H), 6.90–6.75 (m, 3H), 4.25 (t, J=7 Hz, 2H), 3.80 (s, 2H), 3.70 (s, 3H), 3.10 (s, 2H), 3.00 (t, J=7 Hz, 2H), 2.40 (s, 3H), 1.35 (s, 9H).:

EXAMPLE 1(68)

2-(3-(2-(5-methyl-2-(4-cyclohexylphenyl)oxazol-4-
yl)ethoxy)phenylmethylthio)acetic acid.methyl ester

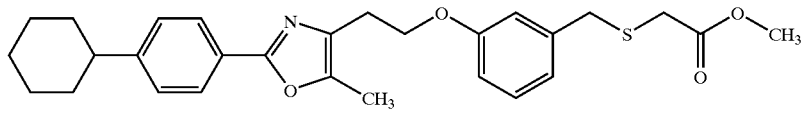

TLC: Rf 0.42: (hexane:ethyl acetate=4:1);

NMR (CDCl$_3$): δ7.88 (d, J=8.3 Hz, 2H), 7.26 (d, J=8.3 Hz, 2H), 7.21 (dd, J=8.0, 8.0 Hz, 1H), 6.87–6.90 (m, 2H), 6.80 (m, 1H), 4.23 (t, J=6.8 Hz, 2H), 3.78 (s, 2H), 3.71 (s, 3H), 3.08 (s, 2H), 2.97 (t, J=6.8 Hz, 2H), 2.53 (m, 1H), 2.37 (s, 3H), 1.70–1.94 (m, 4H), 1.30–1.53 (m, 6H).

EXAMPLE 1(69)

2-(3-(5-methyl-2-(1,3-dioxaindan-5-yl)oxazol-4-ylmethoxy)phenylmethylthio)acetic acid.methyl ester

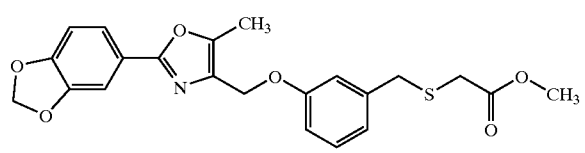

TLC: Rf 0.50 (hexane:ethyl acetate=4:1);

NMR (CDCl$_3$): δ7.55 (dd, J=8.0, 1.8 Hz, 1H), 7.47 (d, J=1.8 Hz, 1H), 7.21 (dd, J=8.0, 8.0 Hz, 1H), 7.08–7.02 (m, 1H), 6.96–6.82 (m, 3H), 6.02 (s, 2H), 5.00 (s, 2H), 3.78 (s, 2H), 3.71 (s, 3H), 3.11 (s, 2H), 2.43 (s, 3H).

EXAMPLE 1(70)

2-(3-(5-methyl-2-(4-isopropylphenyl)oxazol-4-ylmethoxy)phenylmethylthio)acetic acid.methyl ester

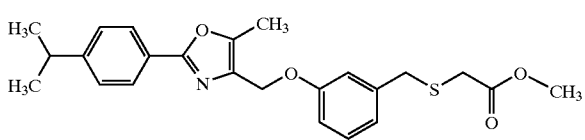

TLC: Rf 0.50 (hexane:ethyl acetate=4:1);

NMR (CDCl$_3$): δ7.93 (dd, J=8.5, 2.0 Hz, 2H), 7.35–7.18 (m, 3H), 7.09–7.03 (m, 1H), 6.96–6.84 (m, 2H), 5.02 (s, 2H), 3.78 (s, 2H), 3.71 (s, 3H), 3.11 (s, 2H), 2.94 (sep., J=7.0 Hz, 1H), 2.43 (s, 3H), 1.27 (d, J=7.0 Hz, 6H).

EXAMPLE 1(71)

2-(3-(2-(4-methyl-2-phenyloxazol-5-yl)ethoxy)phenylmethylthio)acetic acid.methyl ester TLC: Rf 0.37 (hexane:ethyl acetate=3:1);

NMR (CDCl$_3$): δ8.01–7.96 (m, 2H), 7.46–7.39 (m, 3H), 7.22 (t, J=8.2 Hz, 1H), 6.97–6.88 (m, 2H), 6.80 (m, 1H), 4.23 (t, J=6.8 Hz, 2H), 3.78 (s, 2H), 3.71 (s, 3H), 3.16 (t, J=6.8 Hz, 2H), 3.08 (s, 2H), 2.22 (s, 3H).

EXAMPLE 1(72)

2-(3-(2-(5-methyl-2-(3,4-dimethoxyphenyl)oxazol-4-yl)ethoxy)phenylmethylthio)acetic acid.methyl ester

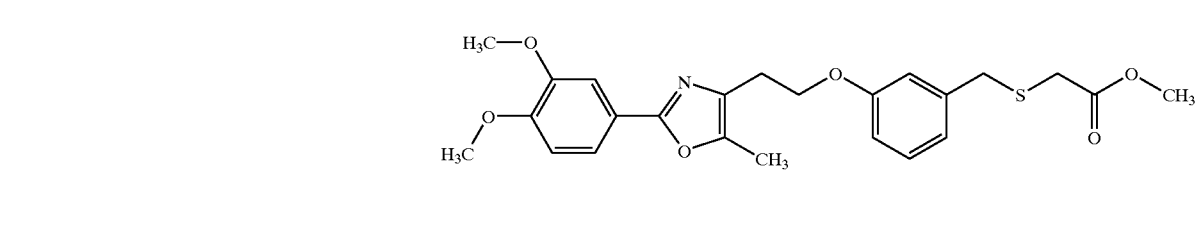

TLC: Rf 0.18 (hexane:ethyl acetate=3:1);

NMR (CDCl$_3$): δ7.56 (dd, J=8.3, 2.0 Hz, 1H), 7.50 (d, J=2.0 Hz, 1H), 7.21 (dd, J=8.1, 8.1 Hz, 1H), 6.91 (d, J=8.3 Hz, 1H), 6.87–6.91 (m, 2H), 6.80 (ddd, J=8.1, 2.5, 1.0 Hz, 1H), 4.24 (t, J=6.7 Hz, 2H), 3.97 (s, 3H), 3.93 (s, 3H), 3.78 (s, 2H), 3.72 (s, 3H), 3.09 (s, 2H), 2.97 (t, J=6.7 Hz, 2H), 2.37 (s, 3H).

EXAMPLE 1(73)

2-(3-(2-(5-methyl-2-(4-trifluoromethoxyphenyl)oxazol-4-yl)ethoxy)phenylmethylthio)acetic acid.methyl ester

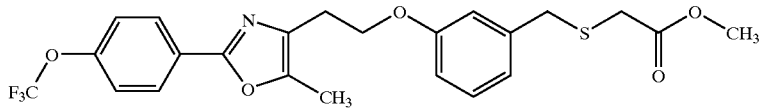

TLC: Rf 0.62 (hexane:ethyl acetate=2:1);

NMR (CDCl$_3$): δ8.00 (d, J=8 Hz, 2H), 7.30–7.15 (m, 3H), 6.95–6.75 (m, 3H), 4.25 (t, J=6.5 Hz, 2H), 3.80 (s, 2H), 3.75 (s, 3H), 3.10 (s, 2H), 3.00 (t, J=6.5 Hz, 2H), 2.40 (s, 3H).

EXAMPLE 1(74)

2-(3-(2-(5-methyl-2-(3,4,5-trimethoxyphenyl)oxazol-4-yl)ethoxy)phenylmethylthio)acetic acid.methyl ester

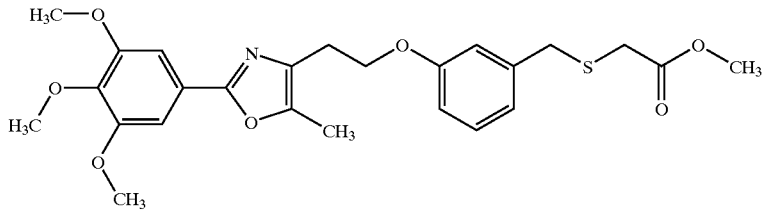

TLC: Rf 0.24 (hexane:ethyl acetate=2:1);

NMR (CDCl$_3$): δ7.25–7.15 (m, 3H), 6.95–6.75 (m, 3H), 4.25 (t, J=7.5 Hz, 2H), 3.95 (s, 6H), 3.90 (s, 3H), 3.80 (s, 2H), 3.70 (s, 3H), 3.10 (s, 2H), 3.00 (t, J=7.5 Hz, 2H), 2.40 (s, 3H).

EXAMPLE 1(75)

2-(3-(2-(5-methyl-2-(4-methylpiperazin-1-yl)oxazol-4-yl)ethoxy)phenylmethylthio)acetic acid.methyl ester

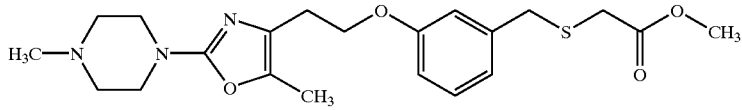

TLC: Rf 0.12 (ethyl acetate);

NMR (CDCl$_3$): δ7.20 (dd, J=8.0, 8.0 Hz, 1H), 6.95–6.75 (m, 3H), 4.20 (t, J=7.0 Hz, 2H), 3.78 (s, 2H), 3.72 (s, 3H), 3.42 (t, J=5.0 Hz, 4H), 3.09 (s, 2H), 2.95 (t, J=7.0 Hz, 2H), 2.50 (t, J=5.0 Hz, 4H), 2.34 (s, 3H), 2.26 (s, 3H).

EXAMPLE 1(76)

2-(3-(2-(5-methyl-2-(4-methylthiophenyl)oxazol-4-yl)ethoxy)phenylmethylthio)acetic acid.methyl ester

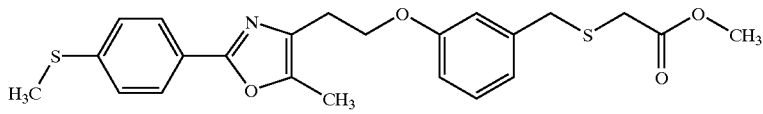

TLC: Rf 0.46 (ethyl acetate:hexane=1:2);

NMR (CDCl₃): δ7.88 (d, J=8.5 Hz, 2H), 7.27 (d, J=8.5 Hz, 2H), 7.21 (dd, J=8.0, 8.0 Hz, 1H), 6.95–6.75 (m, 3H), 4.24 (t, J=6.5 Hz, 2H), 3.78 (s, 2H), 3.71 (s, 3H), 3.08 (s, 2H), 2.97 (t, J=6.5 Hz, 2H), 2.52 (s, 3H), 2.37 (s, 3H).

EXAMPLE 1(77)

2-(3-(2-(5-methyl-2-(pyridin-2-yl)oxazol-4-yl)ethoxy)phenylmethylthio)acetic acid.methyl ester

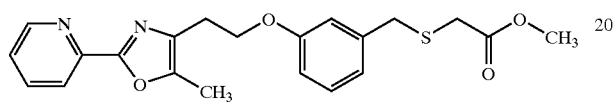

TLC: Rf 0.60 (hexane:ethyl acetate=1:2);

NMR (CDCl₃): δ8.71 (m, 1H), 8.05 (m, 1H), 7.73 (m, 1H), 7.32 (m, 1H), 7.21 (dd, J=8.0, 8.0 Hz, 1H), 6.76–6.92 (m, 3H), 4.27 (t, J=6.6 Hz, 2H), 3.78 (s, 2H), 3.72 (s, 3H), 3.08 (s, 2H), 3.01 (t, J=6.6 Hz, 2H), 2.44 (s, 3H).

EXAMPLE 1(78)

2-(3-(2-(5-methyl-2-(thiophen-2-yl)oxazol-4-yl)ethoxy)phenylmethylthio)acetic acid.methyl ester

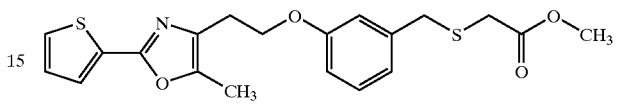

TLC: Rf 0.40 (hexane:ethyl acetate=3:1);

NMR (CDCl₃): δ7.58 (dd, J=3.6, 1.3 Hz, 1H), 7.37 (dd, J=5.0, 1.3 Hz, 1H), 7.21 (dd, J=8.0, 8.0 Hz, 1H), 7.08 (dd, J=5.0, 3.6 Hz, 1H), 6.87–6.91 (m, 2H), 6.79 (m, 1H), 4.22 (t, J=6.6 Hz, 2H), 3.78 (s, 2H), 3.72 (s, 3H), 3.08 (s, 2H), 2.96 (t, J=6.6 Hz, 2H), 2.36 (s, 3H).

EXAMPLE 1(79)

2-(3-(2-(5-methyl-2-(3-nitro-4-methylphenyl)oxazol-4-yl)ethoxy)phenylmethylthio)acetic acid.methyl ester

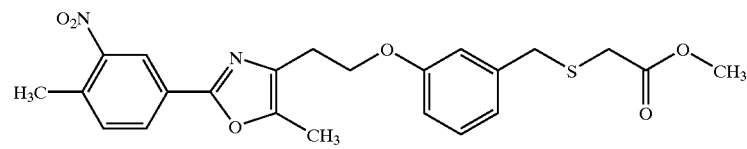

TLC: Rf 0.42 (hexane:ethyl acetate=2:1);

NMR (CDCl₃): δ8.55 (d, J=1 Hz, 1H), 8.10 (dd, J=8, 1 Hz, 1H), 7.40 (d, J=8 Hz, 1H), 7.20 (dd, J=8, 8 Hz, 1H), 6.95–6.80 (m, 3H), 4.25 (t, J=6.5 Hz, 2H), 3.80 (s, 2H), 3.75 (s, 3H), 3.10 (s, 2H), 3.00 (t, J=6.5 Hz, 2H), 2.65 (s, 3H), 2.40 (s, 3H).

EXAMPLE 1(80)

2-(3-(2-(5-methyl-2-(4-dimethylaminophenyl)oxazol-4-yl)ethoxy)phenylmethylthio)acetic acid.methyl ester

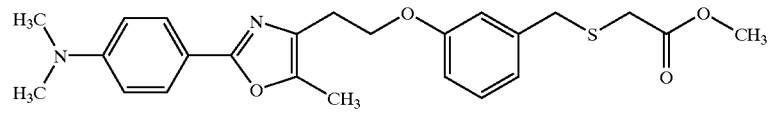

TLC: Rf 0.43 (ethyl acetate:hexane=1:2);

NMR (CDCl₃): δ7.83 (d, J=9.0 Hz, 2H), 7.21 (dd, J=8.0, 8.0 Hz, 1H), 6.95–6.75 (m, 3H), 6.71 (d, J=9.0 Hz, 2H), 4.23 (t, J=7.0 Hz, 2H), 3.78 (s, 2H), 3.71 (s, 3H), 3.08 (s, 2H), 3.01 (s, 6H), 2.96 (t, J=7.0 Hz, 2H), 2.34 (s, 3H).

EXAMPLE 1(81)

2-(3-(2-(5-methyl-2-cyclopentyloxazol-4- yl)ethoxy)phenylmethylthio)acetic acid.methyl ester

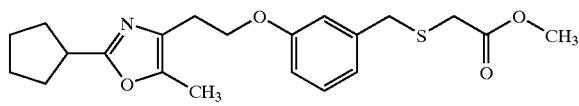

TLC: Rf 0.46 (hexane:ethyl acetate=2:1);

NMR (CDCl$_3$): δ7.20 (m, 1H), 6.95–6.70 (m, 3H), 4.15 (t, J=6.5 Hz, 2H), 3.80 (s, 2H), 3.75 (s, 3H), 3.15 (m, 3H), 2.90 (t, J=6.5 Hz, 2H), 2.25 (s, 3H), 2.20–1.50 (m, 8H).

EXAMPLE 1(82)

2-(3-(2-(5-methyl-2-(4-methylphenyl)oxazol-4-yl)ethoxy)phenyl)acetic acid.methyl ester

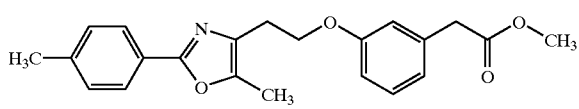

TLC: Rf 0.54 (hexane:ethyl acetate=2:1);

NMR (CDCl$_3$): δ7.86 (d, J=8.0 Hz, 2H), 7.28–7.15 (m, 3H), 6.88–6.76 (m, 3H), 4.23 (t, J=6.6 Hz, 2H), 3.68 (s, 3H), 3.58 (s, 2H), 2.97 (t, J=6.6 Hz, 2H), 2.39 (s, 3H), 2.36 (s, 3H).

EXAMPLE 1(83)

2-(3-(2-(5-methyl-2-(4-ethylphenyl)oxazol-4-yl)ethoxy)phenyl)acetic acid.methyl ester

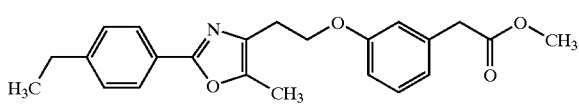

TLC: Rf 0.56 (hexane:ethyl acetate=2:1);

NMR (CDCl$_3$): δ7.90 (d, J=8.0 Hz, 2H), 7.30–7.16 (m, 3H), 6.88–6.76 (m, 3H), 4.23 (t, J=6.6 Hz, 2H), 3.68 (s, 3H), 3.58 (s, 2H), 2.97 (t, J=6.6 Hz, 2H), 2.68 (q, J=7.6 Hz, 2H), 2.37 (s, 3H), 1.26 (t, J=7.6 Hz, 3H).

EXAMPLE 1(84)

2-(3-(2-(5-methyl-2-(4-propylphenyl)oxazol-4-yl)ethoxy)phenyl)acetic acid.methyl ester

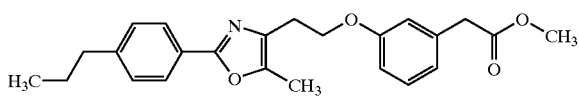

TLC: Rf 0.59 (hexane:ethyl acetate=2:1);

NMR (CDCl$_3$): δ7.88 (d, J=8.4 Hz, 2H), 7.27–7.15 (m, 3H), 6.88–6.76 (m, 3H), 4.23 (t, J=6.6 Hz, 2H), 3.68 (s, 3H), 3.58 (s, 2H), 2.97 (t, J=6.6 Hz, 2H), 2.62 (t, J=7.5 Hz, 2H), 2.36 (s, 3H), 1.66 (m, 2H), 0.94 (t, J=7.5 Hz, 3H).

EXAMPLE 1(85)

2-(3-(2-(5-methyl-2-(4-isopropylphenyl)oxazol-4-yl)ethoxy)phenyl)acetic acid.methyl ester

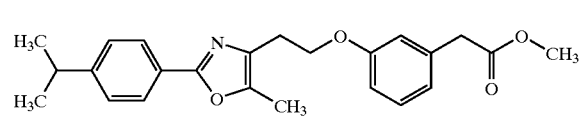

TLC: Rf 0.66 (hexane:ethyl acetate=2:1);

NMR (CDCl$_3$): δ7.89 (d, J=8.4 Hz, 2H), 7.34–7.15 (m, 3H), 6.88–6.75 (m, 3H), 4.23 (t, J=6.8 Hz, 2H), 3.68 (s, 3H), 3.58 (s, 2H), 2.97 (t, J=6.8 Hz, 2H), 3.04–2.86 (m, 1H), 2.36 (s, 3H), 1.28 (s, 3H), 1.25 (s, 3H).

EXAMPLE 1(86)

2-(3-(2-(5-methyl-2-(4-(2-methylpropyl)phenyl)oxazol-4-yl)ethoxy)phenyl)acetic acid.methyl ester

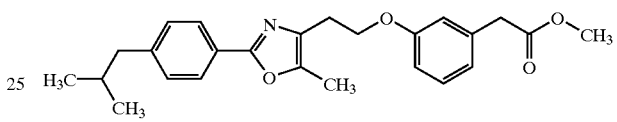

TLC: Rf 0.60 (hexane:ethyl acetate=2:1);

NMR (CDCl$_3$): δ7.88 (d, J=8.2 Hz, 2H), 7.27–7.15 (m, 3H), 6.90–6.76 (m, 3H), 4.23 (t, J=6.6 Hz, 2H), 3.68 (s, 3H), 3.58 (s, 2H), 2.97 (t, J=6.6 Hz, 2H), 2.51 (d, J=5.4 Hz, 2H), 2.36 (s, 3H), 2.00–1.76 (m, 1H), 0.92 (s, 3H), 0.89 (s, 3H).

EXAMPLE 1(87)

2-(3-(2-(5-methyl-2-(4-t-butylphenyl)oxazol-4-yl)ethoxy)phenyl)acetic acid.methyl ester

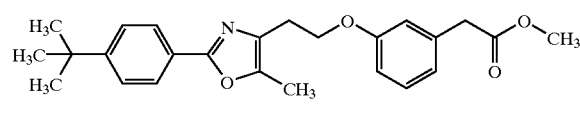

TLC: Rf 0.57 (hexane:ethyl acetate=2:1);

NMR (CDCl$_3$): δ7.90 (d, J=8.6 Hz, 2H), 7.44 (d, J=8.6 Hz, 2H), 7.21 (m, 1H), 6.88–6.76 (m, 3H), 4.23 (t, J=6.6 Hz, 2H), 3.68 (s, 3H), 3.58 (s, 2H), 2.97 (t, J=6.6 Hz, 2H), 2.37 (s, 3H), 1.34 (s, 9H).

EXAMPLE 1(88)

2-(3-(2-(5-methyl-2-cyclopropyloxazol-4-yl)ethoxy)phenylmethylthio)acetic acid.methyl ester

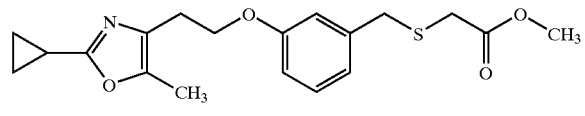

TLC: Rf 0.47 (ethyl acetate:hexane=1:1);

NMR (CDCl$_3$): δ7.20 (dd, J=8.0, 8.0 Hz, 1H), 6.95–6.75 (m, 3H), 4.15 (t, J=7.0 Hz, 2H), 3.79 (s, 2H), 3.72 (s, 3H), 3.09 (s, 2H), 2.84 (t, J=7.0 Hz, 2H), 2.22 (s, 3H), 1.97 (m, 1H), 1.05–0.90 (m, 4H).

EXAMPLE 1(89)

2-(3-(2-(5-methyl-2-(4-(1, 2, 3-thiadiazol-4-yl)phenyl)oxazol-4-yl)ethoxy)phenylmethylthio)acetic acid.methyl ester

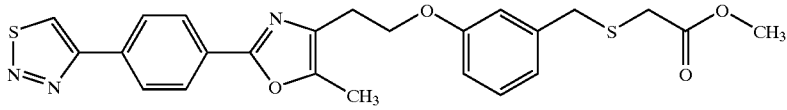

TLC: Rf 0.75 (hexane:ethyl acetate=2 1);

NMR (CDCl$_3$): δ8.72 (s, 1H), 8.13 (s, 4H), 7.22 (t, J=8.0 Hz, 1H), 6.93–6.77 (m, 3H), 4.27 (t, J=6.6 Hz, 2H), 3.78 (s, 2H), 3.71 (s, 3H), 3.09 (s, 2H), 3.00 (t, J=6.6 Hz, 2H), 2.41 (s, 3H).

EXAMPLE 1(90)

2-(3-(2-(5-methyl-2-(4-(4-methyl-1,2,3-thiadiazol-5-yl)phenyl)oxazol-4-yl)ethoxy)phenylmethylthio)acetic acid.methyl ester

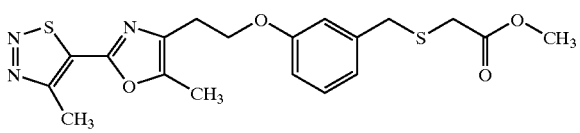

TLC: Rf 0.89 (hexane:ethyl acetate=2:1);

NMR (CDCl$_3$): δ7.21 (t, J=7.4 Hz, 1H), 6.94–6.74 (m, 3H), 4.24 (t, J=6.6 Hz, 2H), 3.78 (s, 2H), 3.72 (s, 3H), 3.09 (s, 2H), 3.02 (s, 3H), 2.99 (t, J=6.6 Hz,, 2H), 2.42 (s, 3H).

EXAMPLE 1(91)

2-(3-(2-(5-methyl-2-(4-methoxyphenyl)oxazol-4-yl)ethoxy)phenyl)acetic acid.methyl ester

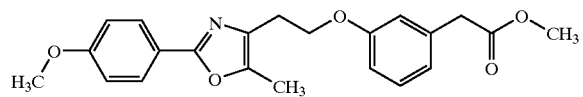

TLC: Rf 0.38 (hexane:ethyl acetate=2:1);

NMR (CDCl$_3$): δ7.91 (d, J=9.0 Hz, 2H), 7.20 (m, 1H), 6.94 (d, J=9.0 Hz, 2H), 6.88–6.77 (m, 3H), 4.23 (t, J=6.6 Hz, 2H), 3.85 (s, 3H), 3.68 (s, 3H), 3.58 (s, 2H), 2.96 (t, J=6.6 Hz, 2H), 2.35 (s, 3H).

EXAMPLE 1(92)

2-(3-(2-(5-methyl-2-(3,4-dimethoxyphenyl)oxazol-4-yl)ethoxy)phenyl)acetic acid.methyl ester

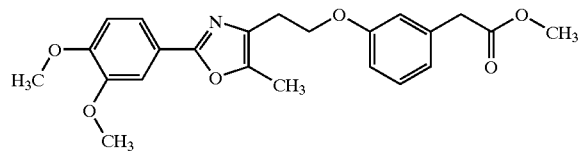

TLC: Rf 0.17 (hexane:ethyl acetate=2:1);

NMR (CDCl$_3$+CD$_3$OD): δ7.56 (dd, J=8.2, 2.0 Hz, 1H), 7.50 (d, J=2.0 Hz, 1H), 7.21 (m, 1H), 6.91 (d, J=8.2 Hz, 1H), 6.89–6.77 (m, 3H), 4.23 (t, J=6.6 Hz, 2H), 3.97 (s, 3H), 3.93 (s, 3H), 3.68 (s, 3H), 3.58 (s, 2H), 2.97 (t, J=6.6 Hz, 2H), 2.37 (s, 3H).

EXAMPLE 1(93)

2-(3-(2-(5-methyl-2-(1,3-dioxaindan-5-yl)oxazol-4-yl)ethoxy)phenyl)acetic acid.methyl ester

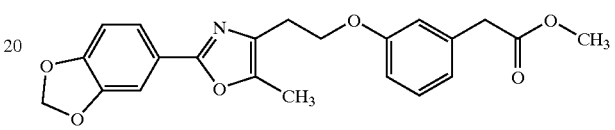

TLC: Rf 0.44 (hexane:ethyl acetate=2:1);

NMR (CDCl$_3$): δ7.52 (dd, J=8.2, 1.8 Hz, 1H), 7.44 (d, J=1.8 Hz, 1H), 7.21 (m, 1H), 6.99–6.76 (m, 4H), 6.01 (s, 2H), 4.22 (t, J=6.6 Hz, 2H), 3.68 (s, 3H), 3.58 (s, 2H), 2.95 (t, J=6.6 Hz, 2H), 2.35 (s, 3H).

EXAMPLE 1(94)

2-(3-(2-(5-methyl-2-(3,4,5-trimethoxyphenyl)oxazol-4-yl)ethoxy)phenyl)acetic acid.methyl ester

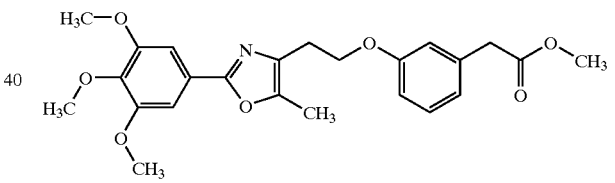

TLC: Rf 0.28 (hexane:ethyl acetate=2:1);

NMR (CDCl$_3$): δ7.28–7.17 (m, 3H), 6.89–6.76 (m, 3H), 4.23 (t, J=6.6 Hz, 2H), 3.94 (s, 6H), 3.89 (s, 3H), 3.68 (s, 3H), 3.58 (s, 2H), 2.97 (t, J=6.6 Hz, 2H), 2.38 (s, 3H).

EXAMPLE 1(95)

2-(3-(2-(5-methyl-2-(4-trifluoromethoxyphenyl)oxazol-4-yl)ethoxy)phenyl)acetic acid.methyl ester

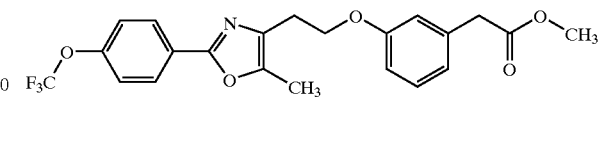

TLC: Rf 0.61 (hexane:ethyl acetate=2:1);

NMR (CDCl$_3$): δ8.01 (d, J=8.6 Hz, 2H), 7.32–7.16 (m, 3H), 6.89–6.76 (m, 3H), 4.23 (t, J=6.6 Hz, 2H), 3.68 (s, 3H), 3.58 (s, 2H), 2.97 (t, J=6.6 Hz, 2H), 2.38 (s, 3H).

EXAMPLE 1(96)

2-(3-(2-(5-methyl-2-(2, 2-difluoro-1,3-dioxaindan-5-yl)oxazol-4-yl)ethoxy)phenyl)acetic acid.methyl ester

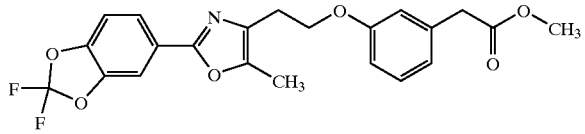

TLC: Rf 0.52 (hexane:ethyl acetate=2:1);
NMR (CDCl₃): δ7.75 (dd, J=8.4, 1.8 Hz, 1H), 7.68 (d, J=1.8 Hz, 1H), 7.21 (m, 1H), 7.10 (d, J=8.4 Hz, 1H), 6.89–6.76 (m, 3H), 4.23 (t, J=6.6 Hz, 2H), 3.68 (s, 3H), 3.58 (s, 2H), 2.96 (t, J=6.6 Hz, 2H), 2.37 (s, 3H).

EXAMPLE 1(97)

2-(3-(2-(5-methyl-2-(4-trifluoromethylthiophenyl)oxazol-4-yl)ethoxy)phenylmethylthio)acetic acid.methyl ester

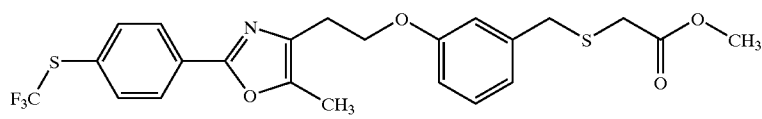

TLC: Rf 0.45 (hexane:ethyl acetate=3:1);
NMR (CDCl₃): δ8.02 (d, J=8.4 Hz, 2H), 7.70 (d, J=8.4 Hz, 2H), 7.21 (t, J=7.8 Hz; 1H), 6.91–6.73 (m, 3H), 4.24 (t, J=6.6 Hz, 2H), 3.78 (s, 2H), 3.71 (s, 3H), 3.08 (s, 2H), 2.98 (t, J=6.6 Hz, 2H), 2.40 (s, 3H).

EXAMPLE 1(98)

2-(3-(2-(5-methyl-2-(4-cyanophenyl)oxazol-4-yl)ethoxy)phenylmethylthio)acetic acid.methyl ester

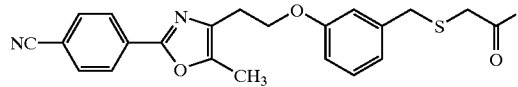

TLC: Rf 0.35 (hexane:ethyl acetate=2:1);
NMR (CDCl₃): δ8.08 (d, J=8.4 Hz, 2H), 7.71 (d, J=8.4 Hz, 2H), 7.21 (m, 1H), 6.75–6.94 (m, 3H), 4.24 (t, J=6.6 Hz, 2H), 3.78 (s, 2H), 3.72 (s, 3H), 3.09 (s, 2H), 2.99 (t, J=6.6 Hz, 2H), 2.41 (s, 3H).

EXAMPLE 1(99)

2-(3-(2-(5-methyl-2-(furan-2-yl)oxazol-4-yl)ethoxy)phenylmethylthio)acetic acid.methyl ester

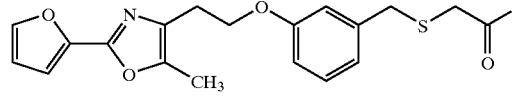

TLC: Rf 0.32 (hexane:ethyl acetate=2:1);
NMR (CDCl₃): δ7.52 (m, 1H), 7.21 (m, 1H), 6.86–6.96 (m, 3H), 6.79 (m, 1H), 6.51 (m, 1H), 4.24 (t, J=6.6 Hz, 2H), 3.78 (s, 2H), 3.72 (s, 3H), 3.08 (s, 2H), 2.97 (t, J=6.6 Hz, 2H), 2.37 (s, 3H).

EXAMPLE 1(100)

2-(3-(5- methyl-2-phenyloxazol-4-ylmethoxy)phenyl)acetic acid.methyl ester

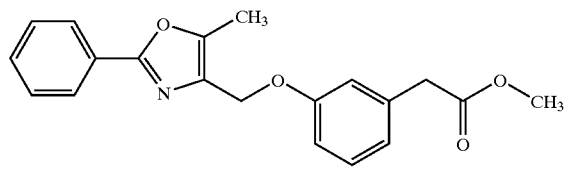

TLC: Rf 0.69 (hexane:ethyl acetate=2:1);
NMR (CDCl₃): δ7.98–8.10 (m, 2H), 7.40–7.54 (m, 3H), 7.26 (m, 1H), 6.86–7.00 (m, 3H), 4.99 (s, 2H), 3.68 (s, 3H), 3.61 (s, 2H), 2.44 (s, 3H).

EXAMPLE 1(101)

2-(3-(2-(5-methyl-2-phenylthiazol-4-yl)ethoxy)phenyl)acetic acid.methyl ester

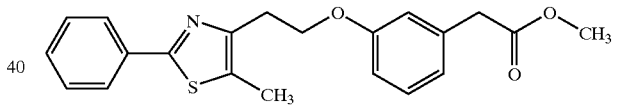

TLC: Rf 0.56 (hexane:ethyl acetate=2:1);
NMR (CDCl₃): δ7.90–7.81 (m, 2H), 7.46–7.35 (m, 3H), 7.25–7.16 (m, 1H), 6.87–6.78 (m, 3H), 4.32 (t, J=6.8 Hz, 2H), 3.68 (s, 3H), 3.58 (s, 2H), 3.19 (t, J=6.8 Hz, 2H), 2.46 (s, 3H).

EXAMPLE 1(102)

2-(3-(3-(5-methyl-2-phenyloxazol-4-yl)propoxy)phenyl)acetic acid.methyl ester

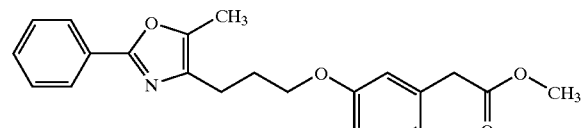

TLC: Rf 0.42 (hexane:ethyl acetate=2:1);
NMR (CDCl₃): δ7.94–8.04 (m, 2H), 7.36–7.50 (m, 3H), 7.22 (m, 1H), 6.76–6.90 (m, 3H), 3.98 (t, J=6.2 Hz, 2H), 3.69 (s, 3H), 3.59 (s, 2H), 2.70 (t, J=7.0 Hz, 2H), 2.28 (s, 3H), 2.15 (m, 2H).

EXAMPLE 1(103)

2-(3-(2-(2-phenyloxazol-4-yl)ethoxy)phenyl)acetic acid.methyl ester

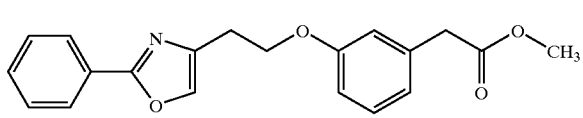

TLC: Rf 0.53 (hexane:ethyl acetate=2:1);

NMR (CDCl$_3$): δ7.96–8.08 (m, 2H), 7.57 (s, 1H), 7.40–7.52 (m, 3H), 7.24 (m, 1H), 6.80–6.92 (m, 3H), 4.28 (t, J=6.6 Hz, 2H), 3.69 (s, 3H), 3.59 (s, 2H), 3.09 (t, J=6.6 Hz, 2H).

EXAMPLE 1(104)

2-(3-(2-(5-methyl-2-(4-cyclohexylphenyl)oxazol-4-yl)ethoxy)phenyl)acetic acid.methyl ester

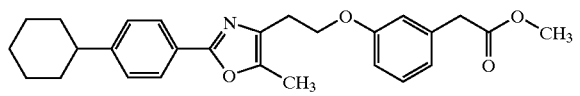

TLC: Rf 0.67 (hexane:ethyl acetate=2:1);

NMR (CDCl$_3$): δ7.88 (d, J=8.4 Hz, 2H), 7.26 (d, J=8.4 Hz, 2H), 7.21 (m, 1H), 6.77–6.86 (m, 3H), 4.23 (t, J=7.0 Hz, 2H), 3.68 (s, 3H), 3.58 (s, 2H), 2.96 (t, J=7.0 Hz, 2H), 2.55 (m, 1H), 2.36 (s, 3H), 1.73–7.87 (m, 4H), 1.30–1.60 (m, 6H).

EXAMPLE 1(105)

2-(3-(2-(5-methyl-2-(3-chloro-4-methylphenyl)oxazol-4-yl)ethoxy)phenyl)acetic acid.methyl ester

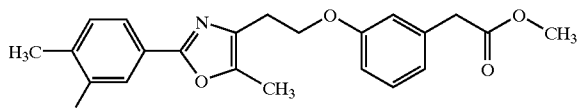

TLC: Rf 0.53 (hexane:ethyl acetate=2:1);

NMR (CDCl$_3$): δ7.96 (d, J=1.8 Hz, 1H), 7.75 (dd, J=8.0, 1.8 Hz, 1H), 7.28 (d, J=8.0 Hz, 1H), 7.22 (m, 1H), 6.78–6.86 (m, 3H), 4.23 (t, J=6.7 Hz, 2H), 3.68 (s, 3H), 3.58 (s, 2H), 2.96 (t, J=6.7 Hz, 2H), 2.40 (s, 3H), 2.37 (s, 3H).

EXAMPLE 1(106)

2-(3-(2-(5-methyl-2-(4-dimethylaminophenyl)oxazol-4-yl)ethoxy)phenyl)acetic acid.methyl ester

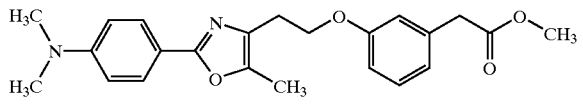

TLC: Rf 0.31 (hexane:ethyl acetate=2:1);

NMR (CDCl$_3$): δ7.84 (d, J=9.0 Hz, 2H), 7.21 (m, 1H), 6.78–6.87 (m, 3H), 6.71 (d, J=9.0 Hz, 2H), 4.23 (t, J=6.8 Hz, 2H), 3.68 (s, 3H), 3.58 (s, 2H), 3.01 (s, 6H), 2.95 (t, J=6.8 Hz, 2H), 2.34 (s, 3H).

EXAMPLE 1(107)

2-(3-(2-(5-ethyl-2-phenyloxazol-4-yl)ethoxy)phenyl)acetic acid.methyl ester

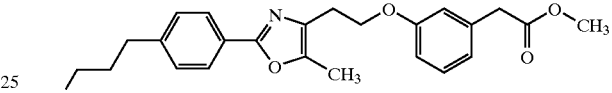

TLC: Rf 0.61 (hexane:ethyl acetate=2:1);

NMR (CDCl$_3$): δ7.94–8.04 (m, 2H), 7.37–7.50 (m, 3H), 7.21 (m, 1H), 6.76–6.89 (m, 3H), 4.23 (t, J=6.6 Hz, 2H), 3.68 (s, 3H), 3.58 (s, 2H), 2.98 (t, J=6.6 Hz, 2H), 2.75 (q, J=7.6 Hz, 2H), 1.31 (t, J=7.6 Hz, 3H).

EXAMPLE 1(108)

2-(3-(2-(5-methyl-2-(4-butylphenyl)oxazol-4-yl)ethoxy)phenyl)acetic acid.methyl ester

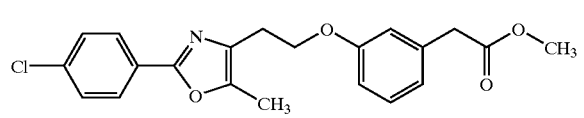

TLC: Rf 0.62 (hexane:ethyl acetate=2:1);

NMR (CDCl$_3$): δ7.88 (d, J=8.6 Hz, 2H), 7.16–7.28 (m, 3H), 6.76–6.90 (m, 3H), 4.23 (t, J=6.8 Hz, 2H), 3.69 (s, 3H), 3.58 (s, 2H), 2.97 (t, J=6.8 Hz, 2H), 2.64 (t, J=7.0 Hz, 2H), 2.36 (s, 3H), 1.62 (m, 2H), 1.34 (m, 2H), ;0.93 (t, J=7.4 Hz, 3H).

EXAMPLE 1(109)

2-(3-(2-(5-methyl-2-(4-chlorophenyl)oxazol-4-yl)ethoxy)phenyl)acetic acid.methyl ester

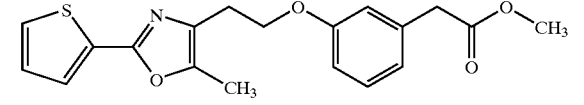

TLC: Rf 0.54 (hexane:ethyl acetate=2:1);

NMR (CDCl$_3$): δ7.91 (d, J=8.6 Hz, 2H), 7.40 (d, J=8.6 Hz, 2H), 7.21 (m, 1H), 6.75–6.89 (m, 3H), 4.23 (t, J=6.6 Hz, 2H), 3.68 (s, 3H), 3.58 (s, 2H), 2.96 (t, J=6.6 Hz, 2H), 2.37 (s, 3H).

EXAMPLE 1(110)

2-(3-(2-(5-methyl-2-(thiophen-2-yl)oxazol-4-yl)ethoxy)phenyl)acetic acid.methyl ester TLC: Rf 0.43 (hexane:ethyl acetate=2:1);

NMR (CDCl$_3$): δ7.58 (dd, J=3.7, 1.2 Hz, 1H), 7.36 (dd, J=5.2, 1.2 Hz, 1H), 7.22 (m, 1H), 7.08 (dd, J=5.2, 3.7 Hz, 1H), 6.77–6.88 (m, 3H), 4.22 (t, J=6.6 Hz, 2H), 3.68 (s, 3H), 3.58 (s, 2H), 2.95 (t, J=6.6 Hz, 2H), 2.35 (s, 3H).

EXAMPLE 1(111)

2-(3-(2-(5-methyl-2-(furan-2-yl)oxazol-4-yl)ethoxy)phenyl)acetic acid.methyl ester

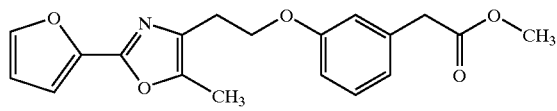

TLC: Rf 0.33 (hexane:ethyl acetate=2:1);

NMR (CDCl$_3$): δ7.51 (m, 1H), 7.21 (m, 1H), 6.92 (d, J=3.4 Hz, 1H), 6.78–6.87 (m, 3H), 6.50 (dd, J=3.4, 1.8 Hz, 1H), 4.23 (t, J=6.6 Hz, 2H), 3.68 (s, 3H), 3.57 (s, 2H), 2.96 (t, J=6.6 Hz, 2H), 2.36 (s, 3H).

EXAMPLE 1(112)

2-(3-(2-(5-methyl-2-(pyridin-2-yl)oxazol-4-yl)ethoxy)phenyl)acetic acid.methyl ester

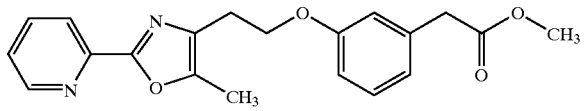

TLC: Rf 0.57 (ethyl acetate);

NMR (CDCl$_3$): δ8.70 (m, 1H), 8.05 (m, 1H), 7.78 (ddd, J=7.8, 7.8, 1.6 Hz, 1H), 7.31 (m, 1H), 7.21 (m, 1H), 6.76–6.86 (m, 3H), 4.25 (t, J=6.6 Hz, 2H), 3.68 (s, 3H), 3.57 (s, 2H), 3.00 (t, J=6.6 Hz, 2H), 2.43 (s, 3H).

EXAMPLE 1(113)

2-(3-(2-(5-methyl-2-(2-methylphenyl)oxazol-4-yl)ethoxy)phenyl)acetic acid.methyl ester

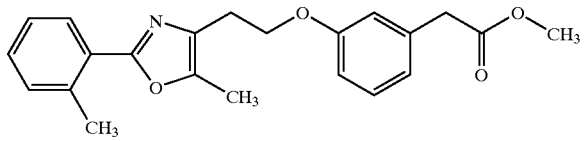

TLC: Rf 0.76 (hexane:ethyl acetate=2:1);

NMR (CDCl$_3$): δ7.91 (m, 1H), 7.19–7.34 (m, 4H), 6.78–6.87 (m, 3H), 4.25 (t, J=6.8 Hz, 2H), 3.68 (s, 3H), 3.58 (s, 2H), 2.98 (t, J=6.8 Hz, 2H), 2.65 (s, 3H), 2.37 (s, 3H).

EXAMPLE 1(114)

2-(3-(2-(5-methyl-2-(3-methylphenyl)oxazol-4-yl)ethoxy)phenyl)acetic acid.methyl ester

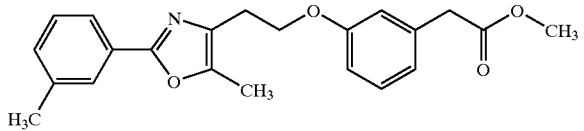

TLC: Rf 0.55 (hexane:ethyl acetate=2:1);

NMR (CDCl$_3$): δ7.75–7.82 (m, 2H), 7.17–7.35 (m, 3H), 6.78–6.86 (m, 3H), 4.24 (t, J=6.6 Hz, 2H), 3.68 (s, 3H), 3.58 (s, 2H), 2.97 (t, J=6.6 Hz, 2H), 2.40 (s, 3H), 2.37 (s, 3H).

EXAMPLE 1(115)

2-(3-(2-(5-methyl-2-(4-trifluoromethylphenyl)oxazol-4-yl)ethoxy)phenyl)acetic acid.methyl ester

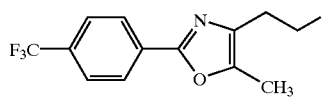

TLC: Rf 0.57 (hexane:ethyl acetate=2:1);

NMR (CDCl$_3$): δ8.09 (d, J=8.4 Hz, 2H), 7.68 (d, J=8.4 Hz, 2H), 7.21 (m, 1H), 6.75–6.90 (m, 3H), 4.24 (t, J=6.6 Hz, 2H), 3.68 (s, 3H), 3.58 (s, 2H), 2.99(t, J=6.6 Hz, 2H), 2.40 (s, 3H).

EXAMPLE 1(116)

2-(3-(2-(5-methyl-2-(4-fluorophenyl)oxazol-4-yl)ethoxy)phenyl)acetic acid.methyl ester

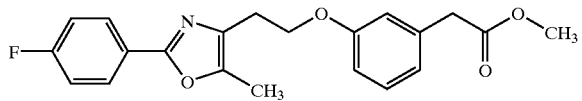

TLC: Rf 0.51 (hexane:ethyl acetate=2:1);

NMR (CDCl$_3$): δ7.91–8.04 (m, 2H), 7.05–7.24 (m, 3H), 6.75–6.92 (m, 3H), 4.23 (t, J=6.6 Hz, 2H), 3.68 (s, 3H), 3.58 (s, 2H), 2.96 (t, J=6.6 Hz, 2H), 2.37 (s, 3H).

EXAMPLE 1(117)

2-(3-(2-(5-methyl-2-(4-cyanophenyl)oxazol-4-yl)ethoxy)phenyl)acetic acid.methyl ester

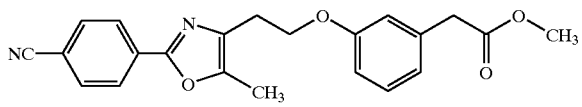

TLC: Rf 0.37 (hexane:ethyl acetate=2:1);

NMR (CDCl$_3$): δ8.07 (d, J=8.8 Hz, 2H), 7.71 (d, J=8.8 Hz, 2H), 7.22 (m, 1H), 6.78–6.87 (m, 3H), 4.24 (t, J=6.6 Hz, 2H), 3.68 (s, 3H), 3.58 (s, 2H), 2.98 (t, J=6.6 Hz, 2H), 2.40 (s, 3H).

EXAMPLE 1(118)

2-(3-(2-(5-methyl-2-(4-methyl-1,2,3-thiadiazol-5-yl)oxazol-4-yl)ethoxy)phenyl)acetic acid.methyl ester

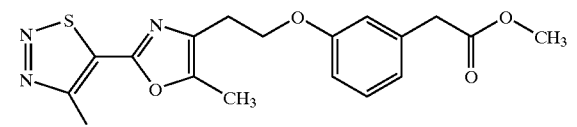

TLC: Rf 0.49 (hexane:ethyl acetate=2:1);

NMR (CDCl$_3$): δ7.22 (m, 1H), 6.78–6.87 (m, 3H), 4.23 (t, J=6.2 Hz, 2H), 3.68 (s, 3H), 3.58 (s, 2H), 3.02 (s, 3H), 2.98 (t, J=6.2 Hz, 2H), 2.41 (s, 3H).

EXAMPLE 1(119)

2-(3-(2-(5-methyl-2-(2,3,5,6-tetrafluoro-4-methylphenyl)oxazol-4-yl)ethoxy)phenyl)acetic acid.methyl ester

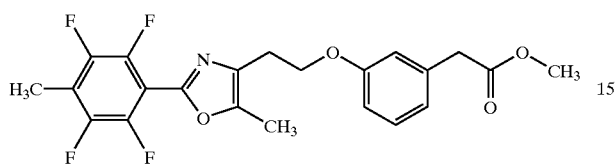

TLC: Rf 0.58 (hexane:ethyl acetate=2:1);

NMR (CDCl$_3$): δ7.20 (m, 1H), 6.75–6.90 (m, 3H), 4.24 (t, J=6.6 Hz, 2H), 3.68 (s, 3H), 3.58 (s, 2H), 3.02 (t, J=6.6 Hz, 2H), 2.41 (s, 3H), 2.33 (s, 3H).

EXAMPLE 1(120)

2-(3-(2-(5-methyl-2-(3-nitro-4-methylphenyl)oxazol-4-yl)ethoxy)phenyl)acetic acid.methyl ester

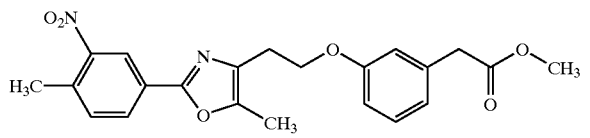

TLC: Rf 0.33 (hexane:ethyl acetate=2:1);

NMR (CDCl$_3$): δ8.55 (d, J=1.6 Hz, 1H), 8.09 (dd, J=8.0, 1.6 Hz, 1H), 7.41 (d, J=8.0 Hz, 1H), 7.19 (m, 1H), 6.70–6.88 (m, 3H), 4.24 (t, J=6.6 Hz, 2H), 3.68 (s, 3H), 3.58 (s, 2H), 2.98 (t, J=6.6 Hz, 2H), 2.64 (s, 3H), 2.40 (s, 3H).

EXAMPLE 1(121)

2-(3-(2-(5-methyl-2-cyclohexyloxazol-4-yl)ethoxy)phenyl)acetic acid.methyl ester

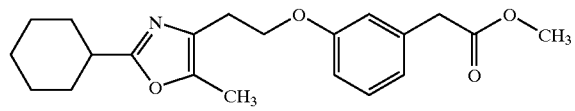

TLC: Rf 0.50 (hexane:ethyl acetate=2:1);

NMR (CDCl$_3$): δ7.21 (m, 1H), 6.76–6.86 (m, 3H), 4.15 (t, J=6.7 Hz, 2H), 3.69 (s, 3H), 3.58 (s, 2H), 2.87 (t, J=6.7 Hz, 2H), 2.69 (m, 1H), 2.24 (s, 3H), 1.96–2.08 (m, 2H), 1.20–1.86 (m, 8H).

EXAMPLE 1(122)

2-(3-(2-(5-methyl-2-cyclopentyloxazol-4-yl)ethoxy)phenyl)acetic acid.methyl ester

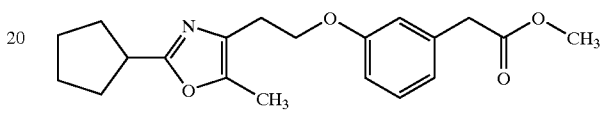

TLC: Rf 0.50 (hexane:ethyl acetate=2:1);

NMR (CDCl$_3$): δ7.21 (m, 1H), 6.76–6.86 (m, 3H), 4.15 (t, J=6.7 Hz, 2H), 3.69 (s, 3H), 3.58 (s, 2H), 3.11 (m, 1H), 2.86 (t, J=6.7 Hz, 2H), 2.24 (s, 3H), 1.58–2.12 (m, 8H).

EXAMPLE 1(123)

2-(3-(2-(5-methyl-2-(4-pentylphenyl)oxazol-4-yl)ethoxy)phenyl)acetic acid.methyl ester

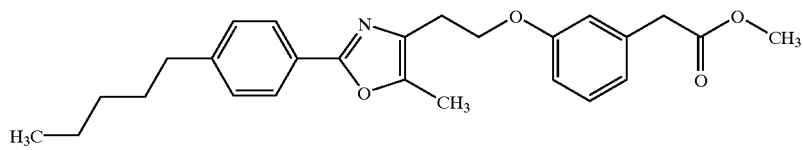

TLC: Rf 0.55 (hexane:ethyl acetate=2:1);

NMR (CDCl$_3$): δ7.88 (d, J=8.0 Hz, 2H), 7.29 (d, J=8.0 Hz, 2H), 7.17 (m, 1H), 6.70–6.88 (m, 3H), 4.23 (t, J=6.8 Hz, 2H), 3.68 (s, 3H), 3.57 (s, 2H), 2.96 (t, J=6.8 Hz, 2H), 2.63 (t, J=7.6 Hz, 2H), 2.36 (s, 3H), 1.64 (m, 2H), 1.20–1.42 (m, 4H), 0.89 (t, J=6.6 Hz, 3H).

EXAMPLE 1(124)

2-(3-(2-(5-methyl-2-(pyridin-4-yl)oxazol-4-yl)ethoxy)phenylmethylthio)acetic acid.methyl ester

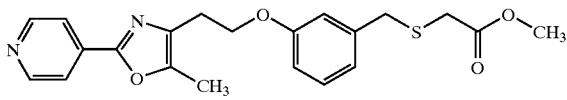

TLC: Rf 0.22.(hexane:ethyl acetate=1:1);

NMR (CDCl$_3$): δ8.90 (d, J=6 Hz, 2H), 7.85 (d, J=6 Hz, 2H), 7.20 (dd, J=8, 8 Hz, 1H), 6.95–6.80 (m, 3H), 4.25 (t, J=6.5 Hz, 2H), 3.80 (s, 2H), 3.75 (s, 3H), 3.10 (s, 2H), 3.00 (t, J=6.5 Hz, 2H), 2.45 (s, 3H).

EXAMPLE 1(125)

2-(3-(2-(5-methyl-2-(pyridin-3-yl)oxazol-4-yl)ethoxy)phenyl)acetic acid.methyl ester

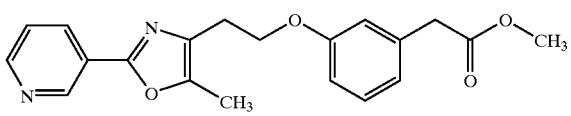

TLC: Rf 0.33 (hexane:ethyl acetate=1:3);

NMR (CDCl$_3$): δ9.22–9.18 (m, 1H), 8.61 (dd, J=5.0 Hz, 1.8 Hz, 1H), 8.25–8.19 (m, 1H), 7.37–7.16 (m, 2H), 6.85–6.76 (m, 3H), 4.23 (t, J=6.6 Hz, 2H), 3.66 (s, 3H), 3.56 (s, 2H), 2.96 (t, J=6.6 Hz, 2H), 2.38 (s, 3H).

EXAMPLE 1(126)

2-(3-(2-(5-methyl-2-(pyridin-4-yl)oxazol-4-yl)ethoxy)phenyl)acetic acid.methyl ester

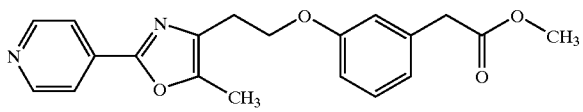

Rf 0.25 (hexane:ethyl acetate=1:3);

NMR (CDCl$_3$): δ8.71–8.67 (m, 2H), 7.83–7.80 (m, 2H), 7.26–7.17 (m, 1H), 6.86–6.79 (m, 3H), 4.24 (t, J=6.4 Hz, 2H), 3.68 (s, 3H), 3.58 (s, 2H), 2.99 (t, J=6.4 Hz, 2H), 2.40 (s, 3H).

EXAMPLE 1(127)

2-(3-(2-(5-methyl-2-(4-methylpiperazin-1-yl)thiazol-4-yl)ethoxy)phenyl)acetic acid.methyl ester

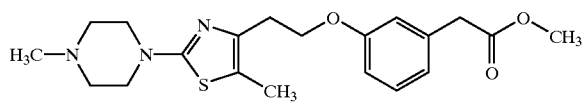

TLC: Rf 0.39 (chloroform:methanol=20:1);

NMR (CDCl$_3$): δ7.21 (m, 1H), 6.77–6.85 (m, 3H), 4.19 (t, J=7.1 Hz, 2H), 3.68 (s, 3H), 3.58 (s, 2H), 3.42 (m, 4H), 2.94 (t, J=7.1 Hz, 2H), 2.50 (m, 4H), 2.33 (s, 3H), 2.25 (s, 3H).

EXAMPLE 1(128)

2-(3-(2-(5-methyl-2-phenyloxazol-4-yl)ethoxy)phenylmethoxy)acetic acid.t-butyl ester

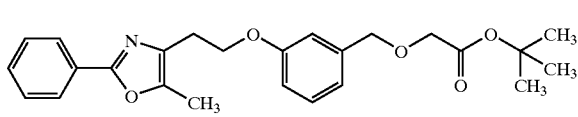

TLC: Rf 0.79 (ethyl acetate:hexane=1:1);

NMR (CDCl$_3$): δ7.98 (m, 2H), 7.50–7.35 (m, 3H), 7.24 (dd, J=8.0, 8.0 Hz, 1H), 6.95–6.80 (m, 3H), 4.58 (s, 2H), 4.25 (t, J=6.5 Hz, 2H), 3.96 (s, 2H), 2.98 (t, J=6.5 Hz, 2H), 2.38 (s, 3H), 1.47 (s, 9H).

EXAMPLE 1(129)

2-(3-(2-(5-methyl-2-(pyridin-3-yl)oxazol-4-yl)ethoxy)phenylmethylthio)acetic acid.methyl ester

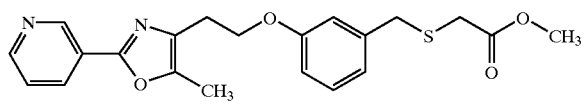

TLC: Rf 0.14 (hexane:ethyl acetate=1:2);

NMR (CDCl$_3$): δ9.20 (d, J=2 Hz, 1H), 8.65 (dd, J=5, 2 Hz, 1H), 8.25 (m, 1H), 7.35 (m, 1H), 7.20 (dd, J=8, 8 Hz, 1H), 6.95–6.75 (m, 3H), 4.25 (t, J=6.5 Hz, 2H), 3.80 (s, 2H), 3.75 (s, 3H), 3.10 (s, 2H), 3.00 (t, J=6.5 Hz, 2H), 2.40 (s, 3H).

EXAMPLE 1(130)

2-(3-(2-(5-methyl-2-(4-methylthiophenyl)oxazol-4-yl)ethoxy)phenyl)acetic acid.methyl ester

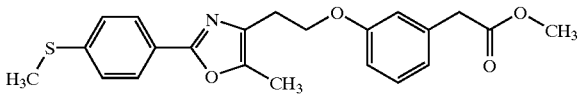

TLC: Rf 0.39 (hexane:ethyl acetate=2:1);

NMR (CDCl$_3$): δ7.88 (d, J=8.6 Hz, 2H), 7.27 (d, J=8.6 Hz, 2H), 7.17 (dd, J=7.8, 7.6 Hz, 1H), 6.70–6.88 (m, 3H), 4.22 (t, J=6.6 Hz, 2H), 3.68 (s, 3H), 3.58 (s, 2H), 2.96 (t, J=6.6 Hz, 2H), 2.51 (s, 3H), 2.37 (s, 3H).

EXAMPLE 1(131)

2-(3-(2-(5-methyl-2-cyclopropyloxazol-4-yl)ethoxy)phenyl)acetic acid.methyl ester

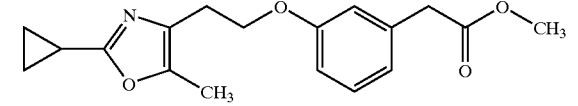

TLC: Rf 0.39 (hexane:ethyl acetate=1:1);

NMR (CDCl$_3$): δ7.26–7.16 (m, 1H), 6.85–6.76 (m, 3H), 4.14 (t, J=6.8 Hz, 2H), 3.68 (s, 3H), 3.57 (s, 2H), 2.83 (t, J=6.8 Hz, 2H), 2.21 (s, 3H), 2.04–1.90 (m, 1H), 1.01–0.89 (m, 4H).

EXAMPLE 1(132)

2-(3-(2-(5-methyl-2-(4-nitrophenyl)oxazol-4-yl)ethoxy)phenyl)acetic acid.methyl ester

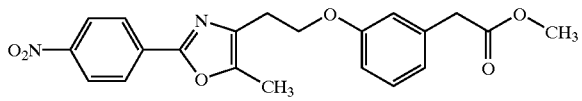

TLC: Rf 0.57 (hexane:ethyl acetate=4:3);

NMR (CDCl$_3$): δ8.29 (d, J=9.0 Hz, 2H), 8.13 (d, J=9.0 Hz, 2H), 7.22 (m, 1H), 6.77–6.87 (m, 3H), 4.25 (t, J=6.6 Hz, 2H), 3.86 (s, 3H), 3.58 (s, 2H), 3.00 (t, J=6.6 Hz, 2H), 2.42 (s, 3H).

EXAMPLE 1(133)

2-(3-(2-(5-methyl-2-(quinolin-2-yl)oxazol-4-yl)ethoxy)phenyl)acetic acid.methyl ester

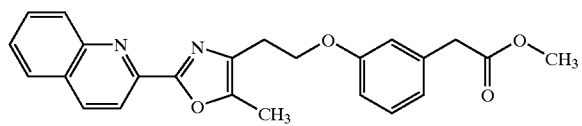

TLC: Rf 0.38 (hexane:ethyl acetate=4:3);

NMR (CDCl$_3$): δ8.17–8.29 (m, 3H), 7.83 (m, 1H), 7.75 (m, 1H), 7.57 (m, 1H), 7.22 (m, 1H), 6.78–6.86 (m, 3H), 4.29 (t, J=6.6 Hz, 2H), 3.68 (s, 3H), 3.58 (s, 2H), 3.05 (t, J=6.6 Hz, 2H), 2.49 (s, 3H).

EXAMPLE 1(134)

2-(3-(2-(5-methyl-2-(3-trifluoromethoxyphenyl)oxazol-4-yl)ethoxy)phenyl)acetic acid.methyl ester

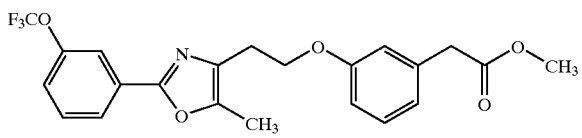

TLC: Rf 0.46 (hexane:ethyl acetate=2:1);

NMR (CDCl$_3$): δ7.91 (dt, J=7.8, 1.2 Hz, 1H), 7.85–7.82 (m, 1H), 7.45 (t, J=7.8 Hz, 1H), 7.28–7.17 (m, 2H), 6.88–6.77 (m, 3H), 4.24 (t, J=6.6 Hz, 2H), 3.68 (s, 3H), 3.58 (s, 2H), 2.97 (t, J=6.6 Hz, 2H), 2.39 (s, 3H).

EXAMPLE 1(135)

2-(3-(2-(5-methyl-2-(2-trifluoromethoxyphenyl)oxazol-4-yl)ethoxy)phenyl)acetic acid.methyl ester

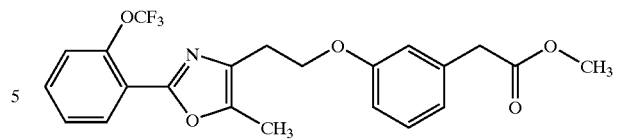

TLC: Rf 0.43 (hexane:ethyl acetate=2:1);

NMR (CDCl$_3$): δ8.11–8.04 (m, 1H), 7.49–7.31 (m, 3H), 7.27–7.16 (m, 1H), 6.88–6.76 (m, 3H), 4.25 (t, J=6.6 Hz, 2H), 3.68 (s, 3H), 3.58 (s, 2H), 2.99 (t, J=6.6 Hz, 2H), 2.39 (s, 3H).

EXAMPLE 1(136)

2-(3-(2-(4-methyl-2-phenyloxazol-5-yl)ethoxy)phenyl)acetic acid.methyl ester

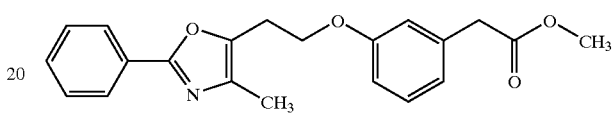

TLC: Rf 0.37 (hexane:ethyl acetate=2:1);

NMR (CDCl$_3$): δ8.02–7.95 (m, 2H), 7.49–7.38 (m, 3H), 7.28–7.18 (m, 1H), 6.90–6.77 (m, 3H), 4.22 (t, J=6.8 Hz, 2H), 3.68 (s, 3H), 3.58 (s, 2H), 3.16 (t, J=6.8 Hz, 2H), 2.22 (s, 3H).

EXAMPLE 1(137)

2-(3-(2-(5-methyl-2-(1,3-dioxaindan-5-yl)oxazol-4-yl)ethoxy)phenylmethoxy)acetic acid.t-butyl ester

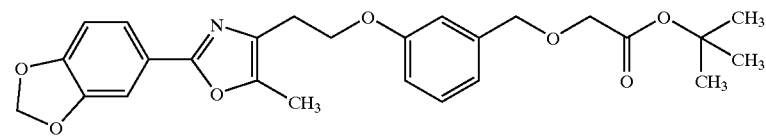

TLC: Rf 0.83 (hexane:ethyl acetate=1:1);

NMR (CDCl$_3$): δ7.51 (dd, J=8.0, 1.8 Hz, 1H), 7.43 (d, J=1.8 Hz, 1H), 7.24 (t, J=7.8 Hz, 1H), 6.97–6.79 (m, 4H), 6.01 (s, 2H), 4.58 (s, 2H), 4.23 (t, J=6.8 Hz, 2H), 3.96 (s, 2H), 2.95 (t, J=6.8 Hz, 2H), 2.35 (s, 3H), 1.48 (s, 9H).

EXAMPLE 2

2-(3-(4-(4-methylphenyl)thiazol-2-ylmethoxy)phenylmethylthio)acetic acid

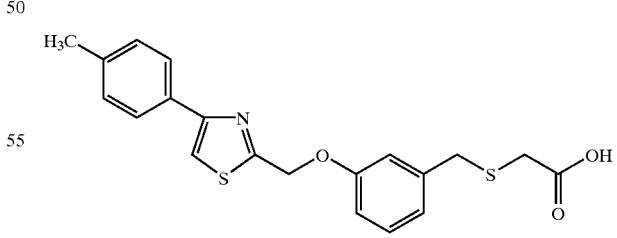

The compound prepared in Example 1 (0.51 g) was dissolved in a mixture of methanol-tetrahydrofuran (8 ml, 1:1), and thereto was added 2N aqueous solution of sodium hydroxide (3.2 ml) and the mixture was stirred at room temperature for 3 hours. The reaction mixture was acidified by adding hydrochloric acid and the solution was extracted with ethyl acetate. The extract was washed with water and a saturated aqueous solution of sodium chloride, successively, dried over anhydrous magnesium sulfate and concentrated. The residue was recrystallized from hexane-ethyl acetate to give the compound of the present invention (0.39 g) having the following physical data.

TLC: Rf 0.37 (ethyl acetate);

NMR (CDCl$_3$+4 drop of CD$_3$OD): δ7.77 (2H, d, J=8.0 Hz), 7.45 (1H, s), 7.23–7.31 (3H, m), 6.91–7.05 (3H, m), 5.42 (2H, s), 3.83 (2H, s), 3.08 (2H, s), 2.39 (3H, s).

EXAMPLE 2(1)~EXAMPLE 2(137)

The following compounds of the present invention were obtained by the same procedure as shown in Example 2, using the compounds prepared in Example 1(1)~Example 1(137) in place of the compound prepared in Example 1, optionally followed by converting them to the corresponding salts by known methods.

EXAMPLE 2(1)

6-(3-(4-(4-methylphenyl)thiazol-2-ylmethoxy)phenyl)hexanoic acid

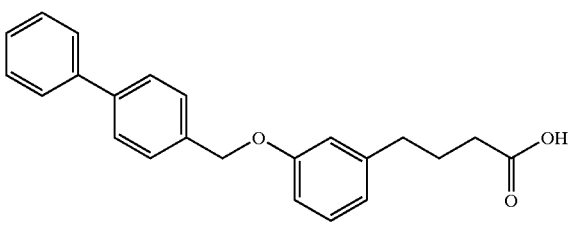

TLC: Rf 0.41 (hexane:ethyl acetate=1:1);

NMR (CDCl$_3$): δ7.78 (2H, d, J=8.0 Hz), 7.43 (1H, s), 7.28–7.16 (3H, m), 6.90–6.78 (3H, m), 5.42 (2H, s), 2.60 (2H, t, J=7.5 Hz), 2.39 (3H, s), 2.34 (2H, t, J=7.5 Hz), 1.76–1.54 (4H, m), 1.46–1.24 (2H, m).

EXAMPLE 2(2)

5-(3-(biphenyl-4-ylmethoxy)phenyl)pentanoic acid

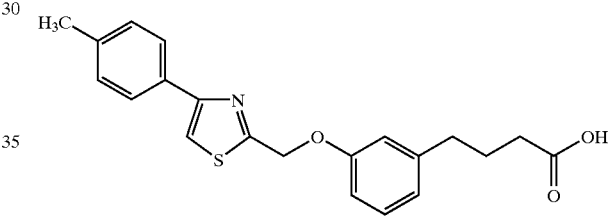

TLC: Rf 0.49 (ethyl acetate);

NMR (CDCl$_3$): δ7.58–7.64 (4H, m), 7.35–7.53 (5H, m), 7.21 (1H, m), 6.78–6.84 (3H, m), 5.09 (2H, s), 2.62 (2H, t, J=7.0 Hz), 2.38 (2H, t, J=7.0 Hz), 1.64–1.72 (4H, m).

EXAMPLE 2(3)

4-(3-(biphenyl-4-ylmethoxy)phenyl)butanoic acid

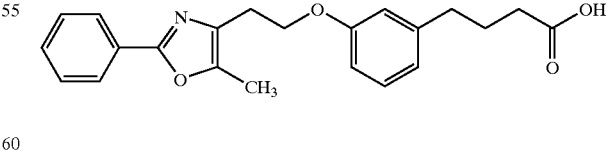

TLC: Rf 0.67 (ethyl acetate);

NMR (d$_6$-DMSO): δ7.62–7.66 (4H, m), 7.31–7.51 (5H, m), 7.14 (1H, dd, J=7.5, 7.5 Hz), 6.71–6.82 (3H, m), 5.07 (2H, s), 2.52 (2H, t, J=7.0 Hz), 2.06 (2H, t, J=7.0 Hz), 1.74 (2H, tt, J=7.0, 7.0 Hz).

EXAMPLE 2(4)

4-(3-(4-(4-methylphenyl)thiazol-2-ylmethoxy)phenyl)butanoic acid

TLC: Rf 0.63 (ethyl acetate);

NMR (CDCl$_3$): δ7.78 (2H, d, J=8.0 Hz), 7.43 (1H, s), 7.23 (2H, d, J=8.0 Hz), 7.22 (1H, m), 6.81–6.88 (3H, m), 5.41 (2H, s), 2.66 (2H, t, J=7.5 Hz), 2.38 (3H, s), 2.36 (2H, t, J=7.5 Hz), 1.96 (2H, tt, J=7.5, 7.5 Hz).

EXAMPLE 2(5)

4-(3-(2-(5-methyl-2-phenyloxazol-4-yl)ethoxy)phenyl)butanoic acid

TLC: Rf 0.47 (ethyl acetate);

NMR (CDCl$_3$): δ7.94–8.02 (2H, m), 7.39–7.48 (3H, m), 7.18 (1H, m), 6.72–6.78 (3H, m), 4.23 (2H, t, J=6.6 Hz), 2.98 (2H, t, J=6.6 Hz), 2.64 (2H, t, J=7.2 Hz), 2.38 (3H, s), 2.35 (2H, t, J=7.2 Hz), 1.95 (2H, tt, J=7.2, 7.2 Hz.).

EXAMPLE 2(6)

6-(3-(2-(5-methyl-2-phenyloxazol-4-yl)ethoxy)phenyl)hexanoic acid

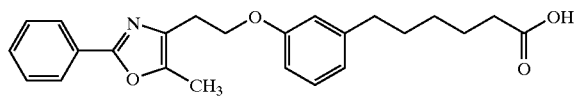

TLC: Rf 0.41 (chloroform:methanol=15:1);

NMR (CDCl₃): δ8.02–7.91 (2H, m), 7.49–7.36 (3H, m), 7.16 (1H, t, J=8.0 Hz), 6.78–6.69 (3H, m), 4.24 (2H, t, J=7.0 Hz), 2.98 (2H, t, J=7.0 Hz), 2.58 (2H, t, J=7.5 Hz), 2.38 (3H, s), 2.34 (2H, t, J=7.5 Hz), 1.75–1.54 (4H, m), 1.45–1.25 (2H, m).

EXAMPLE 2(7)

5-(3-(2-(5-methyl-2-phenyloxazol-4-yl)ethoxy)phenyl)pentanoic acid

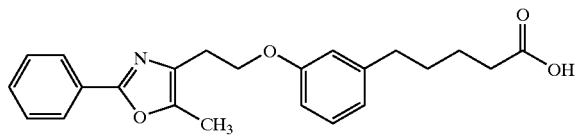

TLC: Rf 0.36 (chloroform:methanol=15:1);

NMR (CDCl₃): δ8.04–7.92 (2H, m), 7.49–7.36 (3H, m), 7.17 (1H, t, J=8.0 Hz), 6.78–6.68 (3H, m), 4.24 (2H, t, J=7.0 Hz), 2.98 (2H, t, J=7.0 Hz), 2.68–2.53 (2H, m), 2.45–2.30 (5H, m), 1.79–1.56 (4H, m).

EXAMPLE 2(8)

2-(3-(3-(biphenyl-4-ylmethoxy)phenyl)propylthio)acetic acid

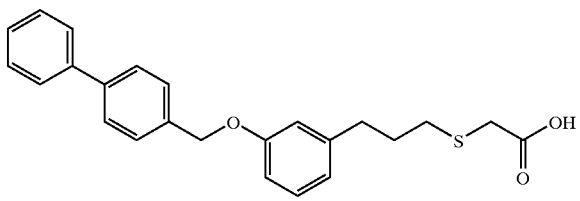

TLC: Rf 0.38 (chloroform:methanol=10:1);

NMR (CDCl₃): δ7.35–7.64 (9H, m), 7.22 (1H, m), 6.78–6.86 (3H, m), 5.09 (2H, s), 3.25 (2H, s), 2.70 (2H, t, J=7.5 Hz), 2.67 (2H, t, J=7.5 Hz), 1.94 (2H, tt, J=7.5, 7.5 Hz).

EXAMPLE 2(9)

2-(3-(3-(4-(4-methylphenyl)thiazol-2-ylmethoxy)phenyl)propylthio)acetic acid

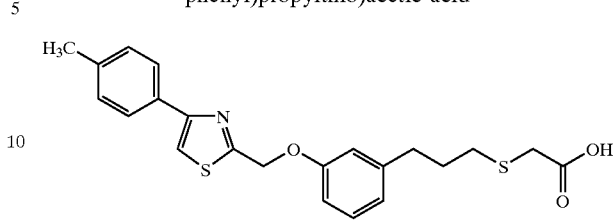

TLC: Rf 0.41 (chloroform:methanol=10:1);

NMR (CDCl₃): δ7.75 (2H, d, J=8.0 Hz), 7.43 (1H, s), 7.18–7.26 (3H, m), 6.80–6.91 (3H, m), 5.44 (2H, s), 3.23 (2H, s), 2.71 (2H, t, J=7.4 Hz), 2.65 (2H, t, J=7.4 Hz), 2.38 (3H, s), 1.93 (2H, tt, J=7.4, 7.4 Hz).

EXAMPLE 2(10)

6-(2-(2-(5-methyl-2-phenyloxazol-4-yl)ethoxy)phenyl)hexanoic acid

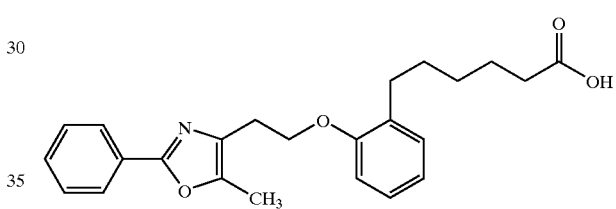

TLC: Rf 0.50 (chloroform:methanol=10:1);

NMR (CDCl₃): δ7.95–8.00 (2H, m), 7.39–7.44 (3H, m), 7.07–7.17 (2H, m), 6.81–6.88 (2H, m), 4.23 (2H, t, J=6.7 Hz), 3.00 (2H, t, J=6.7 Hz), 2.57 (2H, t, J=7.3 Hz), 2.37 (3H, s), 2.30 (2H, t, J=7.4 Hz), 1.46–1.69 (4H, m), 1.22–1.40 (2H, m).

EXAMPLE 2(11)

2-(3-(biphenyl-4-ylmethoxy)phenylmethylthio)acetic acid

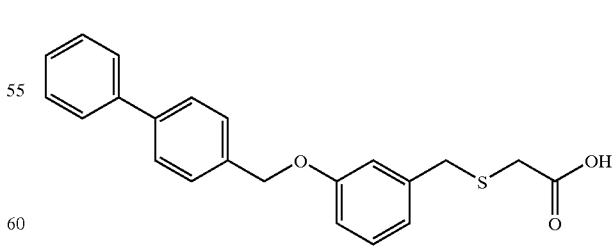

TLC: Rf 0.39 (ethyl acetate);

NMR (CDCl₃): δ7.60–7.64 (4H, m), 7.22–7.53 (6H, m), 6.89–7.02 (3H, m), 5.11 (2H, s), 3.83 (2H, s), 3.10 (2H, s).

EXAMPLE 2(12)

2-(3-(2-(5-methyl-2-phenyloxazol-4-yl)ethoxy)phenylmethylthio)acetic acid

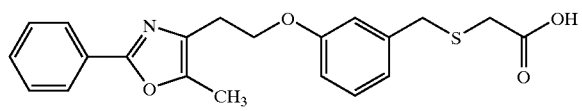

TLC: Rf 0.33 (ethyl acetate);

NMR (CDCl₃): δ7.95–8.00 (2H, m), 7.40–7.47 (3H, m), 7.21 (1H, dd, J=8.0, 8.0 Hz), 7.03 (1H, dd, J=2.0, 1.0 Hz), 6.88 (1H, ddd, J=8.0, 3.0, 2.0 Hz), 6.81 (1H, ddd, J=8.0, 3.0, 1.0 Hz), 4.28 (2H, t, J=7.5 Hz), 3.86 (2H, s), 3.16 (2H, s), 2.98 (2H, t, J=7.5 Hz), 2.39 (3H, s).

EXAMPLE 2(13)

5-(2-(2-(5-methyl-2-phenyloxazol-4-yl)ethoxy)phenyl)pentanoic acid

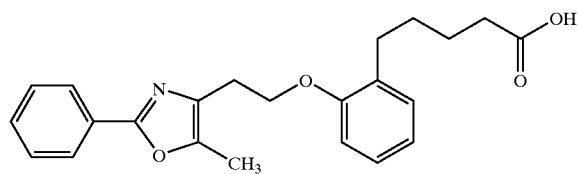

TLC: Rf 0.5,8 (chloroform:methanol=9:1);

NMR (CDCl₃): δ8.00–7.95 (2H, m), 7.50–7.35 (3H, m), 7.20–7.05 (2H, m), 6.90–6.80 (2H, m), 4.25 (2H, t, J=7 Hz), 3.05 (2H, t, J=7 Hz), 2.60 (2H, t, J=7 Hz), 2.40 (3H, s), 2.35 (2H, t, J=6 Hz), 1.80–1.50 (4H, m).

EXAMPLE 2(14)

6-(2-(4-(4-methylphenyl)thiazol-2-ylmethoxy)phenyl)hexanoic acid

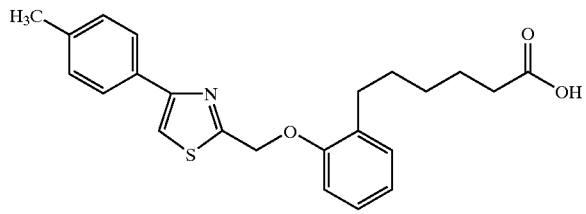

TLC: Rf 0.76 (ethyl acetate);

NMR (CDCl₃): δ7.79 (2H, d, J=8.4 Hz), 7.44 (1H, s), 7.15–7.26 (4H, m), 6.91–6.98 (2H, m), 5.41 (2H, s), 2.73 (2H, t, J=7.4 Hz), 2.38 (3H, s), 2.36 (2H, t, J=7.3 Hz), 1.62–1.78 (4H, m), 1.37–1.52 (2H, m).

EXAMPLE 2(15)

2-(3-(3-(2-(5-methyl-2-phenyloxazol-4-yl)ethoxy)phenyl)propylthio)acetic acid

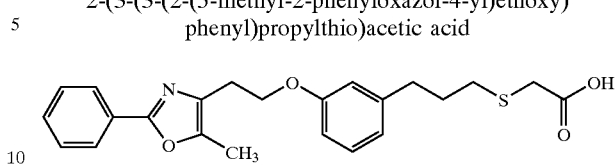

TLC: Rf 0.42 (chloroform:methanol=10:1);

NMR (CDCl₃): δ7.94–7.98 (m, 2H), 7.41–7.44 (m, 3H), 7.16 (dd, J=7.7, 7.7 Hz, 1H), 6.89 (m, 1H), 6.72–6.76 (m, 2H), 4.29 (t, J=7.2 Hz, 2H), 3.23 (s, 2H), 3.01 (t, J=7.2 Hz, 2H), 2.72 (t, J=6.7 Hz, 2H), 2.66 (t, J=6.7 Hz, 2H), 2.40 (s, 3H), 1.94 (tt, J=6.7, 6.7 Hz, 2H).

EXAMPLE 2(16)

2-(3-(2-(biphenyl-4-yl)ethoxy)phenylmethylthio)acetic acid

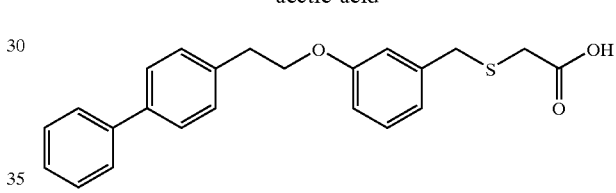

TLC: Rf 0.43 (chloroform:methanol=10:1);

NMR (CDCl₃): δ7.52–7.61 (m, 4H), 7.34–7.47 (m, 5H), 7.23 (dd, J=8.0, 8.0 Hz, 1H), 6.80–6.92 (m, 3H), 4.21 (t, J=6.8 Hz, 2H), 3.81 (s, 2H), 3.14 (t, J=6.8 Hz, 2H), 3.11 (s, 2H).

EXAMPLE 2(17)

2-(4-chloro-3-(2-(5-methyl-2-phenyloxazol-4-yl)ethoxy)phenylmethylthio)acetic acid

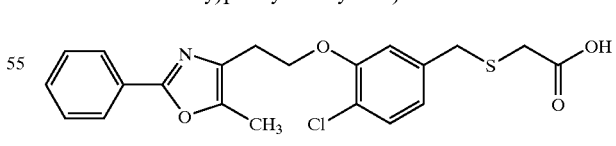

TLC: Rf 0.38 (water:methanol:chloroform=1:10:100);

NMR (CDCl₃): δ7.99 (m, 2H), 7.50–7.40 (m. 3H), 7.28 (d, J=8.0 Hz, 1H), 7.15 (d, J=2.0 Hz, 1H), 6.82 (dd, J=8.0, 2.0 Hz, 1H), 6.30 (br., 1H), 4.38 (t, J=6.5 Hz, 2H), 3.85 (s, 2H), 3.18 (s, 2H), 3.03 (t, J=6.5 Hz, 2H), 2.42 (s, 3H).

EXAMPLE 2(18)

2-(4-chloro-3-(4-(4-methylphenyl)thiazol-2-ylmethoxy)phenylmethylthio)acetic acid

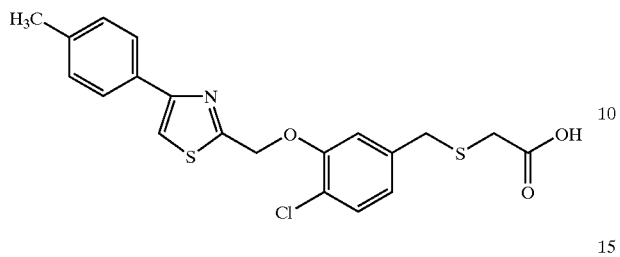

TLC: Rf 0.42 (water:methanol:chloroform=1:10:100);

NMR (CDCl$_3$): δ7.73 (d, J=8.0 Hz, 2H), 7.44 (s. 1H), 7.33 (d, J=8.0 Hz, 1H), 7.22 (d, J=8.0 Hz, 2H), 7.11 (d, J=2.0 Hz, 1H), 6.91 (dd, J=8.0, 2.0 Hz, 1H), 5.50 (s, 2H), 3.80 (s, 2H), 3.04 (s, 2H), 2.37 (s, 3H).

EXAMPLE 2(19)

2-(3-(biphenyl-4-ylmethoxy)-4-chlorophenylmethylthio)acetic acid

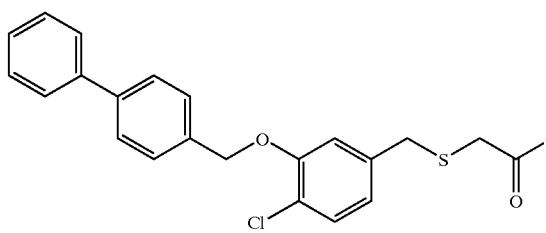

TLC: Rf 0.34 (water:methanol:chloroform=1:10:100);

NMR (CDCl$_3$): δ7.65–7.35 (m, 9H), 7.33 (d, J=8.0 Hz, 1H), 7.01 (d, J=2.0 Hz, 1H), 6.87 (dd, J=8.0, 2.0 Hz, 1H), 5.20 (s, 2H), 3.79 (s, 2H), 3.02 (s, 2H).

EXAMPLE 2(20)

2-(3-((2E)-3-(biphenyl-4-yl)propenyloxy)phenylmethylthio)acetic acid

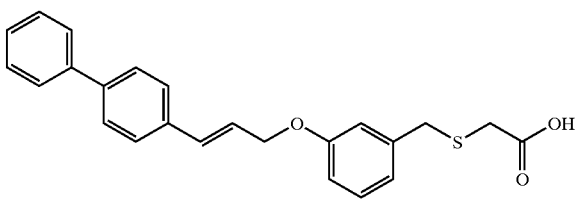

TLC: Rf 0.29 (chloroform:methanol=10:1);

NMR (CDCl$_3$): δ7.22–7.62 (m, 10H), 6.74–6.97 (m, 4H), 6.45 (dt, J=16.0, 5.6 Hz, 1H), 4.73 (d, J=5.6 Hz, 2H), 3.84 (s, 2H), 3.12 (s, 2H).

EXAMPLE 2(21)

2-(3-(3-(biphenyl-4-yl)propoxy)phenylmethylthio)acetic acid

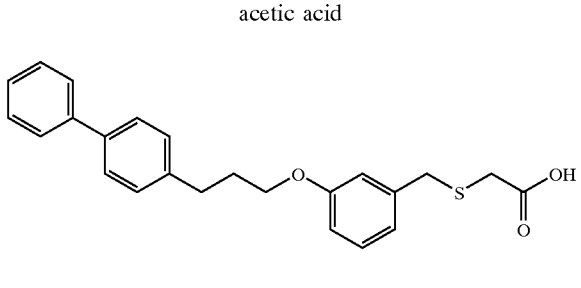

TLC: Rf 0.29 (chloroform:methanol=20:1);

NMR (CDCl$_3$): δ7.19–7.61 (m, 10H), 6.78–6.93 (m, 3H), 4.00 (t, J=6.1 Hz, 2H), 3.82 (s, 2H), 3.12 (s, 2H), 2.86 (t, J=7.6 Hz, 2H), 2.14 (tt, J=7.6, 6.1 Hz, 2H).

EXAMPLE 2(22)

2-(3-(2-(5-methyl-2-phenyloxazol-4-yl)ethoxy)phenyl)acetic acid.methyl ester

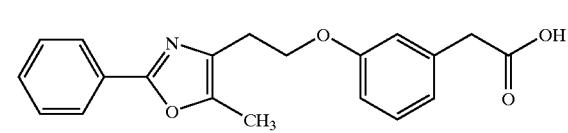

TLC: Rf 0.52 (chloroform:methanol=9:1);

NMR (CDCl$_3$): δ8.00–7.90 (m, 2H), 7.45–7.35 (m, 3H), 7.20 (t, J=7.5 Hz, 1H), 6.90–6.75 (m, 3H), 4.20 (t, J=7 Hz, 2H, ), 3.60 (s, 2H), 2.95 (t, J=7 Hz, 2H), 2.35(s, 3H).

EXAMPLE 2(23)

2-(3-(biphenyl-4-ylmethoxy)pyridin-5-ylmethylthio)acetic acid

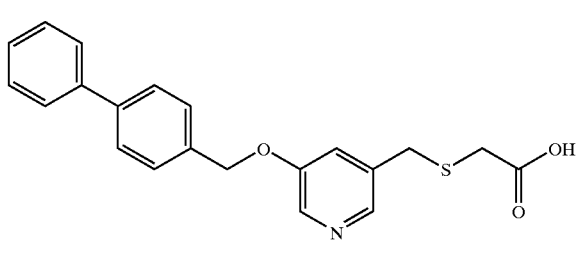

TLC: Rf 0.14 (water:methanol:chloroform=1:10:100);

NMR (DMSO-d$_6$): δ8.27 (d, J=3.0 Hz, 1H), 8.12 (d, J=1.5 Hz, 1H), 7.75–7.30 (m, 10H), 5.23 (s, 2H), 3.83 (s, 2H), 3.15 (s, 2H).

EXAMPLE 2(24)

2-(3-(4'-propylbiphenyl-4-ylmethoxy)phenylmethylthio)acetic acid

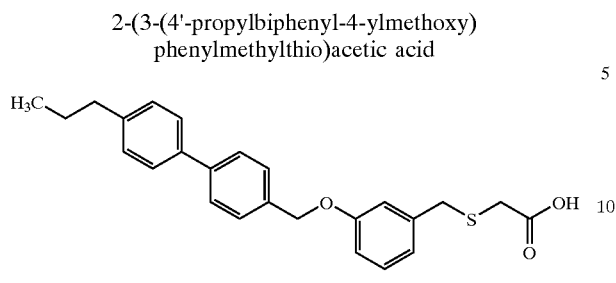

TLC: Rf 0.41 (ethyl acetate);

NMR (CDCl₃): δ7.60 (d, J=8.3 Hz, 2H), 7.51 (d, J=8.2 Hz, 2H), 7.48 (d, J=8.3 Hz, 2H), 7.26 (dd, J=7.8, 7.8 Hz, 1H), 7.25 (d, J=8.2 Hz, 2H), 6.88–7.01 (m, 3H), 5.10 (s, 2H), 3.83 (s, 2H), 3.10 (s, 2H), 2.63 (t, J=7.4 Hz, 2H), 1.68 (tq, J=7.4, 7.4 Hz, 2H), 0.97 (t, J=7.4 Hz, 3H).

EXAMPLE 2(25)

2-(3-(4-(pyridin-4-yl)phenylmethoxy)phenylmethylthio)acetic acid

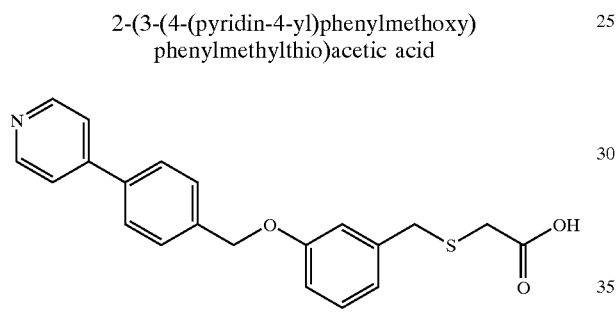

TLC: Rf 0.47 (chloroform:methanol=5:1);

NMR (CDCl₃+17 drops of CD₃OD): δ8.53 (d, J=5.8 Hz, 2H), 7.61 (d, J=8.0 Hz, 2H), 7.49–7.52 (m, 4H), 7.18 (dd, J=7.7, 7.7 Hz, 1H), 6.80–6.95 (m, 3H), 5.07 (s, 2H), 3.76 (s, 2H), 3.02 (s, 2H).

EXAMPLE 2(26)

2-(3-(4-(pyridin-3-yl)phenylmethoxy)phenylmethylthio)acetic acid

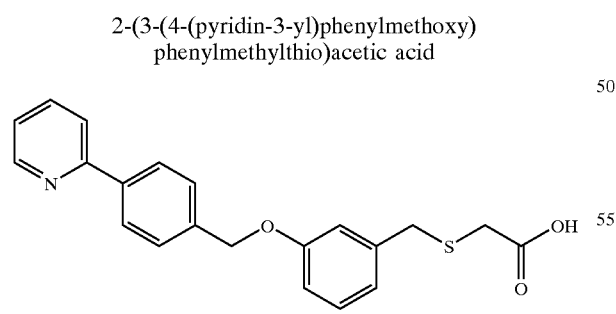

TLC: Rf 0.44 (chloroform:methanol=5:1);

NMR (DMSO-d₆): δ8.88 (d, J=1.5 Hz, 1H), 8.56 (dd, J=4.8, 1.5 Hz, 1H), 8.05 (m, 1H), 7.72 (d, J=8.0 Hz, 2H), 7.54 (d, J=8.0 Hz, 2H), 7.48 (m, 1H), 7.19 (dd, J=8.0, 8.0 Hz, 1H), 6.86–6.99 (m, 3H), 5.11 (s, 2H), 3.73 (s, 2H), 2.99 (s, 2H).

EXAMPLE 2(27)

2-(3-(4-(1,3-dioxaindan-5-yl)phenylmethoxy)phenylmethylthio)acetic acid

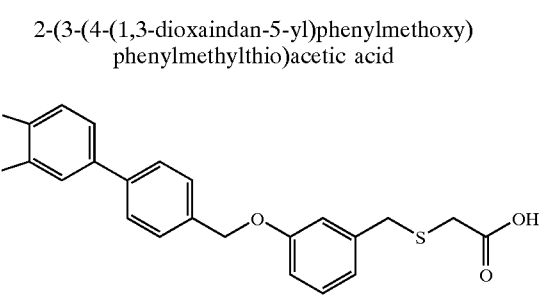

TLC: Rf 0.28 (chloroform:methanol=10:1);

NMR (CDCl₃): δ7.53 (d, J=8.1 Hz, 2H), 7.47 (d, J=8.1 Hz, 2H), 7.26 (dd, J=7.8, 7.8 Hz, 1H), 6.86–7.07 (m, 6H), 6.00 (s, 2H), 5.09 (s, 2H), 3.83 (s, 2H), 3.10 (s, 2H).

EXAMPLE 2(28)

2-(3-(4-(pyridin-2-yl)phenylmethoxy)phenylmethylthio)acetic acid

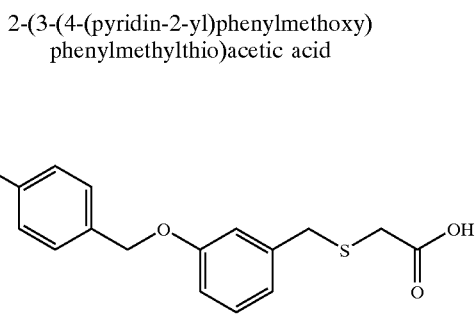

TLC: Rf 0.50 (chloroform:methanol=10:1);

NMR (CDCl₃+3 drops of CD₃OD): δ8.64 (ddd, J=5.0, 1.6, 1.4 Hz, 1H), 7.90 (d, J=8.6 Hz, 2H), 7.67–7.82 (m, 2H), 7.51 (d, J=8.6 Hz, 2H), 7.18–7.29 (m, 2H), 6.84–6.94 (m, 3H), 5.13 (s, 2H), 3.77 (s, 2H), 3.00 (s, 2H).

EXAMPLE 2(29)

2-(5-(biphenyl-4-ylmethoxy)-2-nitrophenylmethylthio)acetic acid

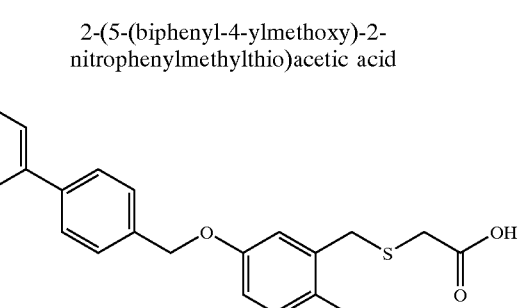

TLC: Rf 0.40 (chloroform:methanol=10:1);

NMR (CDCl₃): δ8.16 (d, J=9.0 Hz, 1H), 7.56–7.65 (m, 4H), 7.32–7.51 (m, 5H), 7.04 (d, J=2.8 Hz, 1H), 6.99 (dd, J=9.0, 2.8 Hz, 1H), 5.21 (s, 2H), 4.25 (s, 2H), 3.09 (s, 2H).

EXAMPLE 2(30)

2-(3-(biphenyl-4-ylmethoxy)-4-nitrophenylmethylthio)acetic acid

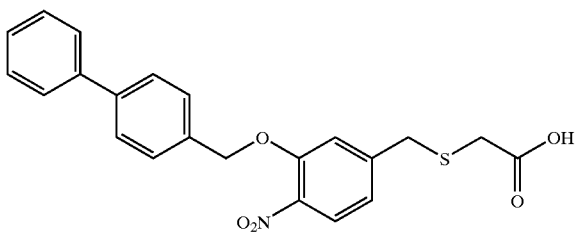

TLC: Rf 0.25 (chloroform:methanol=10:1);

NMR (CDCl$_3$): δ7.85 (d, J=8.4 Hz, 1H), 7.35–7.64 (m, 9H), 7.17 (d, J=1.6 Hz, 1H), 7.00 (dd, J=8.4, 1.6 Hz, 1H), 5.29 (s, 2H), 3.84 (s, 2H), 3.03 (s, 2H).

EXAMPLE 2(31)

2-(3-(4-(1,3-dioxaindan-4-yl)phenylmethoxy)phenylmethylthio)acetic acid

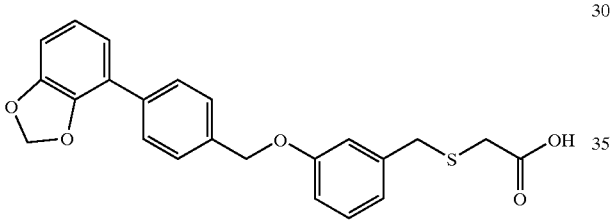

TLC: Rf 0.35 (chloroform:methanol=10:1);

NMR (CDCl$_3$): δ7.73 (d, J=8.5 Hz, 2H), 7.50 (d, J=8.5 Hz, 2H), 7.25 (dd, J=8.0, 8.0 Hz, 1H), 6.80–7.08 (m, 6H), 6.01 (s, 2H), 5.11 (s, 2H), 3.82 (s, 2H), 3.08 (s, 2H).

EXAMPLE 2(32)

2-(3-(2-phenylthiazol-4-ylmethoxy)phenylmethylthio)acetic acid

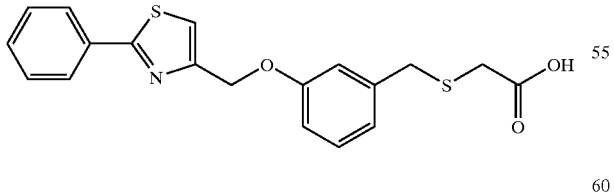

TLC: Rf 0.42 (chloroform:methanol=10:1);

NMR (CDCl$_3$): δ8.80 (brs, 1H), 7.90–7.96 (m, 2H), 7.40–7.45 (m, 3H), 7.32 (s, 1H), 7.25 (dd, J=7.8, 7.8 Hz, 1H), 6.89–7.03 (m, 3H), 5.27 (s, 2H), 3.82 (s, 2H), 3.09 (s, 2H).

EXAMPLE 2(33)

2-(3-(2-(5-methyl-2-(4-methylphenyl)oxazol-4-yl)ethoxy)phenylmethylthio)acetic acid

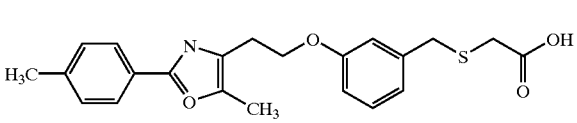

TLC: Rf 0.42 (chloroform:methanol=10:1);

NMR (CDCl$_3$): δ7.86 (d, J=8.0 Hz, 2H), 7.25–7.17 (m, 3H), 7.07 (s, 1H), 6.88 (d, J=7.8 Hz, 1H), 6.80 (dd, J=8.0, 1.4 Hz, 1H), 4.29 (t, J=7.7 Hz, 2H), 3.87 (s, 2H), 3.18 (s, 2H), 2.96 (t, J=7.7 Hz, 2H), 2.39 (s, 3H), 2.37 (s, 3H).

EXAMPLE 2(34)

2-(3-(2-(2-phenylthiazol-4-yl)ethoxy)phenylmethylthio)acetic acid

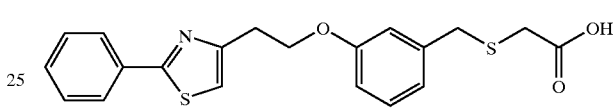

TLC: Rf 0.46 (chloroform:methanol=10:1);

NMR (CDCl$_3$): δ7.90–7.95 (m, 2H), 7.39–7.46 (m, 3H), 7.23 (dd, J=7.8, 7.8 Hz, 1H), 7.08 (s, 1H), 6.81–6.98 (m, 3H), 4.38 (t, J=7.0 Hz, 2H), 3.83 (s, 2H), 3.30 (t, J=7.0 Hz, 2H), 3.12 (s, 2H).

EXAMPLE 2(35)

2-(3-(2-(5-methyl-2-(4-trifluoromethylphenyl)oxazol-4-yl)ethoxy)phenylmethylthio)acetic acid

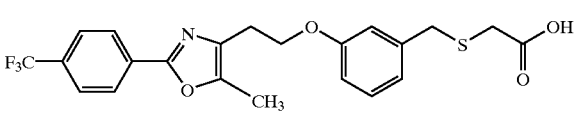

TLC: Rf 0.27 (chloroform:methanol=10:1);

NMR (CDCl$_3$): δ8.09 (d, J=9.0 Hz, 2H), 7.70 (d, J=9.0 Hz, 2H), 7.22–6.79 (m, 4H), 4.29 (t, J=7.5 Hz, 2H), 3.86 (s, 2H), 3.17 (s, 2H), 2.99 (t, J=7.5 Hz, 2H), 2.42 (s, 3H).

EXAMPLE 2(36)

2-(3-(2-(2-phenyloxazol-4-yl)ethoxy)phenylmethylthio)acetic acid

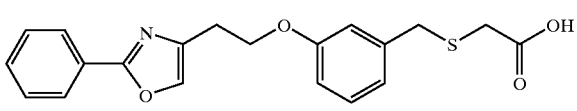

TLC: Rf 0.34 (chloroform:methanol=10:1);

NMR (CDCl$_3$): δ7.99–8.04 (m, 2H), 7.58 (s, 1H), 7.42–7.47 (m, 3H), 7.23 (dd, J=7.7, 7.7 Hz, 1H), 6.89–6.95 (m, 2H), 6.83 (dd, J=7.7, 2.5 Hz, 1H), 4.30 (t, J=7.1 Hz, 2H), 3.84 (s, 2H), 3.14 (s, 2H), 3.08 (t, J=7.1 Hz, 2H).

EXAMPLE 2(37)

2-(3-(2-(5-methyl-2-(4-fluorophenyl)oxazol-4-yl)ethoxy)phenylmethylthio)acetic acid

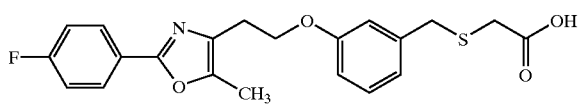

TLC: Rf 0.39 (chloroform:methanol=10:1);

NMR (CDCl$_3$): δ7.97 (dd, J=8.8, 5.2 Hz, 2H), 7.24–7.07 (m, 3H), 6.97 (m, 1H), 6.89 (d, J=7.6 Hz, 1H), 6.79 (dd, J=8.0, 1.8 Hz, 1H), 4.25 (t, J=7.1 Hz, 2H), 3.82 (s, 2H), 3.13 (s, 2H), 2.97 (t, J=7.1 Hz, 2H), 2.37 (s, 3H).

EXAMPLE 2(38)

2-(3-(2-(5-methyl-2-(1,3-dioxaindan-5-yl)oxazol-4-yl)ethoxy)phenylmethylthio)acetic acid

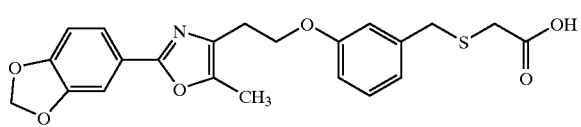

TLC: Rf 0.30 (chloroform:methanol=10:1);

NMR (CDCl$_3$): δ7.53 (d, J=8.4 Hz, 1H), 7.44 (d, J=2.0 Hz, 1H), 7.21 (t, J=7.9 HZ, 1H), 7.05 (s, 1H), 6.90–6.78 (m, 3H), 6.02 (s, 2H), 4.27 (t, J=7.4 Hz, 2H), 3.87 (s, 2H), 3.18 (s, 2H), 2.95 (t, J=7.4 Hz, 2H), 2.36 (s, 3H).

EXAMPLE 2(39)

5-(3-(3-(5-methyl-2-phenyloxazol-4-yl)propoxy)phenyl)pentanoic acid

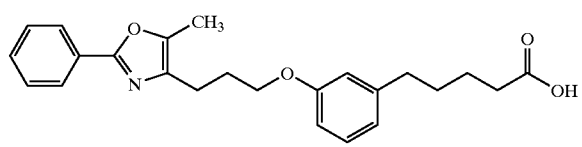

TLC: Rf 0.63 (chloroform:methanol=9:1);

NMR (CDCl$_3$): δ8.05–7.95 (m, 2H), 7.50–7.40 (m, 3H), 7.15 (m, 1H), 6.80–6.70 (m, 3H), 4.00 (t, J=6 Hz, 2H), 2.75 (t, J=7 Hz, 2H), 2.60 (m, 2H), 2.35 (m, 2H), 2.30 (s, 3H), 2.15 (m, 2H), 1.75–1.60 (m, 4H).

EXAMPLE 2(40)

2-(3-(2-(5-methyl-2-(4-chlorophenyl)oxazol-4-yl)ethoxy)phenylmethylthio)acetic acid

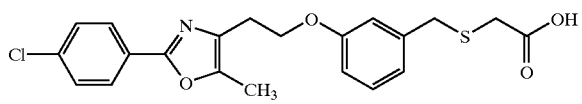

TLC: Rf 0.29 (chloroform:methanol=10:1);

NMR (CDCl$_3$): δ7.92 (d, J=8.8 Hz, 2H), 7.41 (d, J=8.8 Hz, 2H), 7.21 (t, J=7.9 Hz, 1H), 7.02 (m, 1H), 6.89 (d, J=8.0 Hz, 1H), 6.81 (d, J=8.0 Hz, 1H), 4.27 (t, J=7.8 Hz, 2H), 3.86 (s, 2H), 3.16 (s, 2H) 2.97 (t, J=7.8 Hz, 2H), 2.39 (s, 3H).

EXAMPLE 2(41)

2-(3-(5-methyl-2-phenyloxazol-4-ylmethoxy)phenylmethylthio)acetic acid

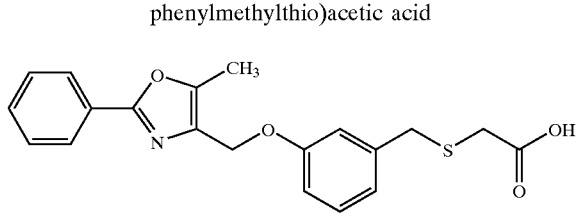

TLC: Rf 0.37 (chloroform:methanol=9:1);

NMR (CDCl$_3$): δ8.05–7.95 (m, 2H), 7.50–7.40 (m, 3H), 7.25 (dd, J=7.5, 7.5 Hz, 1H), 7.05 (m, 1H), 6.95–6.85 (m, 2H), 5.05 (s, 2H), 3.80 (s, 2H), 3.15 (s, 2H), 2.45 (s, 3H).

EXAMPLE 2(42)

2-(3-(3-(5-methyl-2-phenyloxazol-4-yl)propoxy)phenylmethylthio)acetic acid

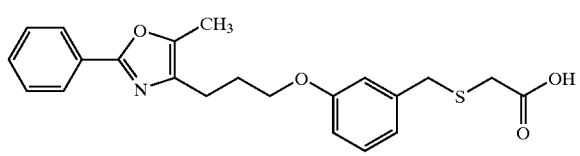

TLC: Rf 0.42 (chloroform:methanol=9:1);

NMR (CDCl$_3$): δ8.00–7.90 (m, 2H), 7.45–7.40 (m, 3H), 7.25 (dd, J=8, 8 Hz, 1H), 6.95–6.85 (m, 2H), 6.80 (m, 1H), 4.15 (t, J=6.5 Hz, 2H), 3.85 (s, 2H), 3.10 (s, 2H), 2.65 (t, J=7.5 Hz, 2H), 2.30 (s, 3H), 2.10 (m, 2H).

EXAMPLE 2(43)

2-(3-(2-(5-methyl-2-phenyloxazol-4-yl)ethoxy)phenyl)-2-methylpropanoic acid

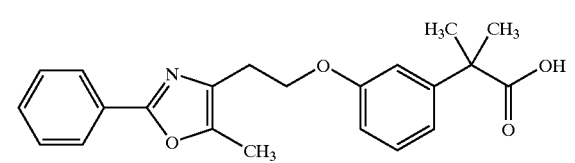

TLC: Rf 0.51 (chloroform:methanol=10:1);

NMR (CDCl$_3$): δ7.96–8.01 (m, 2H), 7.40–7.45 (m, 3H), 7.22 (dd, J=8.0, 8.0 Hz, 1H), 6.92–6.98 (m, 2H), 6.78 (m, 1H), 4.22 (t, J=6.6 Hz, 2H), 2.98 (t, J=6.6 Hz, 2H), 2.36 (s, 3H), 1.57 (s, 6H ).

EXAMPLE 2(44)

2-(3-(2-(5-methyl-2-(2-methylphenyl)oxazol-4-yl)ethoxy)phenylmethylthio)acetic acid

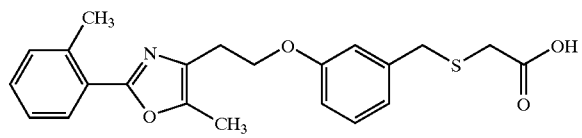

TLC: Rf 0.38 (chloroform:methanol=10:1);

NMR (CDCl$_3$): δ7.89 (m, 1H), 7.33–7.17 (m, 4H), 6.99–6.79 (m, 3H), 4.29 (t, J=7.2 Hz, 2H), 3.83 (s, 2H), 3.12 (s, 2H), 2.99 (t, J=7.2 Hz, 2H), 2.61 (s, 3H), 2.39 (s, 3H).

EXAMPLE 2(45)

2-(3-(2-(5-methyl-2-(3-methylphenyl)oxazol-4-yl)ethoxy)phenylmethylthio)acetic acid

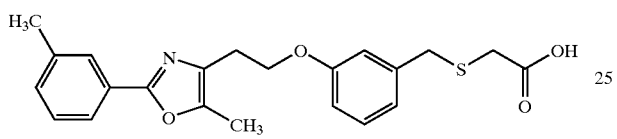

TLC: Rf 0.39 (chloroform:methanol=10:1);

NMR (CDCl$_3$): δ7.79 (m, 2H), 7.37–7.17 (m, 3H), 7.03 (m, 1H), 6.88 (d, J=7.4 Hz, 1H), 6.81 (m, 1H), 4.28 (t, J=7.2 Hz, 2H), 3.86 (s, 2H), 3.16 (s, 2H), 2.98 (t, J=7.2 Hz, 2H), 2.40 (s, 3H), 2.39 (s, 3H).

EXAMPLE 2(46)

2-(3-(2-(5-methyl-2-(4-methoxyphenyl)oxazol-4-yl)ethoxy)phenylmethylthio)acetic acid

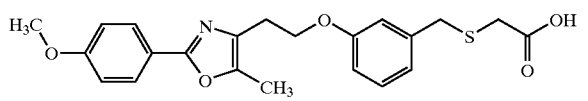

TLC: Rf 0.43 (chloroform:methanol=10:1);

NMR (CDCl$_3$): δ7.92 (d, J=9.0 Hz, 2H), 7.20 (dd, J=7.9, 7.9 Hz, 1H), 7.05 (m, 1H), 6.95 (d, J=9.0 Hz, 2H), 6.78–6.90 (m, 2H), 4.27 (t, J=7.4 Hz, 2H), 3.86 (s, 2H), 3.85 (s, 3H), 3.17 (s, 2H), 2.96 (t, J=7.4 Hz, 2H), 2.36 (s, 3H).

EXAMPLE 2(47)

2-(3-(2-(5-methyl-2-(4-nitrophenyl)oxazol-4-yl)ethoxy)phenylmethylthio)acetic acid

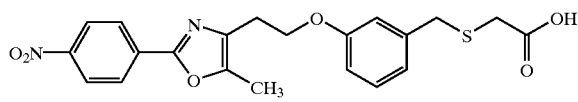

TLC: Rf 0.48 (chloroform:methanol=9:1);

NMR (CDCl$_3$): δ8.29 (d, J=9.0 Hz, 2H), 8.13 (d, J=9.0 Hz, 2H), 7.22 (dd, J=8.0, 8.0 Hz, 1H), 6.88–6.94 (m, 2H), 6.80 (dd, J=8.0, 1.6 Hz, 1H), 4.27 (t, J=6.5 Hz, 2H), 3.82 (s, 2H), 3.13 (s, 2H), 3.00 (t, J=6.5 Hz, 2H), 2.43 (s, 3H).

EXAMPLE 2(48)

2-(3-(2-(5-methyl-2-phenyloxazol-4-yl)ethoxy)-5-chlorophenylmethylthio)acetic acid

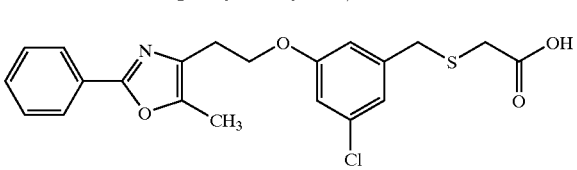

TLC: Rf 0.26 (chloroform:methanol water=100:10:1);

NMR (CDCl$_3$): δ7.95–8.00 (m, 2H), 7.41–7.47 (m, 3H), 6.93 (m, 1H), 6.89 (m, 1H), 6.81 (dd, J=2.0, 2.0 Hz, 1H), 4.27 (t, J=7.2 Hz, 2H), 3.81 (s, 2H), 3.17 (s, 2H), 2.97 (t, J=7.2 Hz, 2H), 2.39 (s, 3H).

EXAMPLE 2(49)

2-(3-(2-(5-methyl-2-phenyloxazol-4-yl)ethoxy)-2-methylphenylmethylthio)acetic acid

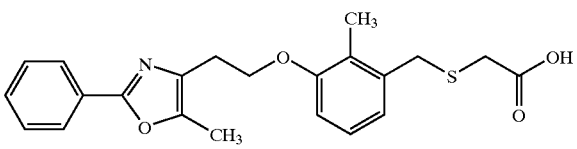

TLC: Rf 0.29 (chloroform:methanol=10:1);

NMR (CDCl$_3$): δ8.00–7.95 (m, 2H), 7.45–7.40 (m, 3H), 7.06 (t, J=8.0 Hz, 1H), 6.85–6.78 (m, 2H), 4.23 (t, J=6.5 Hz, 2H), 3.84 (s, 2H), 3.13 (s, 2H), 3.01 (t, J=6.5 Hz, 2H), 2.38 (s, 3H), 2.22 (s, 3H).

EXAMPLE 2(50)

2-(1-(3-(2-(5-methyl-2-phenyloxazol-4-yl)ethoxy)phenyl)ethylthio)acetic acid

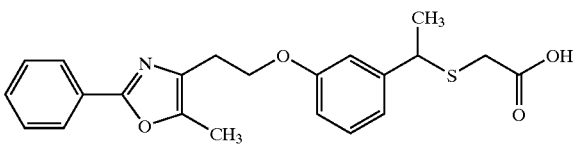

TLC: Rf 0.38 (chloroform:methanol=10:1);

NMR (CDCl$_3$): δ8.00–7.94 (m, 2H), 7.46–7.39 (m, 3H), 7.23 (t, J=7.8 Hz, 1H), 7.01 (brs, 1H), 6.93 (brd, J=8.0 Hz, 1H), 6.83–6.78 (m, 1H), 4.27 (t, J=7.2 Hz, 2H), 4.18 (q, J=7.0 Hz, 1H), 3.06 (d, J=15.6 Hz, 1H), 3.04 (d, J=15.6 Hz, 1H), 2.96 (t, J=7.2 Hz, 2H), 2.38 (s, 3H), 1.58 (d, J=7.0 Hz, 3H).

EXAMPLE 2(51)

2-(3-(2-(5-methyl-2-phenyloxazol-4-yl)-1-methylethoxy)phenylmethylthio)acetic acid

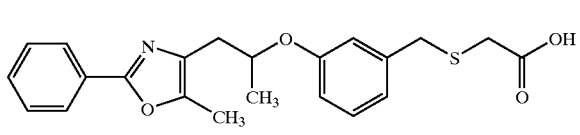

TLC: Rf 0.37 (chloroform:methanol=10:1);
NMR (CDCl$_3$): δ8.00–7.94 (m, 2H), 7.45–7.38 (m, 3H), 7.18 (t, J=7.2 Hz, 1H), 7.04 (brs, 1H), 6.89–6.77 (m, 2H), 4.77 (m, 1H), 3.83 (s, 2H), 3.16 (d, J=15.0 Hz, 1H), 3.10 (d, J=15.0 Hz, 1H), 3.01 (dd, J=14.2, 5.4 Hz, 1H), 2.63 (dd, J=14.2, 7.8 Hz, 1H), 2.35 (s, 3H), 1.34 (d, J=6.2 Hz, 3H).

EXAMPLE 2(52)

2-(3-(2-(5-trifluoromethyl-2-phenyloxazol-4-yl)ethoxy)phenylmethylthio)acetic acid

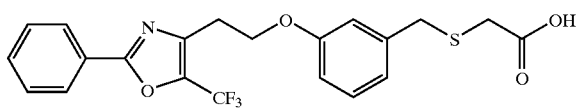

TLC: Rf 0.23 (chloroform:methanol=20:1);
NMR (CDCl$_3$): δ8.10–8.01 (m, 2H), 7.58–7.42 (m, 3H), 7.22 (t, J=8.0 Hz, 1H), 6.96–6.87 (m, 2H), 6.81 (m, 1H), 4.31 (t, J=7.0 Hz, 2H), 3.81 (s, 2H), 3.20 (t, J=7.0 Hz, 2H), 3.10 (s, 2H).

EXAMPLE 2(53)

2-(3-(2-(5-methyl-2-phenyloxazol-4-yl)propoxy)phenylmethylthio)acetic acid

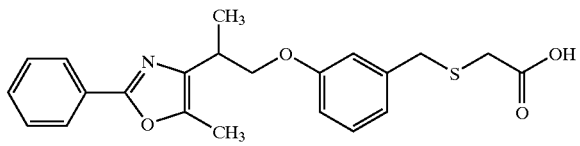

TLC: Rf 0.38 (hexane:ethyl acetate=1:3);
NMR (CDCl$_3$): δ8.00–7.91 (m, 2H), 7.38–7.33 (m, 3H), 7.06 (t, J=8.0 Hz, 1H), 6.83–6.67 (m, 3H), 4.18–3.94 (m, 2H), 3.67 (s, 2H), 3.15 (m, 1H), 3.08 (s, 2H), 2.31 (s, 3H), 1.34 (d, J=7.0 Hz, 3H).

EXAMPLE 2(54)

2-(3-(2-(5-methyl-2-phenyloxazol-4-yl)ethoxy)phenylmethylthio)propanoic acid.sodium salt

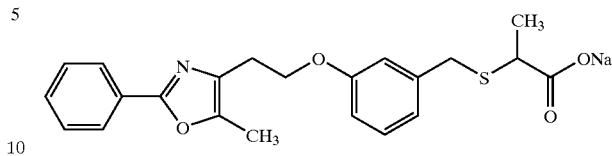

TLC: Rf 0.37 (chloroform:methanol=10:1);
NMR (CD$_3$OD): δ7.98–7.93 (m, 2H), 7.50–7.41 (m, 3H), 7.15 (t, J=7.8 Hz, 1H), 6.94–6.86 (m, 2H), 6.76 (m, 1H), 4.24 (t, J=6.6 Hz, 2H), 3.73 (s, J=13.2 Hz, 1H) 3.72 (d, 13.2 Hz, 1H) 3.72 (q, J=7.0 Hz, 1H), 2.96 (t, J=6.6 Hz, 2H), 2.37 (s, 3H), 1.34 (d, J=7.0 Hz, 3H).

EXAMPLE 2(55)

2-(3-(2-(5-methyl-2(4-ethylphenyl)oxazol-4-yl)propoxy)phenylmethylthio)acetic acid

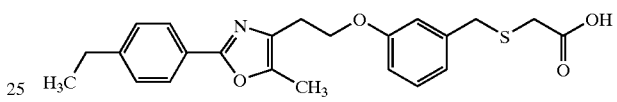

TLC: Rf 0.33 (water:methanol:chloroform=1:10:100);
NMR (CDCl$_3$): δ7.88 (d, J=8.5 Hz, 2H), 7.26 (d, J=8.5 Hz, 2H), 7.20 (dd, J=8.0, 8.0 Hz, 1H), 7.01 (d, J=2.5 Hz, 1H), 6.88 (d, J=8.0 Hz, 1H), 6.80 (dd, J=8.0, 2.5 Hz, 1H), 4.26 (t, J=7.0 Hz, 2H), 3.8 4 (s, 2H), 3.15 (s, 2H), 2.97 (t, J=7.0 Hz, 2H), 2.68 (q, J=7.5 Hz, 2H), 2.37 (s, 3H), 1.25 (t, J=7.5 Hz, 3H).

EXAMPLE 2(56)

2-(3-(2-(5-methyl-2-(2,2fifluoro-1,3-dioxaindan-5-yl)oxazol-4-yl)ethoxy)phenylmethylthio)acetic acid

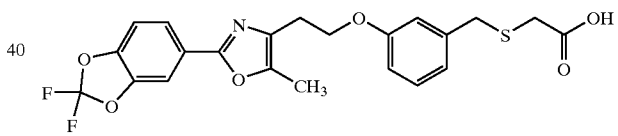

TLC: Rf 0.31 (water:methanol:chloroform=1:10:100);
NMR (CDCl$_3$): δ7.75 (dd, J=8.5, 2.0 Hz, 1H), 7.69 (d, J=2.0 Hz, 1H), 7.21 (dd, J=8.0, 8.0 Hz, 1H), 7.11 (d, J=8.5 Hz, 1H), 6.96 (d, J=2.5 Hz, 1H), 6.89 (d, J=8.0 Hz, 1H), 6.80 (dd, J=8.0, 2.5 Hz, 1H), 4.25 (t, J=7.0 Hz, 2H), 3.83 (s, 2H), 3.14 (s, 2H), 2.97 (t, J=7.0 Hz, 2H), 2.38 (s, 3H).

EXAMPLE 2(57)

2-(3-(2-(5-methyl-2-(4-propylphenyl)oxazol-4-yl)ethoxy)phenylmethylthio)acetic acid

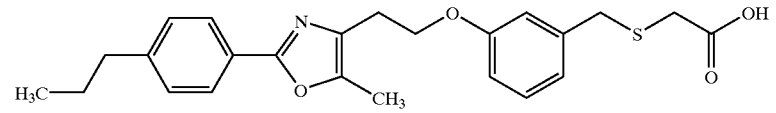

TLC: Rf 0.50 (water:methanol:chloroform=1:10:100);
NMR (CDCl$_3$): δ7.88 (d, J=8.5 Hz, 2H), 7.24 (d, J=8.5 Hz, 2H), 7.20 (dd, J=8.0, 8.0 Hz, 1H), 7.02 (d, J=2.5 Hz, 1H), 6.88 (d, J=8.0 Hz, 1H), 6.80 (dd, J=8.0, 2.5 Hz, 1H), 4.27 (t, J=7.5 Hz, 2H), 3.85 (s, 2H), 3.16 (s, 2H), 2.97 (t, J=7.5 Hz, 2H), 2.62 (t, J=7.5 Hz, 2H), 2.37 (s, 3H), 1.65 (m, 2H), 0.94 (t, J=7.5 Hz, 3H).

EXAMPLE 2(58)

2-(3-(2-(5-methyl-2-(4-isopropylphenyl)oxazol-4-yl)ethoxy)phenylmethylthio)acetic acid

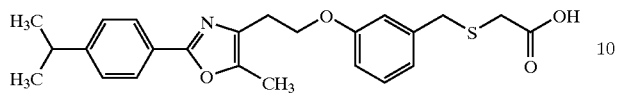

TLC: Rf 0.53 (water:methanol:chloroform=1:10:100);

NMR (CDCl$_3$): δ7.89 (d, J=8.0 Hz, 2H), 7.29 (d, J=8.0 Hz, 2H), 7.21 (dd, J=8.0, 8.0 Hz, 1H), 7.06 (d, J=2.5 Hz, 1H), 6.88 (d, J=8.0 Hz, 1H), 6.81 (dd, J=8.0, 2.5 Hz, 1H), 4.28 (t, J=7.5 Hz, 2H), 3.87 (s, 2H), 3.17 (s, 2H), 2.97 (t, J=7.5 Hz, 2H), 2.94 (m, 1H), 2.38 (s, 3H), 1.26 (d, J=7.0 Hz, 6H).

EXAMPLE 2(59)

2-(3-(2-(5-methyl-2-phenylthiazol-4-yl)ethoxy)phenylmethylthio)acetic acid

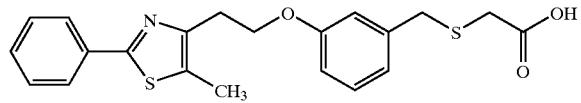

TLC: Rf 0.32 (chloroform:methanol=10:1);

NMR (CDCl$_3$): δ7.88–7.82 (m, 2H), 7.45–7.34 (m, 3H), 7.21 (t, J=7.8 Hz, 1H), 6.98 (m, 1H), 6.92–6.77 (m, 2H), 4.33 (t, J=7.2 Hz, 2H), 3.83 (s, 2H), 3.20 (t, J=7.2 Hz, 2H), 3.12 ((s, 2H), 2.47 (s, 3H).

EXAMPLE 2(60)

2-(3-(2-(5-methyl-2-(4-butylphenyl)oxazol-4-yl)ethoxy)phenylmethylthio)acetic acid

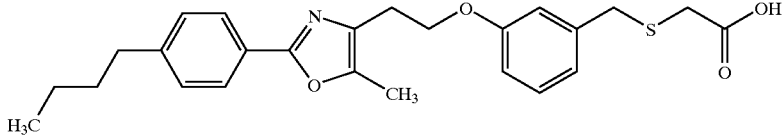

TLC: Rf 0.43 (chloroform:methanol=9:1);

NMR (CDCl$_3$): δ7.85 (d, J=7 Hz, 2H), 7.30–7.05 (m, 3H), 7.05 (brs, 1H), 6.90–6.75 (m, 2H), 4.30 (t, J=8 Hz, 2H), 3.85 (s, 2H), 3.20 (s, 2H), 2.95 (t, J=8 Hz, 2H), 2.60 (t, J=8 Hz, 2H), 2.40 (s, 3H), 1.60 (m, 2H), 1.35 (m, 2H), 0.95 (t, J=7 Hz, 3H).

EXAMPLE 2(61)

2-(3-(2-(5-ethyl-2-phenyloxazol-4-yl)ethoxy)phenylmethylthio)acetic acid

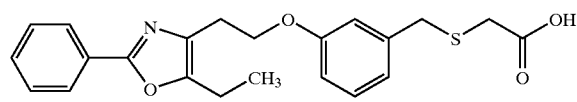

TLC: Rf 0.63 (chloroform:methanol=5:1);

NMR (CDCl$_3$): δ7.96–8.01 (m, 2H), 7.40–7.47 (m, 3H), 7.21 (dd, J=7.8, 7.8 Hz, 1H), 7.04 (m, 1H), 6.88 (d, J=7.8 Hz, 1H), 6.81 (dd, J=7.8, 2.4 Hz, 1H), 4.28 (t, J=7.5 Hz, 2H), 3.86 (s, 2H), 3.17 (s, 2H), 2.98 (t, J=7.5 Hz, 2H), 2.75 (q, J=7.4 Hz, 2H), 1.31 (t, J=7.4 Hz, 3H).

EXAMPLE 2(62)

2-(3-(2-(5-methyl-2-(2,3,5,6-tetrafluoro-4-methylphenyl)oxazol-4-yl)ethoxy)phenylmethylthio)acetic acid

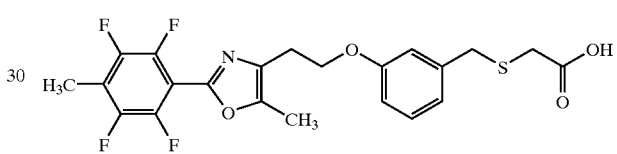

TLC: Rf 0.33 (chloroform:methanol=15:1);

NMR (CDCl$_3$): δ7.21 (t, J=7.8 Hz, 1H), 6.97–6.75 (m, 3H), 4.26 (t, J=7.0 Hz, 2H), 3.82 (s, 2H), 3.12 (s, 2H), 3.02 (t, J=7.0 Hz, 2H), 2.42 (s, 3H), 2.33 (m, 3H).

EXAMPLE 2(63)

2-(3-(2-(5-methyl-2-(4-pentylphenyl)oxazol-4-yl)ethoxy)phenylmethylthio)acetic acid

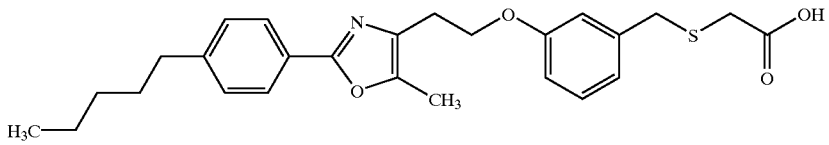

TLC: Rf 0.50 (chloroform:methanol=9:1);

NMR (CDCl$_3$): δ7.90 (d, J=8 Hz, 2H), 7.30–7.15 (m, 3H), 7.05 (br., 1H), 6.90–6.75 (m, 2H), 4.30 (t, J=8 Hz, 2H), 3.90 (s, 2H), 3.20 (s, 2H), 3.00 (t, J=8 Hz, 2H), 2.65 (t, J=8 Hz, 2H), 2.40 (s, 3H), 1.60 (m, 2H), 1.45–1.20 (m, 4H), 0.90 (t, J=7 Hz, 3H).

EXAMPLE 2(64)

2-(3-(2-(5-methyl-2-(3-chloro-4-methylphenyl)oxazol-4-yl)ethoxy)phenylmethylthio)acetic acid

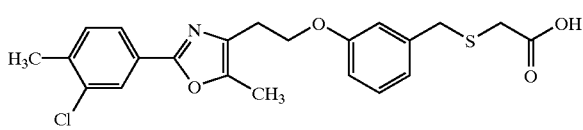

TLC: Rf 0.63 (chloroform:methanol=5:1);

NMR (CDCl$_3$): δ7.95 (d, J=1.8 Hz, 1H), 7.76 (dd, J=8.0, 1.8 Hz, 1H), 7.29 (d, J=8.0 Hz, 1H), 7.21 (dd, J=7.8, 7.8 Hz, 1H), 6.99 (m, 1H), 6.89 (m, 1H), 6.80 (m, 1H), 4.26 (t, J=7.1 Hz, 2H), 3.84 (s, 2H), 3.15 (s, 2H), 2.97 (t, J=7.1 Hz, 2H), 2.40 (s, 3H), 2.38 (s, 3H).

EXAMPLE 2(65)

2-(3-(2-(5-methyl-2-cyclohexyloxazol-4-yl)ethoxy)phenylmethylthio)acetic acid

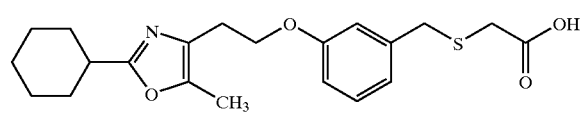

TLC: Rf 0.38 (chloroform:methanol=9:1);

NMR (CDCl$_3$): δ7.20 (dd, J=7.5, 7.5 Hz, 1H), 7.05 (br. 1H), 6.90–6.75 (m, 2H), 4.20 (t, J=8 Hz, 2H), 3.90 (s, 2H), 3.20 (s, 2H), 2.85 (t, J=8 Hz, 2H), 2.25 (s, 3H), 2.10–1.20 (m, 10H).

2-(3-(2-(5-methyl-2-cyclohexyloxazol-4-yl)ethoxy)phenylmethylthio)acetic acid.sodium salt

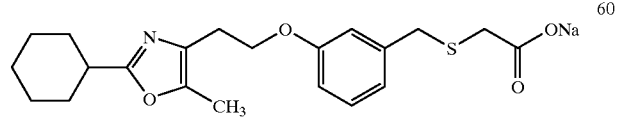

TLC: Rf 0.22 (chloroform:methanol=10:1);

NMR (CDCl$_3$): δ6.96 (m, 1H), 6.76–6.66 (m, 2H), 6.58 (m, 1H), 4.00 (m, 2H), 3.48 (s, 2H), 3.07 (s, 2H), 2.74 (m, 2H), 2.62 (m, 1H), 2.15 (s, 3H), 2.01–1.89 (m, 2H), 1.80–1.15 (m, 8H).

EXAMPLE 2(66)

2-(3-(2-(5-methyl-2-(4-(2-methylpropyl)phenyl)oxazol-4-yl)ethoxy)phenylmethylthio)acetic acid

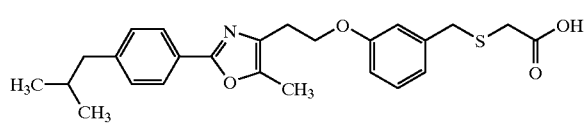

TLC: Rf 0.44 (chloroform:methanol=9:1);

NMR (CDCl$_3$): δ7.90 (d, J=7 Hz, 2H), 7.30–7.15 (m, 3H), 7.05 (m, 1H), 6.95–6.75 (m, 2H), 4.25 (t, J=7.5 Hz, 2H), 3.85 (s, 2H), 3.20 (s, 2H), 3.00 (t, J=7.5 Hz, 2H), 2.50 (d, J=8 Hz, 2H), 2.40 (s, 3H), 1.90 (m, 1H), 0.90 (d, J=8 Hz, 6H).

EXAMPLE 2(67)

2-(3-(2-(5-methyl-2-(4-t-butylphenyl)oxazol-4-yl)ethoxy)phenylmethylthio)acetic acid

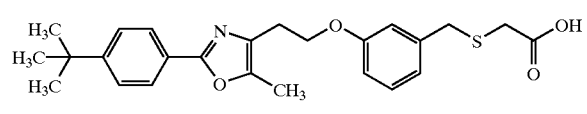

TLC: Rf 0.50 (chloroform:methanol=9:1);

NMR (CDCl$_3$): δ7.90 (d, J=9 Hz, 2H), 7.45 (d, J=9 Hz, 2H), 7.20 (dd, J=8, 8 Hz, 1H), 7.05 (br., 1H), 6.90–6.80 (m, 2H), 4.30 (t, J=7.5 Hz, 2H), 3.85 (s, 2H), 3.20 (s, 2H), 3.00 (t, J=7.5 Hz, 2H), 2.40 (s, 3H), 1.35 (s, 9H).

EXAMPLE 2(68)

2-(3-(2-(5-methyl-2-(4-cyclohexylphenyl)oxazol-4-yl)ethoxy)phenylmethylthio)acetic acid

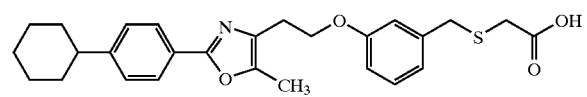

TLC: Rf 0.65 (chloroform:methanol=9:1);

NMR (CDCl$_3$): δ7.89 (d, J=8.5 Hz, 2H), 7.27 (d, J=8.5 Hz, 2H), 7.20 (dd, J=8.0, 8.0 Hz, 1H), 7.03 (m, 1H), 6.88 (d, J=8.0 Hz, 1H), 6.80 (dd, J=8.0, 2.2 Hz, 1H), 4.27 (t, J=7.5 Hz, 2H), 3.85 (s, 2H), 3.16 (s, 2H), 2.97 (t, J=7.5 Hz, 2H), 2.53 (m, 1H), 2.37 (s, 3H), 1.70–1.90 (m, 4H), 1.20–1.52 (m, 6H).

EXAMPLE 2(69)

2-(3-(5-methyl-2-(1,3-dioxaindan-5-yl)oxazol-4-ylmethoxy)phenylmethylthio)acetic acid

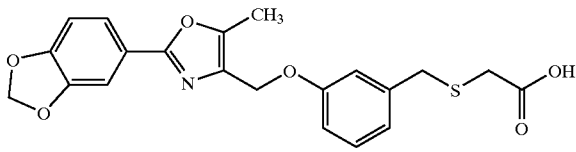

TLC: Rf 0.40 (chloroform:methanol=10:1);

NMR (CDCl₃): δ7.54 (dd, J=8.0, 1.8 Hz, 1H), 7.46 (d, J=1.8 Hz, 1H), 7.21 (d, J=8.0 Hz, 1H), 7.07–7.02 (m, 1H), 6.96–6.82 (m, 3H), 6.02 (s, 2H), 5.00 (s, 2H), 3.78 (s, 2H), 3.11 (s, 2H), 2.42 (s, 3H).

EXAMPLE 2(70)

2-(3-(5-methyl-2-(4-isopropylphenyl)oxazol-4-ylmethoxy)phenylmethylthio)acetic acid

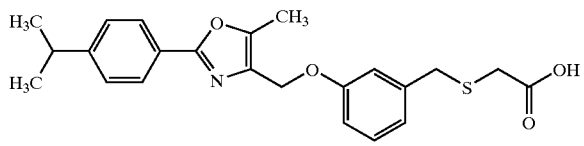

TLC: Rf 0.48 (chloroform:methanol=10:1);

NMR (CDCl₃): δ7.92 (d, J=8.5 Hz, 2H), 7.34–7.17 (m, 3H), 7.08–7.03 (m, 1H), 6.96–6.84 (m, 2H), 5.02 (s, 2H), 3.78 (s, 2H), 3.11 (s, 2H), 2.94 (sep., J=7.0 Hz, 1H), 2.44 (s, 3H), 1.26 (d, J=7.0 Hz, 6H).

EXAMPLE 2(71)

2-(3-(2-(4-methyl-2-phenyloxazol-5-yl)ethoxy)phenylmethylthio)acetic acid

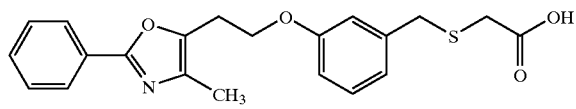

TLC: Rf 0.38 (chloroform:methanol=10:1);

NMR (CDCl₃): δ8.00–7.95 (m, 2H), 7.49–7.37 (m, 3H), 7.22 (t, J=8.0 Hz, 1H), 6.95–6.76 (m, 3H), 4.23 (t, J=7.0 Hz, 2H), 3.81 (s, 2H), 3.15 (t, J=7.0 Hz, 2H), 3.10 (s, 2H), 2.22 (s, 3H).

EXAMPLE 2(72)

2-(3-(2-(5-methyl-2-(3,4-dimethoxyphenyl)oxazol-4-yl)ethoxy)phenylmethylthio)acetic acid

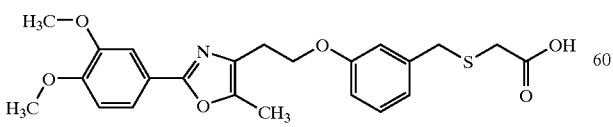

TLC: Rf 0.62 (chloroform:methanol=5:1);

NMR (CDCl₃): δ7.57 (dd, J=8.5, 2.0 Hz, 1H), 7.51 (d, J=2.0 Hz, 1H), 7.21 (dd, J=8.0, 8.0 Hz, 1H), 7.04 (m, 1H), 6.91 (d, J=8.5 Hz, 1H), 6.78–6.90 (m, 2H), 4.28 (t, J=7.5 Hz, 2H), 3.95 (s, 3H), 3.93 (s, 3H), 3.86 (s, 2H), 3.16 (s, 2H), 2.96 (t, J=7.5 Hz, 2H), 2.38 (s, 3H).

EXAMPLE 2(73)

2-(3-(2-(5-methyl-2-(4-trifluoromethoxyphenyl)oxazol-4-yl)ethoxy)phenylmethylthio)acetic acid

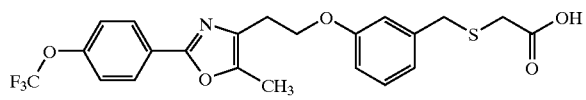

TLC: Rf 0.39 (chloroform:methanol=9:1);

NMR (CDCl₃): δ8.00 (d, J=8 Hz, 2H), 7.30 (d, J=8 Hz, 2H), 7.20 (dd, J=7.5, 7.5 Hz, 1H), 7.00 (br. 1H) 6.90 (d, J=7.5 Hz, 1H), 6.80 (dd, J=7.5, 7.5 Hz, 1H), 4.25 (t, J=7 Hz, 2H), 3.85 (s, 2H), 3.15 (s, 2H), 3.00 (t, J=7 Hz, 2H), 2.40 (s, 3H).

EXAMPLE 2(74)

2-(3-(2-(5-methyl-2-(3,4,5-trimethoxyphenyl)oxazol-4-yl)ethoxy)phenylmethylthio)acetic acid

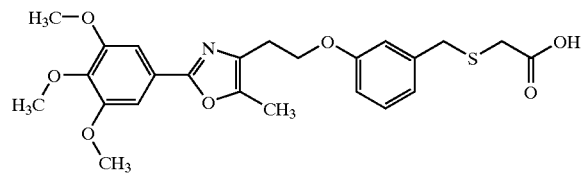

TLC: Rf 0.39 (chloroform:methanol=9:1);

NMR (CDCl₃): δ7.25–7.15 (m, 3H), 7.05 (m, 1H), 6.90–6.75 (m, 2H), 4.25 (t, J=7.5 Hz, 2H), 3.95 (s, 6H), 3.90 (s, 3H), 3.85 (s, 2H), 3.15 (s, 2H), 2.95 (t, J=7.5 Hz, 2H), 2.40 (s, 3H).

EXAMPLE 2(75)

2-(3-(2-(5-methyl-2-(4-methylpiperazin-1-yl)oxazol-4-yl)ethoxy)phenylmethylthio)acetic acid

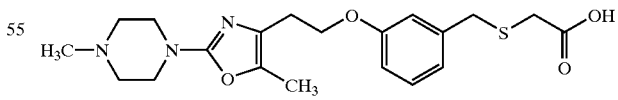

TLC: Rf 0.26 (water:methanol chloroform=1:10:100);

NMR (CDCl₃): δ7.14 (dd, J=7.5, 7.5 Hz, 1H), 6.88 (d, J=7.5 Hz, 1H), 6.73 (dd, J=7.5, 2.0 Hz, 1H), 6.70 (d, J=2.0 Hz, 1H), 4.27 (t, J=6.5 Hz, 2H), 3.78 (s, 2H), 3.55 (t, J=5.0 Hz, 4H), 3.14 (s, 2H), 2.90 (t, J=6.5 Hz, 2H), 2.85 (t, J=5.0 Hz, 4H), 2.51 (s, 3H), 2.19 (s, 3H).

EXAMPLE 2(76)

2-(3-(2-(5-methyl-2-(4-methylthiophenyl)oxazol-4-yl)ethoxy)phenylmethylthio)acetic acid

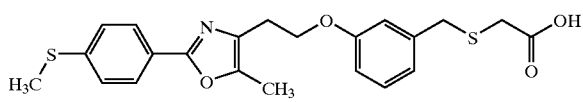

TLC: Rf 0.33 (water:methanol:chloroform=1:10:100);

NMR (CDCl$_3$): δ7.88 (d, J=8.5 Hz, 2H), 7.27 (d, J=8.5 Hz, 2H), 7.20 (dd, J=8.0, 8.0 Hz, 1H), 7.03 (dd, J=2.5, 2.0 Hz, 1H), 6.88 (ddd, J=8.0, 2.0, 1.0 Hz, 1H), 6.80 (ddd, J=8.0, 2.5, 1.0 Hz, 1H), 4.27 (t, J=7.5 Hz, 2H), 3.85 (s, 2H), 3.16 (s, 2H), 2.96 (t, J=7.5 Hz, 2H), 2.51 (s, 3H), 2.37 (s, 3H).

EXAMPLE 2(77)

2-(3-(2-(5-methyl-2-(pyridin-2-yl)oxazol-4-yl)ethoxy)phenylmethylthio)acetic acid

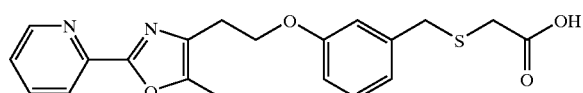

TLC: Rf 0.55 (chloroform:methanol=5:1);

NMR (CDCl$_3$): δ8.77 (ddd, J=4.9, 1.8, 0.8 Hz, 1H), 8.04 (ddd, J=8.0, 1.2, 0.8 Hz, 1H), 7.84 (ddd, J=8.0, 7.6, 1.8 Hz, 1H), 7.38 (ddd, J=7.6, 4.9., 1.2 Hz, 1H), 7.23 (dd, J=7.8, 7.8 Hz, 1H), 7.10 (m, 1H), 6.92 (m, 1H), 6.81 (m, 1H), 4.34 (t, J=7.0 Hz, 2H), 3.85 (s, 2H), 3.13 (s, 2H), 2.99 (t, J=7.0 Hz, 2H), 2.42 (s, 3H).

EXAMPLE 2(78)

2-(3-(2-(5-methyl-2-(thiophen-2-yl)oxazol-4-yl)ethoxy)phenylmethylthio)acetic acid

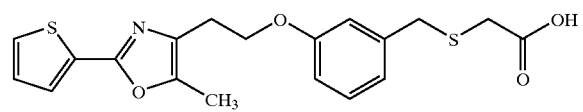

TLC: Rf 0.52 (chloroform:methanol=5:1);

NMR (CDCl$_3$): δ7.64 (dd, J=3.6, 1.2 Hz, 1H), 7.39 (dd, J=5.0, 1.2 Hz, 1H), 7.20 (dd, J=7.8, 7.8 Hz, 1H), 7.09 (dd, J=5.0, 3.6 Hz, 1H), 7.00 (m, 1H), 6.88 (m, 1H), 6.80 (m, 1H), 4.25 (t, J=7.4 Hz, 2H), 3.85 (s, 2H), 3.16 (s, 2H), 2.95 (t, J=7.4 Hz, 2H), 2.36 (s, 3H).

EXAMPLE 2(79)

2-(3-(2-(5-methyl-2-(3-nitro-4-methylphenyl)oxazol-4-yl)ethoxy)phenylmethylthio)acetic acid

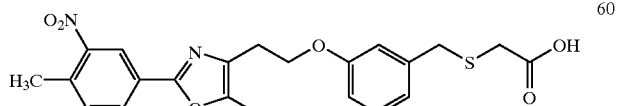

TLC: Rf 0.40 (ethyl acetate);

NMR (CDCl$_3$): δ8.52 (s, 1H), 8.07 (d, J=8.0 Hz, 1H), 7.39 (d, J=8.0 Hz, 1H), 7.18 (m, 1H), 6.70–7.00 (m, 3H), 4.23 (t, J=6.6 Hz, 2H), 3.78 (s, 2H), 3.11 (s, 2H), 2.97 (t, J=6.6 Hz, 2H), 2.61 (s, 3H), 2.39 (s, 3H).

EXAMPLE 2(80)

2-(3-(2-(5-methyl-2-(4-dimethylaminophenyl)oxazol-4-yl)ethoxy)phenylmethylthio)acetic acid

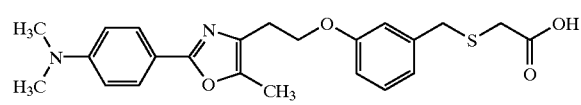

TLC: Rf 0.47 (water:methanol:chloroform=1:10:100);

NMR (CDCl$_3$): δ7.84 (d, J=9.0 Hz, 2H), 7.20 (dd, J=8.0, 8.0 Hz, 1H), 7.11 (dd, J=2.0, 1.0 Hz, 1H), 6.87 (dd, J=8.0, 1.0 Hz, 1H), 6.80 (dd, J=8.0, 2.0 Hz, 1H), 6.71 (d, J=9.0 Hz, 2H), 4.29 (t, J=8.0 Hz, 2H), 3.88 (s, 2H), 3.19 (s, 2H), 3.02 (s, 6H), 2.94 (t, J=8.0 Hz, 2H), 2.35 (s, 3H).

EXAMPLE 2(81)

2-(3-(2-(5-methyl-2-cyclopentyloxazol-4-yl)ethoxy)phenylmethylthio)acetic acid

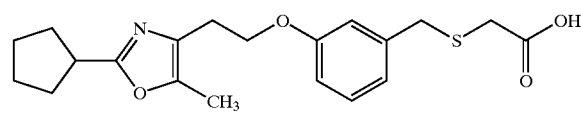

TLC: Rf 0.44 (chloroform:methanol=9:1);

NMR (CDCl$_3$): δ7.20 (dd, J=7.5, 7.5 Hz, 1H), 7.10 (br., 1H), 6.85 (d, J=7.5 Hz, 1H), 6.80 (dd, J=7.5, 1.5 Hz, 1H), 4.20 (t, J=7.5 Hz, 2H), 3.85 (s, 2H), 3.20 (s, 2H), 3.15 (m, 1H), 2.85 (t, J=7.5 Hz, 2H), 2.25 (s, 3H), 2.20–1.60 (m, 8H).

Bis(2-(3-(2-(5-methyl-2-cyclopentyloxazol-4-yl)ethoxy)phenylmethylthio)acetic acid) .ethylenediamine salt

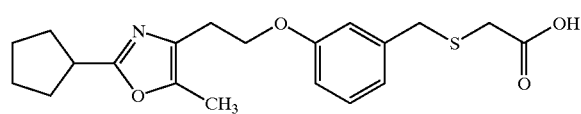

TLC: Rf 0.29 (chloroform:methanol=10:1);

NMR (DMSO-d$_6$): δ7.18 (t, J=8.0 Hz, 1H), 6.88–6.72 (m, 3H), 4.09 (t, J=6.8 Hz, 2H), 3.69 (s, 2H), 3.19–3.00 (m, 1H), 2.96 (s, 2H), 2.84 (s, 2H), 2.78 (t, J=6.8 Hz, 2H), 2.21 (s, 3H), 2.06–1.48 (m, 8H).

EXAMPLE 2(82)

2-(3-(2-(5-methyl-2-(4-methylphenyl)oxazol-4-yl)ethoxy)phenyl)acetic acid

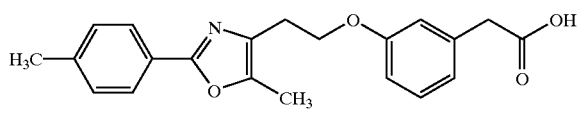

TLC: Rf 0.46 (chloroform:methanol=10:1);

NMR (CDCl$_3$): δ7.85 (d, J=8.4 Hz, 2H), 7.27–7.14 (m, 3H), 6.89–6.75 (m, 3H), 4.20 (t, J=6.6 Hz, 2H), 3.59 (s, 2H), 2.96 (t, J=6.6 Hz, 2H), 2.38 (s, 3H), 2.35 (s, 3H).

EXAMPLE 2(83)

2-(3-(2-(5-methyl-2-(4-ethylphenyl)oxazol-4-yl)ethoxy)phenyl)acetic

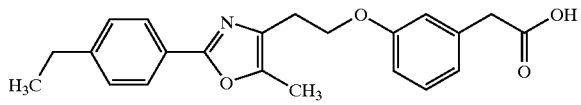

TLC: Rf 0.54 (chloroform:methanol=10:1);

NMR (CDCl$_3$): δ7.88 (d, J=8.2 Hz, 2H), 7.29–7.15 (m, 3H), 6.89–6.75 (m, 3H), 4.20 (t, J=6.6 Hz, 2H), 3.60 (s, 2H), 2.96 (t, J=6.6 Hz, 2H), 2.68 (q, J=7.6 Hz, 2H), 2.35 (s, 3H), 1.25 (t, J=7.6 Hz, 3H).

EXAMPLE 2(84)

2-(3-(2-(5-methyl-2-(4-propylphenyl)oxazol-4-yl)ethoxy)phenyl)acetic acid

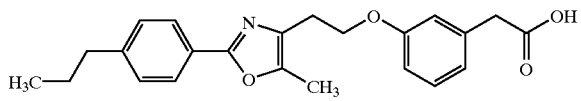

TLC: Rf 0.57 (chloroform:methanol=10:1);

NMR (CDCl$_3$): δ7.87 (d, J=8.2 Hz, 2H), 7.28–7.15 (m, 3H), 6.88–6.76 (m, 3H), 4.20 (t, J=6.6 Hz, 2H), 3.59 (s, 2H), 2.96 (t, J=6.6 Hz, 2H), 2.61 (t, J=7.5 Hz, 2H), 2.35 (s, 3H), 1.65 (sixtet, J=7.5 Hz, 2H), 0.94 (t, J=7.5 Hz, 3H).

EXAMPLE 2(85)

2-(3-(2-(5-methyl-2-(4-isopropylphenyl)oxazol-4-yl)ethoxy)phenyl)acetic acid

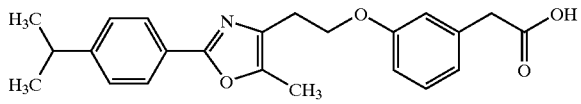

TLC: Rf 0.52 (chloroform:methanol=10:1);

NMR (CDCl$_3$): δ7.88 (d, J=8.2 Hz, 2H), 7.32–7.15 (m, 3H), 6.88–6.76 (m, 3H), 4.19 (t, J=6.6 Hz, 2H), 3.59 (s, 2H), 2.96 (t, J=6.6 Hz, 2H), 2.93 (sept, J=7.2 Hz, 1H), 1.25 (d, J=7.2 Hz, 6H).

EXAMPLE 2(86)

2-(3-(2-(5-methyl-2-(4-(2-methylpropyl)phenyl)oxazol-4-yl)ethoxy)phenyl)acetic acid

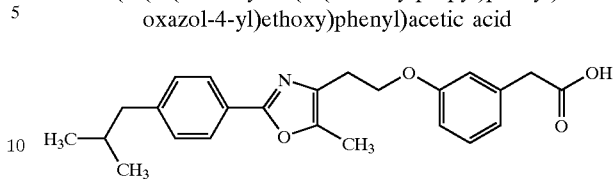

TLC: Rf 0.50 (chloroform:methanol=10:1);

NMR (CDCl$_3$): δ7.87 (d, J=8.2 Hz, 2H), 7.26–7.15 (m, 3H), 6.89–6.76 (m, 3H), 4.20 (t, J=6.6 Hz, 2H), 3.59 (s, 2H), 2.96 (t, J=6.6 Hz, 2H), 2.50 (d, J=7.0 Hz, 2H), 2.35 (s, 3H), 1.88 (m, 1H), 0.90 (d, J=6.6 Hz, 6H).

EXAMPLE 2(87)

2-(3-(2-(5-methyl-2-(4-t-butylphenyl)oxazol-4-yl)ethoxy)phenyl)acetic acid

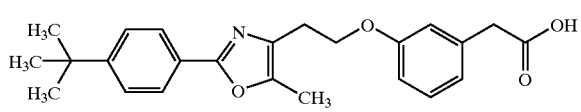

TLC: Rf 0.44 (chloroform:methanol=10:1);

NMR (CDCl$_3$): δ7.89 (d, J=8.2 Hz, 2H), 7.43 (d, J=8.2 Hz, 2H), 7.20 (t, J=8.0 Hz, 1H), 6.89–6.76 (m, 3H), 4.20 (t, J=6.6 Hz, 2H), 3.60 (s, 2H), 2.96 (t, J=6.6 Hz, 2H), 2.35 (s, 3H), 1.33 (s, 9H).

EXAMPLE 2(88)

2-(3-(2-(5-methyl-2-cyclopropyloxazol-4-yl)ethoxy)phenylmethylthio)acetic acid

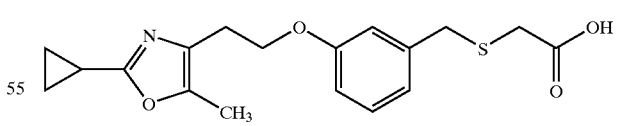

TLC: Rf 0.39 (water:methanol:chloroform=1:10:100);

NMR (CDCl$_3$): δ7.18 (dd, J=8.0, 8.0 Hz, 1H), 7.00 (d, J=2.5 Hz, 1H), 6.86 (d, J=8.0 Hz, 1H), 6.77 (dd, J=8.0, 2.5 Hz, 1H), 4.19 (t, J=7.5 Hz, 2H), 3.83 (s, 2H), 3.15 (s, 2H), 2.84 (t, J=7.5 Hz, 2H), 2.22 (s, 3H), 2.06 (m, 1H), 1.10–0.95 (m, 4H).

EXAMPLE 2(89)

2-(3-(2-(5-methyl-2-(4-(1,2,3-thiadiazol-4-yl)phenyl)oxazol-4-yl)ethoxy)phenylmethylthio)acetic acid

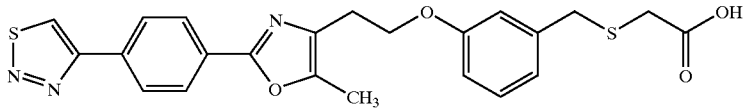

TLC: Rf 0.30 (chloroform:methanol=10:1);

NMR (CD$_3$OD): δ9.35 (d, J=0.8 Hz, 1H), 8.24 (d, J=8.2 Hz, 2H), 8.11 (d, J=8.2 Hz, 2H), 7.20 (t, J=7.6 Hz, 1H), 6.95–6.78 (m, 3H), 4.27 (t, J=6.2 Hz, 2H), 3.78 (s, 2H), 3.06 (s, 2H), 3.00 (t, J=6.2 Hz 2H), 2.41 (s, 3H).

EXAMPLE 2(90)

2-(3-(2-(5-methyl-2-(4-(4-methyl-1,2,3-thiadiazol-5-yl)phenyl)oxazol-4-yl)ethoxy)phenylmethylthio)acetic acid

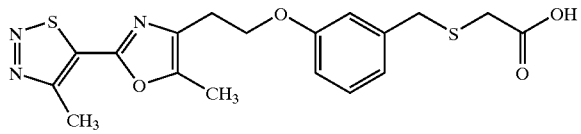

TLC: Rf 0.34 (chloroform:methanol=10:1);

NMR (CDCl$_3$): δ7.22 (t, J=8.0 Hz, 1H), 6.95–6.74 (m, 3H), 4.24 (t, J=6.2 Hz, 2H), 3.81 (s, 2H), 3.11 (s, 2H), 3.02 (s, 3H), 2.99 (t, J=6.2 Hz, 2H), 2.42 (s, 3H).

EXAMPLE 2(91)

2-(3-(2-(5-methyl-2-(4-methoxyphenyl)oxazol-4-yl)ethoxy)phenyl)acetic acid

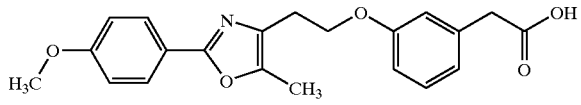

TLC: Rf 0.67 (chloroform:methanol=10:1);

NMR (CDCl$_3$): δ7.90 (d, J=9.0 Hz, 2H), 7.20 (t, J=8.0 Hz, 1H), 6.93 (d, J=9.0 Hz, 2H), 6.89–6.76 (m, 3H), 4.19 (t, J=6.6 Hz, 2H), 3.84 (s, 3H), 3.59 (s, 2H), 2.95 (t, J=6.6 Hz, 2H), 2.34 (s, 3H).

EXAMPLE 2(92)

2-(3-(2-(5-methyl-2-(3,4-dimethoxyphenyl)oxazol-4-yl)ethoxy)phenyl)acetic acid

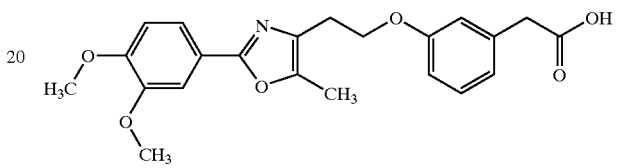

TLC: Rf 0.54 (chloroform:methanol=10:1);

NMR (CDCl$_3$+CD$_3$OD): δ7.56 (dd, J=8.2, 2.0 Hz, 1H), 7.51 (d, J=2.0 Hz, 1H), 7.22 (t, J=8.0 Hz, 1H), 6.93 (d, J=8.2 Hz, 1H), 6.90–6.77 (m, 3H), 4.22 (t, J=6.6 Hz, 2H), 3.97 (s, 3H), 3.93 (s, 3H), 3.57 (s, 2H), 2.96 (t, J=6.6 Hz, 2H), 2.38 (s, 3H).

EXAMPLE 2(93)

2-(3-(2-(5-methyl-2-(1,3-dioxaindan-5-yl)oxazol-4-yl)ethoxy)phenyl)acetic acid

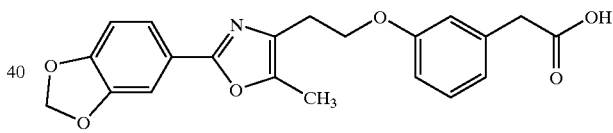

TLC: Rf 0.53 (chloroform:methanol=10:1);

NMR (CDCl$_3$): δ7.51 (dd, J=8.2, 1.8 Hz, 1H), 7.43 (d, J=1.8 Hz, 1H), 7.21 (t, J=7.6 Hz, 1H), 6.89–6.76 (m, 4H), 6.00 ( s, 2H), 4.19 (t, J=6.6 Hz, 2H), 3.60 (s, 2H), 2.94 (t, J=6.6 Hz, 2H), 2.34 (s, 3H).

EXAMPLE 2(94)

2-(3-(2-(5-methyl-2-(3,4,5-trimethoxyphenyl)oxazol-4-yl)ethoxy)phenyl)acetic acid

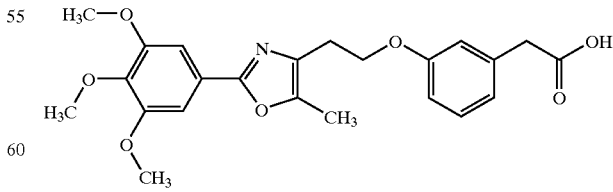

TLC: Rf 0.47 (chloroform:methanol=10:1);

NMR (CDCl$_3$): δ7.21 (t, J=8.0 Hz, 1H), 7.20 (s, 2H), 6.89–6.76 (m, 3H), 4.21 (t, J=6.6 Hz, 2H), 3.91 (s, 6H), 3.88 (s, 3H), 3.60 (s, 2H), 2.97 (t, J=6.6 Hz, 2H), 2.38 (s, 3H).

EXAMPLE 2(95)

2-(3-(2-(5-methyl-2-(4-trifluoromethoxyphenyl)oxazol-4-yl)ethoxy)phenyl)acetic acid

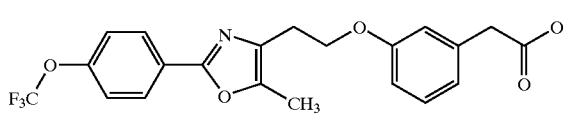

TLC: Rf 0.57 (chloroform:methanol=10:1);

NMR (CDCl$_3$): δ8.00 (d, J=8.8 Hz, 2H), 7.30–7.16 (m, 3H), 6.89–6.76 (m, 3H), 4.21 (t, J=6.6 Hz, 2H), 3.60 (s, 2H), 2.96 (t, J=6.6 Hz, 2H), 2.37 (s, 3H).

EXAMPLE 2(96)

2-(3-(2-(5-methyl-2-(2,2-difluoro-1,3-dioxaindan-5-yl)oxazol-4-yl)ethoxy)phenyl)acetic acid

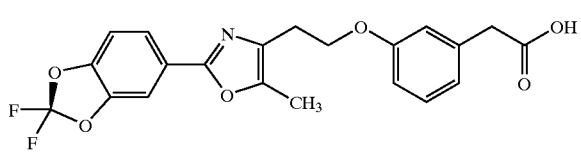

TLC: Rf 0.53 (chloroform:methanol=10:1);

NMR (CDCl$_3$): δ7.74 (dd, J=8.4, 1.5 Hz, 1H), 7.68 (d, J=1.5 Hz, 1H), 7.22 (dd, J=9.4, 7.4 Hz, 1H), 7.09 (d, J=8.4 Hz, 1H), 6.89–6.76 (m, 3H), 4.21 (t, J=6.6 Hz, 2H), 3.60 (s, 2H), 2.95 (t, J=6.6 Hz, 2H), 2.36 (s, 3H).

EXAMPLE 2(97)

2-(3-(2-(5-methyl-2-(4-trifluoromethylthiophenyl)oxazol-4-yl)ethoxy)phenylmethylthio)acetic acid

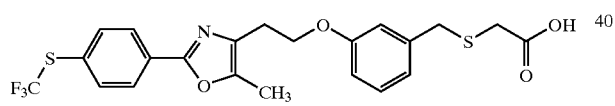

TLC: Rf 0.47 (chloroform:methanol=10:1);

NMR (DMSO-d$_6$): δ8.02 (d, J=8.1 Hz, 2H), 7.81 (d, J=8.1 Hz, 2H), 7.20 (t, J=7.8 Hz, 1H), 6.86–6.80 (m, 3H), 4.20 (t, J=6.6 Hz, 2H), 3.74 (s, 2H), 3.09 (s, 2H), 2.94 (t, J=6.6 Hz, 2H), 2.37 (s, 3H).

EXAMPLE 2(98)

2-(3-(2-(5-methyl-2-(4-cyanophenyl)oxazol-4-yl)ethoxy)phenylmethylthio)acetic acid

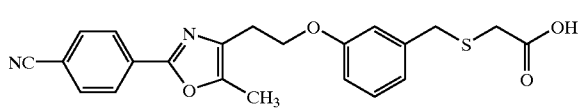

TLC: Rf 0.24 (hexane:ethyl:acetate=1:1);

NMR (CDCl$_3$): δ8.08 (d, J=8.0 Hz, 2H), 7.72 (d, J=8.0 Hz, 2H), 7.22 (m, 1H), 6.76–6.98 (m, 3H), 4.26 (t, J=6.6 Hz, 2H), 3.83 (s, 2H), 3.13 (s, 2H), 2.99 (t, J=6.6 Hz, 2H), 2.42 (s, 3H).

EXAMPLE 2(99)

2-(3-(2-(5-methyl-2-(furan-2-yl)oxazol-4-yl)ethoxy)phenylmethylthio)acetic acid

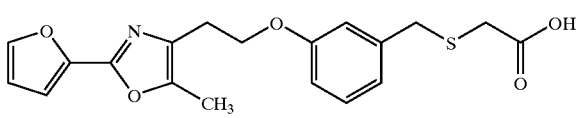

TLC: Rf 0.24 (hexane:ethyl:acetate=1:1);

NMR (CDCl$_3$): δ7.52 (m, 1H), 7.20 (m, 1H), 6.74–7.03 (m, 4H), 6.51 (dd, J=3.4, 1.6 Hz, 1H), 4.25 (t, J=6.8 Hz, 2H), 3.82 (s, 2H), 3.13 (s, 2H), 2.97 (t, J=6.8 Hz, 2H), 2.37 (s, 3H).

EXAMPLE 2(100)

2-(3-(5-methyl-2-phenyloxazol-4-yl)methoxy)phenyl)acetic acid

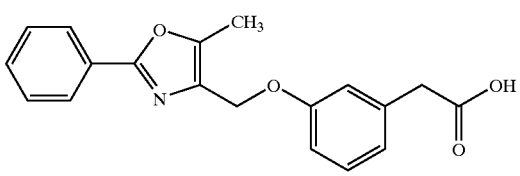

TLC: Rf 0.31 (chloroform:methanol=8:1);

NMR (CDCl$_3$): δ8.00 (m, 2H), 7.42 (m, 3H), 7.24 (m, 1H), 6.85–6.98 (m, 3H), 4.98 (s, 2H), 3.61 (s, 2H), 2.42 (s, 3H).

EXAMPLE 2(101)

2-(3-(2-(5-methyl-2-phenylthiazol-4-yl)ethoxy)phenyl)acetic acid

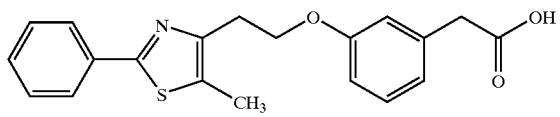

TLC: Rf 0.43 (chloroform:methanol=9:1);

NMR (CDCl): δ7.89–7.81 (m, 2H), 7.46–7.34 (m, 3H), 7.26–7.16 (m, 1H), 6.87–6.78 (m, 3H), 4.30 (t, J=6.8 Hz, 2H), 3.59 (s, 2H), 3.18 (t, J=6.8 Hz, 2H), 2.45 (s, 3H).

EXAMPLE 2(102)

2-(3-(3-(5-methyl-2-phenyloxazol-4-yl)propoxy)phenyl)acetic acid

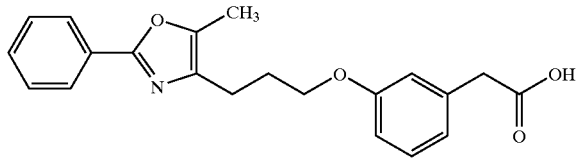

TLC: Rf 0.50 (chloroform:methanol=8:1);

NMR (CDCl$_3$): δ7.97 (m, 2H), 7.41 (m, 3H), 7.22 (m, 1H), 6.74–6.92 (m, 3H), 3.94 (t, J=6.0 Hz, 2H), 3.61 (s, 2H), 2.68 (t, J=7.0 Hz, 2H), 2.27 (s, 3H), 2.11 (m, 2H).

EXAMPLE 2(103)

2-(3-(2-(2-phenyloxazol-4-yl)ethoxy)phenyl)acetic acid

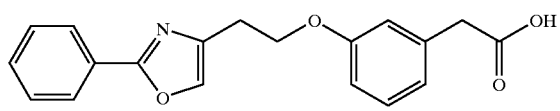

TLC: Rf 0.39 (chloroform:methanol=8:1);

NMR (CDCl$_3$): δ8.01 (m, 2H), 7.55 (s, 1H), 7.43 (m, 3H), 7.23 (m, 1H), 6.85 (m, 3H), 4.25 (t, J=6.4 Hz, 2H), 3.60 (s, 2H), 3.07 (t, J=6.4 Hz, 2H).

EXAMPLE 2(104)

2-(3-(2-(5-methyl-2-(4-cyclohexylphenyl)oxazol-4-yl)ethoxy)phenyl)acetic acid

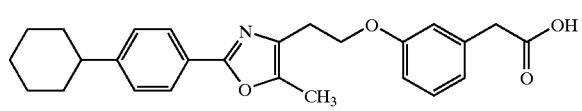

TLC: Rf 0.62 (chloroform:methanol=5:1);

NMR (CDCl$_3$): δ7.88 (d, J=8.2 Hz, 2H), 7.25 (d, J=8.2 Hz, 2H), 7.21 (m, 1H), 6.78–6.87 (m, 3H), 4.20 (t, J=6.6 Hz, 2H), 3.60 (s, 2H), 2.96 (t, J=6.6 Hz, 2H), 2.52 (m, 1H), 2.35 (s, 3H), 1.70–1.95 (m, 4H), 1.20–1.53 (m, 6H).

EXAMPLE 2(105)

2-(3-(2-(5-methyl-2-(3-chloro-4-methylphenyl)oxazol-4-yl)ethoxy)phenyl)acetic acid

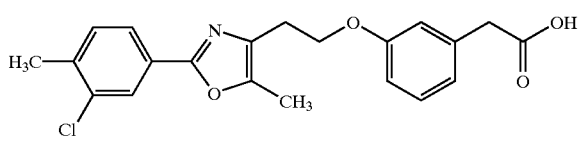

TLC: Rf 0.67 (chloroform:methanol=5:1);

NMR (CDCl$_3$): δ7.95 (d, J=1.7 Hz, 1H), 7.75 (dd, J=8.0, 1.7 Hz, 1H), 7.27 (d, J=8.0 Hz, 1H), 7.21 (m, 1H), 6.78–6.88 (m, 3H), 4.21 (t, J=6.6 Hz, 2H), 3.60 (s, 2H), 2.96 (t, J=6.6 Hz, 2H), 2.40 (s, 3H), 2.36 (s, 3H).

EXAMPLE 2(106)

2-(3-(2-(5-methyl-2-(4-dimethylaminophenyl)oxazol-4-yl)ethoxy)phenyl)acetic acid

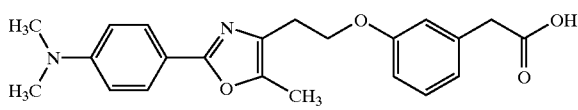

TLC: Rf 0.55 (chloroform:methanol=5:1);

NMR (CDCl$_3$): δ7.83 (d, J=9.0 Hz, 2H), 7.09 (dd, J=8.0, 8.0 Hz, 1H), 6.76–6.87 (m, 3H), 6.70 (d, J=9.0 Hz, 2H), 4.18 (t, J=6.8 Hz, 2H), 3.60 (s, 2H), 3.01 (s, 6H), 2.94 (t, J=6.8 Hz, 2H), 2.32 (s, 3H).

EXAMPLE 2(107)

2-(3-(2-(5-ethyl-2-phenyloxazol-4-yl)ethoxy)phenyl) acetic acid

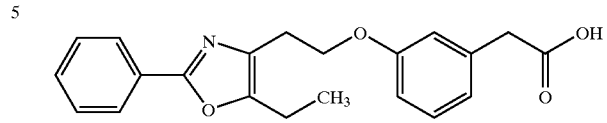

TLC: Rf 0.44 (chloroform methanol=8:1);

NMR (CDCl$_3$): δ7.97 (m, 2H), 7.41 (m, 3H), 7.20 (m, 1H), 6.82 (m, 3H), 4.20 (t, J=6.6 Hz, 2H), 3.59 (s, 2H), 2.98 (t, J=6.6 Hz, 2H), 2.73 (q, J=7.6 Hz, 2H), 1.29 (t, J=7.6 Hz, 3H).

EXAMPLE 2(108)

2-(3-(2-(5-methyl-2-(4-butylphenyl)oxazol-4-yl)ethoxy)phenyl)acetic acid

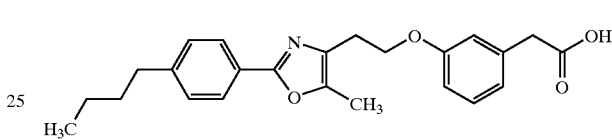

TLC: Rf 0.54 (chloroform:methanol=8:1);

NMR (CDCl$_3$): δ7.87 (d, J=8.2 Hz, 2H), 7.22 (d, J=8.2 Hz, 2H), 7.14–7.28 (m, 1H), 6.82 (m, 3H), 4.19 (t, J=6.6 Hz, 2H), 3.59 (s, 2H), 2.96 (t, J=6.6 Hz, 2H), 2.63 (t, J=7.6 Hz, 2H), 2.34 (s, 3H), 1.61 (m, 2H), 1.35 (m, 2H), 0.92 (t, J=7.2 Hz, 3H).

EXAMPLE 2(109)

2-(3-(2-(5-methyl-2-(4-chlorophenyl)oxazol-4-yl)ethoxy)phenyl)acetic acid

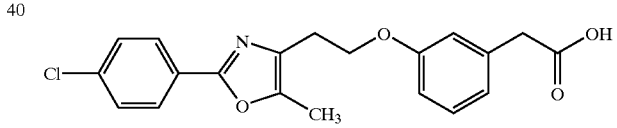

TLC: Rf 0.57 (chloroform:methanol=8:1);

NMR (CDCl$_3$): δ7.90 (d, J=8.8Hz, 2H), 7.38 (d, J=8.8 Hz, 2H), 7.16–7.28 (m, 1H), 6.83 (m, 3H), 4.20 (t, J=6.6 Hz, 2H), 3.59 (s, 2H), 2.96 (t, J=6.6 Hz, 2H), 2.36 (s, 3H).

EXAMPLE 2(110)

2-(3-(2-(5-methyl-2-(thiophen-2-yl)oxazol-4-yl)ethoxy)phenyl)acetic acid

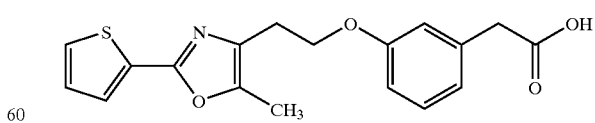

TLC: Rf 0.70 (chloroform:methanol=5:1);

NMR (CDCl$_3$): δ7.59 (dd, J=3.6, 1.2 Hz, 1H), 7.36 (dd, J=4.8, 1.2 Hz, 1H), 7.21 (m, 1H), 7.07 (dd, J=4.8, 3.6 Hz, 1H), 6.77–6.87 (m, 3H), 4.20 (t, J=6.6 Hz, 2H), 3.60 (s, 2H), 2.95 (t, J=6.6 Hz, 2H), 2.34 (s, 3H).

EXAMPLE 2(111)

2-(3-(2-(5-methyl-2-(furan-2-yl)oxazol-4-yl)ethoxy)phenyl)acetic acid

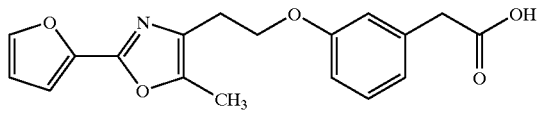

TLC: Rf 0.69 (chloroform:methanol=5:1);

NMR (CDCl$_3$): δ7.51 (m, 1H), 7.21 (m, 1H), 6.93 (d, J=3.5 Hz, 1H), 6.78–6.87 (m, 3H), 6.50 (dd, J=3.5, 1.9 Hz, 1H), 4.22 (t, J=6.6 Hz, 2H), 3.59 (s, 2H), 2.95 (t, J=6.6 Hz, 2H), 2.35 (s, 3H).

EXAMPLE 2(112)

2-(3-(2-(5-methyl-2-(pyridin-2-yl)oxazol-4-yl)ethoxy)phenyl)acetic acid

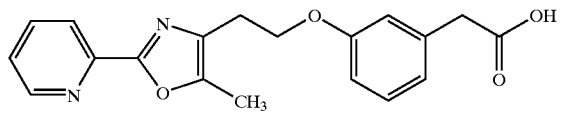

TLC: Rf 0.67 (chloroform:methanol=5:1);

NMR (CDCl$_3$): δ8.71 (d, J=4.8 Hz, 1H), 8.05 (d, J=7.8 Hz, 1H), 7.79 (ddd, J=7.8, 7.8, 1.8 Hz, 1H), 7.32 (ddd, J=7.8, 4.8, 1.8 Hz, 1H), 7.21 (dd, J=7.8, 7.8 Hz, 1H), 6.78–6.87 (m, 3H), 4.26 (t, J=6.8 Hz, 2H), 3.61 (s, 2H), 2.99 (t, J=6.8 Hz, 2H), 2.41 (s, 3H).

EXAMPLE 2(113)

2-(3-(2-(5-methyl-2-(2-methylphenyl)oxazol-4-yl)ethoxy)phenyl)acetic acid

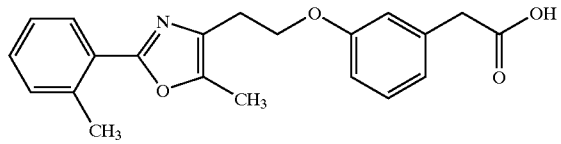

TLC: Rf 0.68 (chloroform:methanol=5:1);

NMR (CDCl$_3$): δ7.90 (m, 1H), 7.18–7.30 (m, 4H), 6.80–6.87 (m, 3H), 4.24 (t, J=6.7 Hz, 2H), 3.60 (s, 2H), 2.98 (t, J=6.7 Hz, 2H), 2.64 (s, 3H), 2.37 (s, 3H).

EXAMPLE 2(114)

2-(3-(2-(5-methyl-2-(3-methylphenyl)oxazol-4-yl)ethoxy)phenyl)acetic acid

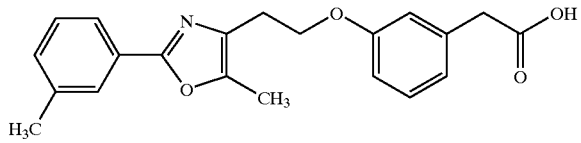

TLC: Rf 0.71 (chloroform:methanol=5:1);

NMR (CDCl$_3$): δ7.74–7.81 (m, 2H), 7.17–7.35 (m, 3H), 6.78–6.87 (m, 3H), 4.21 (t, J=6.6 Hz, 2H), 3.60 (s, 2H), 2.97 (t, J=6.6 Hz, 2H), 2.39 (s, 3H), 2.36 (s, 3H).

EXAMPLE 2(115)

2-(3-(2-(5-methyl-2-(4-trifluoromethylphenyl)oxazol-4-yl)ethoxy)phenyl)acetic acid

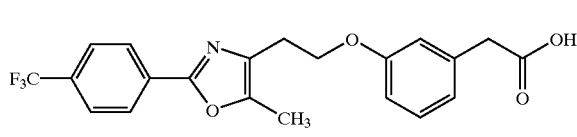

TLC: Rf 0.54 (chloroform:methanol=8:1);

NMR (CDCl$_3$): δ8.08 (d, J=8.0 Hz, 2H), 7.67 (d, J=8.0 Hz, 2H), 7.17–7.24 (m, 1H), 6.83 (m, 3H), 4.23 (t, J=6.6 Hz, 2H), 3.60 (s, 2H), 2.98 (t, J=6.6 Hz, 2H), 2.39 (s, 3H).

EXAMPLE 2(116)

2-(3-(2-(5-methyl-2-(4-fluorophenyl)oxazol-4-yl)ethoxy)phenyl)acetic acid

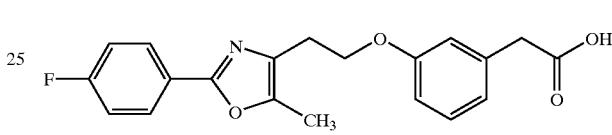

TLC: Rf 0.59 (chloroform:methanol=8:1);

NMR (CDCl$_3$): δ7.95 (m, 2H), 7.03–7.26 (m, 3H), 6.83 (m, 3H), 4.20 (t, J=6.6 Hz, 2H), 3.59 (s, 2H), 2.96 (t, J=6.6 Hz, 2H), 2.35 (s, 3H).

EXAMPLE 2(117)

2-(3-(2-(5-methyl-2-(4-cyanophenyl)oxazol-4-yl)ethoxy)phenyl)acetic acid

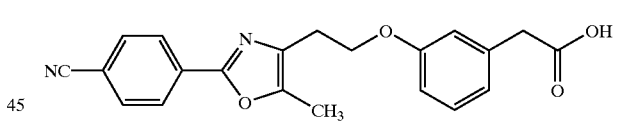

TLC: Rf 0.52 (chloroform:methanol=9:1);

NMR (CDCl$_3$): δ8.06 (d, J=8.6 Hz, 2H), 7.70 (d, J=8.6 Hz, 2H), 7.22 (m, 1H), 6.78–6.87 (m, 3H), 4.23 (t, J=6.4 Hz, 2H), 3.60 (s, 2H), 2.98 (t, J=6.4 Hz, 2H), 2.40 (s, 3H)

EXAMPLE 2(118)

2-(3-(2-(5-methyl-2-(4-methyl-1,2,3-thiadiazol-5-yl)oxazol-4-yl)ethoxy)phenyl)acetic acid

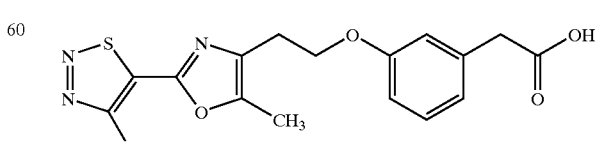

TLC: Rf 0.54 (chloroform:methanol=9:1);

NMR (CDCl$_3$): δ7.23 (m, 1H), 6.78–6.88 (m, 3H), 4.23 (t, J=6.5 Hz, 2H), 3.60 (s, 2H), 3.02 (s, 3H), 2.98 (t, J=6.5 Hz, 2H), 2.40 (s, 3H).

EXAMPLE 2(119)

2-(3-(2-(5-methyl-2-(2,3,5,6-tetrafluoro-4-methylphenyl)oxazol-4-yl)ethoxy)phenyl)acetic acid

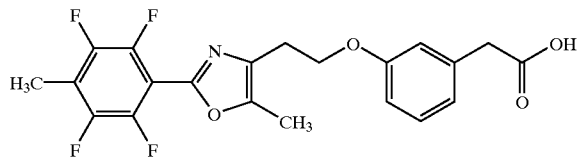

TLC: Rf 0.34 (chloroform:methanol=8:1);

NMR (CDCl$_3$): δ7.22 (m, 1H), 6.76–6.90 (m, 3H), 4.23 (t, J=6.4 Hz, 2H), 3.60 (s, 2H), 3.01 (t, J=6.4 Hz, 2H), 2.40 (s, 3H), 2.33 (s, 3H).

EXAMPLE 2(120)

2-(3-(2-(5-methyl-2-(3-nitro-4-methylphenyl)oxazol-4-yl)ethoxy)phenyl)acetic acid

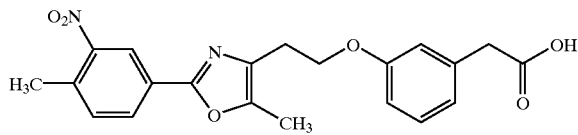

TLC: Rf 0.31 (chloroform:methanol=8:1);

NMR (CDCl$_3$): δ8.54 (d, J=1.6 Hz, 1H), 8.08 (dd, J=8.0, 1.6 Hz, 1H), 7.39 (d, J=8.0 Hz, 1H), 7.17 (m, 1H), 6.66–6.90 (m, 3H), 4.21 (t, J=6.4 Hz, 2H), 3.59 (s, 2H), 2.97 (t, J=6.4 Hz, 2H), 2.63 (s, 3H), 2.39 (s, 3H).

EXAMPLE 2(121)

2-(3-(2-(5-methyl-2-cyclohexyloxazol-4-yl)ethoxy)phenyl)acetic acid

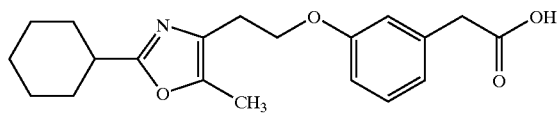

TLC: Rf 0.44 (chloroform:methanol=9:1);

NMR (CDCl$_3$): δ7.19 (dd, J=8.0, 8.0 Hz, 1H), 6.74–6.87 (m, 3H), 4.10 (t, J=6.6 Hz, 2H), 3.59 (s, 2H), 2.85 (t, J=6.6 Hz, 2H), 2.71 (m, 1H), 2.23 (s, 3H), 1.96–2.04 (m, 2H), 1.19–1.86 (m, 8H).

EXAMPLE 2(122)

2-(3-(2-(5-methyl-2-cyclopentyloxazol-4-yl)ethoxy)phenyl)acetic acid

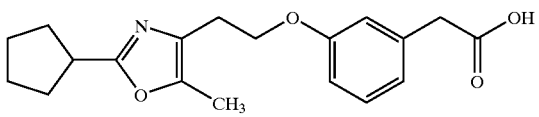

TLC: Rf 0.46 (chloroform:methanol=9:1);

NMR (CDCl$_3$): δ7.19 (dd, J=7.9, 7.9 Hz, 1H), 6.74–6.87 (m, 3H), 4.11 (t, J=6.6 Hz, 2H), 3.59 (s, 2H), 3.14 (m, 1H), 2.86 (t, J=6.6 Hz, 2H), 2.24 (s, 3H), 1.56–2.12 (m, 8H).

EXAMPLE 2(123)

2-(3-(2-(5-methyl-2-(4-pentylphenyl)oxazol-4-yl)ethoxy)phenyl)acetic acid

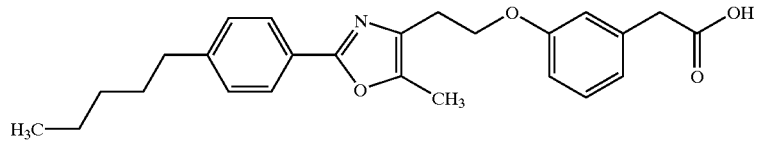

TLC: Rf 0.44 (chloroform:methanol=8:1);

NMR (CDCl$_3$): δ7.87 (d, J=8.4 Hz, 2H), 7.22 (d, J=8.4 Hz, 2H), 7.20 (m, 1H), 6.75–6.90 (m, 3H), 4.19 (t, J=6.6 Hz, 2H), 3.59 (s, 2H), 2.96 (t, J=6.6 Hz, 2H), 2.62 (t, J=7.6 Hz, 2H), 2.35 (s, 3H), 1.62 (m, 2H), 1.23–1.44 (m, 4H), 0.89 (t, J=6.8 Hz, 3H).

EXAMPLE 2(124)

2-(3-(2-(5-methyl-2-(pyridin-4-yl)oxazol-4-yl)ethoxy)phenylmethylthio)acetic acid

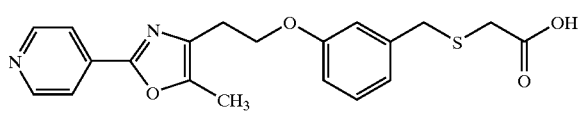

TLC: Rf 0.36 (chloroform:methanol=4:1);

NMR (DMSO-d$_6$): δ8.75 (d, J=6 Hz, 2H), 7.80 (d, J=6 Hz, 2H), 7.20 (dd, J=8, 8 Hz, 1H), 6.95–6.80 (m, 3H), 4.20 (t, J=7 Hz, 2H), 3.75 (s, 2H), 3.05 (s, 2H), 2.95 (t, J=7 Hz, 2H), 2.40 (s, 3H).

EXAMPLE 2(125)

2-(3-(2-(5-methyl-2-(pyridin-3-yl)oxazol-4-yl)ethoxy)phenyl)acetic acid

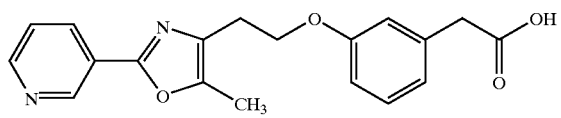

TLC: Rf 0.39 (chloroform:methanol=9:1);

NMR (DMSO-d$_6$): δ12.28 (brs, 1H), 9.07 (d, J=1.5 Hz, 1H), 8.65 (d, J=4.8 Hz, 1H), 8.24 (d, J=8.4 Hz, 1H), 7.52 (dd, J=8.4 Hz, 4.8 Hz, 1H), 7.21–7.16 (m, 1H), 6.82–6.79 (m, 3H), 4.18 (t, J=6.6 Hz, 2H), 3.50 (s, 2H), 2.93 (t, J=6.6 Hz, 2H), 2.37 (s, 3H).

EXAMPLE 2(126)

2-(3-(2-(5-methyl-2-(pyridin-4-yl)oxazol-4-yl)ethoxy)phenyl)acetic acid

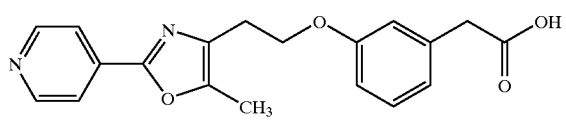

TLC: Rf 0.34 (chloroform:methanol=9:1);

NMR (DMSO-d$_6$): δ12.29 (brs, 1H), 8.69 (d, J=6.0 Hz, 2H), 7.80 (d, J=6.0 Hz, 2H), 7.21–7.16 (m, 1H), 6.82–6.78 (m, 3H), 4.19 (t, J=6.6 Hz, 2H), 3.50 (s, 2H), 2.95 (t, J=6.6 Hz, 2H), 2.38 (s, 3H).

EXAMPLE 2(127)

2-(3-(2-(5-methyl-2-(4-methylpiperazin-1-yl)thiazol-4-yl)ethoxy)phenyl)acetic acid

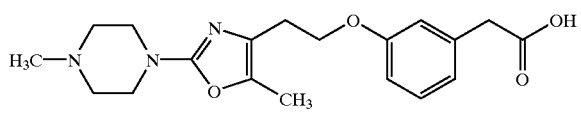

TLC: Rf 0.40 (chloroform:methanol=3:1);

NMR (CDCl$_3$): δ7.00–7.20 (m, 2H), 6.70–6.85 (m, 3H), 4.19 (t, J=6.6 Hz, 2H), 3.46–3.55 (m, 4H), 2.91 (t, J=6.6 Hz, 2H), 2.75–2.83 (m, 4H), 2.47 (s, 3H), 2.24 (s, 3H).

EXAMPLE 2(128)

2-(3-(2-(5-methyl-2-phenyloxazol-4-yl)ethoxy)phenylmethoxy)acetic acid

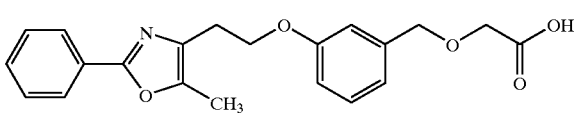

TLC: Rf 0.31 (water:methanol:chloroform=1:10:100);

NMR (CDCl$_3$): δ7.98 (m, 2H), 7.50–7.40 (m, 3H), 7.24 (dd, J=8.0, 8.0 Hz, 1H), 7.00 (m, 1H), 6.95–6.80 (m, 2H), 4.62 (s, 2H), 4.26 (t, J=7.0 Hz, 2H), 4.11 (s, 2H), 2.99 (t, J=7.0 Hz, 2H), 2.39 (s, 3H).

EXAMPLE 2(129)

2-(3-(2-(5methyl-2-(pyridin-3-yl)oxazol-4-yl)ethoxy)phenylmethylthio)acetic acid

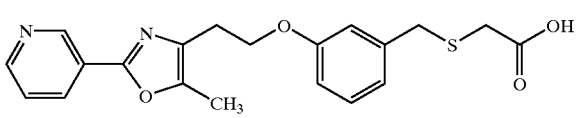

TLC: Rf 0.41 (chloroform:methanol=4:1);

NMR (DMSO-d$_6$): δ9.05 (s, 1H), 8.65 (d, J=4 Hz, 1H), 8.25 (d, J=7 Hz, 1H), 7.55 (m, 1H), 7.20 (dd, J=7, 7 Hz, 1H), 6.95–6.80 (m, 3H), 4.20 (t, J=6 Hz, 2H), 3.80 (s, 2H), 3.10 (s, 2H), 2.95 (t, J=6 Hz, 2H), 2.40 (s, 3H).

EXAMPLE 2(130)

2-(3-(2-(5-methyl-2-(4-methylthiophenyl)oxazol-4-yl)ethoxy)phenyl)acetic acid

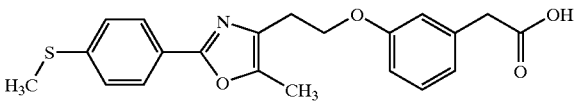

TLC: 0.44 (chloroform:methanol=8:1);

NMR (CDCl$_3$): δ7.87 (d, J=8.6 Hz, 2H), 7.26 (d, J=8.6 Hz, 2H), 7.21 (m, 1H), 6.75–6.89 (m, 3H), 4.20 (t, J=6.6 Hz, 2H), 3.59 (s, 2H), 2.96 (t, J=6.6 Hz, 2H), 2.51 (s, 3H), 2.35 (s, 3H).

EXAMPLE 2(131)

2-(3-(2-(5-methyl-2-cyclopropyloxazol-4-yl)ethoxy)phenyl)acetic acid

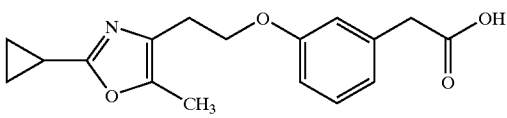

TLC: Rf 0.43 (chloroform:methanol=9:1);

NMR CDCl$_3$): δ7.25–7.10 (m, 1H), 6.86–6.74 (m, 3H), 4.10 (t, J=6.6 Hz, 2H), 3.58 (s, 2H), 2.82 (t, J=6.6 Hz, 2H), 2.20 (s, 3H), 2.04–1.98 (m, 1H), 1.01–0.94 (m, 4H).

EXAMPLE 2(132)

2-(3-(2-(5-methyl-2-(4-nitrophenyl)oxazol-4-yl)ethoxy)phenyl)acetic acid

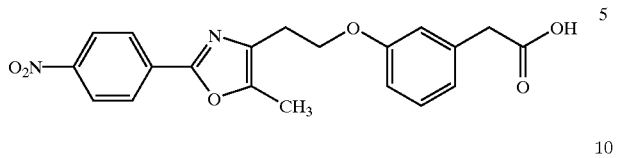

TLC: Rf 0.53 (chloroform:methanol=9:1);

NMR (CDCl$_3$): δ8.30 (d, J=9.0 Hz, 2H), 8.14 (d, J=9.0 Hz, 2H), 7.22 (dd, J=8.0, 8.0 Hz, 1H), 6.77–6.90 (m, 3H), 4.25 (t, J=6.6 Hz, 2H), 3.57 (s, 2H), 3.00 (t, J=6.6 Hz, 2H), 2.43 (s, 3H).

EXAMPLE 2(133)

2-(3-(2-(5-methyl-2-(quinolin-2-yl)oxazol-4-yl)ethoxy)phenyl)acetic acid

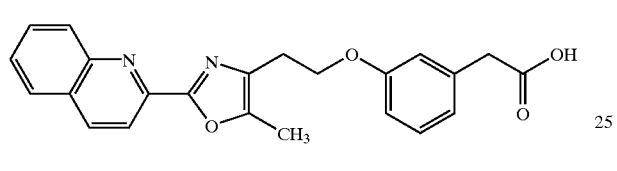

TLC: Rf 0.51 (chloroform:methanol=9:1);

NMR (CDCl$_3$): δ8.16–8.28 (m, 3H), 7.83 (m, 1H), 7.75 (m, 1H), 7.57 (m, 1H), 7.22 (dd, J=8.2, 8.2 Hz, 1H), 6.78–6.87 (m, 3H), 4.29 (t, J=6.6 Hz, 2H), 3.61 (s, 2H), 3.04 (t, J=6.6 Hz, 2H), 2.46 (s, 3H).

EXAMPLE 2(134)

2-(3-(2-(5-methyl-2-(3-trifluoromethoxyphenyl)oxazol-4-yl)ethoxy)phenyl)acetic acid

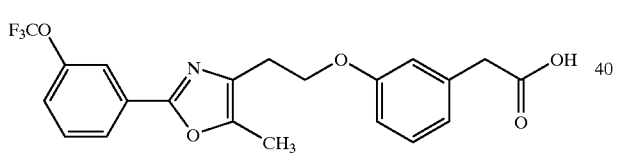

TLC: Rf 0.37 (chloroform:methanol=9:1);

NMR (CDCl$_3$): δ7.91 (dt, J=7.8, 1.2 Hz, 1H), 7.85–7.80 (m, 1H), 7.45 (t, J=7.8 Hz, 1H), 7.28–7.17 (m, 2H), 6.89–6.78 (m, 3H), 4.22 (t, J=6.6 Hz, 2H), 3.60 (S, 2H), 2.97 (t, J=6.6 Hz, 2H), 2.38 (s, 3H).

EXAMPLE 2(135)

2-(3-(2-(5-methyl-2-(2-trifluoromethoxyphenyl)oxazol-4-yl)ethoxy)phenyl)acetic acid

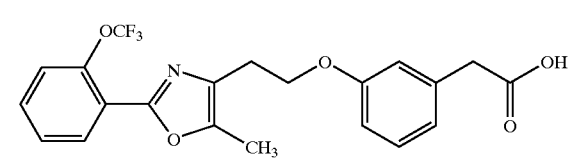

TLC: Rf 0.42 (chloroform:methanol=9:1);

NMR (CDCl$_3$): δ8.06 (dd, J=7.8, 2.0 Hz, 1H), 7.49–7.31 (m, 3H), 7.27–7.17 (m, 1H), 6.88–6.78 (m, 3H), 4.23 (t, J=6.8 Hz, 2H), 3.60 (s, 2H), 2.98 (t, J=6.8 Hz, 2H), 2.38 (s, 3H).

EXAMPLE 2(136)

2-(3-(2-(4-methyl-2-phenyloxazol-5-yl)ethoxy)phenyl)acetic acid

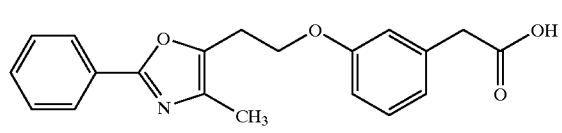

TLC: Rf 0.44 (chloroform:methanol=9:1);

NMR (CDCl$_3$): δ8.00–7.93 (m, 2H), 7.46–7.37 (m, 3H), 7.28–7.18 (m, 1H), 6.90–6.78 (m, 3H), 4.22 (t, J=6.8 Hz, 2H), 3.61 (s, 2H), 3.14 (t, J=6.8 Hz, 2H), 2.20 (s, 3H).

EXAMPLE 2(137)

2-(3-(2-(5-methyl-2-(1,3-dioxaindan-5-yl)oxazol-4-yl)ethoxy)phenylmethoxy)acetic acid

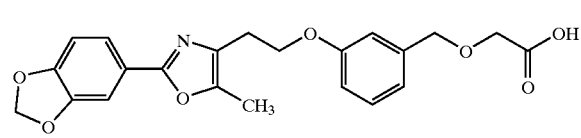

TLC: Rf 0.20 (chloroform:methanol:water=100:10:1);

NMR (CD$_3$OD): δ7.49 (dd, J=8.4, 1.8 Hz, 1H), 7.38 (d, J=1.8 Hz, 1H), 7.22 (t, J=7.8 Hz, 1H), 6.97–6.79 (m, 4H), 6.01 (s, 2H), 4.54 (s, 2H), 4.26 (t, J=6.4 Hz, 2H), 4.06 (s, 2H), 2.93 (t, J=6.4 Hz, 2H), 2.33 (s, 3H).

EXAMPLE 3

2-(3-(2-(5-methyl-2-phenyloxazol-4-yl)ethylthio)phenyl)acetic acid.methyl ester

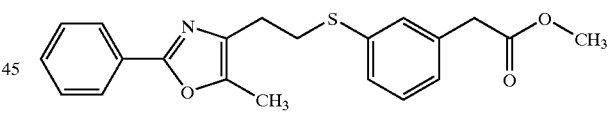

2-(5-methyl-2-phenyloxazol-4-yl)ethylbromide (136 mg) and 3-mercaptophenylacetic acid.methyl ester (78 mg) were dissolved in acetonitrile (5 ml) and thereto was added potassium carbonate and the mixture was stirred at room temperature for 1 hour. The reaction mixture was poured into ice water and the mixture was extracted with ether. The extract was washed with an aqueous solution of sodium hydroxide, water and a saturated aqueous solution of sodium chloride, successively, dried over anhydrous magnesium sulfate and concentrated. The residue was purified by column chromatography on silica gel (chloroform:ethyl acetate=200:1→50:1) to give the compound of the present invention (92 mg) having the following physical data.

TLC: Rf 0.33 (ethyl acetate:hexane=1:3);

NMR (CDCl$_3$): δ7.96 (m, 2H), 7.50–7.35 (m. 3H) 7.30–7.15 (m, 3H), 7.06 (m, 1H), 3.69 (s, 3H), 3.57 (s, 2H), 3.28 (t, J=7.0 Hz, 2H), 2.82 (t, J=7.0 Hz, 2H), 2.27 (s, 3H).

EXAMPLE 4

2-(3-(2-(5-methyl-2-phenyloxazol-4-yl)ethoxy)phenylmethylthio-2-methylpropanoic acid.ethyl ester

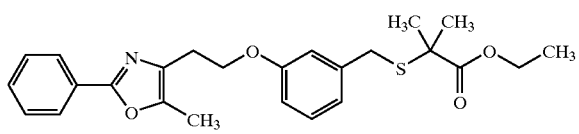

To a solution of 3-(2-(5-methyl-2-phenyloxazol-4-yl)ethoxy)benzylthiol (1.15 g) in ethanol (35 ml) were added 2-bromo-2-methylpropanoic acid.ethyl ester (0.64 ml) and sodium methylate (290 mg) at 0° C. and the mixture was refluxed for 3 hours. The reaction mixture was cooled to room temperature and then filtered. The filtrate was poured into water and the aqueous layer was extracted with ethyl acetate. The extract was washed with a saturated aqueous solution of sodium chloride, dried over anhydrous magnesium sulfate and concentrated. The residue was purified by column chromatography on silica gel (hexane:ethyl acetate=5:1) to give the compound of the present invention (1.69 g) having the following physical data.

TLC: Rf 0.46 (hexane:ethyl acetate=4:1);

NMR (CDCl$_3$): δ8.01–7.94 (m, 2H), 7.46–7.37 (m, 3H), 7.18 (t, J=8.0 Hz, 1H), 6.89–6.72 (m, 3H), 4.23 (t, J=6.8 Hz, 2H), 4.12 (q, J=7.0 Hz, 2H), 3.79 (s, 2H), 2.97 (t, J=6.8 Hz, 2H), 2.38 (s, 3H), 1.53 (s, 6H), 1.26 (t, J=7.0 Hz, 3H).

EXAMPLE 5~EXAMPLE 5(1)

The following compounds of the present invention were obtained by the same procedure as shown in Example 2, using the compounds prepared in Example 3 or Example 4 in place of the compound prepared in Example 1, optionally followed by converting them to the corresponding salts by known methods.

EXAMPLE 5

2-(3-(2-(5-methyl-2-phenyloxazol-4-yl)ethylthio)phenyl)acetic acid

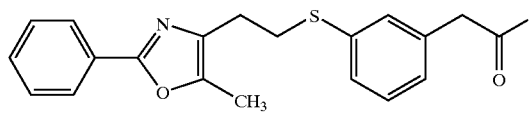

TLC: Rf 0.50 (water:methanol:chloroform=1:10:100);

NMR (CDCl$_3$): δ7.94 (m, 2H), 7.45–7.35 (m, 3H), 7.30–7.15 (m, 3H), 7.07 (m, 1H), 3.58 (s, 2H), 3.25 (t, J=7.0 Hz, 2H), 2.81 (t, J=7.0 Hz, 2H), 2.25 (s, 3H).

EXAMPLE 5(1)

2-(3-(2-(5-methyl-2-phenyloxazol-4-yl)ethoxy)phenylmethylthio)-2-methylpropanoic acid

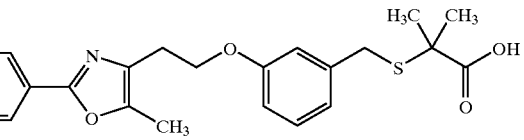

TLC: Rf 0.53 (hexane:ethyl acetate=1:3);

NMR (CDCl$_3$): δ8.00–7.94 (m, 2H), 7.46–7.41 (m, 3H), 7.15 (t, J=7.8 Hz, 1H), 7.08 (m, 1H), 6.84–6.74 (m, 2H), 4.29 (t, J=7.2 Hz, 2H), 3.88 (s, 2H), 2.99 (t, J=7.2 Hz, 1H), 2.38 (s, 3H), 1.58 (s, 6H).

2-(3-(2-(5-methyl-2-phenyloxazol-4-yl)ethoxy)phenylmethylthio)-2-methylpropanoic acid.sodium salt

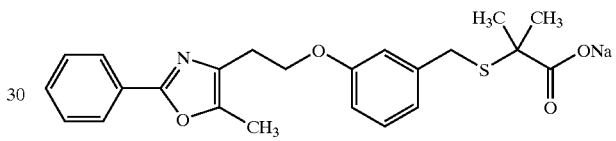

TLC: Rf 0.53 (hexane:ethyl acetate=1:3);

NMR (CD$_3$OD): δ7.98–7.93 (m, 2H), 7.49–7.43 (m, 3H), 7.13 (t, J=7.4 Hz, 1H), 6.92–6.85 (m, 2H), 6.78–6.70 (m, 1H), 4.23 (t, J=6.6 Hz, 2H), 3.78 (s, 2H,), 2.96 (t, J=6.6 Hz, 2H), 2.36 (s, 3H), 1.46 (s, 6H).

REFERENCE EXAMPLE 6

3-(2-(5-methyl-2-phenyloxazol-4-yl)ethoxy)benzaldehyde

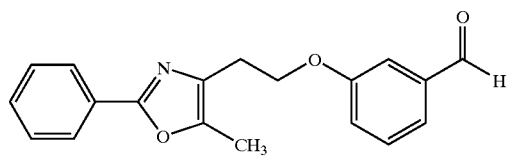

2-(5-methyl-2-phenyloxazol-4-yl)ethanol (1.02 g), 3-hydroxybenzaldehyde (0.73 g) and triphenylphosphine (1.57 g) were dissolved in dichloromethane (10 ml) and thereto was added 1,1'(azodicarbonyl)dipiperidine (1.74 g) at 0° C. and the mixture was stirred at room temperature for 2 hours. To the reaction mixture was added hexane and the solid was filtered off. The filtrate was concentrated. The residue was purified by column chromatography on silica gel (methanol:chloroform=1:100) to give the title compound (1.30 g) having the following physical data.

TLC: Rf 0.77 (methanol:chloroform=1:20);

NMR (CDCl₃): δ9.96 (s, 1H), 7.98 (m, 2H), 7.50–7.35 (m, 6H), 7.17 (m, 1H), 4.31 (t, J=6.0 Hz, 2H), 3.01 (t, J=6.0 Hz, 2H), 2.38 (s, 3H).

REFERENCE EXAMPLE 7

3-(2-(5-methyl-2-phenyloxazol-4-yl)ethoxy)mandelonitrile

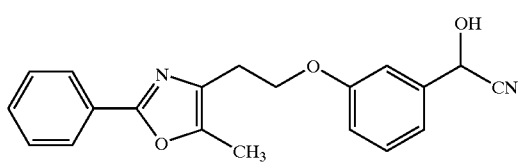

The compound prepared in Reference Example 6 (135 mg) and zinc iodide (13 mg) were dissolved in dichloromethane (3 ml). Thereto was added trimethylsilylnitrile (0.14 ml) at 0° C. and the mixture was stirred at 0° C. for 4 hours. To the reaction mixture were added cold water and a saturated aqueous solution of sodium bicarbonate and the organic layer was separated. The organic layer was dried over anhydrous magnesium sulfate and concentrated. The residue was dissolved in dioxane (3 ml) and thereto was added 2N hydrochloric acid (0.5 ml) and the mixture was stirred at room temperature overnight. The reaction mixture was poured into cold water and extracted with ethyl acetate. The extract was washed with water and a saturated aqueous solution of sodium chloride, successively, dried over anhydrous magnesium sulfate and concentrated to give the title compound (140 mg) having the following physical data.

TLC: Rf 0.27 (ethyl acetate:hexane=1:2);

NMR (CDCl₃): δ7.94 (m, 2H), 7.45–7.35 (m, 3H), 7.29 (dd, J=8.0, 8.0 Hz, 1H), 7.10–7.00 (m, 2H), 6.90 (m, 1H), 5.49 (d, J=6.0 Hz, 1H), 4.73 (d, J=6.0 Hz, 1H), 4.16 (t, J=6.5 Hz, 2H), 2.92 (t, J=6.5 Hz, 2H), 2.37 (s, 3H).

REFERENCE EXAMPLE 8

α-cyano-3-(2-(5-methyl-2-phenyloxazol-4-yl)ethoxy)benzyl chloride

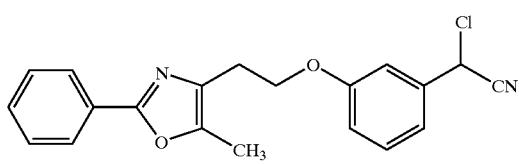

The compound prepared in Reference Example 7 (93 mg) was dissolved in dichloromethane (3 ml), thereto were added thionyl chloride (61 ml) and dimethylformamide (1 drop) and the mixture was stirred at room temperature for 30 minutes. To the reaction mixture was added cold water and the solution was extracted with ethyl acetate. The extract was washed with a saturated aqueous solution of sodium bicarbonate and a saturated aqueous solution of sodium chloride, successively, dried over anhydrous magnesium sulfate and concentrated to give the title compound (99 mg) having the following physical data.

TLC: Rf 0.74 (ethyl acetate:hexane=1:1);

NMR (CDCl₃): δ7.97 (m, 2H), 7.50–7.35 (m, 3H), 7.33 (dd, J=8.0, 8.0 Hz, 1H), 7.10–7.00 (m, 2H), 6.98 (m, 1H), 5.75 (s, 1H), 4.23 (t, J=6.5 Hz, 2H), 2.93 (t, J=6.5 Hz, 2H), 2.36 (s, 3H).

EXAMPLE 6

5-(3-(2-(5-methyl-2-phenyloxazol-4-yl)ethoxy)phenyl)-2,4-thiazolidinedione

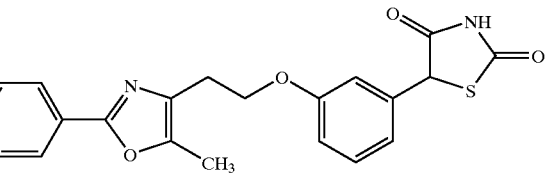

The compound prepared in Reference Example 8 (99 mg) was dissolved in ethanol (1 ml) and thereto was added thiourea (26 mg) and the mixture was refluxed for 3 hours. To the reaction mixture was added 2N hydrochloric acid (1.5 ml) and the mixture was refluxed overnight. The reaction mixture was poured into cold water and the solution was extracted with ethyl acetate. The extract was washed with water and a saturated aqueous solution of sodium chloride, successively, dried over anhydrous magnesium sulfate and concentrated. The residue was recrystallized from methanol to give the compound of the present invention (60 mg) having the following physical data.

TLC: Rf 0.31 (ethyl acetate:hexane=1:1);

NMR (d₆-DMSO): δ7.90 (m, 2H), 7.60–7.40 (m, 3H), 7.31 (dd, J=8.0, 8.0 Hz, 1H), 7.00–6.90 (m, 3H), 5.75 (s, 1H), 4.23 (t, J=6.5 Hz, 2H), 2.93 (t, J=6.5 Hz, 2H), 2.36 (s, 3H).

Formulation Example

Formulation Example 1

The following components were admixed in a conventional method and punched out to give 100 tablets each containing 100 mg of active ingredient.

2-(3-(4-(4-methylphenyl)thiazol-2-ylmethoxy)phenylmethylthio)acetic acid . . . 10.0 g
carboxymethylcellulose calcium (disintegrating agent) . . . 0.2 g
Magnesium stearate (Lubricating agent) . . . 0.1 g
Microcrystaline cellulose . . . 9.7 g

Formulation Example 2

The following components were admixed in a conventional method. The solution was sterilized in a conventional method, placed 5 ml portions into ampoules and freezedried to give 100 ampoules each containing 20 mg of active ingredient.

2-(3-(4-(4-methylphenyl)thiazol-2-ylmethoxy)phenylmethylthio)acetic acid . . . 2 g
mannitol . . . 5 g
distilled water . . . 100 ml

What is claimed is:

1. A method for treatment in animals of diseases induced by a peroxisome proliferator activated receptor, which comprises administering to a subject in need thereof an effective amount of the compound of formula (I)

(I)

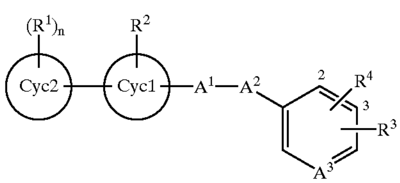

wherein $A^1$ is C1~4 alkylene or C2~4 alkenylene, $A^2$ is —O— or —S—, $A^3$ is CH, n is 1~5, $R^1$ is (i) hydrogen, (ii) C1~8 alkyl, (iii) halogen, (iv) C1~4 alkoxy, (v) nitro, (vi) trihalomethyl, (vii) trihalomethoxy, (viii) trihalomethylthio, (ix) cyano, (x) C1~4 alkylthio, (xi) $NR^5R^6$ wherein $R^5$ and $R^6$ are each independently hydrogen or C1~4 alkyl, (xii) carbocyclic ring or (xiii) hetero ring, $R^2$ is (i) hydrogen, (ii) C1~4 alkyl, (iii) halogen or (iv) trihalomethyl, $Cyc^1$ is (ii)

, or

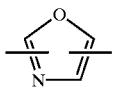 (iii)

CYc² is
(i) a carbocyclic ring or
(ii) a hetero ring,
R³ is
(i) hydrogen,
(ii) C1~alkyl,
(iii) halogen,
(iv) C1~4 alkoxy,
(v) nitro,
(vi) trihalomethyl,
(vii) trihalomethoxy,
(viii) trihalomethylthio,
(ix) cyano or
(x) C1~4 alkylthio,
R⁴ is

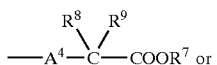 (i)

(ii) 2,4-thiazolidindion-5-yl,
A⁴ is
(i) a bond,
(ii) C1~4 alkylene,
(iii) —C1~4 alkylene —O— or
(iv) —C1~4 alkylene —S—,
R⁷, R⁸ and R⁹ are each independently hydrogen or C1~4 alkyl, with the proviso that
(1) R⁴ is attached to the 2- or 3-position,
(2) when R⁴ is attached to the 3-position, A⁴ is a bond or methylene, and Cyc¹ is benzene, then A¹ is methylene, ethylene or vinylene,
a non-toxic salt thereof or a hydrate thereof.

2. A compound according to claim 1, which is
1) 4-(3-(2-(5-methyl-2-phenyloxazol-4-yl)ethoxy)phenyl)butanoic acid.methyl ester,
2) 6-(3-(2-(5-methyl-2-phenyloxazol-4-yl)ethoxy)phenyl)hexanoic acid.methyl ester,
3) 5-(3-(2-(5-methyl-2-phenyloxazol-4-yl)ethoxy)phenyl)pentanoic acid.methyl ester,
4) 6-(2-(2-(5-methyl-2-phenyloxazol-4-yl)ethoxy)phenyl)hexanoic acid.methyl ester,
5) 5-(2-(2-(5-methyl-2-phenyloxazol-4-yl)ethoxy)phenyl)pentanoic acid.methyl ester,
6) 2-(3-(2-(5-methyl-2-phenyloxazol-4-yl)ethoxy)phenyl)acetic acid.methyl ester,
7) 5-(3-(3-(5-methyl-2-phenyloxazol-4-yl)propoxy)phenyl)pentanoic acid.methyl ester,
8) 2-(3-(2-(5-methyl-2-(4-methylphenyl)oxazol-4-yl)ethoxy)phenyl)acetic acid.methyl ester,
9) 2-(3-(2-(5-methyl-2-(4-ethylphenyl)oxazol-4-yl)ethoxy)phenyl)acetic acid.methyl ester,
10) 2-(3-(2-(5-methyl-2-(4-propylphenyl)oxazol-4-yl)ethoxy)phenyl)acetic acid.methyl ester,
11) 2-(3-(2-(5-methyl-2-(4-isopropylphenyl)oxazol-4-yl)ethoxy)phenyl)acetic acid.methyl ester,
12) 2-(³-(2-(5-methyl-2-(4-(2-methylpropyl)phenyl)oxazol-4-yl)ethoxy)phenyl)acetic acid.methyl ester,
13) 2(3-(2-(5-methyl-2-(4-t-butylphenyl)oxazol-4-yl)ethoxy)phenyl)acetic acid.methyl ester, 14) 2-(3-(2-(5-methyl-2-(4-methoxyphenyl)oxazol-4-yl)ethoxy)phenyl)acetic acid.methyl ester,
15) 2-(3-(2-(5-methyl-2-C3,4-dimethoxyphenyl)oxazol-4-yl)ethoxy)phenyl)acetic acid.methyl ester,
16) 2-(3-(5-methyl-2-phenyloxazol-4-yl)methoxy)phenyl)acetic acid.methyl ester,
17) 2-(3-(2-(5-methyl-2-phenylthiazol-4-yl)ethoxy)phenyl)acetic acid.methyl ester,
18) 2-(3-(3-(5-methyl-2-phenyloxazol-4-yl)propoxy)phenyl)acetic acid.methyl ester,
19) 2-(3-(2-(2-phenyloxazol-4-yl)ethoxy)phenyl)acetic acid.methyl ester,
20) 2-(3-(2-(5-methyl-2-(3-chloro-4-methylphenyl)oxazol-4-yl)ethoxy)phenyl)acid.methyl ester,
21) 2-(3-(2-(5-ethyl-2-phenyloxazol-4-yl)ethoxy)phenyl)acetic acid.methyl ester,
22) 2-(3-(2-(5-methyl-2-(4-butylphenyl )oxazol-4-yl)ethoxy)phenyl)acetic acid.methyl ester,
23) 2-(3-(2-(5-methyl-2-(4-chlorophenyl)oxazol-4-yl)ethoxy)phenyl)acetic acid.methyl
24) 2-(3-(2-(5-methyl-2-(2-methylphenyl)oxazol-4-yl)ethoxy)phenyl)acetic acid.methyl ester,
25) 2-(3-(2-(5-methyl-2-(3-methylphenyl)oxazol-4-yl)ethoxy)phenyl)acetic acid.methyl ester,
26) 2-(3-(2-(5-methyl-2-(4-trifluoromethylphenyl)oxazol-4-yl)ethoxy)phenyl)acetic acid.methyl ester,
27) 2-(3-(2-(5-methyl-2-(4-fluorophenyl)oxazol-4-yl)ethoxy)phenyl)acetic acid.methyl ester,
28) 2-(3-(2-(5-methyl-2-(4-cyanophenyl)oxazol-4-yl)ethoxy)phenyl)acetic acid.methyl ester,
29) 2-(3-(2-(5-methyl-2-(3-nitro-4-methylphenyl)oxazol-4-yl)ethoxy)phenyl)acetic acid.methyl ester,
30) 2-(3-(2-(5-methyl-2-(4-pentylphenyl)oxazol-4-yl)ethoxy)phenyl)acetic acid.methyl ester,
31) 2-(3-(2-(5-methyl-2-(4-nitrophenyl)oxazol-4-yl)ethoxy)phenyl)acetic acid.methyl ester,
32) 4-(3-(2-(5-methyl-2-phenyloxazol-4-yl)ethoxy)phenyl)butanoic acid,
33) 6-(3-(2-(5-methyl-2-phenyloxazol-4-yl)ethoxy)phenyl)hexanoic acid,
34) 5-(3-(2-(5-methyl-2-phenyloxazol-4-yl)ethoxy)phenyl)pentanoic acid,
35) 6-(2-(2-(5-methyl-2-phenyloxazol-4-yl)ethoxy)phenyl)hexanoic acid,
36) 5-(2-(2-(5-methyl-2-phenyloxazol-4-yl)ethoxy)phenyl)pentanoic acid,
37) 2-(3(2-(5-methyl-2-phenyloxazol-4-yl)ethoxy)phenyl)acetic acid.[methyl ester],
38) 5-(3-(3-(5-methyl-2-phenyloxazol-4-yl)propoxy)phenyl)pentanoic acid,
39) 2-(3-(2-(5-methyl-2-(4-methylphenyl)oxazol-4-yl)ethoxy)phenyl)acetic acid,
40) 2-(3-(2-(5-methyl-2-(4-ethylphenyl)oxazol-4-yl)ethoxy)phenyl)acetic acid,
41) 2-(3-(2-(5-methyl-2-(4-propylphenyl)oxazol-4-yl)ethoxy)phenyl)acetic acid,
42) 2-(3-(2-(5-methyl-2-(4-isopropylphenyl)oxazol-4-yl)ethoxy)phenyl)acetic acid,
43) 2-(3-(2-(5-methyl-2-(4-(2-methylpropyl)phenyl)oxazol-4-yl)ethoxy)phenyl)acetic acid,
44) 2-(3-(2-(5-methyl-2-(4-t-butylphenyl)oxazol-4-yl)ethoxy)phenyl)acetic acid,
45) 2-(3-(2-(5-methyl-2-(4-methoxyphenyl)oxazol-4-yl)ethoxy)phenyl)acetic acid,
46) 2-(3-(2-(5-methyl-2-(3,4-dimethoxyphenyl)oxazol-4-yl)ethoxy)phenyl)acetic acid,
47) 2-(3-(5-methyl-2-phenyloxazol-4-yl)methoxy)phenyl)acetic acid, 48) 2-(3-(2-(5-methyl-2-phenylthiazol-4-yl)ethoxy)phenyl) acetic acid,
49) 2-(3-(3-(5-methyl-2-phenyloxazol-4-yl)propoxy) phenyl)acetic acid,
50) 2-(3-(2-(2-phenyloxazol-4-yl)ethoxy)phenyl)acetic acid,
51) 2-(3-(2-(5-methyl-2-(3-chloro-4-methylphenyl)oxazol-4-yl)ethoxy)phenyl)acetic acid,
52) 2-(3-(2-(5-ethyl-2-phenyloxazol-4-yl)ethoxy)phenyl) acetic acid,
53) 2-(3-(2-(5-methyl-2-(4-butylphenyl)oxazol-4-yl) ethoxy)phenyl)acetic acid,
54) 2-(3-(2-(5-methyl-2-(4-chlorophenyl)oxazol-4-yl) ethoxy)phenyl)acetic acid,
55) 2-(3-(2-(5-methyl-2-(2-methylphenyl)oxazol-4-yl) ethoxy)phenyl)acetic acid,
56) 2-(3-(2-(5-methyl-2-(3-methylphenyl)oxazol-4-yl) ethoxy)phenyl)acetic acid,
57) 2-(3-(2-(5-methyl-2-(4-trifuoromethylphenyl)oxazol-4-yl)ethoxy)phenyl)acetic acid,
58) 2-(3-(2-(5-methyl-2-(4-fluorophenyl)oxazol-4-yl) ethoxy)phenyl)acetic acid,
59) 2-(3-(2-(5-methyl-2-(4-cyanophenyl)oxazol-4-yl) ethoxy)phenyl)acetic acid,
60) 2-(3-(2-(5-methyl-2-(3-nitro-4-methylphenyl)oxazol-4-yl)ethoxy)phenyl)acetic acid,
61) 2-(3-(2-(5-methyl-2-(4-pentylphenyl)oxazol-4-yl) ethoxy)phenyl )acetic acid,
62) 2-(3-(2-(5-methyl-2-(4-nitrophenyl)oxazol-4-yl)ethoxy) phenyl)acetic acid,
63) 2-(3-(2-(5-methyl-2-phenyloxazol-4-yl)ethylthio) phenyl)acetic acid.methyl ester,
64) 2-(3-(2-(5-methyl-2-phenyloxazol-4-yl)ethylthio) phenyl)acetic acid, a non-toxic salt thereof or a hydrate thereof.

3. A compound according to claim 1 which is
1) 2-(3-(4-(4-methylphenyl)thiazol-2-ylmethoxy) phenylmethylthio)acetic acid.methyl ester,
2) 2-(3-(3-(4-(4-methylphenyl)thiazol-2-ylmethoxy)phenyl) propylthio)acetic acid.methyl ester,
3) 2-(3-(2-(5-methyl-2-phenyloxazol-4-yl)ethoxy) phenylmethylthio)acetic acid.methyl ester,
4) 2-(3-(3-(2-(5-methyl-2-phenyloxazol-4-yl)ethoxy) phenyl)propylthio)acetic acid.methyl ester,
5) 2-(4-chloro-3-(2-(5-methyl-2-phenyloxazol-4-yl)ethoxy) phenylmethylthio)acetic acid.methyl ester,
6) 2-(4-chloro-3-(4-(4-methylphenyl)thiazol-2-yimethoxy) phenylmethylthio)acetic acid.methyl ester,
7) 2-(3-(2-phenylthiazol-4-ylmethoxy)phenylmethylthio) acetic acid.methyl ester,
8) 2-(3-(2-(5-methyl-2-(4-methylphenyl)oxazol-4-yl) ethoxy)phenylmethylthio)acetic acid.methyl ester,
9) 2-(3-(2-(2-phenylthiazol-4-yl)ethoxy)phenylmethylthio) acetic acid.methyl ester,
10) 2-(3-(2-(2-phenyloxazol-4-yl)ethoxy)phenylmethylthio) acetic acid.methyl ester,
11) 2-(3-(2-(5-methyl-2-(1,3-dioxaindan-5-yl)oxazol-4-yl) ethoxy)phenylmethylthio)acetic acid.methyl ester,
12) 2-(3-(5-methyl-2-phenyloxazol-4-ylmethoxy) phenylmethylthio)acetic acid.methyl ester,
13) 2-(3-(3-(5-methyl-2-phenyloxazol-4-yl)propoxy) phenylmethylthio)acetic acid.methyl ester,
14) 2-(3-(2-(5-methyl-2-(2-methylphenyl)oxazol-4-yl) ethoxy)phenylmethylthio)acetic acid.methyl ester,
15) 2-(3-(2-(5-methyl-2-(3-methylphenyl)oxazol-4-yl) ethoxy)phenylmethylthio)acetic acid.methyl ester,
16) 2-(3-(2-(5-methyl-2-(4-methoxyphenyl)oxazol-4-yl) ethoxy)phenylmethylthio)acetic acid.methyl ester,
17) 2-(3-(2-(5-methyl-2-phenyloxazol-4-yl)etkoxy)-5-chlorophenylmethylthio)acetic acid.methyl ester,
18) 2-(3-(2-(5-methyl-2-phenyloxazol-4-yl)ethoxy)-2-methylphenylmethylthio)acetic acid.methyl ester,
19) 2-3-2-5-methyl-2-phenyloxazol-4-yl)-1-methylethoxy) phenylmethylthio)acetic acid.methyl ester,
20) 2-(3-(2-(5-methyl-2-phenyloxazol-4-yl)propoxy) phenylmethylthio)acetic acid.methyl ester,
21) 2-(3-(2-(5-methyl-2-phenyloxazol-4-yl)ethoxy) phenylmethylthio)propanoic acid.ethyl ester
22) 2-(3-(2-(5-methyl-2-(4-ethylphenyl)oxazol-4-yl) ethoxy)phenylmethylthio)acetic acid.methyl ester,
23) 2-(3-(2-(5-methyl-2-(4-propylphenyl)oxazol-4-yl) ethoxy)phenylmethylthio)acetic acid.methyl ester,
24) 2-(3-(2-(5-methyl-2-(4-isopropylphenyl)oxazol-4-yl) ethoxy)phenylmethylthio)acetic.acid methyl ester,
25) 2-(3-(2-(5-methyl-2-phenylthiazol-4-yl)ethoxy) phenylmethylthio)acetic acid methyl.ester,
26) 2-(3-(2-(5-methyl-2-(4-butylphenyl)oxazol-4-yl) ethoxy)phenylmethylthio)acetic acid.methyl ester,
27) 2-(3-(2-(5-ethyl-2-phenyloxazol-4-yl)ethoxy) phenylmethylthio)acetic acid.methyl ester,
28) 2-(3-(2-(5-methyl-2-(4-pentylphenyl)oxazol-4-yl) ethoxy)phenylmethylthio)acetic acid.methyl ester,
29) 2-(3-(2-(5-methyl-2-cyclohexyloxazol-4-yl)ethoxy) phenylmethylthio)acetic acid.methyl ester,
30) 2-(3-(2-(5-methyl-2-(4-(2-methylpropyl)phenyl)oxazol-4-yl)ethoxy)phenylmethylthio)acetic acid.methyl ester,
31) 2-(3-(2-(5-methyl-2-(4-t-butylphenyl)oxazol-4-yl) ethoxy)phenylmethylthio)acetic acid.methyl ester,
32) 2-(3-(2-(5-methyl-2-(4-cyclohexylphenyl)oxazol-4-yl) ethoxy)phenylmethylthio)acetic acid. methyl ester,
33) 2-(3-(5-methyl-2-(1,3-dioxaindan-5-yl)oxazol-4-yl) methoxy)phenylmethylthio)acetic acid.methyl ester,
34) 2-(3-(5-methyl-2-(4-isopropylphenyl)oxazol-4-yl) methoxy)phenylmethylthio)acetic acid.methyl ester,
35) 2-(3-(2-(4-methyl-2-phenyloxazol-5-yl)ethoxy) phenylmethylthio)acetic acid.methyl ester,
36) 2-(3-(2-(5-methyl-2-(3,4-dimethoxyphenyl)oxazol-4-yl) ethoxy)phenylmethylthio)acetic acid methyl ester,
37) 2-(3-(2-(5-methyl-2-(4-methylpiperazin-1-yl)oxazol-4-yl)ethoxy)phenylmethylthio)acetic acid.methyl ester,
38) 2-(3-(2-(5-methyl-2-(pyridin-2-yl)oxazol-4-yl)ethoxy) phenylmethylthio)acetic acid.methyl ester,
39) 2-(3-(2-(5-methyl-2-(thiophen-2-yl)oxazol-4-yl)ethoxy) phenylmethylthio)acetic acid.methyl ester,
40) 2-(3-(2-(5-methyl-2-(4-dimethylaminophenyl)oxazol-4-ly)ethoxy)phenylmethylthio)acetic acid.methyl ester,
41) 2-(3-(2-(5-methyl-2-cyclopentyloxazol-4-yl)ethoxy) phenylmethylthio)acetic acid.methyl ester,
42) 2-(3-(2-(5-methyl-2-cyclopropyloxazol-4-yl)ethoxy) phenylmethylthio)acetic acid.methyl ester,
43) 2-(3-(2-(5-methyl-2-(4-(1,2,3-thiadiazo-4-yl)phenyl) oxazol-4-yl)ethoxy)phenylmethylthio)acetic acid.methyl ester,
44) 2-(3-(2-(5-methyl-2-(4-(4-methyl-1,2,3-thiadiazol-5-yl) phenyl)oxazol-4-yl)ethoxy)phenylmethylthio)acetic acid-.methyl ester,
45) 2-(3-(2-(5-methyl-2-(furan-2-yl)oxazol-4-yl)ethoxy) phenylmethylthio)acetic acid.methyl ester,
46) 2-(3-(2-(-methyl-2-(pyridin-4-yl)oxazol-4-yl)ethoxy) phenylmethylthio)acetic acid.methyl ester,
47) 2-(3-(2-(5-methyl-2-phenyloxazol-4-yl)ethoxy) phenylmethoxy)acetic acid.t-butyl ester,
48) 2-(3-(2-(5-methyl-2-(pyridin-3-yl)oxazol-4-yl)ethoxy) phenylmethylthio)acetic acid.methyl ester,
49) 2-(3-(4-(4-methylphenyl)thiazol-2-ylmethoxy) phenylmethylthio)acetic acid, 50) 2-(3-(3-(4-(4-methylphenyl)thiazol-2-ylmethoxy) phenyl)propylthio)acetic acid,
51) 2-(3-(2-(5-methyl-2-phenyloxazol-4-yl)ethoxy) phenylmethylthio)acetic acid,
52) 2-(3-(3-(2-(5-methyl-2-phenyloxazol-4-yl)ethoxy) phenyl)propylthio)acetic acid,
53) 2-(4-chloro-3-(2-(5-methyl-2-phenyloxazol-4-yl) ethoxy)phenylmethylthio)acetic acid,
54) 2-(4-chloro-3-(4-(4-methylphenyl)thiazol-2-ylmethoxy) phenylmethylthio)acetic acid,
55) 2-(3-(2-(2-phenylthiazol-4-yl)ethoxy) phenylmethylthio)acetic acid,
56) 2-(3-(2-(2-phenyloxazol-4-yl)ethoxy)phenylmethylthio) acetic acid
57) 2-(3-(2-(5-methyl-2-(1,3-dioxaindan-5-yl)oxazol-4-yl) ethoxy)phenylmethylthio)acetic acid,
58) 2-(3-(5-methyl-2-phenyloxazol-4-ylmethoxy) phenylmethylthio)acetic acid,
59) 2-(3-(3-(5-methyl-2-phenyloxazol-4-yl)propoxy) phenylmethylthio)acetic acid,
60) 2-(3-(2-(5-methyl-2-(2-methylphenyl)oxazol-4-yl) ethoxy)phenylmethylthio)acetic acid,
61) 2-(3-(2-(5-methyl-2-(3-methylphenyl)oxazol-4-yl) ethoxy)phenylmethylthio)acetic acid,
62) 2-(3-(2-(5-methyl-2-(4-methoxyphenyl)oxazol-4-yl) ethoxy)phenylmethylthio)acetic acid,
63) 2-(3-(2-(5-methyl-2-phenyloxazol-4-yl)ethoxy)-5-chlorophenylmethylthio)acetic acid,
64) 2-(3-(2-(5-methyl-2-phenyloxazol-4-yl)ethoxy)-2-methylphenylmethylthio)acetic acid,
65) 2-(3-(2-(5-methyl-2-phenyloxazol-4-yl)-1-methylethoxy)phenylmethylthio)acetic acid,
66) 2-(3-(2-(5-methyl-2-phenyloxazol-4-yl)propoxy) phenylmethylthio)acetic acid,
67) 2-(3-(2-(5-methyl-2-phenyloxazol-4-yl)ethoxy) phenylmethylthio)propanoic acid.sodium salt,
68) 2-(3-(2-(5-methyl-2-(4-ethylphenyl)oxazol-4-yl) ethoxy)phenylmethylthio)acetic acid,
69) 2-(3-(2-(5-methyl-2-(4-propylphenyl)oxazol-4-yl) ethoxy)phenylmethylthio)acetic acid,
70) 2-(3-(2-(5-methyl-2-(4-isopropylphenyl)oxazol-4-yl) ethoxy)phenylmethylthio)acetic acid,
71) 2-(3-(2-(5-methyl-2-phenylthiazol-4-yl)ethoxy) phenylmethylthio)acetic acid,
72) 2-(3-(2-(5-methyl-2-(4-butylphenyl)oxazol-4-yl) ethoxy)phenylmethylthio)acetic acid,
73) 2-(3-(2-(5-ethyl-2-phenyloxazol-4-yl)ethoxy) phenylmethylthio)acetic acid,
74) 2-(3-(2-(5-methyl-2-(4-pentylphenyl)oxazol-4-yl) ethoxy)phenylmethylthio)acetic acid,
75) 2-(3-(2-(5-methyl-2-cyclohexyloxazol-4-yl)ethoxy) phenylmethylthio)acetic acid,
76) 2-(3-(2-(5-methyl-2-(4-(2-methylpropyl)phenyl)oxazol-4-yl)ethoxy)phenylmethylthio)acetic acid,
77) 2-(3-(2-(5-methyl-2-(4-t-butylphenyl)oxazol-4-yl) ethoxy)phenylmethylthio)acetic acid,
78) 2-(3-(2-(5-methyl-2-(4-cyclohexylphenyl)oxazol-4-yl) ethoxy)phenylmethylthio)acetic acid,
79) 2-(3-(5-methyl-2-(1,3-dioxaindan-5-yl)oxazol-4-yl) methoxy)phenylmethylthio)acetic acid,
80) 2-(3-(5-methyl-2-(4-isopropylphenyl)oxazol-4-yl) methoxy)phenylmethylthio)acetic acid,
81) 2-(3-(2-(4-methyl-2-phenyloxazol-5-yl)ethoxy) phenylmethylthio)acetic acid,
82) 2-(3-(2-(5-methyl-2-(3,4-dimethoxyphenyl)oxazol-4-yl) ethoxy)phenylmethylthio)acetic acid,
83) 2-(3-(2-(5-methyl-2-(4-methylpiperazin-1-yl)oxazol-4-yl)ethoxy)phenylmethylthio)acetic acid,
84) 2-(3-(2-(5-methyl-2-(pyridin-2-yl)oxazol-4-yl)ethoxy) phenylmethylthio)acetic acid,
85) 2-(3-(2-(5-methyl-2-(thiophen-2-yl)oxazol-4-yl)ethoxy) phenylmethylthio)acetic acid,
86) 2-(3-(2-(5-methyl-2-(4-dimethylaminophenyl)oxazol-4-yl)ethoxy)phenylmethylthio)acetic acid,
87) 2-(3-(2-(5-methyl-2-cyclopentyloxazol-4-yl)ethoxy) phenylmethylthio)acetic acid,
88) 2-(3-(2-(5-methyl-2-cyclopropyloxazol-4-yl)ethoxy) phenylmethylthio)acetic acid,
89) 2-(3-(2-(5-methyl-2-(4-(1,2,3-thiadiazol-4-yl)phenyl) oxazol-4-yl)ethoxy)phenylmethylthio)acetic acid,
90) 2-(3-(2-(5-methyl-2-(4-(4-methyl-1,2,3-thiadiazol-5-yl) phenyl)oxazol-4-yl)ethoxy)phenylmethylthio)acetic acid,
91) 2-(3-(2-(5-methyl-2-(furan-2-yl)oxazol-4-yl)ethoxy) phenylmethylthio)acetic acid,
92) 2-(3-(2-(5-methyl-2-(pyridin-4-yl)oxazol-4-yl)ethoxy) phenylmethylthio)acetic acid,
93) 2-(3-(2-(5-methyl-2-phenyloxazol-4-yl)ethoxy) phenylmethoxy)acetic acid,
94) 2-(3-(2-(5-methyl-2-(pyridin-3-yl)oxazol-4-yl)ethoxy) phenylmethylthio)acetic acid,
95) 2-(3-(2-(5-methyl-2-phenyloxazol-4-yl)ethoxy) phenylmethylthio)-2-methylpropanoic acid.ethyl ester,
96) 2-(3-(2-(5-methyl-2-phenyloxazol-4-yl)ethoxy) phenylmethylthio)-2-methylpropanoic acid,
97) 2-(3-(2-(5-methyl-2-(1,3-dioxaindan-5-yl)oxazol-4-yl) ethoxy)phenylmethoxy)acetic.t-butyl ester,
98) 2-(3-(2-(5-methyl-2-(1,3-dioxaindan-5-yl)oxazol-4-yl) ethoxy)phenylmethoxy)acetic acid, a non-toxic salt thereof or a hydrate thereof.

4. A compound according to claim 1 which is
1) 6-(3-(4-(4-methylphenyl)thiazol-2-ylmethoxy)phenyl) hexanoic acid.methyl ester,
2) 4-(3-(4-(4-methylphenyl)thiazol-2-ylmethoxy)phenyl) butanoic acid.methyl ester,
3) 6-(2-(4-(4-methylphenyl)thiazol-2-ylmethoxy)phenyl) hexanoic acid.methyl ester,
4) 2-(3-(2-(5-methyl-2-(4-trifluoromethylphenyl)oxazol-4-yl)ethoxy)phenylmethylthio)acetic acid.methyl ester,
5) 2-(3-(2-(5-methyl-2-(4-fluorophenyl)oxazol-4-yl)ethoxy) phenylmethylthio)acetic acid.methyl ester,
6) 2-(3-(2-(5-methyl-2-(4-chlorophenyl)oxazol-4-yl) ethoxy)phenylmethylthio)acetic acid.methyl ester,
7) 2-(3-(2-(5-methyl-2-phenyloxazol-4-yl)ethoxy)phenyl)-2-methylpropanoic acid.methyl ester,
8) 2-(3-(2-(5-methyl-2-(4-nitrophenyl)oxazol-4-yl)ethoxy) phenylmethylthio)acetic acid.methyl ester,
9) 2-(1-(3-(2-(5-methyl-2-phenyloxazol-4-yl)ethoxy) phenyl)ethylthio)acetic acid.methyl ester,
10) 2-(3-(2-(5-trifluoromethyl-2-phenyloxazol-4-yl)ethoxy) phenylthio)acetic acid.methyl ester,
11) 2-(3-(2-(5-methyl-2-(2,2-difluoro-1,3-dioxaindan-5-yl) oxazol-4-yl)ethoxy)phenylmethylthio)acetic acid.methyl ester,
12) 2-(3-(2-(5-methyl-2-(2,3,5,6-tetrafluoro-4-methylphenyl)oxazol-4-yl)ethoxy)phenylmethylthio) acetic acid methyl ester,
13) 2-(3-(2-(5-methyl-2-(3-chloro-4-methylphenyl)oxazol-4-yl)ethoxy)phenylmethylthio)acetic acid.methyl ester,
14) 2-(3-(2-(5-methyl-2-(4-trifluoromethoxyphenyl)oxazol-4-yl)ethoxy)phenylmethylthio)acetic acid.methyl ester,
15) 2-(3-(2-(5-methyl-2-(3,4,5-trimethoxyphenyl)oxazol-4-yl)ethoxy)phenylmethylthio)acetic acid.methyl ester,
16) 2-(3-(2-(5-methyl-2-(4-methylthiophenyl)oxazol-4-yl) ethoxy)phenylmethylthio)acetic acid.methyl ester,
17) 2-(3-(2-(5-methyl-2-(3-nitro-4-methylphenyl)oxazol-4-yl)ethoxy)phenylmethylthio)acetic acid.methyl ester, 18) 2-(3-(2-(5-methyl-2-(1,3-dioxaindan-5-yl)oxazol-4-yl)ethoxy)phenyl)acetic acid.methyl ester,
19) 2-(3-(2-(5-methyl-2-(3,4,5-trimethoxyphenyl)oxazol-4-yl)ethoxy)phenyl)acetic acid.methyl ester,
20) 2-(3-(2-(5-methyl-2-(4-trifluoromethoxyphenyl)oxazol-4-yl)ethoxy)phenyl)acetic acid.methyl ester,
21) 2-(3-(2-(5-methyl-2-(2,2-difluoro-1,3-dioxaindan-5-yl)oxazol-4-yl)ethoxy)phenyl)acetic acid.methyl ester,
22) 2-(3-(2-(5-methyl-2-(4-trifluoromethylthiophenyl)oxazol-4-yl)ethoxy)phenylmethylthio)acetic acid.methyl ester,
23) 2-(3-(2-(5-methyl-2-(4-cyanophenyl)oxazol-4-yl)ethoxy)phenylmethylthio)acetic acid.methyl ester,
24) 2-(3-(2-(5-methyl-2-(4-cyclohexylphenyl)oxazol-4-yl)ethoxy)phenyl)acetic acid.methyl ester,
25) 2-(3-(2-(5-methyl-2-(4-dimethylaminophenyl)oxazol-4-yl)ethoxy)phenyl)acetic acid.methyl ester,
26) 2-(3-(2-(5-methyl-2-(thiophen-2-yl)oxazol-4-yl)ethoxy)phenyl)acetic acid.methyl ester,
27) 2-(3-(2-(5-methyl-2-(furan-2-yl)oxazol-4-yl)ethoxy)phenyl)acetic acid.methyl ester,
28) 2-(3-(2-(5-methyl-2-(pyridin-2-yl)oxazol-4-yl)ethoxy)phenyl)acetic acid.methyl ester,
29) 2-(3-(c2-(5-methyl-2-(4-methyl-1,2,3-thiadiazol-5-yl)oxazol 4-yl)ethoxy)phenyl)acetic acid.methyl ester,
30) 2-(3-(2-(5-methyl-2-(2,3,5,6-tetrafluoro-4-methylphenyl)oxazol-4-yl)ethoxy)phenyl)acetic acid.methyl ester,
31) 2-(3-(2-(5-methyl-2-cyclohexyloxazol-4-yl)ethoxy)phenyl)acetic acid.methyl ester,
32) 2-(3-(2-(5-methyl-2-cyclopentyloxazol-4-yl)ethoxy)phenyl)acetic acid.methyl ester,
33) 2-(3-(2-(5-methyl-2-(pyridin-3-yl)oxazol-4-yl)ethoxy)phenyl)acetic acid.methyl ester,
34) 2-(3-(2-(5-methyl-2-(pyridin-4-yl)oxazol-4-yl)ethoxy)phenyl)acetic acid.methyl ester,
35) 2-(3-(2-(5-methyl-2-(4-methylpiperazin-1-yl)thiazo-4-yl)ethoxy)phenyl)acetic acid.methyl ester,
36) 2-(3-(2-(5-methyl-2-(4-methylthiophenyl)oxazo-4-yl)ethoxy)phenyl)acetic acid.methyl ester,
37) 2-(3-(2-(5-methyl-2-cyclopropyloxazol-4-yl)ethoxy)phenyl)acetic acid.methyl ester,
38) 2-(3-(2-(5-methyl-2-(quinolin-2-yl)oxazol-4-yl)ethoxy)phenyl)acetic acid.methyl ester,
39) 6-(3-(4-(4-methylphenyl)thiazol-2-ylmethoxy)phenyl)hexanoic acid,
40) 4-(3-(4-(4-methylphenyl)thiazol-2-ylmethoxy)phenyl)butanoic acid,
41) 6-(2-(4-(4-methylphenyl)thiazol..2ylmethoxy)phenyl)hexanoic acid,
42) 2-(3-(2-(5-methyl-2-(4-trifluoromethylphenyl)oxazol-4-yl)ethoxy)phenylmethylthio)acetic acid,
43) 2-(3-(2-(5-methyl-2-(4-fluorophenyl)oxazol-4-yl)ethoxy)phenylmethylthio)acetic acid,
44) 2-(3-(2-(5-methyl-2-(4-chlorophenyl)oxazol-4-yl)ethoxy)phenylmethylthio)acetic acid,
45) 2-(3-(2-(5-methyl-2-phenyloxazol-4-yl)ethoxy)phenyl)-2-methylpropanoic acid,
46) 2-(3-(2-(5methyl-2-(4-nitrophenyl)oxazol-4-yl)ethoxy)phenylmethylthio)acetic acid,
47) 2-(1-(3-(2-(5-methyl-2-phenyloxazol-4-yl)ethoxy)phenyl)ethylthio)acetic acid,
48) 2-(3-(2-(5-trifluoromethyl-2-phenyloxazol-4-yl)ethoxy)phenylthio)acetic acid,
49) 2-(3-(2-(5-methyl-2-(2,2-difluoro-1,3-dioxaindan-5-yl)oxazol-4-yl)ethoxy)phenylmethylthio)acetic acid,
50) 2-(3-(2-(5-methyl-2-(2,3,5,6-tetrafluoro-4-methylphenyl)oxazol-4-yl)ethoxy)phenylmethylthio)acetic acid,
51) 2-(3-(2-(5-methyl-2-(3-chloro-4-methylphenyl)oxazol-4-yl)ethoxy)phenylmethylthio)acetic acid,
52) 2-(3-(2-(5-methyl-2-(4-trifluoromethoxyphenyl)oxazol-4-yl)ethoxy)phenylmethylthio)acetic acid,
53) 2-(3-(2-(5-methyl-2-(3,4,5-trimethoxyphenyl)oxazol-4-yl)ethoxy)phenylmethylthio)acetic acid,
54) 2-(3-(2-(5-methyl-2-(4-methylthiophenyl)oxazol-4-yl)ethoxy)phenylmethylthio)acetic acid,
55) 2-(3-(2-(5-methyl-2-c3-nitro-4-methylphenyl)oxazol-4-yl)ethoxy)phenylmethylthio)acetic acid,
56) 2-(3-(2-(5-methyl-2-(1,3-dioxaindan-5-yl)oxazol-4-yl)ethoxy)phenyl)acetic acid,
57) 2-(3-(2-(5-methyl-2-(3,4,5-trimethoxyphenyl)oxazol-4-yl)ethoxy)phenyl)acetic acid,
58) 2-(3-(2-(5-methyl-2-(4-trifluoromethoxyphenyl)oxazol-4-yl)ethoxy)phenyl)acetic acid,
59) 2-(3-(2-(5-methyl-2-(2,2-difluoro-1,3-dioxaindan-5-yl)oxazol-4-yl)ethoxy)phenyl)acetic acid,
60) 2-(3-(2-(5-methyl-2-(4-trifluoromethylthiophenyl)oxazol-4-yl)ethoxy)phenylmethylthio)acetic acid,
61) 2-(3-(2-(5-methyl-2-(4-cyanophenyl)oxazol-4-yl)ethoxy)phenylmethylthio)acetic acid,
62) 2-(3-(2-(5-methyl-2-(4-cyclohexylphenyl)oxazol-4-yl)ethoxy)phenyl)acetic acid,
63) 2-(3-(2-(5-methyl-2-(4-dimethylaminophenyl)oxazol-4-yl)ethoxy)phenyl)acetic acid,
64) 2-(3-(2-(5-methyl-2-(thiophen-2-yl)oxazol-4-yl)ethoxy)phenyl)acetic acid,
65) 2-(3-(2-(5-methyl-2-(furan-2-yl)oxazol-4-yl)ethoxy)phenyl)acetic acid,
66) 2-(3-(2-(5-methyl-2-(pyridin-2-yl)oxazol-4-yl)ethoxy)phenyl)acetic acid,
67) 2-(3-(2-(5-methyl-2-(4-methyl-1,2,3-thiadiazol-5-yl)oxazol-4-yl)ethoxy)phenyl)acetic acid,
68) 2-(3-(2-(5-methyl-2-(2,3,5,6-tetrafluoro-4-methylphenyl)oxazol-4-yl)ethoxy)phenyl)acetic acid,
69) 2-(3-(2-(5-methyl-2-cyclohexyloxazol-4-yl)ethoxy)phenyl)acetic acid,
70) 2-(3-(2-(5-methyl-2-cyclopentyloxazol-4-yl)ethoxy)phenyl)acetic acid,
71) 2-(3-(2-(5-methyl-2-(pyridin-3-yl)oxazol-4-yl)ethoxy)phenyl)acetic acid,
72) 2-(3-(2-(5-methyl-2-(pyridin-4-yl)oxazol-4-yl)ethoxy)phenyl)acetic acid,
73) 2-(3-(2-(5-methyl-2-(4-methylpiperazin-1-yl)thiazol-4-yl)ethoxy)phenyl)acetic acid,
74) 2-(3-(2-(5-methyl-2-(4-methylthiophenyl)oxazol-4-yl)ethoxy)phenyl)acetic acid,
75) 2-(3-(2-(5-methyl-2-cyclopropyloxazol-4-yl)ethoxy)phenyl)acetic acid,
76) 2-(3-(2-(5-methyl-2-(quinolin-2-yl)oxazol-4-yl)ethoxy)phenyl)acetic acid,
77) 5-(3-(2-(5-methyl-2-phenyloxazol-4-yl)ethoxy)phenyl)2,4-thiazolidindione,
78) 2-(3-(2-(5-methyl-2-(3-trifluoromethoxyphenyl)oxazol-4-yl)ethoxy)phenyl)acetic.acid methyl ester,
79) 2-(3-(2-(5-methyl-2-(2-trifluoromethoxyphenyl)oxazol-4-yl)ethoxy)phenyl)acetic acid.methyl ester,
80) 2-(3-(2-(4-methyl-2-phenyloxazol-5-yl)ethoxy)phenyl)acetic acid.methyl ester,
81) 2-(3-(2-(5-methyl-2-(3-trifluoromethoxyphenyl)oxazol-4-yl)ethoxy)phenyl)acetic acid,
82) 2-(3-(2-(5-methyl-2-(2-trifluoromethoxyphenyl)oxazol-4-yl)ethoxy)phenyl)acetic acid,
83) 2-(3-(2-(4-methyl-2-phenyloxazol-5-yl)ethoxy)phenyl)acetic acid, a non-toxic salt thereof or a hydrate thereof.

5. A method for treatment in animals of diseases induced by a peroxisome proliferator activated receptor, which comprises administering to a subject in need thereof an effective amount of the compound of formula (I)

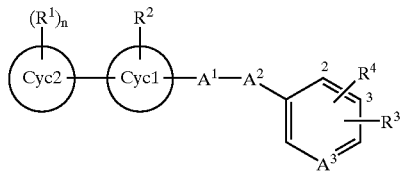

wherein $A^1$ is C1~4 alkylene or C2~4 alkenylene,
$A^2$ is —O— or —S—,
$A^3$ is CH,
n is 1~5,
$R^1$ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano,
(x) C1~4 alkylthio,
(xi) $NR^5R^6$ wherein $R^5$ and $R^6$ are each independently, hydrogen or C1~4 alkyl,
(xii) carbocyclic ring or
(xiii) hetero ring,
$R^2$ is
(i) hydrogen,
(ii) C1~4 alkyl,
(iii) halogen or
(iv) trihalomethyl,
$Cyc^1$ is

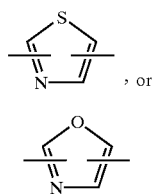

$Cyc^2$ is
(i) carbocyclic ring or
(ii) hetero ring,
$R^3$ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano or
(x) C1~4 alkylthio, $R^4$ is

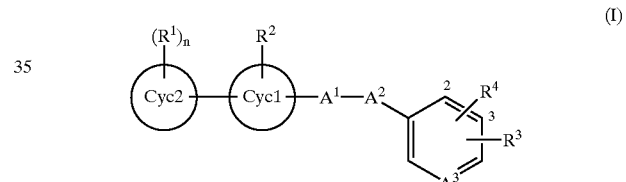

(ii) 2,4-thiazolidindion-5-yl,
$A^4$ is
(i) bond,
(ii) C1~4 alkylene,
(iii) —C1~4 alkylene —o— or
(iv) —C1~4 alkylene —S—,
$R^7$, $R^8$ and $R^9$ are each independently hydrogen or C1~4 alkyl, with the proviso that
(1) $R^4$ is attached to 2- or 3-position and
(2) when $R^4$ is attached to the 3-position, $A^4$ is a bond or methylene, and $Cyc^1$ is benzene, then $A^1$ is methylene, ethylene or vinylene, a non-toxic salt thereof or a hydrate thereof.

6. The method of claim 5, wherein said disease is hyperglycemia or hyperlipidemia.

7. The method of claim 5, wherein said disease is a metabolic disorder selected from the group consisting of diabetes, obesity, syndrome X, hypercholesterolemia, and hyperlipoproteinemia, hyperlipidemia, artherosclerosis, hypertension, circulatory diseases, overeating, and ischemic heart diseases.

8. A method for elevating HDL cholesterol, which comprises administering to a subject in need therof an effective amount of the compound of formula (I):

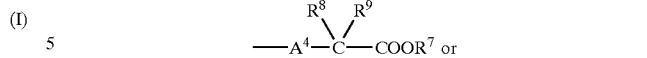

wherein $A^1$ is C1~4 alkylene or C2~4 alkenylene,
$A^2$ is —O— or —S—,
$A^3$ is CH,
n is 1~5,
$R^1$ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano,
(x) C1~4 alkylthio,
(xi) $NR^5R^6$ wherein $R^5$ and $R^6$ are each independently, hydrogen or C1~4 alkyl,
(xii) carbocyclic ring or
(xiii) hetero ring,
$R^2$ is
(i) hydrogen,
(ii) C1~4 alkyl,
(iii) halogen or
(iv) trihalomethyl, Cyc¹ is

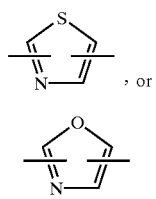

Cyc² is
(i) carbocyclic ring or
(ii) hetero ring,
R³ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano or
(x) C1~4 alkylthio,
R⁴ is

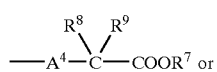

(ii) 2,4-thiazolidindion-5-yl,
A⁴ is
(i) bond,
(ii) C1~4 alkylene,
(iii) —C1~4 alkylene —o— or
(iv) —C1~4 alkylene —S—,
R⁷, R⁸ and R⁹ are each independently hydrogen or C1~4 alkyl, with the proviso that
(1) R⁴ is attached to 2- or 3-position and
(2) when R⁴ is attached to the 3-position, A⁴ is a bond or methylene, and Cyc¹ is benzene, then A¹ is methylene, ethylene or vinylene,
a non-toxic salt thereof or a hydrate thereof.

9. A method for lowering LDL cholesterol or VDL cholesterol, which comprises administering to subject in need thereof an effective amount of the compound of formula (I):

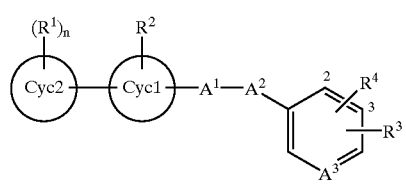

wherein
A¹ is C1~4 alkylene or C2~4 alkenylene,
A² is —O— or —S—,
A³ is CH,
n is 1~5,
R¹ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano,
(x) C1~4 alkylthio,
(xi) NR⁵R⁶ wherein R⁵ and R⁶ are each independently, hydrogen or C1~4 alkyl,
(xii) carbocyclic ring or
(xiii) hetero ring,
R² is
(i) hydrogen,
(ii) C1~4 alkyl,
(iii) halogen or
(iv) trihalomethyl,
Cyc¹ is

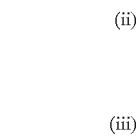

Cyc² is
(i) carbocyclic ring or
(ii) hetero ring,
R³ is
(i) hydrogen,
(ii) C1~8 alkyl,
(iii) halogen,
(iv) C1~4 alkoxy,
(v) nitro,
(vi) trihalomethyl,
(vii) trihalomethoxy,
(viii) trihalomethylthio,
(ix) cyano or
(x) C1~4 alkylthio,
R⁴ is

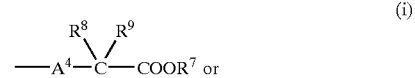

(ii) 2,4-thiazolidindion-5-yl,
A⁴ is
(i) bond,
(ii) C1~4 alkylene,
(iii) —C1~4 alkylene —o— or
(iv) —C1~4 alkylene —S—,
R⁷, R⁸ and R⁹ are each independently hydrogen or C1~4 alkyl, with the proviso that
(1) R⁴ is attached to 2- or 3-position and
(2) when R⁴ is attached to the 3-position, A⁴ is a bond or methylene, and Cyc¹ is benzene, then A¹ is methylene, ethylene or vinylene,
a non-toxic salt thereof or a hydrate thereof.

10. A method for relief from risk factor of diabetes or syndrome X, which comprises administering to a subject in need thereof an effective amount of the compound of formula (I):

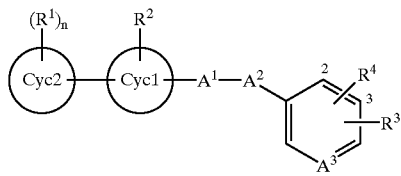
(I)

wherein $A^1$ is C1~4 alkylene or C2~4 alkenylene,
$A^2$ is —O— or —S—,
$A^3$ is CH,
n is 1~5,
$R^1$ is
  (i) hydrogen,
  (ii) C1~8 alkyl,
  (iii) halogen,
  (iv) C1~4 alkoxy,
  (v) nitro,
  (vi) trihalomethyl,
  (vii) trihalomethoxy,
  (viii) trihalomethylthio,
  (ix) cyano,
  (x) C1~4 alkylthio,
  (xi) $NR^5R^6$ wherein $R^5$ and $R^6$ are each independently, hydrogen or C1~4 alkyl,
  (xii) carbocyclic ring or
  (xiii) hetero ring,
$R^2$ is
  (i) hydrogen,
  (ii) C1~4 alkyl,
  (iii) halogen or
  (iv) trihalomethyl,
$Cyc^1$ is

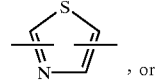
(ii)
, or

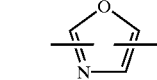
(iii)

$Cyc^2$ is
  (i) carbocyclic ring or
  (ii) hetero ring,
$R^3$ is
  (i) hydrogen,
  (ii) C1~8 alkyl,
  (iii) halogen,
  (iv) C1~4 alkoxy,
  (v) nitro,
  (vi) trihalomethyl,
  (vii) trihalomethoxy,
  (viii) trihalomethylthio,
  (ix) cyano or
  (x) C1~4 alkylthio,
$R^4$ is

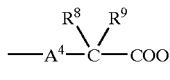
(i)

(ii) 2,4-thiazolidindion-5-yl,
$A^4$ is
  (i) bond,
  (ii) C1~4 alkylene,
  (iii) —C1~4 alkylene —o— or
  (iv) —C1~4 alkylene —S—,
$R^7$, $R^8$ and $R^9$ are each independently hydrogen or C1~4 alkyl, with the proviso that
  (1) $R^4$ is attached to 2- or 3-position and
  (2) when $R^4$ is attached to the 3-position, $A^4$ is a bond or methylene, and $Cyc^1$ is benzene, then $A^1$ is methylene, ethylene or vinylene,
a non-toxic salt thereof or a hydrate thereof.

* * * * *

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

<u>Column 183, lines 41-67, Column 184, and Column 185, lines 1-40,</u>
Delete claim 2 and insert:
2. The method of claim 1, wherein said disease is hyperglycemia or hyperlipidemia.

<u>Column 185, lines 41-67, Column 186, Column 187 and Column 188, lines 1-30,</u>
Delete claim 3 and insert:
3. The Method of claim 1, wherein said disease is a metabolic disorder selected from the group consisting of diabetes, obesity, syndrome X, hypercholesterolemia, and hyperlipoproteinemia, hyperlipidemia, artherosclerosis, hypertension, circulatory diseases, overeating, and ischemic heart diseases.

<u>Column 188, lines 31-67, Column 89 and Column 190, lines 1-65,</u>
Delete claim 4 and insert:

4. A compound of formula (I)

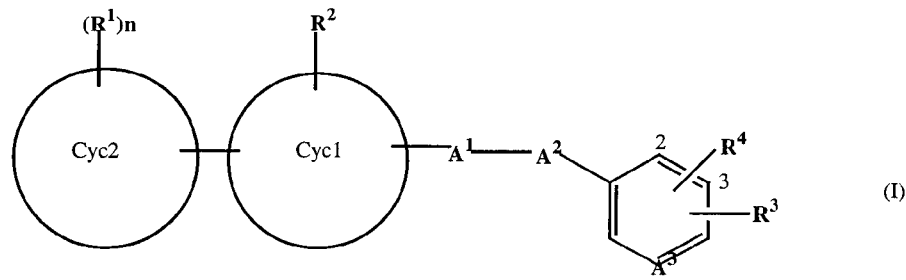

wherein $A^1$ is C1~4 alkylene or C2~4 alkenylene, $A^2$ is -O- or -S-,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

$A^3$ is CH, n is 1~5, $R^1$ is (i) hydrogen, (ii) C1~8 alkyl, (iii) halogen, (iv) C1~4 alkoxy, (v) nitro, (vi) trihalomethyl, (vii) trihalomethoxy, (viii) trihalomethylthio, (ix) cyano, (x) C1~4 alkylthio, (xi) $NR^5R^6$ wherein $R^5$ and $R^6$ are each independently hydrogen or C1~4 alkyl, (xii) carbocyclic ring or (xiii) hetero ring, $R^2$ is (i) hydrogen,

UNITED STATES PATENT AND TRADEMARK OFFICE
CERTIFICATE OF CORRECTION

PATENT NO. : 6,506,757 B1  Page 3 of 22
DATED : January 14, 2003
INVENTOR(S) : Tajima, Hisao et al.

It is certified that error appears in the above-identified patent and that said Letters Patent is hereby corrected as shown below:

(ii) C1~4 alkyl, (iii) halogen or (iv) trihalomethyl,

Cyc$^1$ is (ii) 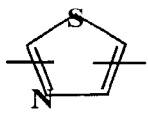 or (iii) 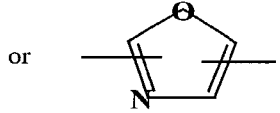,

Cyc$^2$ is (i) a carbocyclic ring or (ii) a hetero ring,

R$^3$ is (i) hydrogen, (ii) C1~8 alkyl, (iii) halogen, (iv) C1~4 alkoxy, (v) nitro, (vi) trihalomethyl, (vii) trihalomethoxy, (viii) trihalomethylthio, (ix) cyano or (x) C1~4 alkylthio, $R^4$ is (i)

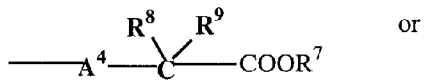

or (ii) 2, 4-thiazolidindion-5-yl, $A^4$ is (i) a bond, (ii) C1~4 alkylene, (iii) -C1~4 alkylene -O- or (iv) -C1~4 alkylene-S-, $R^7$, $R^8$ and $R^9$ are each independently hydrogen or C1~4 alkyl, with the proviso that (1) $R^4$ is attached to the 2- or 3-position, (2) when $R^4$ is attached to the 3-position, $A^4$ is a bond or methylene, and $Cyc^1$ is benzene, $A^1$ is methylene, ethylene or vinylene, and (3) when $R^4$ is attached to 2-position, $-A^1-A^2$ is $-CH_2-O-$, $R^7$ is methyl, and $R^8$ and $R^9$ are hydrogen,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

then $A^4$ is C1~4 alkylene, C1~4 alkylene –O-, or -C1~4 alkylene -S-, a non-toxic salt thereof or a hydrate thereof.

<u>Column 191, lines 66 and 67, Column 191 and Column 192, lines 1-20,</u>
Delete claim 5 and insert:

5. A compound according to claim 4, which is 1) 4-(3-(2-(5-methyl-2-phenyloxazol-4-yl)ethoxy)phenyl)butanoic acid · methyl ester, 2) 6-(3-(2-(5-methyl-2-phenyloxazol-4-yl)ethoxy)phenyl)hexanoic acid · methyl ester, 3) 5-(3-(2-(5-methyl-2-phenyloxazol-4- yl)ethoxy)phenyl)pentanoic acid · methyl ester, 4) 6-(2-(2-(5-methyl-2-phenyloxazol-4-yl)ethoxy)phenyl)hexanoic acid · methyl ester, 5) 5-(2-(2-(5-methyl-2-phenyloxazol-4-yl)ethoxy)phenyl)pentanoic acid · methyl ester, 6) 2-(3-(2-(5-methyl-2-phenyloxazol-4-yl)ethoxy)phenyl)acetic acid · methyl ester, 7) 5-(3-(3-(5-methyl-2-phenyloxazol-4-yl)propoxy)phenyl)pentanoic acid · methyl ester, 8) 2-(3-(2-(5-methyl-2-(4-methylphenyl)oxazol-4-yl)ethoxy)phenyl)acetic acid · methyl ester, 9) 2-(3-(2-(5-methyl-2-(4-ethylphenyl)oxazol-4-yl)ethoxy)phenyl)acetic acid · methyl ester, 10) 2-(3-(2-(5-methyl-2-(4-propylphenyl)oxazol-4-yl)ethoxy)phenyl)acetic acid · methyl ester, 11) 2- (3-(2-(5-methyl-2-(4-isopropylphenyl)oxazol-4-yl)ethoxy)phenyl)acetic acid · methyl ester, 12) 2-(3-(2-(5-methyl-2-(4-(2-methylpropyl)phenyl)oxazol-4-yl)ethoxy)phenyl)acetic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

13) 2(3-(2-(5-methyl-2-(4-t-butylphenyl)oxazol-4-yl)ethoxy)phenyl)acetic acid · methyl ester, 14) 2-(3-(2-(5-methyl-2-(4-methoxyphenyl)oxazol-4-yl)ethoxy)phenyl)acetic acid · methyl ester, 15) 2-(3-(2-(5-methyl-2-(3,4-dimethoxyphenyl)oxazol-4-yl)ethoxy)phenyl)acetic acid · methyl ester, 16) 2-(3-(5-methyl-2-phenyloxazol-4-yl)methoxy)phenyl)acetic acid · methyl ester, 17) 2-(3-(2-(5-methyl-2-phenylthiazol-4-yl)ethoxy)phenyl)acetic acid · methyl ester, 18) 2-(3-(3-(5-methyl-2-phenyloxazol-4-yl)propoxy)phenyl)acetic acid · methyl ester, 19) 2-(3-(2-(2-phenyloxazol-4-yl)ethoxy)phenyl)acetic acid · methyl ester, 20) 2-(3-(2-(5-methyl-2-(3-chloro-4-methylphenyl)oxazol-4-yl)ethoxy)phenyl) acid · methyl ester, 21) 2-(3-(2-(5-ethyl-2-phenyloxazol-4-yl)ethoxy)phenyl)acetic acid · methyl ester, 22) 2-(3- (2- (5-methyl-2-(4-butylphenyl )oxazol-4-yl)ethoxy)phenyl)acetic acid · methyl ester, 23) 2-(3-(2-(5-methyl-2-(4-chlorophenyl)oxazol-4-yl)ethoxy)phenyl)acetic acid · methyl ester, 24) 2-(3-(2-(5-methyl-2-(2-methylphenyl)oxazol-4-yl)ethoxy)phenyl)acetic acid · methyl ester, 25) 2-(3-(2-(5-methyl-2-(3-methylphenyl)oxazol-4-yl)ethoxy)phenyl)acetic acid . methyl ester, 26) 2-(3-(2-(5-methyl-2-(4-trifluoromethylphenyl)oxazol-4-yl)ethoxy)phenyl)acetic acid · methyl ester, 27) 2-(3-(2-(5-methyl-2-(4-fluorophenyl)oxazol-4-yl)ethoxy)phenyl)acetic acid · methyl ester, 28) 2-(3-(2-(5-methyl-2-(4-cyanophenyl)oxazol-4-yl)ethoxy)phenyl)acetic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

29) 2-(3-(2-(5-methyl-2-(3-nitro-4-methylphenyl)oxazol-4-yl)ethoxy)phenyl)acetic acid · methyl ester, 30) 2-(3-(2-(5-methyl-2-(4-pentylphenyl)oxazol-4-yl)ethoxy)phenyl)acetic acid · methyl ester, 31) 2-(3-(2-(5-methyl-2-(4-nitrophenyl)oxazol-4-yl)ethoxy)phenyl)acetic acid · methyl ester, 32) 4-(3-(2-(5-methyl-2-phenyloxazol-4-yl)ethoxy)phenyl)butanoic acid, 33) 6-(3-(2-(5-methyl-2-phenyloxazol-4-yl)ethoxy)phenyl)hexanoic acid, 34) 5-(3-(2-(5-methyl-2-phenyloxazol-4-yl)ethoxy)phenyl)pentanoic acid, 35) 6-(2-(2-(5-methyl-2-phenyloxazol-4-yl)ethoxy)phenyl)hexanoic acid, 36) 5-(2-(2-(5-methyl-2-phenyloxazol-4-yl)ethoxy)phenyl)pentanoic acid, 37) 2-(3(2-(5-methyl-2-phenyloxazol-4-yl)ethoxy)phenyl)acetic acid, 38) 5- (3-( 3- (5-methyl-2-phenyloxazol-4-yl)propoxy)phenyl)pentanoic acid, 39) 2-(3-(2-(5-methyl-2-(4-methylphenyl)oxazol-4-yl)ethoxy)phenyl)acetic acid, 40) 2-(3-(2-(5-methyl-2-(4-ethylphenyl)oxazol-4-yl)ethoxy)phenyl)acetic acid, 41) 2-(3-(2-(5-methyl-2-(4-propylphenyl)oxazol-4-yl)ethoxy)phenyl) acetic acid, 42) 2-(3-(2-(5-methyl-2-(4-isopropylphenyl)oxazol-4-yl)ethoxy)phenyl) acetic acid, 43) 2-(3-(2-(5-methyl-2-(4-(2-methylpropyl)phenyl)oxazol-4-yl)ethoxy)phenyl)acetic acid, 44) 2-(3-(2-(5-methyl-2-(4-t-butylphenyl)oxazol-4-yl)ethoxy)phenyl)acetic acid, 45) 2-(3-(2-(5-methyl-2-(4-methoxyphenyl)oxazol-4-yl)ethoxy)phenyl)acetic acid, 46) 2-(3-(2-(5-methyl-2-(3,4-dimethoxyphenyl)oxazol-4-yl)ethoxy)phenyl) acetic acid,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

47) 2-(3-(5-methyl-2-phenyloxazol-4-yl)methoxy)phenyl)acetic acid, 48) 2-(3-(2-(5-methyl-2-phenylthiazol-4-yl)ethoxy)phenyl)acetic acid, 49) 2-(3-(3-(5-methyl-2-phenyloxazol-4-yl)propoxy)phenyl)acetic acid, 50) 2-(3-(2-(2-phenyloxazol-4-yl)ethoxy)phenyl)acetic acid, 51) 2-(3-(2-(5-methyl-2-(3-chloro-4-methylphenyl)oxazol-4-yl)ethoxy)phenyl) acetic acid, 52) 2-(3-(2-(5-ethyl-2-phenyloxazol-4-yl)ethoxy)phenyl)acetic acid, 53) 2-(3-(2-(5-methyl-2-(4-butylphenyl)oxazol-4-yl)ethoxy)phenyl)acetic acid, 54) 2-(3-(2-(5-methyl-2-(4-chlorophenyl)oxazol-4-yl)ethoxy)phenyl)acetic acid, 55) 2-(3- (2-(5-methyl-2-(2-methylphenyl)oxazol-4-yl)ethoxy)phenyl)acetic acid, 56) 2-(3-(2-(5-methyl-2-(3-methylphenyl)oxazol-4-yl)ethoxy)phenyl )acetic acid, 57) 2-(3-(2-(5-methyl-2-(4-trifluoromethylphenyl)oxazol-4-yl)ethoxy)phenyl) acetic acid, 58) 2-(3-(2-(5-methyl-2-(4-fluorophenyl)oxazol-4-yl)ethoxy)phenyl)acetic acid, 59) 2-(3-(2-(5-methyl-2-(4-cyanophenyl)oxazol-4-yl)ethoxy)phenyl )acetic acid, 60) 2-(3-(2-(5-methyl-2-(3-nitro-4-methylphenyl)oxazol-4-yl)ethoxy)phenyl)acetic acid, 61) 2-(3-(2-(5-methyl-2-(4-pentylphenyl)oxazol-4-yl)ethoxy)phenyl )acetic acid, 62) 2-(3-(2-(5-methyl-2-(4-nitrophenyl)oxazol-4-yl)ethoxy)phenyl)acetic acid, 63) 2-(3-(2-(5-methyl-2-phenyloxazol-4-yl)ethylthio)phenyl)acetic acid · methyl ester, 64) 2-(3-(2-(5-methyl-2-phenyloxazol-4-yl)ethylthio)phenyl)acetic acid, a non-toxic salt thereof or a hydrate thereof.

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

Delete claim 6 and insert:

6. A compound according to claim 4 which is 1) 2-(3-(4-(4-methylphenyl)thiazol-2-ylmethoxy)phenylmethylthio)acetic acid · methyl ester, 2) 2-(3-(3-(4-(4-methylphenyl)thiazol-2-ylmethoxy)phenyl)propylthio)acetic acid · methyl ester, 3) 2-(3-(2-(5-methyl-2-phenyloxazol-4-yl)ethoxy)phenylmethylthio)acetic acid · methyl ester, 4) 2-(3-(3-(2-(5-methyl-2-phenyloxazol-4-yl)ethoxy)phenyl)propylthio)acetic acid · methyl ester, 5) 2-(4-chloro-3-(2-(5-methyl-2-phenyloxazol-4-yl)ethoxy)phenylmethylthio)acetic acid · methyl ester, 6) 2-(4-chloro-3-(4-(4-methylphenyl)thiazol-2-ylmethoxy)phenylmethylthio)acetic acid · methyl ester, 7) 2-(3-(2-phenylthiazol-4-ylmethoxy)phenylmethylthio)acetic acid · methyl ester, 8) 2-(3- (2- (5-methyl-2-(4-methylphenyl)oxazol-4-yl)ethoxy)phenylmethylthio)acetic acid · methyl ester, 9) 2-(3-(2-(2-phenylthiazol-4-yl)ethoxy)phenylmethylthio)acetic acid · methyl ester, 10) 2-(3-(2-(2-phenyloxazol-4-yl)ethoxy)phenylmethylthio)acetic acid · methyl ester, 11) 2-(3-(2-(5-methyl-2-(1,3-dioxaindan-5-yl)oxazol-4- yl)ethoxy)phenylmethylthio)acetic acid · methyl ester, 12) 2-(3-(5-methyl-2-phenyloxazol-4-ylmethoxy)phenylmethylthio)acetic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

13) 2-(3-(3-(5-methyl-2-phenyloxazol-4-yl)propoxy)phenylmethylthio)acetic acid · methyl ester, 14) 2-(3-(2-(5-methyl-2-(2-methylphenyl)oxazol-4-yl)ethoxy)phenylmethylthio)acetic acid · methyl ester, 15) 2-(3-(2-(5-methyl-2-(3-methylphenyl)oxazol-4-yl)ethoxy)phenylmethylthio)acetic acid · methyl ester, 16) 2-(3-(2-(5-methyl-2-(4-methoxyphenyl)oxazol-4- yl)ethoxy)phenylmethylthio)acetic acid · methyl ester, 17) 2-(3-(2-(5-methyl-2-phenyloxazol-4-yl)ethoxy)-5-chlorophenylmethylthio)acetic acid · methyl ester, 18) 2-(3-(2-(5-methyl-2-phenyloxazol-4-yl)ethoxy)-2-methylphenylmethylthio)acetic acid · methyl ester, 19) 2-(3-(2-(5-methyl-2-phenyloxazol-4-yl)-1-methylethoxy)phenylmethylthio)acetic acid · methyl ester, 20) 2-(3-(2-(5-methyl-2-phenyloxazol-4-yl)propoxy)phenylmethylthio)acetic acid · methyl ester, 21) 2-(3-(2-(5-methyl-2-phenyloxazol-4-yl)ethoxy)phenylmethylthio)propanoic acid · ethyl ester 22) 2-(3-(2-(5-methyl-2-(4-ethylphenyl)oxazol-4-yl)ethoxy)phenylmethylthio)acetic

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

acid · methyl ester, 23) 2-(3-(2-(5-methyl-2-(4-propylphenyl)oxazol-4-yl)ethoxy)phenylmethylthio)acetic acid · methyl ester, 24) 2-(3-(2-(5-methyl-2-(4-isopropylphenyl)oxazol-4- yl)ethoxy)phenylmethylthio)acetic acid · methyl ester, 25) 2-(3-(2-(5-methyl-2-phenylthiazol-4-yl)ethoxy)phenylmethylthio)acetic acid methyl · ester, 26) 2-(3-(2-(5-methyl-2-(4-butylphenyl)oxazol-4- yl)ethoxy)phenylmethylthio)acetic acid · methyl ester, 27) 2-(3-(2-(5-ethyl-2-phenyloxazol-4- yl)ethoxy)phenylmethylthio)acetic acid · methyl ester, 28) 2-(3-(2-(5-methyl-2-(4-pentylphenyl)oxazol-4-yl)ethoxy)phenylmethylthio)acetic acid · methyl ester, 29) 2-(3-(2-(5-methyl-2-cyclohexyloxazol-4-yl)ethoxy)phenylmethylthio)acetic acid · methyl ester, 30) 2-(3-(2-(5-methyl-2-(4-(2-methylpropyl)phenyl)oxazol-4-yl)ethoxy)phenylmethylthio)acetic acid · methyl ester, 31) 2-(3-(2-(5-methyl-2-(4-t-butylphenyl)oxazol-4-yl)ethoxy)phenylmethylthio)acetic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

32) 2-(3-(2-(5-methyl-2-(4-cyclohexylphenyl)oxazol-4-yl)ethoxy)phenylmethylthio)acetic acid · methyl ester, 33) 2-(3-(5-methyl-2-(1,3-dioxaindan-5-yl)oxazol-4-yl)methoxy)phenylmethylthio)acetic acid · methyl ester, 34) 2-(3-(5-methyl-2-(4-isopropylphenyl)oxazol-4-yl)methoxy)phenylmethylthio)acetic acid · methyl ester, 35) 2-(3-(2-(4-methyl-2-phenyloxazol-5-yl)ethoxy)phenylmethylthio)acetic acid · methyl ester, 36) 2-(3-(2-(5-methyl-2-(3,4-dimethoxyphenyl)oxazol-4-yl)ethoxy)phenylmethylthio)acetic acid · methyl ester, 37) 2-(3-(2-(5-methyl-2-(4-methylpiperazin-1-yl)oxazol-4-yl)ethoxy)phenylmethylthio)acetic acid · methyl ester, 38) 2-(3-(2-(5-methyl-2-(pyridin-2-yl)oxazol-4-yl)ethoxy)phenylmethylthio)acetic acid · methyl ester, 39) 2-(3-(2-(5-methyl-2-(thiophen-2-yl)oxazol-4-yl)ethoxy)phenylmethylthio)acetic acid · methyl ester, 40) 2-(3-(2-(5-methyl-2-(4-dimethylaminophenyl)oxazol-4-ly)ethoxy)phenylmethylthio)acetic acid · methyl ester, 41) 2-(3-(2-(5-methyl-2-cyclopentyloxazol-4-yl)ethoxy)phenylmethylthio)acetic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

42) 2-(3-(2-(5-methyl-2-cyclopropyloxazol-4-yl)ethoxy)phenylmethylthio)acetic acid · methyl ester, 43) 2-(3-(2-(5-methyl-2-(4-(1,2,3-thiadiazol-4-yl)phenyl)oxazol-4-yl)ethoxy)phenylmethylthio)acetic acid · methyl ester, 44) 2-(3-(2-(5-methyl-2-(4-(4-methyl-1,2,3-thiadiazol-5-yl)phenyl)oxazol-4-yl)ethoxy)phenylmethylthio)acetic acid · methyl ester, 45) 2-(3-(2-(5-methyl-2-(furan-2-yl)oxazol-4-yl)ethoxy)phenylmethylthio)acetic acid · methyl ester, 46) 2-(3-(2-(5-methyl-2-(pyridin-4-yl)oxazol-4-yl)ethoxy)phenylmethylthio)acetic acid · methyl ester, 47) 2-(3-(2-(5-methyl-2-phenyloxazol-4-yl)ethoxy)phenylmethoxy)acetic acid · t-butyl ester, 48) 2-(3-(2-(5-methyl-2-(pyridin-3-yl)oxazol-4-yl)ethoxy)phenylmethylthio)acetic acid · methyl ester, 49) 2-(3-(4-(4-methylphenyl)thiazol-2-ylmethoxy)phenylmethylthio )acetic acid, 50) 2-(3-(3-(4-(4-methylphenyl)thiazol-2-ylmethoxy)phenyl )propylthio)acetic acid, 51) 2-(3-(2-(5-methyl-2-phenyloxazol-4- yl)ethoxy)phenylmethylthio)acetic acid, 52) 2-(3-(3-(2-(5-methyl-2-phenyloxazol-4-yl)ethoxy)phenyl)propylthio)acetic acid, 53) 2-(4-chloro-3-(2-(5-methyl-2-phenyloxazol-4-yl)ethoxy)phenylmethylthio)acetic acid, 54) 2-(4-chloro-3-(4-(4-methylphenyl)thiazol-2-ylmethoxy)phenylmethylthio)acetic acid, 55) 2-(3-(2-phenylthiazol-4-ylmethoxy)phenylmethylthio)acetic acid

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

56) 2-(3-(2-(5-methyl-2-(4-methylphenyl)oxazol-4-yl)ethoxy)phenylmethylthio)acetic acid 57) 2-(3-(2-(2-phenylthiazol-4-yl)ethoxy)phenylmethylthio)acetic acid, 58) 2-(3-(2-(2-phenyloxazol-4-yl)ethoxy)phenylmethylthio)acetic acid 59) 2-(3-(2-(5-methyl-2-(1,3-dioxaindan-5-yl)oxazol-4-yl)ethoxy)phenylmethylthio)acetic acid, 60) 2-(3-(5-methyl-2-phenyloxazol-4-ylmethoxy)phenylmethylthio) acetic acid, 61) 2-(3-(3-(5-methyl-2-phenyloxazol-4-yl)propoxy)phenylmethylthio) acetic acid, 62) 2-(3-(2-(5-methyl-2-(2-methylphenyl)oxazol-4-yl)ethoxy)phenylmethylthio)acetic acid, 63) 2-(3-(2-(5-methyl-2-(3-methylphenyl)oxazol-4-yl)ethoxy)phenylmethylthio) acetic acid, 64) 2-(3-(2-(5-methyl-2-(4-methoxyphenyl)oxazol-4-yl)ethoxy)phenylmethylthio)acetic acid, 65) 2-(3-(2-(5-methyl-2-phenyloxazol-4-yl)ethoxy)-5-chlorophenylmethylthio)acetic acid, 66) 2-(3-(2-(5-methyl-2-phenyloxazol-4-yl)ethoxy)-2-methylphenylmethylthio)acetic acid, 67) 2-(3-(2-(5-methyl-2-phenyloxazol-4-yl)-1-methylethoxy)phenylmethylthio)acetic acid, 68) 2-(3-(2-(5-methyl-2-phenyloxazol-4-yl)propoxy)phenylmethylthio)acetic acid, 69) 2-(3-(2-(5-methyl-2-phenyloxazol-4- yl)ethoxy)phenylmethylthio)propanoic acid · sodium salt, 70) 2-(3-(2-(5-methyl-2-(4-ethylphenyl)oxazol-4-yl)ethoxy)phenylmethylthio)acetic acid, 71) 2-(3-(2-(5-methyl-2-(4-propylphenyl)oxazol-4-yl)ethoxy)phenylmethylthio)acetic acid, 72) 2-(3-(2-(5-methyl-2-(4-isopropylphenyl)oxazol-4-yl)ethoxy)phenylmethylthio)acetic acid, 73) 2-(3-(2-(5-methyl-2-phenylthiazol-4-yl)ethoxy)phenylmethylthio)acetic acid,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

74) 2-(3-(2-(5-methyl-2-(4-butylphenyl)oxazol-4-yl)ethoxy)phenylmethylthio)acetic acid, 75) 2-(3-(2-(5-ethyl-2-phenyloxazol-4-yl)ethoxy)phenylmethylthio)acetic acid, 76) 2-(3-(2-(5-methyl-2-(4-pentylphenyl)oxazol-4-yl)ethoxy)phenylmethylthio)acetic acid, 77) 2-(3-(2-(5-methyl-2-cyclohexyloxazol-4-yl)ethoxy)phenylmethylthio)acetic acid, 78) 2-(3-(2-(5-methyl-2-(4-(2-methylpropyl)phenyl)oxazol-4-yl)ethoxy)phenylmethylthio) acetic acid, 79) 2-(3-(2-(5-methyl-2- (4-t-butylphenyl)oxazol-4-yl)ethoxy)phenylmethylthio)acetic acid, 80) 2-(3-(2-(5-methyl-2-(4-cyclohexylphenyl)oxazol-4-yl)ethoxy)phenylmethylthio)acetic acid, 81) 2-(3-(5-methyl-2-(1,3-dioxaindan-5-yl)oxazol-4-yl)methoxy)phenylmethylthio)acetic acid, 82) 2-(3-(5-methyl-2-(4-isopropylphenyl)oxazol-4-yl)methoxy)phenylmethylthio)acetic acid, 83) 2-(3-(2-(4-methyl-2-phenyloxazol-5-yl)ethoxy)phenylmethylthio)acetic acid, 84) 2-(3-(2-(5-methyl-2-(3,4-dimethoxyphenyl)oxazol-4-yl)ethoxy)phenylmethylthio)acetic acid, 85) 2-(3-(2-(5-methyl-2-(4-methylpiperazin-1-yl)oxazol-4-yl)ethoxy)phenylmethylthio)acetic acid, 86) 2-(3-(2-(5-methyl-2-(pyridin-2-yl)oxazol-4-yl)ethoxy)phenylmethylthio)acetic acid, 87) 2-(3-(2-(5-methyl-2-(thiophen-2-yl)oxazol-4-yl)ethoxy)phenylmethylthio)acetic acid, 88) 2-(3-(2-(5-methyl-2-(4-dimethylaminophenyl)oxazol-4-yl)ethoxy)phenylmethylthio)acetic acid, 89) 2-(3-(2-(5-methyl-2-cyclopentyloxazol-4-yl)ethoxy)phenylmethylthio)acetic acid, 90) 2-(3-(2-(5-methyl-2-cyclopropyloxazol-4-yl)ethoxy)phenylmethylthio)acetic acid,

UNITED STATES PATENT AND TRADEMARK OFFICE
CERTIFICATE OF CORRECTION

PATENT NO.    : 6,506,757 B1
DATED         : January 14, 2003
INVENTOR(S)   : Tajima, Hisao et al.

It is certified that error appears in the above-identified patent and that said Letters Patent is hereby corrected as shown below:

91) 2-(3-(2-(5-methyl-2-(4-(1,2,3-thiadiazol-4-yl)phenyl)oxazol-4-yl)ethoxy)phenylmethylthio)acetic acid, 92) 2-(3-(2-(5-methyl-2- (4- (4-methyl-1,2,3-thiadiazol-5-yl)phenyl)oxazol-4-yl)ethoxy)phenylmethylthio)acetic acid, 93) 2-(3-(2-(5-methyl-2-(furan-2-yl)oxazol-4-yl)ethoxy)phenylmethylthio)acetic acid, 94) 2-(3-(2-(5-methyl-2-(pyridin-4-yl)oxazol-4-yl)ethoxy)phenylmethylthio)acetic acid, 95) 2-(3-(2-(5-methyl-2-phenyloxazol-4-yl)ethoxy)phenylmethoxy)acetic acid, 96) 2-(3-(2-(5-methyl-2-(pyridin-3-yl)oxazol-4-yl)ethoxy)phenylmethylthio)acetic acid, 97) 2-(3-(2-(5-methyl-2-phenyloxazol-4-yl)ethoxy)phenylmethylthio)-2-methylpropanoic acid · ethyl ester, 98) 2-(3-(2-(5-methyl-2-phenyloxazol-4-yl)ethoxy)phenylmethylthio)-2-methylpropanoic acid, 99) 2-(3-(2-(5-methyl-2-(1,3-dioxaindan-5-yl)oxazol-4-yl)ethoxy)phenylmethoxy)acetic acid · t-butyl ester, 100) 2-(3-(2-(5-methyl-2-(1,3-dioxaindan-5-yl)oxazol-4-yl)ethoxy)phenylmethoxy)acetic acid, a non-toxic salt thereof or a hydrate thereof.

Column 192,
Lines 23-28, delete claim 7 and insert:
   7.    A compound according to claim 4 which is 1) 6-(3-(4-(4-methylphenyl)thiazol-2-ylmethoxy)phenyl)hexanoic acid · methyl ester, 2) 4-(3-(4-(4-methylphenyl)thiazol-2-ylmethoxy)phenyl)butanoic acid · methyl ester, 3) 6-(2-(4-(4-methylphenyl)thiazol-2-ylmethoxy)phenyl)hexanoic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

4) 2-(3-(2-(5-methyl-2-(4-trifluoromethylphenyl)oxazol-4-yl)ethoxy)phenylmethylthio)acetic acid · methyl ester, 5) 2-(3-(2-(5-methyl-2-(4-fluorophenyl)oxazol-4-yl)ethoxy)phenylmethylthio)acetic acid · methyl ester, 6) 2-(3-(2-(5-methyl-2-(4-chlorophenyl)oxazol-4-yl)ethoxy)phenylmethylthio)acetic acid · methyl ester, 7) 2-(3-(2-(5-methyl-2-phenyloxazol-4-yl)ethoxy)phenyl)-2-methylpropanoic acid · methyl ester, 8) 2-(3-(2-(5-methyl-2-(4-nitrophenyl)oxazol-4- yl)ethoxy)phenylmethylthio)acetic acid · methyl ester, 9) 2-(1-(3-(2-(5-methyl-2-phenyloxazol-4-yl)ethoxy)phenyl)ethylthio)acetic acid · methyl ester, 10) 2-(3-(2-(5-trifluoromethyl-2-phenyloxazol-4-yl)ethoxy)phenylthio)acetic acid · methyl ester, 11) 2-(3-(2-(5-methyl-2-(2,2-difluoro-1,3-dioxaindan-5-yl)oxazol-4-yl)ethoxy)phenylmethylthio)acetic acid · methyl ester, 12) 2-(3-(2-(5-methyl-2-(2,3,5,6-tetrafluoro-4- methylphenyl)oxazol-4-yl)ethoxy)phenylmethylthio)acetic acid · methyl ester, 13) 2-(3-(2-(5-methyl-2-(3-chloro-4-methylphenyl)oxazol-4-yl)ethoxy)phenylmethylthio)acetic acid · methyl ester, 14) 2-(3-(2-(5-methyl-2-(4-trifluoromethoxyphenyl)oxazol-4-yl)ethoxy)phenylmethylthio)acetic acid · methyl ester, 15) 2-(3-(2-(5-methyl-2-(3,4,5-trimethoxyphenyl)oxazol-4-yl)ethoxy)phenylmethylthio)acetic acid

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

· methyl ester, 16) 2-(3-(2-(5-methyl-2-(4-methylthiophenyl)oxazol-4-yl)ethoxy)phenylmethylthio)acetic acid · methyl ester, 17) 2-(3-(2-(5-methyl-2-(3-nitro-4-methylphenyl)oxazol-4-yl)ethoxy)phenylmethylthio)acetic acid · methyl ester, 18) 2-(3-(2-(5-methyl-2-(1,3-dioxaindan-5-yl)oxazol-4-yl)ethoxy)phenyl)acetic acid · methyl ester, 19) 2-(3-(2-(5-methyl-2-(3,4,5-trimethoxyphenyl)oxazol-4-yl)ethoxy)phenyl)acetic acid · methyl ester, 20) 2-(3-(2-(5-methyl-2-(4-trifluoromethoxyphenyl)oxazol-4-yl)ethoxy)phenyl)acetic acid · methyl ester, 21) 2-(3-(2-(5-methyl-2-(2,2-difluoro-1,3-dioxaindan-5-yl)oxazol-4-yl)ethoxy)phenyl)acetic acid · methyl ester, 22) 2-(3-(2-(5-methyl-2-(4-trifluoromethylthiophenyl)oxazol-4-yl)ethoxy)phenylmethylthio)acetic acid · methyl ester, 23) 2-(3-(2-(5-methyl-2-(4-cyanophenyl)oxazol-4-yl)ethoxy)phenylmethylthio)acetic acid · methyl ester, 24) 2-(3-(2-(5-methyl-2-(4-cyclohexylphenyl)oxazol-4-yl)ethoxy)phenyl)acetic acid · methyl ester, 25) 2-(3-(2-(5-methyl-2-(4-dimethylaminophenyl)oxazol-4-yl)ethoxy)phenyl)acetic acid · methyl ester, 26) 2-(3-(2-(5-methyl-2-(thiophen-2-yl)oxazol-4-yl)ethoxy)phenyl)acctic acid · methyl ester,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

27) 2-(3-(2-(5-methyl-2-(furan-2-yl)oxazol-4-yl)ethoxy)phenyl)acetic acid · methyl ester, 28) 2-(3-(2-(5-methyl-2-(pyridin-2-yl)oxazol-4-yl)ethoxy)phenyl)acetic acid · methyl ester, 29) 2-(3-(2-(5-methyl-2-(4-methyl-1,2,3-thiadiazol-5-yl)oxazol 4-yl)ethoxy)phenyl)acetic acid · methyl ester, 30) 2-(3-(2-(5-methyl-2-(2,3,5,6-tetrafluoro-4-methylphenyl)oxazol-4-yl)ethoxy)phenyl)acetic acid · methyl ester, 31) 2-(3-(2-(5-methyl-2-cyclohexyloxazol-4-yl)ethoxy)phenyl)acetic acid · methyl ester, 32) 2-(3-(2-(5-methyl-2-cyclopentyloxazol-4-yl)ethoxy)phenyl)acetic acid · methyl ester, 33) 2-(3-(2-(5-methyl-2-(pyridin-3-yl)oxazol-4-yl)ethoxy)phenyl)acetic acid · methyl ester, 34) 2-(3-(2-(5-methyl-2-(pyridin-4-yl)oxazol-4-yl)ethoxy)phenyl)acetic acid · methyl ester, 35) 2-(3-(2-(5-methyl-2-(4-methylpiperazin-1-yl)thiazol-4-yl)ethoxy)phenyl)acetic acid · methyl ester, 36) 2-(3-(2-(5-methyl-2-(4-methylthiophenyl)oxazol-4-yl)ethoxy)phenyl)acetic acid · methyl ester, 37) 2-(3-(2-(5-methyl-2-cyclopropyloxazol-4-yl)ethoxy)phenyl)acetic acid · methyl ester, 38) 2-(3-(2-(5-methyl-2-(quinolin-2-yl)oxazol-4-yl)ethoxy)phenyl)acetic acid · methyl ester, 39) 6-(3-(4-(4-methylphenyl)thiazol-2-ylmethoxy)phenyl)hexanoic acid, 40) 4-(3-(4-(4-methylphenyl)thiazol-2-ylmethoxy)phenyl)butanoic acid, 41) 6-(2-(4-(4-methylphenyl)thiazol-2-ylmethoxy)phenyl)hexanoic acid, 42) 2-(3-(2-(5-methyl-2-(4-trifluoromethylphenyl)oxazol-4-yl)ethoxy)phenylmethylthio)acetic

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

acid, 43) 2-(3-(2-(5-methyl-2-(4-fluorophenyl)oxazol-4-yl)ethoxy)phenylmethylthio)acetic acid, 44) 2-(3-(2-(5-methyl-2-(4-chlorophenyl)oxazol-4-yl )ethoxy)phenylmethylthio )acetic acid, 45) 2-(3-(2-(5-methyl-2-phenyloxazol-4-yl)ethoxy)phenyl)-2-methylpropanoic acid, 46) 2-(3-(2-(5-methyl-2-(4-nitrophenyl)oxazol-4-yl)ethoxy)phenylmethylthio)acetic acid, 47) 2-(1-(3-(2-(5-methyl-2-phenyloxazol-4-yl )ethoxy)phenyl)ethylthio)acetic acid, 48) 2-(3-(2-(5-trifluoromethyl-2-phenyloxazol-4-yl)ethoxy)phenylthio)acetic acid, 49) 2-(3-(2-(5-methyl-2-(2,2-difluoro-1,3-dioxaindan-5-yl)oxazol-4-yl)ethoxy)phenylmethylthio)acetic acid, 50) 2-(3-(2-(5-methyl-2-(2,3,5,6-tetrafluoro-4-methylphenyl)oxazol-4-yl)ethoxy)phenylmethylthio)acetic acid, 51) 2-(3-(2-(5-methyl-2-(3-chloro-4-methylphenyl)oxazol-4-yl)ethoxy)phenylmethylthio)acetic acid, 52) 2-(3-(2-(5-methyl-2-(4-trifluoromethoxyphenyl)oxazol-4-yl)ethoxy)phenylmethylthio)acetic acid, 53) 2-(3-(2-(5-methyl-2-(3,4,5-trimethoxyphenyl)oxazol-4-yl)ethoxy)phenylmethylthio)acetic acid, 54) 2-(3-(2-(5-methyl-2-(4-methylthiophenyl)oxazol-4-yl)ethoxy)phenylmethylthio)acetic acid,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

55) 2-(3-(2-(5-methyl-2-(3-nitro-4-methylphenyl)oxazol-4-yl)ethoxy)phenylmethylthio)acetic acid, 56) 2-(3-(2-(5-methyl-2-(1,3-dioxaindan-5-yl)oxazol-4-yl)ethoxy)phenyl)acetic acid, 57) 2-(3-(2-(5-methyl-2-(3,4,5-trimethoxyphenyl)oxazol-4-yl)ethoxy)phenyl)acetic acid, 58) 2-(3-(2-(5-methyl-2-(4-trifluoromethoxyphenyl)oxazol-4-yl)ethoxy)phenyl)acetic acid, 59) 2-(3-(2-(5-methyl-2-(2,2-difluoro-1,3-dioxaindan-5-yl)oxazol-4-yl)ethoxy)phenyl)acetic acid, 60) 2-(3-(2-(5-methyl-2-(4-trifluoromethylthiophenyl)oxazol-4-yl)ethoxy)phenylmethylthio)acetic acid, 61) 2-(3-(2-(5-methyl-2-(4-cyanophenyl)oxazol-4-yl)ethoxy)phenylmethylthio)acetic acid, 62) 2-(3-(2-(5-methyl-2-(4-cyclohexylphenyl)oxazol-4-yl)ethoxy)phenyl)acetic acid, 63) 2-(3-(2-(5-methyl-2-(4-dimethylaminophenyl)oxazol-4-yl)ethoxy)phenyl)acetic acid, 64) 2-(3-(2-(5-methyl-2-(thiophen-2-yl)oxazol-4-yl)ethoxy)phenyl)acetic acid, 65) 2- (3- (2- (5-methyl-2- (furan-2-yl)oxazol-4-yl)ethoxy)phenyl)acetic acid, 66) 2-(3-(2-(5-methyl-2-(pyridin-2-yl)oxazol-4-yl)ethoxy)phenyl)acetic acid, 67) 2-(3-(2-(5-methyl-2-(4-methyl-1,2,3-thiadiazol-5-yl)oxazol-4-yl)ethoxy)phenyl )acetic acid, 68) 2-(3-(2-(5-methyl-2-(2,3,5,6-tetrafluoro-4-methylphenyl)oxazol-4-yl)ethoxy)phenyl)acetic acid, 69) 2-(3-(2-(5-methyl-2-cyclohexyloxazol-4-yl)ethoxy)phenyl) acetic acid, 70) 2-(3-(2-(5-methyl-2-cyclopentyloxazol-4-yl)ethoxy)phenyl)acetic acid, 71) 2-(3-(2-(5-methyl-2-(pyridin-3-yl)oxazol-4-yl)ethoxy)phenyl)acetic acid,

UNITED STATES PATENT AND TRADEMARK OFFICE
CERTIFICATE OF CORRECTION

PATENT NO. : 6,506,757 B1
DATED : January 14, 2003
INVENTOR(S) : Tajima, Hisao et al.

It is certified that error appears in the above-identified patent and that said Letters Patent is hereby corrected as shown below:

72) 2-(3-(2-(5-methyl-2-(pyridin-4-yl)oxazol-4-yl)ethoxy)phenyl)acetic acid, 73) 2-(3-(2-(5-methyl-2-(4-methylpiperazin-1-yl)thiazol-4-yl)ethoxy)phenyl)acetic acid, 74) 2-(3-(2-(5-methyl-2-(4-methylthiophenyl)oxazol-4-yl)ethoxy)phenyl)acetic acid, 75) 2-(3-(2-(5-methyl-2-cyclopropyloxazol-4-yl)ethoxy)phenyl)acetic acid, 76) 2-(3-(2-(5-methyl-2-(quinolin-2-yl)oxazol-4-yl)ethoxy)phenyl)acetic acid, 77) 5-(3-(2-(5-methyl-2-phenyloxazol-4-yl)ethoxy)phenyl)-2,4-thiazolidindione, 78) 2-(3-(2-(5-methyl-2-(3-trifluoromethoxyphenyl)oxazol-4-yl)ethoxy)phenyl)acetic acid · methyl ester, 79) 2-(3-(2-(5-methyl-2-(2-trifluoromethoxyphenyl)oxazol-4-yl)ethoxy)phenyl)acetic acid · methyl ester, 80) 2-(3-(2-(4-methyl-2-phenyloxazol-5-yl)ethoxy)phenyl)acetic acid · methyl ester, 81) 2-(3-(2-(5-methyl-2-(3-trifluoromethoxyphenyl)oxazol-4-yl)ethoxy)phenyl) acetic acid, 82) 2-(3-(2-(5-methyl-2-(2-trifluoromethoxyphenyl)oxazol-4-yl)ethoxy)phenyl) acetic acid, 83) 2-(3-(2-(4-methyl-2-phenyloxazol-5-yl)ethoxy)phenyl)acetic acid, a non-toxic salt thereof or a hydrate thereof.

Signed and Sealed this

Seventh Day of October, 2003

JAMES E. ROGAN
*Director of the United States Patent and Trademark Office*

SEQUENCE LISTING

<160> NUMBER OF SEQ ID NOS: 3

<210> SEQ ID NO 1
<211> LENGTH: 85
<212> TYPE: DNA
<213> ORGANISM: Artificial Sequence
<220> FEATURE:
<223> OTHER INFORMATION: Description of Artificial Sequence: Enhancer sequence including 4 times repeated Gal4 protein response sequence

<400> SEQUENCE: 1
tcgacggagt actgtcctcc gcgacggagt actgtcctcc gcgacggagt actgtcctcc 60
gcgacggagt actgtcctcc gagct 85

<210> SEQ ID NO 2
<211> LENGTH: 9
<212> TYPE: PRT
<213> ORGANISM: Unknown Organism
<220> FEATURE:
<223> OTHER INFORMATION: Description of Unknown Organism:Nuclear localization signal derived from SV-40 T-antigen

<400> SEQUENCE: 2

Ala Pro Lys Lys Lys Arg Lys Val Gly
1 5

<210> SEQ ID NO 3
<211> LENGTH: 9
<212> TYPE: PRT
<213> ORGANISM: Influenza virus
<220> FEATURE:
<223> OTHER INFORMATION: hemagglutinin epitope

<400> SEQUENCE: 3

Tyr Pro Tyr Asp Val Pro Asp Tyr Ala
1 5